United States Patent
Barnes et al.

(10) Patent No.: US 11,235,123 B2
(45) Date of Patent: Feb. 1, 2022

(54) PRESSURE REGULATING VALVE

(71) Applicant: Fisher & Paykel Healthcare Limited, Auckland (NZ)

(72) Inventors: Thomas Heinrich Barnes, Surrey (GB); Shane Terry Massey, Auckland (NZ); Taylor James Edwards, Auckland (NZ); Arjen David Kat, Auckland (NZ); James Alexander Gordon, Auckland (NZ); Grant Leigh Nelson, Auckland (NZ); Carsten Ma On Wong Corazza, Auckland (NZ)

(73) Assignee: FISHER & PAYKEL HEALTHCARE LIMITED, Auckland (NZ)

( * ) Notice: Subject to any disclaimer, the term of this patent is extended or adjusted under 35 U.S.C. 154(b) by 0 days.

(21) Appl. No.: 16/325,853

(22) PCT Filed: Aug. 16, 2017

(86) PCT No.: PCT/IB2017/054973
§ 371 (c)(1),
(2) Date: Feb. 15, 2019

(87) PCT Pub. No.: WO2018/033863
PCT Pub. Date: Feb. 22, 2018

(65) Prior Publication Data
US 2021/0178110 A1    Jun. 17, 2021

Related U.S. Application Data

(60) Provisional application No. 62/485,846, filed on Apr. 14, 2017, provisional application No. 62/399,643, (Continued)

(51) Int. Cl.
*A61M 16/20*    (2006.01)
*A61M 16/08*    (2006.01)
(Continued)

(52) U.S. Cl.
CPC ....... *A61M 16/209* (2014.02); *A61M 16/0066* (2013.01); *A61M 16/04* (2013.01);
(Continued)

(58) Field of Classification Search
CPC .............. A61M 16/00; A61M 16/0003; A61M 16/0057; A61M 16/0066; A61M 16/022;
(Continued)

(56) References Cited

U.S. PATENT DOCUMENTS

| 2,743,737 A | 5/1956 | Textor |
| 2,286,713 A | 6/1972 | Burks |

(Continued)

FOREIGN PATENT DOCUMENTS

| CN | 101394888 A | 3/2009 |
| EP | 2431065 | 3/2012 |

(Continued)

OTHER PUBLICATIONS

Third party Written Submissions of Publications, Japanese Application No. 2019-508899, dated Sep. 30, 2020, in 6 pages.

(Continued)

*Primary Examiner* — Joseph D. Boecker
(74) *Attorney, Agent, or Firm* — Knobbe Martens Olson & Bear LLP

(57) ABSTRACT

A pressure regulating or pressure relief device comprises an inlet and an outlet chamber with an outlet. The inlet is in fluid communication with the outlet chamber. A valve seat is located between the inlet and the outlet. A valve member is biased to seal against the valve seat, and displaces from the valve seat by an inlet pressure at the inlet increasing above a pressure threshold to allow a flow of gases from the inlet to the outlet via the outlet chamber. The flow of gases through the outlet causes an outlet pressure in the outlet (Continued)

chamber to act on the valve member together with the inlet pressure to displace the valve member from the valve seat.

63 Claims, 58 Drawing Sheets

Related U.S. Application Data filed on Sep. 26, 2016, provisional application No. 62/375,831, filed on Aug. 16, 2016.

(51) Int. Cl.
| | | |
|---|---|---|
| A61M 16/06 | (2006.01) | |
| A61M 16/16 | (2006.01) | |
| A61M 16/00 | (2006.01) | |
| A61M 16/04 | (2006.01) | |

(52) U.S. Cl.
CPC ......... *A61M 16/06* (2013.01); *A61M 16/0672* (2014.02); *A61M 16/0808* (2013.01); *A61M 16/161* (2014.02); *A61M 2016/003* (2013.01); *A61M 2016/0027* (2013.01); *A61M 2202/0208* (2013.01); *A61M 2205/3368* (2013.01); *A61M 2205/42* (2013.01)

(58) Field of Classification Search
CPC .............. A61M 16/06; A61M 16/0666; A61M 16/0672; A61M 16/0858; A61M 16/0866; A61M 16/20; A61M 16/201; A61M 16/202; A61M 16/203; A61M 16/206; A61M 16/207; A61M 2016/0027; A61M 2016/003; A61M 2016/0033; A61M 2016/0039; A61M 2205/3334; F16K 17/0486; F16K 17/06; F16K 17/065; F16K 17/22

See application file for complete search history.

(56) References Cited

U.S. PATENT DOCUMENTS

| | | | |
|---|---|---|---|
| 4,555,719 A | 11/1985 | Arway et al. | |
| 4,712,580 A | 12/1987 | Gilman et al. | |
| 5,360,396 A | 11/1994 | Chan | |
| 5,514,087 A | 5/1996 | Jones | |
| 5,791,339 A | 8/1998 | Winter | |
| 6,006,748 A | 12/1999 | Hollis | |
| 6,253,764 B1 * | 7/2001 | Calluaud ............. | A61M 16/202 128/204.18 |
| 6,425,393 B1 | 7/2002 | Lurie et al. | |
| 7,364,132 B2 | 4/2008 | Browne et al. | |
| 8,196,581 B2 | 6/2012 | Bozanic et al. | |
| 8,307,846 B2 | 11/2012 | Yanagisawa | |
| 8,695,571 B2 | 4/2014 | Suzuki et al. | |
| 8,733,344 B2 | 5/2014 | Bozanic et al. | |
| 8,893,718 B2 | 11/2014 | Heinonen | |
| 9,016,319 B2 | 4/2015 | Spahr | |
| 9,058,042 B2 | 6/2015 | Vu et al. | |
| 9,109,711 B2 | 8/2015 | Mattson et al. | |
| 9,125,721 B2 | 9/2015 | Field | |
| 9,352,086 B2 | 5/2016 | Guala | |
| 9,435,236 B2 | 9/2016 | Zitarosa et al. | |
| 9,476,507 B2 | 10/2016 | Akahane et al. | |
| 9,616,192 B2 | 4/2017 | Chalvignac et al. | |
| 9,684,293 B2 | 6/2017 | Barrow et al. | |
| 9,770,571 B2 | 9/2017 | Hollis | |
| 9,835,255 B2 | 12/2017 | Pears et al. | |
| 10,167,959 B2 | 1/2019 | Pears et al. | |
| 2002/0014239 A1* | 2/2002 | Chalvignac ......... | A61M 16/205 128/204.18 |
| 2002/0017301 A1 | 2/2002 | Lundin | |
| 2003/0127100 A1* | 7/2003 | Hollis ................. | A61M 16/209 128/205.24 |
| 2010/0170509 A1 | 7/2010 | Moody et al. | |
| 2011/0168181 A1* | 7/2011 | Caspary .............. | A61M 16/206 128/205.24 |
| 2013/0061852 A1* | 3/2013 | Heinonen ......... | A61M 16/0081 128/204.21 |
| 2013/0186394 A1* | 7/2013 | Hallett .............. | A61M 16/0666 128/201.13 |
| 2014/0305431 A1 | 10/2014 | Holley et al. | |
| 2015/0190606 A1 | 7/2015 | Hollis | |
| 2016/0169398 A1 | 6/2016 | Takahashi et al. | |
| 2017/0165449 A1 | 6/2017 | Chalvignac et al. | |
| 2017/0167808 A1 | 6/2017 | Han et al. | |
| 2019/0038866 A1 | 2/2019 | Chalvignac et al. | |
| 2019/0111232 A1 | 4/2019 | Holley et al. | |

FOREIGN PATENT DOCUMENTS

| | | |
|---|---|---|
| EP | 2526267 | 11/2012 |
| EP | 2550052 | 1/2013 |
| EP | 2633213 | 9/2013 |
| EP | 2776107 | 9/2014 |
| EP | 2848878 | 3/2015 |
| EP | 2971897 | 1/2016 |
| GB | 1 432 171 A | 4/1976 |
| JP | S58-221078 | 12/1983 |
| JP | 2000-193347 | 7/2000 |
| JP | 2004-218443 | 8/2004 |
| JP | 2008-20141 | 1/2008 |
| JP | 2008-286204 | 11/2008 |
| JP | 2012-107641 | 6/2012 |
| JP | 2015-021518 | 2/2015 |
| JP | 2017-025975 | 2/2017 |
| NZ | 585948 | 3/2013 |
| NZ | 598313 | 11/2013 |
| NZ | 603309 | 2/2014 |
| NZ | 612448 | 10/2014 |
| NZ | 721709 | 1/2017 |
| NZ | 743431 | 6/2018 |
| NZ | 728273 | 7/2018 |
| WO | WO 97/41812 A1 | 11/1997 |
| WO | WO 00/45883 A1 | 8/2000 |
| WO | WO 03/066146 A1 | 8/2003 |
| WO | WO 2012/048364 A1 | 4/2012 |
| WO | WO 2012/140514 | 10/2012 |
| WO | WO 2014/186584 A2 | 11/2014 |
| WO | WO 2016/067147 A1 | 5/2016 |

OTHER PUBLICATIONS

International Search Report and Written Opinion for Application No. PCT/IB2017/054973 dated Nov. 22, 2017 in 16 pages.
Written Opinion for Application No. EP 17 841 177 dated Mar. 6, 2020 in 6 pages.
Supplemental European Search Report for Application No. EP 17 84 1177 dated Feb. 25, 2020 in 3 pages.

* cited by examiner

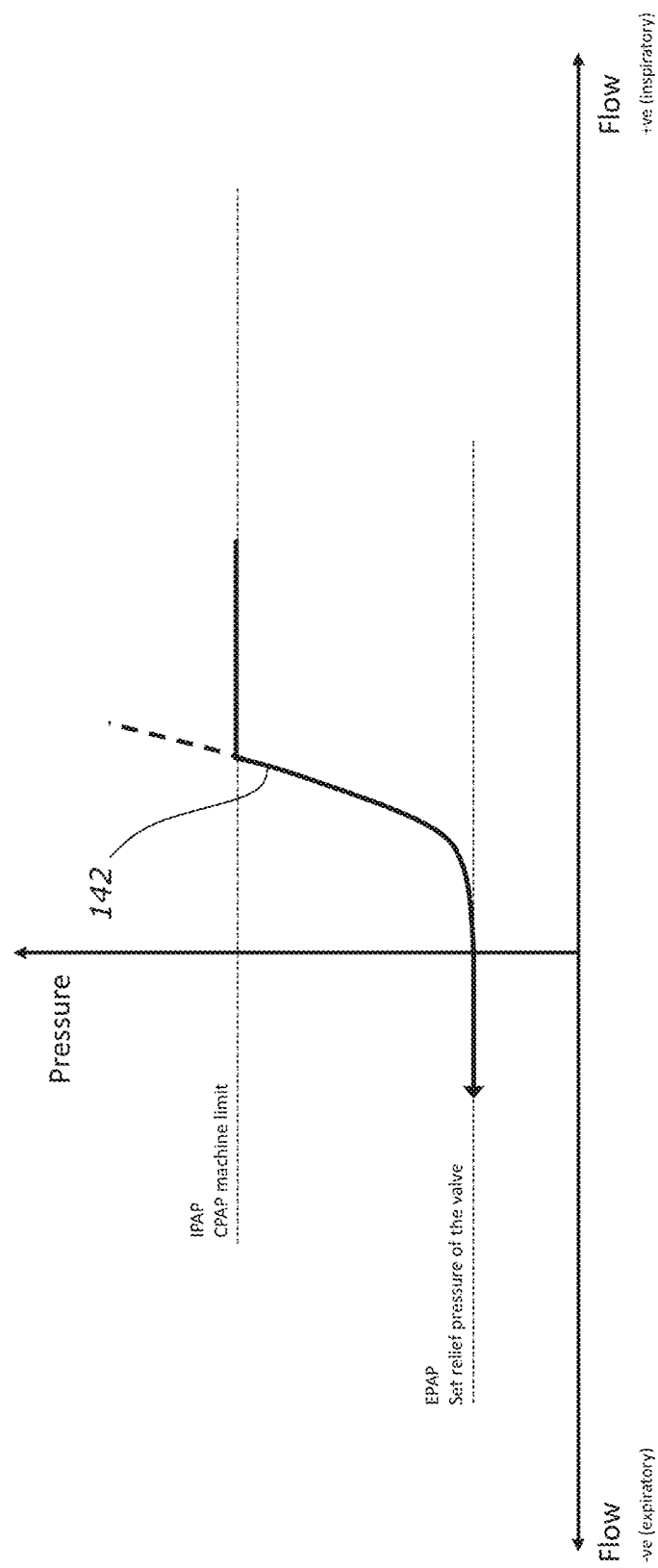

PRESSURE REGULATING VALVE

TECHNICAL FIELD

The present disclosure generally relates to a pressure relief or pressure regulation device, and more specifically a pressure relief or regulation device for use in a respiratory gases system for providing a flow of respiratory gases to a user, for example a high flow respiratory gases system.

BACKGROUND ART

Respiratory gas supply systems provide gas for delivery to a patient. Respiratory gas supply systems typically include a fluid connection between the gas supply and the patient. This may include an inspiratory tube and a patient interface. Such systems may be open, i.e. comprising an unsealed patient interface such as a nasal cannula, or closed, i.e. comprising a sealed patient interface such as a face mask that seals against the user's face. Such systems may receive gases from a pressurised gas supply (such as a gas tank, or hospital wall supply), a blower, or a combination thereof.

Open respiratory gas supply systems may include those employed in nasal high flow therapy, for example. Closed respiratory gas supply systems may include those employed in continuous positive airway pressure (CPAP) or in ventilation, for example.

Respiratory gas supply systems may be susceptible to accidental or inadvertent flow restriction or obstruction. For example, accidental snagging, folding or crushing of the inspiratory tube may create a sudden and/or substantial flow restriction or obstruction. Consequently, a substantial backpressure may be created upstream of the restriction or obstruction.

It should be further appreciated that a sudden and/or substantial backpressure may occur when the patient presents excessive resistance to flow. For example, the shape, size, or anatomy of a patient's nose and/or airway may provide a restriction which creates a substantial backpressure. Furthermore, a substantial backpressure may alternatively and/or concurrently be created as a result of the patient exhaling into to the flow of incoming gases.

Excess backpressure in a respiratory gases supply system may cause damage to tubes, fluid connections, or other components. In particular, tubes, fluid connections, or other components may burst or fail.

Therefore, there is a need to relieve/regulate pressure in a respiratory gases supply system created as the result of a restriction, obstruction, or excessive resistance to flow in order to avoid or prevent damage to components.

Respiratory gas supply systems may place strain on the patient's tissues when inadequate or no pressure limiting means are provided. This may consequently place the patient at risk of barotrauma or gastric distension.

Therefore, there is also a need to provide an upper pressure limit, for patient safety.

A pressure relief valve may be used to provide an upper pressure limit in a respiratory system. A pressure relief valve may allow the discharge of gas pressure when the system pressure exceeds a pressure relief threshold provided by the pressure relief valve. Beyond a pressure relief threshold, as the flow rate is increased, the pressure in the system progressively increase approximately proportionate to flow. As a result, the patient and components in the system may be exposed to increasingly greater pressures as the flow rate is increased.

An example a pressure relief valve is a valve of the plunger and spring type. The plunger is displaced when pressure in the valve provides a force on the plunger that exceeds a force provided by the spring in a return direction. Gas is then allowed to pass through a gap between the plunger and a valve seat until the pressure in the valve is insufficient to generate a force to continue to exceed the return force provided by the spring—at which point, the plunger re-engages the valve seat, closing the gap. Valves of this type may naturally oscillate as the abovementioned function occurs repetitively—as pressure builds and is subsequently released in succession. This may be referred to as valve 'chatter' or valve 'flutter'. In some instances, such oscillations may be erratic. Valve oscillations may create unwanted noise, pressure or flow fluctuations, or wear.

Valves of the plunger and spring type typically also require some means of sealing the plunger inside a housing in which it travels and/or some means of sealing the plunger against a valve seat. Such means may include additional components such as O-rings. Forming a strong fluid tight seal is typically important. Additional components add complexity to the construction of the valve and subsequently increase susceptibility of the valve to failure and/or wear.

A respiratory system presents a resistance to the flow of respiratory gases through the system. The resistance to flow caused by individual components of the system such as the humidifier, conduits, couplings, filters the patient interface and any other system component accumulates throughout the system, resulting in a total pressure drop through the system. Resistance to flow may be attributed to flow direction changes, restrictions, convergences, divergences and/or permeable barriers (such as filters), for example, in the flow path.

In order to increase the flow rate of gases through a system, the pressure provided by a flow source is increased, to account for an increased pressure drop through the system resulting from the increased flow rate. As flow is increased, the system pressure required to achieve the flow rate (the driving pressure) may reach a set relief pressure of a pressure relief valve, for example a predetermined safe pressure limit. Therefore the set relief pressure of the pressure relief valve defines or determines the maximum flow which may be delivered to the patient. In prior art pressure relief valves, the maximum flow rate that can be delivered to the patient is limited by the set relief pressure of the pressure relief valve. This may constrain the design of system components.

It is typically desirable to design a system to minimise resistance to flow in order to minimise pressure drop and maximise the flow that is deliverable to a patient within the set relief pressure of the pressure relief valve. For example, particular tube diameters and lengths may be selected to minimise resistance to flow. However, the system pressure drop may vary in use. For example, tubes may curve, bend, fold or crush, in use, or different patients may present different airway restriction characteristics.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY

It is therefore an object of certain embodiments disclosed herein to provide a pressure relief or pressure regulating device which will go at least some way towards addressing the foregoing problems or which will at least provide the industry with a useful choice.

In accordance with at least one of the embodiments disclosed herein, a pressure regulating or pressure relief device comprises:
an inlet,
an outlet chamber with an outlet, the inlet in fluid communication with the outlet chamber,
a valve seat between the inlet and the outlet, and
a valve member biased to seal against the valve seat,
the valve member adapted to displace from the valve seat by an inlet pressure at the inlet increasing above a pressure threshold to allow a flow of gases from the inlet to the outlet via the outlet chamber, the flow of gases through the outlet causing an outlet pressure (back pressure) in the outlet chamber to act on the valve member together with the inlet pressure to (further) displace the valve member from the valve seat.

In some embodiments, wherein the valve member comprises a membrane biased against the valve seat.

In some embodiments, the valve member comprises a frame supporting the membrane in a tensioned state.

In some embodiments, the frame comprises one or more clipping features to clip the valve member to a body of the device (without significantly altering the tension in the membrane).

In some embodiments, a perimeter portion of the valve member provides a seal, to seal the outlet chamber from ambient or a displacement chamber.

In some embodiments, the membrane is stretched or tensioned over the valve seat so that tension in the membrane biases the membrane to seal against the valve seat.

In some embodiments, a periphery of the membrane is supported by a wall of the outlet chamber.

In some embodiments, the device comprises a spring to bias the membrane against the valve seat, wherein the spring is in compression acting on a non-pressure side of the membrane, or the spring is in tension acting on a pressure side of the membrane.

In some embodiments, the membrane is a resilient or elastomeric material, for example a silicone material, and may be either thermoplastic or thermoset materials.

In some embodiments, the membrane has a thickness of less than 1 mm, for example 0.3 mm.

In some embodiments, the valve seat is provided centrally with respect to the membrane.

In some embodiments, the membrane comprises a thickened portion to contact the valve seat, for example the membrane comprises a thickened central portion to act against the valve seat.

In some embodiments, an area of the valve member is greater than an area of the valve seat.

In some embodiments, the inlet pressure acts on the valve member over a valve seat area and when the valve member is displaced from the valve seat the outlet pressure acts on the valve member over an area outside of the valve seat area.

In some embodiments, the inlet pressure acts on the valve member over an area outside of a valve seat area and when the valve member is displaced from the valve seat the outlet pressure acts on the valve member over a valve seat area.

In some embodiments, a ratio of the area of the valve member and an area of the valve seat is in the range of 1.2 to 1600.

In some embodiments, the inlet comprises an inlet tube, and the valve member is approximately perpendicular to a longitudinal axis of the inlet tube.

In some embodiments, the inlet comprises an inlet tube extending into the outlet chamber.

In some embodiments, the valve seat is provided at an outlet end of the inlet tube within the outlet chamber.

In some embodiments, the outlet comprises at least one aperture in a wall of the outlet chamber and/or at least one aperture through the valve member.

In some embodiments, the at least one aperture is in a wall of the outlet chamber and adjacent to the inlet tube.

In some embodiments, the outlet end of the inlet tube forms the valve seat.

In some embodiments, the outlet end of the inlet tube is bevelled, a bevelled edge of the outlet end of the inlet tube forming the valve seat.

In some embodiments, the outlet is located radially between an outer perimeter of the valve member and an outer perimeter of the valve seat and/or inlet and/or an inlet tube.

In some embodiments, the device comprises an inlet tube surrounding the outlet chamber and the valve seat is provided at an inlet to the outlet chamber.

In some embodiments, the valve member is supported by or seals against a wall of the outlet chamber or wherein the valve inlet comprises an inlet tube and the valve member is supported by or forms a seal with a wall of the inlet tube.

In some embodiments, the device comprises a displacement chamber, the valve member displacing into the displacement chamber when the valve member is displaced from the valve seat.

In some embodiments, the displacement chamber is open to ambient (atmospheric) pressure, such that when the valve member is displaced into the displacement chamber the pressure in the displacement chamber remains substantially at ambient (atmospheric pressure), or
wherein the displacement chamber is sealed or is sealable from the ambient environment.

In some embodiments, the displacement chamber is sealed or is sealable from the ambient environment.

In some embodiments, the device comprises a pressuring device to alter the pressure within the displacement chamber, for example a foot or hand operable pump to increase or decrease the pressure in the displacement chamber.

In some embodiments, the device comprises a pressure reset device to reset the displacement chamber pressure to ambient pressure, for example a poppet valve.

In some embodiments, the inlet, the valve member, the valve seat and the outlet are arranged so that the flow of gases through the outlet chamber is directed against the valve member as the flow of gases enters the chamber to be reflected from the valve member through an angle greater than 90 degrees to exit the chamber via the outlet.

In some embodiments, the outlet comprises at least one aperture in a wall of the outlet chamber opposite to the valve member.

In some embodiments, the outlet chamber surrounds the valve seat (e.g. the valve seat is located within the outlet chamber).

In some embodiments, ambient pressure acts on a non-pressure side of the valve member.

In some embodiments, an area of the outlet is variable.

In some embodiments, the outlet comprises one or more apertures in a wall of the outlet chamber and the one or more apertures may be selectively opened or closed or partially closed to vary the area of the outlet.

In some embodiments, the relative position of the valve seat and the valve member is adjustable to adjust a bias of the member against the valve seat.

In some embodiments, the valve member is a plunger or piston and the device comprises a biasing member to bias the valve member to seal against the valve seat. The biasing member may be a spring or resilient diaphragm or (elastomeric) membrane or other spring element.

In some embodiments, the outlet comprises a gap between a periphery of the valve member and a wall of the outlet chamber and/or the outlet comprises one or more apertures through the valve member.

In some embodiments, the valve member is a piston comprising a sliding seal with a wall of the outlet chamber, and the outlet is one or more apertures through the piston or a wall of the outlet chamber.

In some embodiments, the biasing member is a spring, and wherein tension or compression in the spring is adjustable to vary an amount of bias basing the plunger or piston to seal against the valve seat.

In some embodiments, the device is adapted to maintain a relief pressure range of less than 5cmH$_2$O over a flow rate range of 30 L/min through the device.

In some embodiments, the device comprises at least two outlet chambers in series or parallel.

In some embodiments, the outlet chamber of claim 1 is a first outlet chamber with a first outlet, and the device comprises a second outlet chamber with a second outlet, the second outlet chamber adapted to receive the flow of gases from the first outlet,
the valve member adapted to displace from the valve seat by the inlet pressure at the inlet increasing above the pressure threshold to allow the flow of gases from the inlet to the second outlet via the first outlet chamber, the first outlet and the second outlet chamber, the flow of gases through the first outlet and the second outlet causing the outlet pressure (back pressure) in the first outlet chamber to act on the valve member together with the inlet pressure to (further) displace the valve member from the valve seat.

In some embodiments, the valve member and valve seat provide a dynamically variable flow restriction between the inlet and the outlet chamber that is dependent on the inlet pressure and outlet pressure, the dynamically variable flow restriction decreasing for increasing inlet and/or outlet pressure.

In some embodiments, the outlet provides an outlet restriction to flow that is independent of the inlet and outlet pressures.

In some embodiments, outlet restriction to flow is greater than the dynamically variable flow restriction.

In some embodiments, the valve member is a first valve member and the device comprises a second valve member coupled to the first valve member, the first member to vent a flow of expiratory gases and the second valve member to open and close a nebuliser port, wherein
when venting expiratory gases the first valve member is displaced from the valve seat to displace the second valve member to close the nebuliser port, and
when the valve member is against the valve seat the second valve member is displaced from the nebuliser port to allow medicament to flow from the nebuliser.

In accordance with at least one of the embodiments disclosed herein, a patient interface system or respiratory system comprises:

a patient interface to seal with the patient's airways, an inlet conduit or flow path to the patient interface comprising a nebuliser port, a device as described in the previous statement, the inlet arranged to receive a flow of expiratory gases from the patient interface.

In accordance with at least one of the embodiments disclosed herein, a pressure regulating or pressure relief device comprises:

an inlet, an outlet, a valve seat between the inlet and the outlet, and a valve member biased to seal against the valve seat, the valve member adapted to displace from the valve seat by an inlet pressure at the inlet increasing above a pressure threshold to allow a flow of gases from the inlet to the outlet, wherein the valve member is or comprises a membrane (diaphragm), the membrane stretched or tensioned over the valve seat so that tension in the membrane biases the membrane to seal against the valve seat.

In accordance with at least one of the embodiments disclosed herein, a pressure regulating or pressure relief device comprises:

an inlet, an outlet, a valve seat between the inlet and the outlet, and a valve member biased to seal against the valve seat, the valve member adapted to displace from the valve seat by an inlet pressure at the inlet increasing above a pressure threshold to allow a flow of gases from the inlet to the outlet, and a membrane (diaphragm) stretched or tensioned over the valve member or valve seat to bias the valve member against the valve seat.

A device according to the previous statement may comprise a feature or features of any one or more of the preceding statements relating to a pressure regulating or pressure relief device.

In some embodiments, the valve member is or comprises the membrane (diaphragm), the membrane stretched or tensioned over the valve seat so that tension in the membrane biases the membrane to seal against the valve seat.

In accordance with at least one of the embodiments disclosed herein, a pressure relief device comprises:

an inlet, an outlet chamber with an outlet, the inlet in fluid communication with the outlet chamber, a dynamically variable flow restriction between the inlet and the outlet chamber, and a flow path through the valve from the inlet to the outlet via the dynamic flow restriction and the outlet chamber, wherein the outlet from the outlet chamber comprises or provides an outlet restriction to flow from the device causing an outlet pressure (back pressure) in the outlet chamber, and wherein the dynamically variable flow restriction is dependent on an inlet pressure at the inlet and the outlet pressure in the outlet chamber, the dynamically variable flow restriction decreasing for increasing inlet and/or outlet pressure, and the outlet restriction is independent of the inlet pressure and the outlet pressure.

A device according to the previous statement may comprise a feature or features of any one or more of the preceding statements relating to a pressure regulating or pressure relief device.

In accordance with at least one of the embodiments disclosed herein, a flow compensated pressure regulating or pressure relief device for a system providing a flow of gases, the device comprising:
- a main inlet to receive a flow of gases from a gases source and a main outlet to provide at least a portion of the flow of gases received by the main inlet to flow from the device,
- a pressure relief valve adapted to vent at least a portion of the flow of gases received by the inlet when a pressure of the flow of gases increases above a pressure threshold, and
- a sensing mechanism to dynamically adjust the pressure threshold based on a flow rate of the flow of gases from the main outlet to a patient.

In some embodiments, the pressure relief valve comprises:
- a valve inlet in fluid communication with the main inlet,
- a vent outlet,
- a valve seat between the valve inlet and the vent outlet, and a valve member biased to seal against the valve seat and to displace from the valve seat by an inlet pressure at the valve inlet increasing above a pressure threshold to vent at least a portion of the flow of gases from the valve inlet to the vent outlet, and
- wherein the sensing mechanism comprises:
- a sensing member to sense a differential pressure indicative of a flow rate of the flow of gases through the main outlet, and
- a mechanical link acting between the sensing member and the valve member to transfer a force applied by the sensing member to the valve member to adjust a biasing of the valve member against the valve seat in response to the flow rate of the flow of gases through the main outlet.

In some embodiments, the sensing mechanism comprises a flow restriction or constriction to generate the differential pressure sensed by the sensing member to displace the sensing member in response to the flow rate of the gases through the main outlet.

In some embodiments, the sensing mechanism comprises:
- a flow constriction or restriction downstream of the valve inlet,
- a sensing chamber, and the sensing member located in the sensing chamber dividing the sensing chamber into a first chamber and a second chamber, the first chamber in fluid communication with the flow of gases upstream of the flow constriction or restriction, and the second chamber in fluid communication with the flow of gases at the flow constriction or downstream of the flow restriction, a resulting differential pressure caused by the flow of gases through the flow constriction or restriction and the main outlet sensed by the sensing member.

In some embodiments, the mechanical link is coupled to the valve member and the sensing member to bias the valve member against the valve seat in response to a flow rate of the flow gases through the main outlet.

In some embodiments, the mechanical link uncoupled from the valve member or the sensing member or the valve member and the sensing member, and
- with no flow of gases through the main outlet the valve member is biased against the valve seat and with the mechanical link bearing against the valve member and the sensing member, and
- as the flow of gases through the main outlet increases, the differential pressure across the sensing member increases to reduce a force applied by the mechanical link to the valve member to reduce a bias of the valve member against the valve seat until the mechanical link loses contact with the valve member or the sensing member or both when the flow rate of the flow of gases through the main outlet increases above a threshold.

In some embodiments, the pressure relief valve comprises:
- an outlet chamber comprising the vent outlet,
- the valve member adapted to displace from the valve seat by the inlet pressure at the valve inlet increasing above the pressure threshold to vent at least a portion of the flow of gases received by the main inlet from the valve inlet to the vent outlet via the outlet chamber, the flow of gases through the vent outlet causing an outlet pressure (back pressure) in the outlet chamber to act on the valve member together with the inlet pressure to (further) displace the valve member from the valve seat.

In some embodiments, the valve member comprises a membrane biased against the valve seat In some embodiments, the sensing member comprises a membrane.

In some embodiments, the valve member and/or the sensing member comprises a frame supporting the membrane in a tensioned state.

In some embodiments, the frame comprises one or more clipping features to clip the valve member or sensing member to a body of the device (without significantly altering the tension in the membrane).

In some embodiments, a perimeter portion of the valve member provides a seal, to seal the outlet chamber from ambient or a displacement chamber and/or a perimeter portion of the sensing member provides a seal, to seal the first sensing chamber from the second sensing chamber.

In some embodiments, the membrane is stretched or tensioned over the valve seat so that tension in the membrane biases the membrane to seal against the valve seat.

In some embodiments, the valve member is a plunger or piston.

In some embodiments, an area of the valve member is greater than an area of the valve seat.

In some embodiments, the inlet pressure acts on the valve member over a valve seat area and when the valve member is displaced from the valve seat the outlet pressure acts on the valve member over an area outside of the valve seat area.

In some embodiments, the inlet pressure acts on the valve member over an area outside of a valve seat area and when the valve member is displaced from the valve seat the outlet pressure acts on the valve member over a valve seat area.

In some embodiments, the valve inlet comprises an inlet tube extending into the outlet chamber.

In some embodiments, the valve seat is provided at an outlet end of the inlet tube within the outlet chamber.

In some embodiments, the vent outlet comprises at least one aperture through a wall of the outlet chamber and/or at least one aperture through the valve member.

In some embodiments, the valve member is supported by or forms a seal with a wall of the outlet chamber or wherein the valve inlet comprises an inlet tube and the valve member is supported by or forms a seal with a wall of the inlet tube.

In some embodiments, the sensing member is positioned in a sensing chamber, and the flow restriction is provided by a gap between the sensing member and a side wall of the sensing chamber and/or the flow restriction is provided by one or more apertures through the sensing member, and a flow path for the flow of gases from the main inlet to the main outlet is through the sensing chamber.

In some embodiments, the sensing member is a piston, and the sensing chamber is a cylinder in which the piston moves, and the piston pneumatically seals the first chamber from the second chamber.

In some embodiments, the mechanical link transmits tension and/or compression.

In some embodiments, the mechanical link is a rod or shaft and the device comprises a link guide supporting the mechanical link between the valve member and the sensing member, and wherein the main inlet is in fluid communication with the sensing chamber via an annular space between the link and the link guide.

In some embodiments, the device comprises an opening between the main inlet and the sensing chamber, the mechanical link extending through the opening, the opening with mechanical link received through the opening presenting an annular opening between the main inlet and the sensing chamber.

In some embodiments, the mechanical link is a ribbed rod or shaft.

In some embodiments, the mechanical link comprises a flange at one end to support the valve member against the valve seat.

In some embodiments, the flange has a diameter that is larger than the diameter of the valve seat so that when the valve member is seated against the valve seat the valve member is supported against the valve seat between the flange and the valve seat.

In some embodiments, the mechanical link is length adjustable.

In some embodiments, the device comprises a user interface to allow a user to adjust the length of the mechanical link during use.

In some embodiments, the device comprise a displacement chamber into which the valve member may displace away from the valve seat.

In some embodiments, the displacement chamber is sealed or is sealable from the ambient environment.

In some embodiments, the device comprises a pressuring device to alter the pressure within the displacement chamber, for example a foot or hand operable pump to increase or decrease the pressure in the displacement chamber.

In some embodiments, the device comprises a pressure reset device to reset the displacement chamber pressure to ambient pressure, for example a poppet valve.

In some embodiments, the relative position of the valve seat and the valve member is adjustable to adjust a bias of the member against the valve seat.

In some embodiments, the relative position of the valve seat and the valve member is adjustable during use.

In some embodiments, the device comprises:
a flow constriction and a pressure tap from the flow constriction to the second chamber, or
wherein the device comprises an orifice flow restriction and a pressure tap from a downstream side of the orifice to the second chamber.

In some embodiments, the flow constriction or restriction is adjustable.

In some embodiments, the device is configured to limit an amount of travel or deformation of the sensing member to set an upper pressure limit for the pressure threshold that is independent of flow rate.

In some embodiments, the device comprises a mechanical limit to limit an amount of travel or deformation of the sensing member.

In some embodiments, the mechanical limit is an end stop that acts against the mechanical link or the sensing member.

In some embodiments, a wall of the sensing chamber limits the amount of deformation or travel of the sensing member.

In some embodiments, the sensing mechanism comprises:
one or more electronic sensors to detect the flow rate (e.g. a differential pressure) of gases flowing through the main outlet of the device and a pressure of the flow of gases between the main inlet and main outlet,
an actuator, and
a controller or processor that receives a signal from the sensor(s) and provides an output to drive the actuator to adjust the pressure threshold of the pressure relief valve based on the detected flow rate.

In some embodiments, the actuator drives a member attached to a valve member of the pressure relief valve to adjust an amount of bias of the valve member towards a valve seat of the pressure relief valve.

In some embodiments, the valve member is a plunger or diaphragm.

In some embodiments, the device comprises a housing to enclose the pressure relief valve and the sensing mechanism.

In some embodiments, the device comprises a body, the body comprising the main inlet and the main outlet, and at least an outlet chamber of the device and the first chamber of the sensing chamber, and the housing substantially encloses the body.

In some embodiments, the housing provides a space or cavity around the body, and wherein a displacement chamber of the device and/or the outlet chamber is in fluid communication with the cavity or space.

In some embodiments, the housing comprises a housing outlet from the housing space.

In some embodiments, the housing comprises a housing vent outlet in communication with a vent outlet from the outlet chamber, and where the housing vent outlet is coaxial with the main inlet or the main outlet.

In some embodiments, the housing comprises an outlet in fluid communication with the displacement chamber, and the aperture is coaxial with the main inlet or the main outlet.

In some embodiments, the flow constriction or restriction is a first flow constriction or restriction and the device comprises:
a second flow constriction or restriction upstream of the valve inlet, and
a first port between the second chamber and the first flow constriction or a location adjacent and downstream of the first flow restriction, and
a second port between the second chamber and the second flow constriction or a location adjacent and upstream of the second flow restriction, and
for a flow of gases from the main inlet to the main outlet the second port is blocked by a conduit or connector, and
for a flow of gases from the main outlet to the main inlet the first port is blocked by a conduit or connector.

In some embodiments, the first flow constriction or restriction presents a greater differential pressure than the second flow constriction or restriction or the second flow constriction or restriction presents a greater pressure differential than the first flow constriction or restriction.

In some embodiments, the device comprises an indicator to indicate when a flow of gases is venting from the pressure relief valve.

In some embodiments, the indicator is visually observable when gases vent from the pressure relief valve.

In some embodiments, the indicator provides a binary indication of venting/no venting or a proportional indication of venting that is indicative of a rate of venting.

In some embodiments, the indicator comprises a movable member such as a shuttle or plunger or flap located within a guide or housing, for example a housing enclosing the pressure relief valve and the sensing mechanism.

In some embodiments, the movable member is located proximate a vent outlet of the device.

In some embodiments, the device comprises an indicator to indicate a flow of gases or a flow rate of gases provided from a main outlet of the device.

In some embodiments, the indicator comprises an impeller or flap located in the main outlet of the device.

In some embodiments, the device comprises a flow restriction downstream of the valve inlet, and the indicator comprises a shuttle or plunger received in a guide tube, an inlet end of the guide tube in fluid communication with the main inlet upstream of the flow restriction and an outlet end of the guide tube in fluid communication with the main outlet downstream of the flow restriction.

In accordance with at least one of the embodiments disclosed herein, a flow compensated pressure regulating or pressure relief device for a system providing a flow of gases, the device comprising:
    a main inlet to receive a flow of gases from a gases source and a main outlet to provide at least a portion of the flow of gases received by the main inlet to flow from the device,
    a pressure relief valve comprising:
        a valve inlet in fluid communication with the main inlet,
        a vent outlet,
        a valve seat between the valve inlet and the vent outlet, and
        a valve member biased to seal against the valve seat to displace from the valve seat by an inlet pressure at the valve inlet increasing above a pressure threshold to vent at least a portion of the flow of gases from the valve inlet to the vent outlet,
    a sensing member to sense a differential pressure indicative of a flow rate of the flow of gases through the main outlet, and
    a mechanical link acting between the sensing member and the valve member to transfer a force applied by the sensing member to the valve member to adjust a biasing of the valve member against the valve seat in response to the flow rate of the flow gases through the main outlet.

In some embodiments, the device comprises a flow constriction or restriction downstream of the valve inlet,
    a sensing chamber, the sensing member located in the sensing chamber dividing the sensing chamber into a first chamber and a second chamber, the first chamber in fluid communication with the flow of gases upstream of the flow constriction or restriction, and the second chamber in fluid communication with the flow of gases at the flow constriction or downstream of the flow restriction, a resulting differential pressure caused by the flow of gases through the flow constriction or restriction and the main outlet sensed by the sensing member.

In some embodiments, the pressure relief valve comprises:
    an outlet chamber comprising the vent outlet,
    the valve member adapted to displace from the valve seat by the inlet pressure at the valve inlet increasing above the pressure threshold to vent at least a portion of the flow of gases received by the main inlet from the valve inlet to the vent outlet via the outlet chamber, the flow of gases through the vent outlet causing an outlet pressure in the outlet chamber to act on the valve member together with the inlet pressure to displace the valve member from the valve seat.

In accordance with at least one of the embodiments disclosed herein, a flow compensated pressure regulating or pressure relief device for a system providing a flow of gases comprises:
    a main inlet to receive a flow of gases from a gases source and a main outlet to provide at least a portion of the flow of gases received by the main inlet to flow from the device,
    a valve adapted to vent at least a portion of the flow of gases received by the inlet or to occlude the flow of gases flowing from the main inlet to the main outlet,
    one or more electronic sensors to detect the flow rate of gases flowing through the main outlet of the device and a pressure of the flow of gases,
    an actuator, and
    a controller or processor that receives a signal or signals from the sensor(s) and provides an output to drive the actuator to adjust the valve to vent at least a portion of the flow of gases received by the inlet or to at least partially occlude the flow of gases flowing from the main inlet to the main outlet when the detected pressure goes above a pressure threshold, and wherein the pressure threshold is dependent on the detected flow rate.

In some embodiments, the valve is adapted to occlude the flow of gases from the main inlet to the main outlet, and the device comprises a vent aperture downstream of the valve.

In some embodiments, the device comprises a first valve to vent at least a portion of the flow of gases received by the inlet and a second valve to occlude the flow of gases flowing from the main inlet to the main outlet, a first actuator to drive the first valve and a second actuator to drive the second valve, wherein the second valve is downstream of the first valve, and
    the controller drives the first and second actuators to adjust the first valve to vent at least a portion of the flow of gases received by the inlet and the second valve to at least partially occlude the flow of gases flowing from the main inlet to the main outlet when the detected pressure goes above a pressure threshold, and wherein the pressure threshold is dependent on the detected flow rate.

In accordance with at least one of the embodiments disclosed herein, a respiratory gases system comprises a pressure regulating or pressure relief device or a flow compensated pressure regulating or pressure relief device as described in any one or more of the above statements.

In some embodiments, the system is a bi-level pressure system comprising a said flow compensating pressure regulating or pressure relief device, a pressure gases source and a sealing patient interface, and wherein the flow compensating pressure regulating or pressure relief device is configured so that:
    substantially all of the flow of gases received by the main inlet flow to the main outlet during inspiration so that an inspiratory pressure is determined by a pressure setting of the pressure source, and a portion of the flow of gases received by the main inlet is vented from the vent outlet during expiration so that an expiratory pressure is determined by a venting pressure of the device.

In some embodiments, the device is located adjacent or near to the patient interface.

In some embodiments the pressure gases source comprises a flow gases source and a second pressure regulating or pressure relief device as described above tuned so that the pressure relieve valve of the second device continuously vents a portion of the flow of gases received by the main inlet from the vent outlet during inspiration and expiration.

In some embodiments, the system is a high flow respiratory gases system comprising a flow source and an unsealed patient interface such as a nasal cannula.

In some embodiments, the respiratory gases system is a CPAP system comprising a flow gases source and a sealing patient interface, and wherein the pressure regulating or pressure relief device is tuned so that the pressure relieve valve continuously vents a portion of the flow of gases received by the main inlet from the vent outlet during inspiration and expiration.

In some embodiments, the respiratory gases system is a ventilation or CPAP system, the system comprising a ventilator or flow gases source and a sealing patient interface, and wherein the pressure regulating or pressure relief device is located at or adjacent the patient interface and is tuned to operate as an anti-asphyxiation valve, wherein:
 substantially all of the flow of gases received by the main inlet flow to the main outlet during inspiration, and
 in an event whereby the ventilator or pressure gases source fails or stops functioning a substantial portion of the patient's exhaled breath is vented from the vent outlet.

In some embodiments, the respiratory gases system is a ventilation or bi-level pressure system, the system comprising a flow gases source and a sealing patient interface, and wherein the pressure regulating or pressure relief device is tuned so that the pressure relieve valve continuously vents a portion of the flow of gases received by the main inlet from the vent outlet during inspiration at a first pressure threshold and the pressure relieve valve continuously vents a portion of the flow of gases received by the main inlet from the vent outlet during expiration at a second threshold, the first threshold greater than the second threshold.

In some embodiments, the system comprises an inspiratory conduit, a first pressure regulating or pressure relief device as described above provided to the inspiratory conduit, and a second pressure regulating or pressure relief device as described above provided to an expiratory flow path, the first device configured to provide an inspiratory pressure and the second device configured to provide an expiratory pressure.

In some embodiments, the pressure regulating or pressure relief device comprises a significant pneumatic coupling between the main inlet and the sensing member, so that the valve comprises provides a fast response so that pressure at the patient rapidly changes between an inspiratory pressure and an expiratory pressure determined by the first and second thresholds.

In accordance with at least one of the embodiments disclosed herein, an insufflation system comprises a flow compensated pressure regulating or pressure relief device as described in any one of the preceding statements. The flow compensated pressure regulating or pressure relief device is configured so that the pressure relief valve continuously vents a portion of the flow of gases received by the main inlet from the vent outlet. The system continuously vents from the patient (abdominal cavity) during use. The system preferably vents from the patient via a filter.

"High gas flow" or "high gas flows" as used herein is defined as the volumetric movement of a portion/parcel of gas or mixtures of gases into the patient's airways at rates exceeding the fraction of inspired oxygen requirements at peak inspiratory flow demand. In particular, in one embodiment, high gas flow (or high gas flows) refers to gas flow rate of greater than 15 L/min (Litres per minute), greater than or equal to about 20 L/min, greater than or equal to about 30 L/min, greater than or equal to about 40 L/min, greater than or equal to about 50 L/min, greater than or equal to about 60 L/min, greater than or equal to about 70 L/min, greater than or equal to about 80 L/min, greater than or equal to about 90 L/min, greater than greater than or equal to about 100 L/min, greater than about or equal to 110 L/min, greater than about or equal to 120 L/min, greater than about or equal to 130 L/min, greater than about or equal to 140 L/min or up to about 150 L/min. In certain embodiments, useful ranges of a high gas flow can be selected between any of the aforementioned flow rates including but not limited to from about 40 L/min to about 80 L/min, from about 50 L/min to about 80 L/min, from about 70 L/min to about 100 L/min, about 70 L/min to about 80 L/min, about 100 L/min to about 150 L/min and about greater than 15 L/min to about 150 L/min and about 30 L/min to about 150 L/min. These flow rates can be provided using a patient interface and in certain embodiments through a nasal interface. In a preferred high flow therapy an operating flow range of 30-70 L/min is desired and possible 30-100 L/min, for treating an adult patient. When treating an infant, a 'high flow' therapy may require a flow rate of about 1 to 50 L/min.

Unless the context suggests otherwise a flow source provides a flow of gases at a set flow rate. A set flow rate may be a constant flow rate, or may be an oscillating flow rate, for example a sinusoidal flow rate. Unless the context suggests otherwise a pressure source provides a flow of gases at a set pressure. The set pressure may be a constant pressure, or may be an oscillating pressure, for example a sinusoidal pressure.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the foregoing and also envisages constructions of which the following gives examples only.

BRIEF DESCRIPTION OF THE DRAWINGS

Preferred embodiments will be described by way of example only and with reference to the drawings.

FIG. 1AA illustrates a high flow respiratory system comprising a flow controlled pressure relief valve.

FIGS. 1B-1 and 1B-2 illustrate a continuous positive airway pressure respiratory system comprising a flow controlled pressure relief valve, and FIG. 1B-3 shows a chart of pressure at the FCPRV vs flow rate of gases to a patient.

FIGS. 1C-1 and 1C-2 illustrate a bi-level pressure respiratory system comprising a flow controlled pressure relief valve, and FIG. 1C-3 shows a chart of patient pressure vs flow rate of gases to a patient. FIG. 1C-4 illustrates a patient pressure characteristic of the system over multiple breath cycles.

FIG. 1C-5 illustrates an alternative a bi-level pressure respiratory system comprising two flow controlled pressure relief valves.

FIGS. 1E-1 and 1E-2 illustrate a continuous positive airway pressure respiratory system or ventilator system comprising a flow controlled pressure relief valve configured as an anti-asphyxiation valve.

FIGS. 1F-1 and 1F-2 illustrate system comprising a flow controlled pressure relief valve configured to operate as a ventilator, and FIG. 1F-3 shows a chart of pressure at the FCPRV vs flow rate of gases to a patient.

FIG. 2A shows the PRV with a valve member in a sealed position. FIG. 2B shows the valve member displaced from a valve seat. FIG. 2C shows the valve member further displaced from a valve seat.

FIG. 3 shows a chart of the inlet pressure and outlet chamber pressure of a PRV vs venting flowrate through the PRV according to embodiments described herein.

FIG. 4 shows a chart of the inlet pressure and outlet chamber pressure of a PRV vs venting flowrate through the PRV of the same configuration as the PRV for FIG. 3 but with an outlet area twice the outlet area of the PRV for FIG. 3.

FIG. 5 shows a chart of the inlet pressure and outlet chamber pressure of a PRV vs venting flowrate through the PRV of the same configuration as the as the PRV for FIG. 3 but with an outlet area three times the outlet area of the PRV for FIG. 3.

FIG. 9A shows the PRV with a valve member in a sealed position. FIG. 9B shows the valve member displaced from a valve seat. FIG. 9C shows the valve member further displaced from a valve seat.

FIG. 13A shows the PRV with a valve member in a sealed position. FIG. 13B shows the valve member displaced from a valve seat. FIG. 13C shows the valve member further displaced from a valve seat.

FIG. 14A shows the FCPRV in a no flow configuration, and FIG. 14B shows the FCPRV in a flowing configuration.

FIG. 16A shows the FCPRV in a venting flow configuration, FIG. 16B in a low flow configuration, and FIG. 16C in a higher or higher flow pressure limiting configuration.

FIG. 23A shows a no flow or low flow configuration and FIG. 23B shows a flow or high flow configuration.

FIG. 25A shows a no flow or low flow configuration and FIG. 25B shows a flow or high flow configuration.

FIG. 26A shows a no flow or low flow configuration and FIG. 26B shows a flow or high flow configuration.

FIG. 27D is a cross section of the valve member or sensing member of FIG. 27C.

FIG. 31A illustrates the FCPRV in a lower flow configuration and FIG. 31B higher flow configuration.

FIG. 32A illustrates the FCPRV in a lower flow configuration and FIG. 32B higher flow configuration.

FIG. 33A illustrates the FCPRV in a lower flow configuration and FIG. 33B higher flow configuration.

FIGS. 30 to 32 are cross sectional views of a portion of a FCPRV. FIGS. 33 and 34 are cross sectional views of a body of a FCPRV including a venting flow indicator.

DETAILED DESCRIPTION OF PREFERRED EMBODIMENTS

Figure 1:
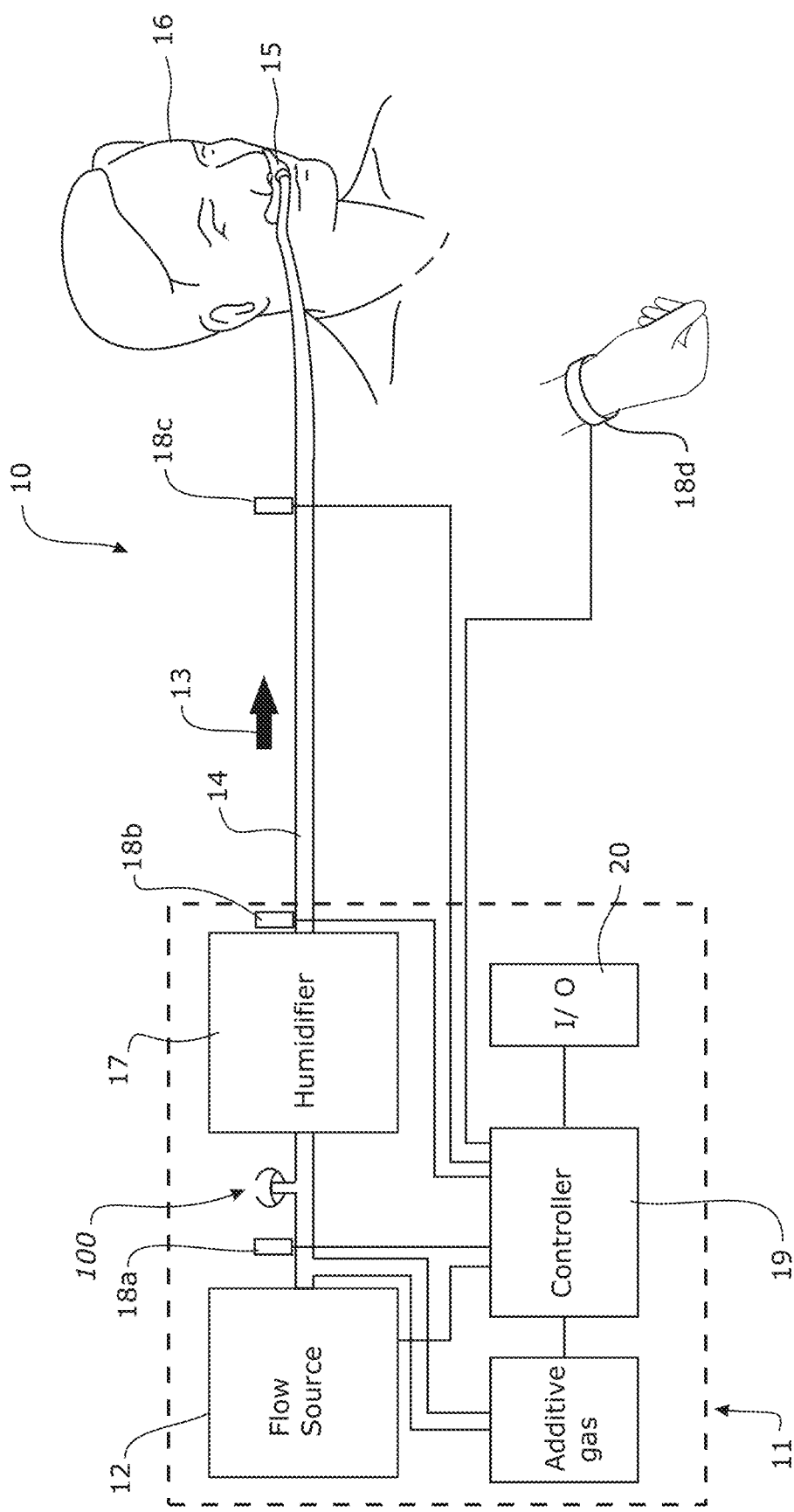
FIG. 1 illustrates a high flow respiratory system comprising a pressure relief or regulating valve (PRV).

Various embodiments are described with reference to the Figures. Throughout the Figures and specification, the same reference numerals may be used to designate the same or similar components, and redundant descriptions thereof may be omitted.

A pressure relief device according to embodiments described herein are particularly adapted for use in respiratory systems such as CPAP or high flow respiratory gas systems, for example a high flow system for use in anaesthesia procedures. Respiratory systems in which the pressure relief valve may be particularly useful are CPAP, BiPAP, High flow therapy, varying high flow therapy, low flow air, low flow O2 delivery, bubble CPAP, apnoeic high flow (i.e. high flow to anesthetized patients), invasive ventilation and non-invasive ventilation. Further, a pressure relief valve as described herein may be useful in systems other than respiratory systems.

By example, a high flow respiratory system 10 is described with reference to FIG. 1. High flow therapy may be used as a means to promote gas exchange and/or respiratory support through the delivery of oxygen and/or other gases, and through the removal of CO2 from the patient's airways. High flow therapy may be particularly useful prior to, during or after a medical procedure.

When used prior to a medical procedure, high gas flow can pre-load the patient with oxygen so that their blood oxygen saturation level and volume of oxygen in the lungs is higher to provide an oxygen buffer while the patient is in an apnoeic phase during the medical procedure.

A continuous supply of oxygen is essential to sustain healthy respiratory function during medical procedures (such as during anaesthesia) where respiratory function might be compromised (e.g. diminishes or stops). When this supply is compromised, hypoxia and/or hypercapnia can occur. During medical procedures such as anaesthesia and/or general anaesthesia where the patient is unconscious, the patient is monitored to detect when this happens. If oxygen supply and/or $CO_2$ removal is compromised the clinician stops the medical procedure and facilitates oxygen supply and/or $CO_2$ removal. This can be achieved for example by manually ventilating the patient through an anesthetic bag and mask, or by providing a high flow of gases to the patient's airway using a high flow therapy system.

Further advantages of high gas flow can include that the high gas flow increases pressure in the airways of the patient, thereby providing pressure support that opens airways, the trachea, lungs/alveolar and bronchioles. The opening of these structures enhances oxygenation, and to some extent assists in removal of $CO_2$.

The increased pressure can also keep structures such as the larynx from blocking the view of the vocal chords during intubation. When humidified, the high gas flow can also prevent airways from drying out, mitigating mucociliary damage, and reducing risk of laryngospasms and risks associated with airway drying such as nose bleeding, aspiration (as a result of nose bleeding), and airway obstruction, swelling and bleeding. Another advantage of high gas flow is that the flow can clear smoke created during surgery in the air passages. In such embodiments, the smoke can be created by lasers and/or cauterizing devices.

A pressure relief or regulating device is particularly desirable for use in a respiratory system such as a high flow system comprising an unsealed patient interface, to provide an upper pressure limit for the system. Most importantly, the upper pressure limit may be configured to provide a patient safety limit, or may be configured to prevent damage to tubes, fluid connections, or other components. A pressure relief or regulating device may be used in a CPAP system to regulate the pressure provided to the patient.

With reference to FIG. 1, the system/apparatus 10 may comprise an integrated or separate component based arrangement, generally shown in the dotted box 11 in FIG. 1. In some configurations the system 10 could comprise a modular arrangement of components. Hereinafter it will be referred to as system, but this should not be considered limiting. The system can include a flow source 12, such as an in-wall source of oxygen, an oxygen tank, a blower, a flow therapy apparatus, or any other source of oxygen or other gas. It may also comprise an additive gas source, comprising one or more other gases that can be combined with the flow source. The flow source 12 can provide a pressurised high gas flow 13 that can be delivered to a patient 16 via a delivery conduit 14, and patient interface 15 (such as a nasal cannula). A controller 19 controls the flow source 12 and additive gas through valves or the like to control flow and other characteristics such as any one or more of pressure, composition, concentration, volume of the high flow gas 13. A humidifier 17 is also optionally provided, which can humidify the gas under control of the controller and control the temperature of the gas. One or more sensors 18a, 18b, 18c, 18d, such as flow, oxygen, pressure, humidity, temperature or other sensors can be placed throughout the system and/or at, on or near the patient 16. The sensors can include a pulse oximeter 18d on the patient for determining the oxygen concentration in the blood.

Figure 1A:
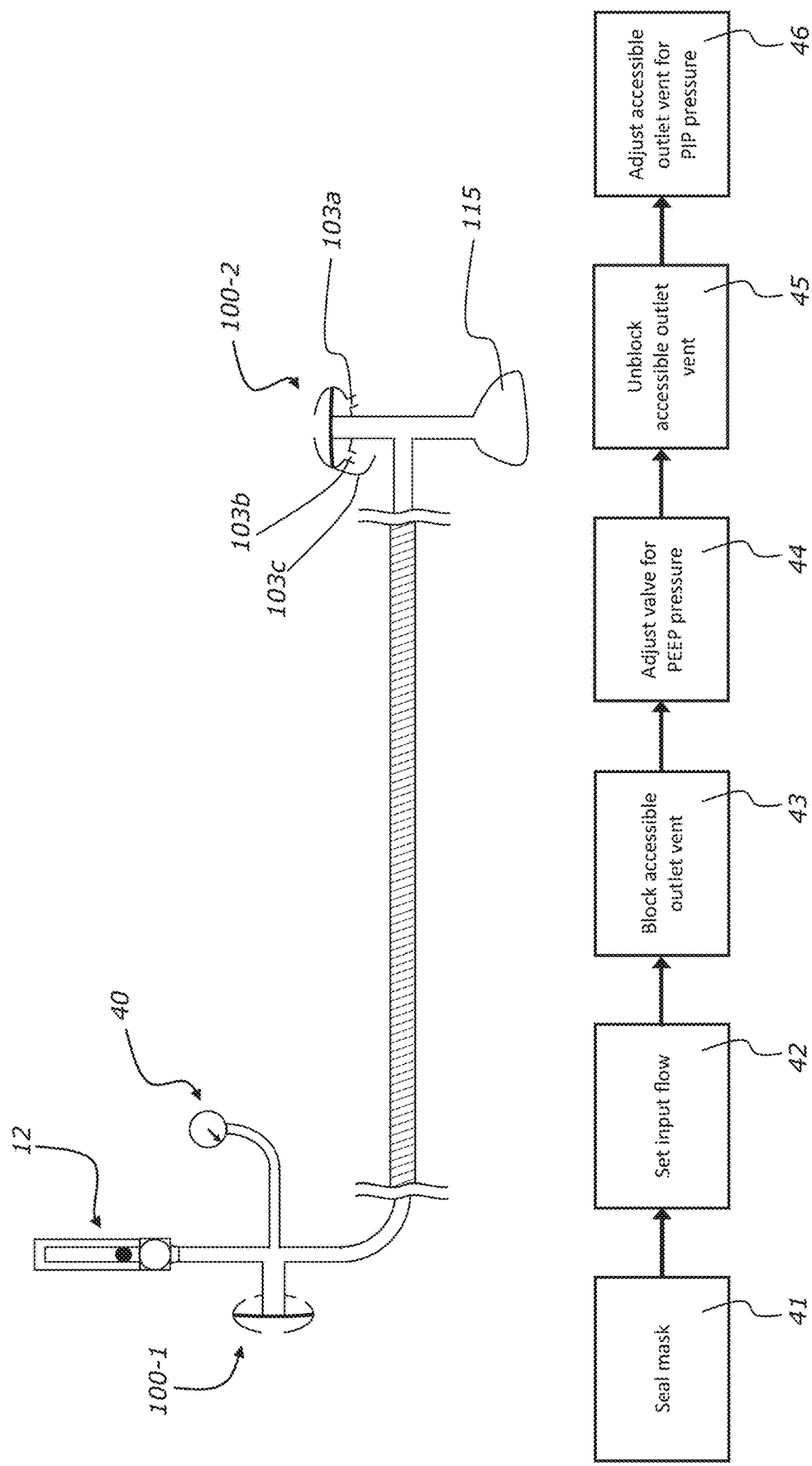
FIG. 1A illustrates an infant resuscitation system comprising a pressure relief or regulating valve (PRV).
Figure 1A:
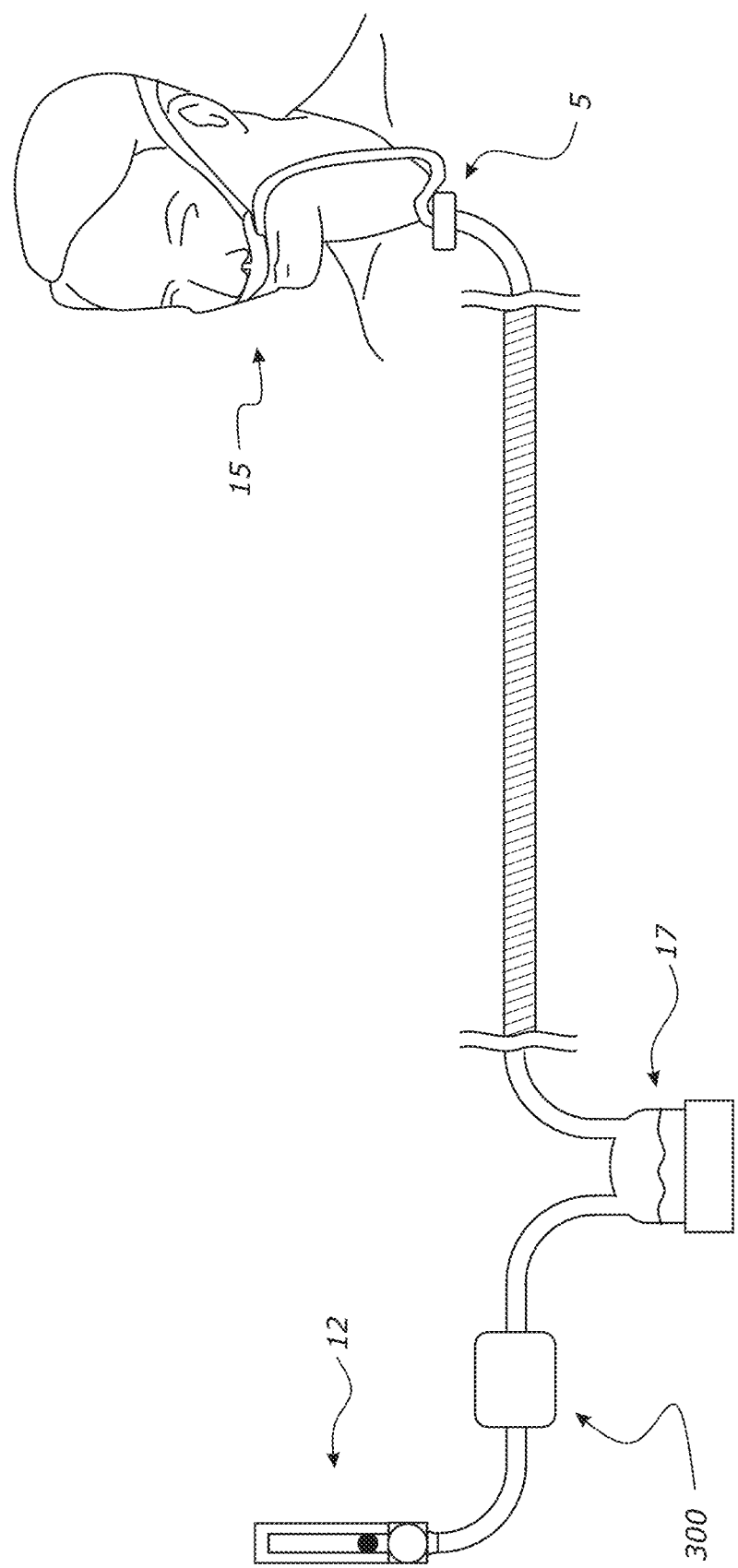

The controller 19 can be coupled to the flow source 12, humidifier 17 and sensors 18a-18d. The controller 19 can operate the flow source to provide the delivered flow of gas. It can control the flow, pressure, composition (where more than one gas is being provided), volume and/or other parameters of gas provided by the flow source based on feedback from sensors. The controller 19 can also control any other suitable parameters of the flow source to meet oxygenation requirements. The controller 19 can also control the humidifier 17 based on feed-back from the sensors 18a-18d. Using input from the sensors, the controller can determine oxygenation requirements and control parameters of the flow source and/or humidifier as required. An input/output interface 20 (such as a display and/or input device) is provided. The input device is for receiving information from a user (e.g. clinician or patient) that can be used for determining oxygenation requirements. In some embodiments the system may be without a controller and/or I/O interface. A medical professional such as a nurse or technician may provide the necessary control function (for example as shown in FIG. 1A).

The pressure may also be controlled. As noted above, the high gas flow (optionally humidified) can be delivered to the patient 16 via a delivery conduit 14 and the patient interface 15 or "interface", such as a cannula, mask, nasal or oral device or combination thereof. A nasal interface as used herein is a device such as a cannula, a nasal mask, nasal pillows, or other type of nasal device or combinations thereof. The patient or nasal interface can be substantially sealed, partially sealed or substantially unsealed. A nasal interface can also be used in combination with a mask or oral device (such as a tube inserted into the mouth) and/or a mask or oral device (such as a tube inserted into the mouth) that can be detached and/or attached to the nasal interface. A nasal cannula is a nasal interface that includes one or more prongs that are configured to be inserted into a patient's nasal passages. A mask refers to an interface that covers a patient's nasal passages and/or mouth and can also include devices in which portions of the mask that cover the patient's mouth are removable, or other patient interfaces such as laryngeal mask airway or endotracheal tube. A mask also refers to a nasal interface that includes nasal pillows that create a substantial seal with the patient's nostrils. The controller controls the system to provide the required oxygenation.

A system 10 according to embodiments herein includes a pressure relief or regulating device, or pressure limiting device 100 (herein a pressure relief valve or PRV). The PRV may be placed anywhere in the system between the gases source 12 and the patient 16. Preferably the PRV is provided at an outlet of the flow source 12, or between the flow source 12 and the humidifier 17, for example near to an inlet of the humidifier. In some embodiments the PRV may be provided at an outlet of the humidifier and/or an inlet to the conduit 14, or at any point along the conduit 14 through a suitable housing or coupling device. The PRV 100 may be located anywhere in the system, for example the PRV could be part of a patient interface assembly. The system may additionally or alternatively include a flow controlled pressure relief or pressure regulating device (FCPRV) 300, as illustrated in FIG. 1AA.

A PRV 100 according to embodiments described herein regulates pressure at an approximately consistent pressure across a given range of flow rates. The PRV 100 may be used to provide an upper limit for patient safety, and/or to prevent damage to system components caused by overpressure. For example, an occlusion in the system may cause a substantial back pressure in the system upstream of the occlusion, and the PRV may operate to ensure the back pressure does not increase above a limit to protect the patient and/or system components from damage. A blockage in the patient's nares or exhaling conduit can result in an increased patient pressure. An occlusion in the system may be caused by for example inadvertent folding or crushing of the conduit 14, or may be caused deliberately, for example by occluding the conduit 14 (e.g. by pinching a portion of the conduit closed) to prevent a flow of gases from reaching the patient.

Figure 2A:
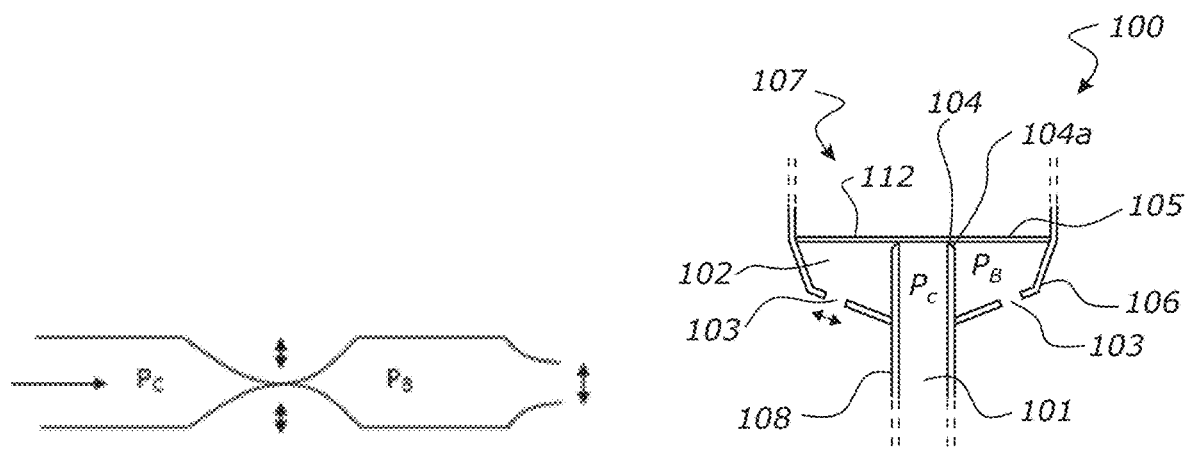
FIGS. 2A to 2C each illustrate a PRV cross section and corresponding schematic representation.
Figure 2B:
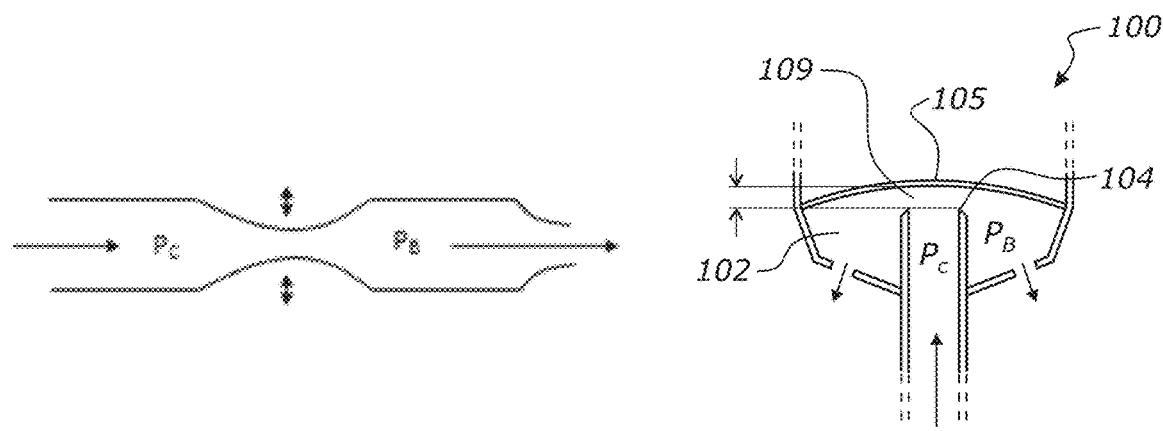
Figure 2C:
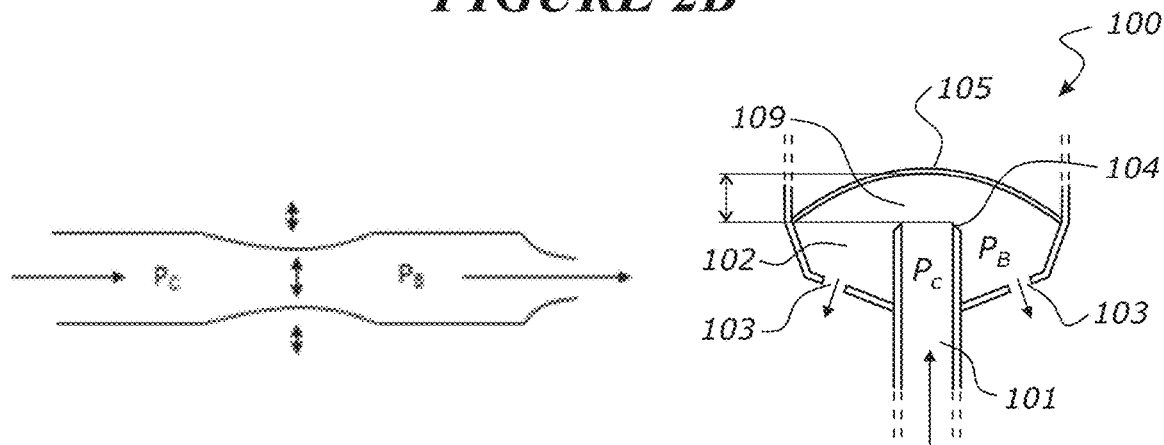
Figure 12A:
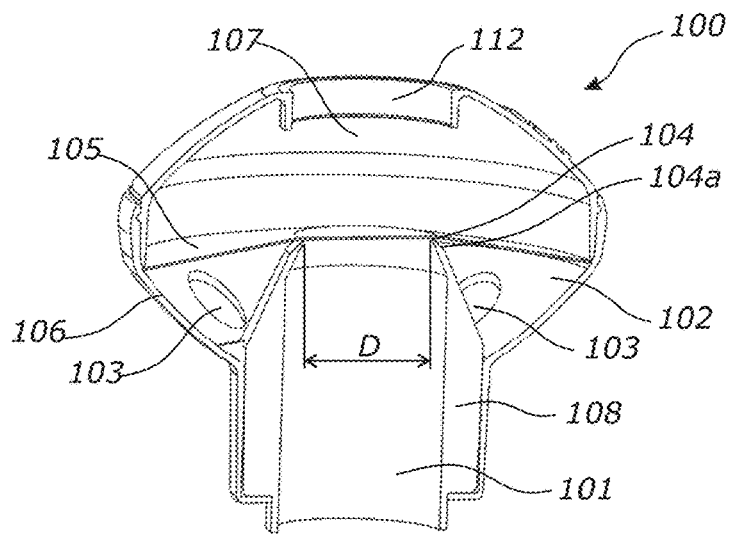
FIGS. 12A to 12E show sectional views of further example embodiments for a PRV.

With reference to FIGS. 2A and 12A, in some embodiments the PRV 100 comprises an inlet 101, an outlet chamber 102 with an outlet 103, a valve seat 104 between the inlet 101 and the outlet chamber 102, and a valve member 105 biased to seal against the valve seat 104. The valve member is adapted to displace from the valve seat by pressure Pc at the inlet increasing above a pressure threshold. The pressure Pc acts on the valve member 105 to force the member away from the valve seat 104 once the pressure Pc reaches the threshold, for example as shown in FIG. 2B. As the member displaces from the valve seat, a flow of gases flows from the inlet into the outlet chamber 102, and then from the outlet chamber via the outlet 103 to ambient pressure/atmospheric pressure. The outlet from the chamber is configured so that the flow of gases through the outlet causes a (back) pressure Pb in the outlet chamber that acts on the valve member 105 to further displace the valve member from the valve seat, for example as shown in FIG. 2C. As the member is further displaced from the valve seat a gap 109 between the valve member and valve seat increases. Further explanation of the valve operation is provided below.

As shown in FIGS. 2A to 2C, in some embodiments the valve member is an elastomeric membrane 105. The membrane may be suspended across the outlet chamber 102. The membrane is preferably stretched or tensioned over the valve seat 104 so that tension in the membrane causes the membrane to be biased against the valve seat to form a seal with the valve seat and close a flow path from the inlet to the outlet chamber. Alternatively a separate biasing member or spring may be provided to bias the membrane against the valve seat. For example, a compression spring may be provided to act on a non-pressure side (non system pressure side) of the membrane to push the membrane against or towards the valve seat. Alternatively a spring in tension may be provided to act on a system pressure side of the membrane. A periphery of the membrane may be supported or held by a wall 106 of the outlet chamber with the membrane stretched or tensioned over the valve seat. For example the valve may comprise a housing. The housing may comprise a first housing part forming the outlet chamber and a second housing part, a periphery of the membrane sandwiched between the first and second housing parts. The second housing part may form a displacement chamber 107. The valve member may be bonded/glued or welded to the housing.

In some embodiments the PRV may comprise a displacement chamber 107 into which the valve member may displace, away from the valve seat. The membrane separates the outlet chamber and the displacement chamber. The PRV may comprise a housing that is separated into the outlet chamber and the displacement chamber. The outlet chamber may be considered as a pressure side of the housing, and the displacement chamber may be considered as an ambient side of the housing. Preferably the displacement chamber is open to atmospheric/ambient pressure (e.g. the displacement chamber is not sealed closed). For example the displacement chamber may have a relatively large opening (e.g. opening 112 in FIG. 12A) that maintains an ambient pressure within the displacement chamber. With the displacement chamber at ambient pressure, when the valve member is displaced from the valve seat the displacement chamber remains at ambient pressure, such that displacement of the valve member into the displacement chamber does not result in an increase in pressure in the displacement chamber that would act against displacement of the membrane away from the valve seat. The displacement chamber might enclose the membrane but with an opening to maintain atmospheric pressure within the displacement chamber. The opening of the displacement chamber is of sufficient area such that no pressure increase occurs in the displacement chamber when the valve member is displaced from the valve seat. Ambient (atmospheric) pressure acts on a non-pressure side 112 of the valve member. The non-pressure side is the side of the valve member opposite to a side of the member that seals over the valve seat. The size of the opening to atmosphere may be reduced in order to reduce valve oscillation/change valve response. A smaller opening reduces a response time of the valve. Alternatively, the displacement chamber may be sealed. One benefit of having the displacement chamber open to atmosphere/ambient is that any leak across the valve member will not cause operational failure of the valve due to an increased pressure in the displacement chamber.

In a preferred embodiment, the outlet discharges the flow of gases from the inlet via the outlet chamber to atmosphere/the ambient environment.

In some embodiments, as shown in FIGS. 2A to 2C, the inlet comprises an inlet tube 108 extending into the outlet chamber 102. The valve seat 104 is preferably provided at an end of the inlet tube. In some embodiments an end of the inlet tube 108 forms the valve seat. In some embodiments the membrane 105 is approximately perpendicular to the inlet tube (e.g. perpendicular to a longitudinal axis of the inlet tube). In some embodiments, the inlet tube abuts the membrane to cause the elastomeric membrane to deflect when in contact with the valve seat, so that the membrane is biased by tension in the membrane against the valve seat to create a seal with the valve seat.

The outlet chamber 102 surrounds the valve seat 104. When the valve member (i.e. membrane 105) seals against the valve seat the inlet pressure acts over a first area or portion of the valve member determined by the geometry of the valve seat 104. When the valve member is displaced from the valve seat, the inlet pressure Pc acts on the valve member over the valve seat area (first area) and the back pressure Pb in the outlet chamber acts over a second area that is an area of the valve member outside of the valve seat area. In some embodiments the second area of the valve member is greater than the first area of the valve member. A difference in pressure between the inlet pressure Pc and the back pressure Pb is created by a pressure drop of the flow of gases passing through a gap 109 between the valve member 105 and the valve seat 104. The area of the valve member is greater than the area of the valve seat, so that when the valve member is displaced from the valve seat the inlet pressure and the outlet pressure act on the larger area of the valve member.

In some embodiments, the abutting end 104 of the inlet tube 108 is bevelled about its periphery to form the valve seat 104. The bevel 104a reduces the amount of surface area of the end of the inlet tube in contact with the elastomeric membrane, which may assist with ensuring a tight seal between the valve seat and membrane. The bevelled edge of the tube is not so sharp that it might cause damage to the membrane. The bevel may be on an external periphery of the tube. The abutting end 104 of the tube may be any number of shapes, including curved, flat, triangular, sloped, or a combination thereof.

Figure 12B:
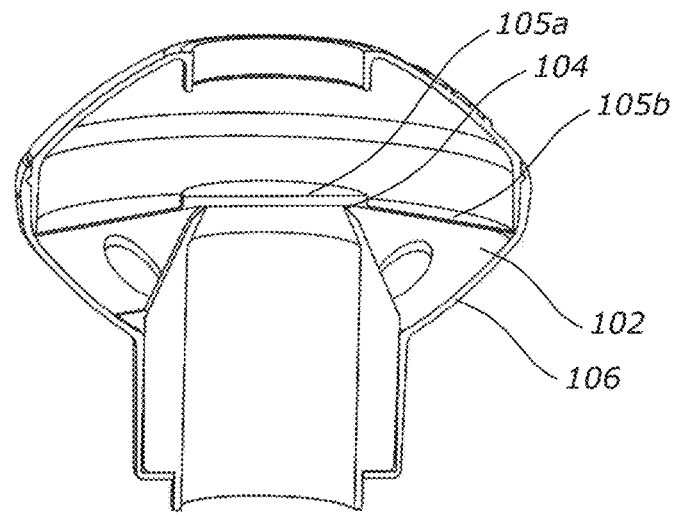
Figure 12C:
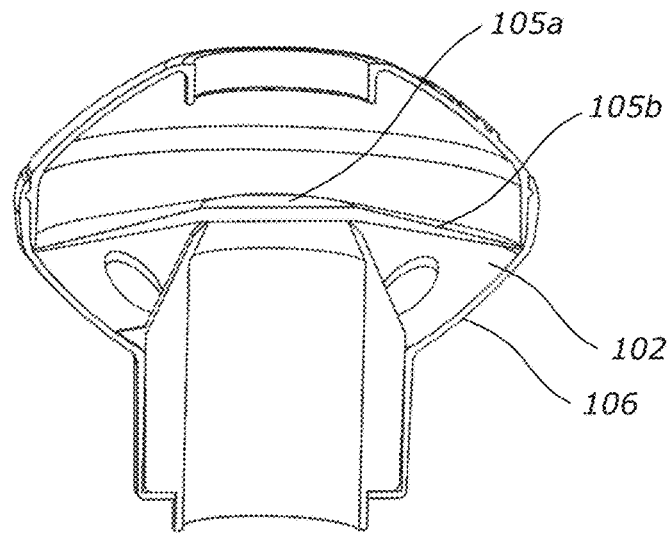
Figure 12D:
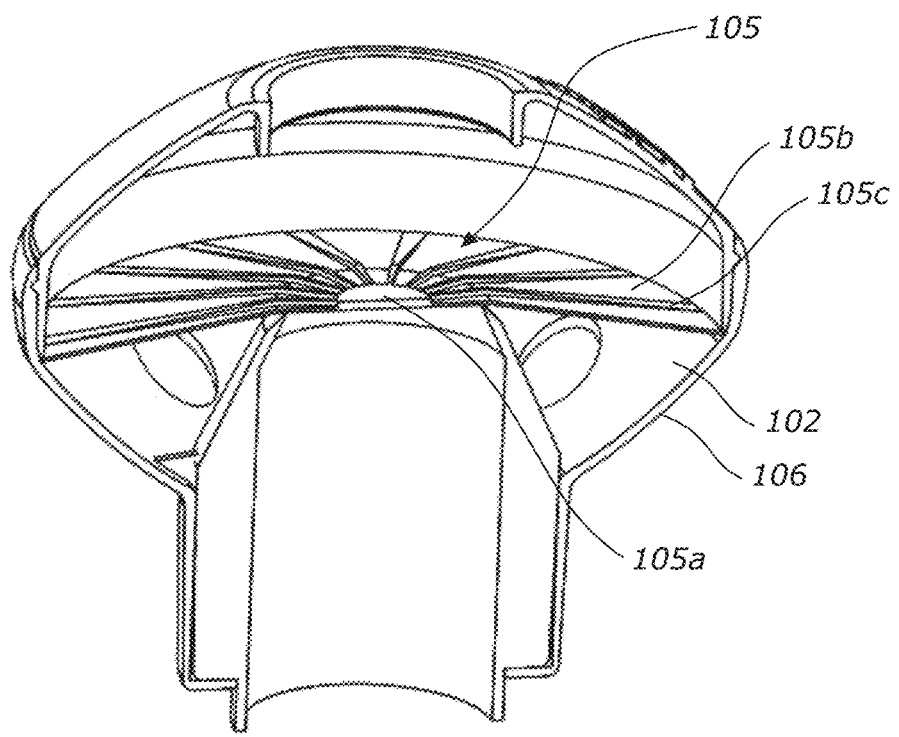
Figure 12E:
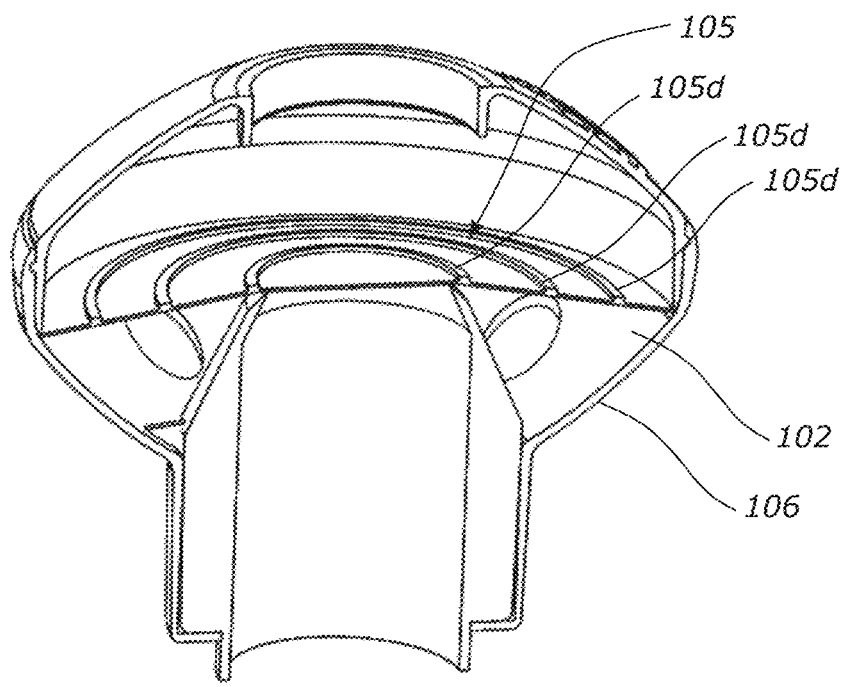

The membrane (i.e. valve member) 105 may be formed from a suitable elastomeric material, for example a rubber or silicone material or other elastic material. The material may be a thermoplastic or thermoset material, or a thermoplastic film. The membrane material may be non-porous or in some embodiments may be porous, for example to allow a continuous venting flow through the valve member for pressure above a threshold. One prototype valve was constructed using a rubber material with a thickness in the order of 0.4 mm. Other prototypes have a thicknesses of 0.1 mm to 0.3 mm with 0.3 mm being preferred. It should be appreciated that alternative membranes of different material composition and/or geometry may also be employed. Different materials may include, for example, rubber, thermoplastic, silicone, or the like having different respective modulus of elasticity. Different geometries may include membranes of different thickness, shape, or combinations thereof. For example, the membrane may include thickened regions. Thickened regions may be formed as a thickened circular centre of the membrane, or thickened radial ribs. For example, a membrane with a thickened central portion 105a to bear against the valve seat 104 is shown in FIGS. 12B and 12C. A portion 105b of the membrane extending around the thickened central portion 105a is of a suitable thickness to provide a desired characteristic of the PRV. The thinner portion 105b may provide the required bias of the valve member 105 against the valve seat 104. In FIG. 12B, the cross sectional thickness of the thinner portion 105b is constant over its radial length. In FIG. 12C, the thickness of the thinner portion 105b decreases along its radial length from the central thickened portion 105a to the outer perimeter of the membrane 105 at the wall 106 of the outlet chamber 102. The example embodiments of FIGS. 12D and 12E provide a membrane 105 with ribs 105c, 105d. In FIG. 12D, the ribs 105c are radial ribs 105c. The radial ribs may have a constant width along their radial length, or as shown may increase in width along their length towards the outer perimeter of the membrane. In FIG. 12E, the ribs 105d are concentric ribs 105d. The ribs 105d may be applied to achieve a desired characteristic of the PRV, e.g. to affect the way in which the membrane is elastically deformed.

The outlet 103 from the outlet chamber 102 provides a resistance to flow from the outlet chamber of the PRV. The resistance to flow generates the pressure Pb (a back pressure) in the outlet chamber 102 that acts on the valve member to push or force the member away from the valve seat 104. In some embodiments there may be more than one outlet, or in other words the outlet 103 may comprise a plurality of outlet holes or apertures 103. The chamber pressure Pb is a back pressure caused in the outlet chamber 102 by flow though the chamber 102 and a restriction provided by the configuration of the outlet 103 from the chamber 102. To cause a back pressure in the chamber 102, in some embodiments, the outlet 103 from the chamber is configured to have a greater resistance to flow than the gap 109 between the valve seat 104 and the valve member 105. A difference in pressure between the inlet pressure Pc and the back pressure Pb is created by a pressure drop in the flow of gases flowing through the gap 109 between the valve member 105 and the valve seat 104.

The valve member and valve seat provide a dynamically variable flow restriction 109 between the inlet 101 and the outlet chamber 102. The dynamically variable flow restriction is dependent on the inlet pressure at the inlet of the PRV, and the outlet pressure or back pressure in the outlet chamber. As the inlet pressure and/or outlet pressure increases, the dynamically variable flow restriction 109 decreases. The outlet 103 provides a 'fixed' flow restriction, or a flow restriction that is independent the inlet and outlet pressures. In other words, the outlet restriction does not change with changing inlet or outlet pressure. However, in some embodiments, the restriction of the outlet may be adjusted by a user, as described in more detail below.

In the embodiment of FIGS. 2A to 2C, the valve seat is at the end of the inlet 101, such that the inlet pressure Pc acts on the valve member over a valve seat area defined by the diameter of the valve seat (D in FIG. 12A). Once the valve member 105 is displaced from the valve seat 104, the inlet pressure continues to act against the valve member 105 over the valve seat area, and the back pressure Pb acts on the valve member over an area outside of the valve seat. Thus the back pressure Pb acts against an area of the valve member equal to the valve member area minus the valve seat area.

Figure 13A:
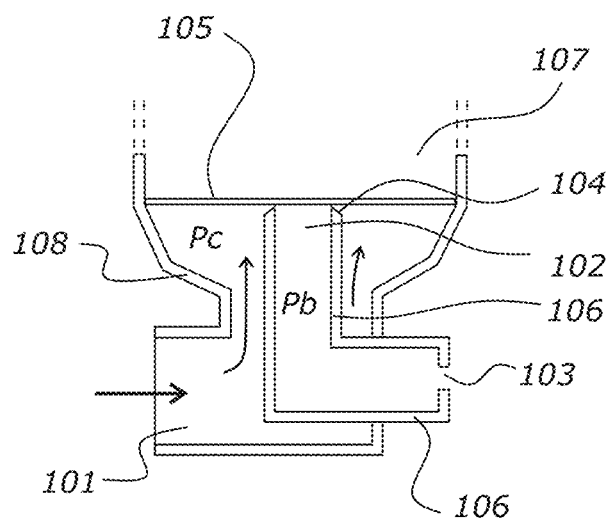
FIGS. 13A to 13C each illustrate a PRV cross section.
Figure 13B:
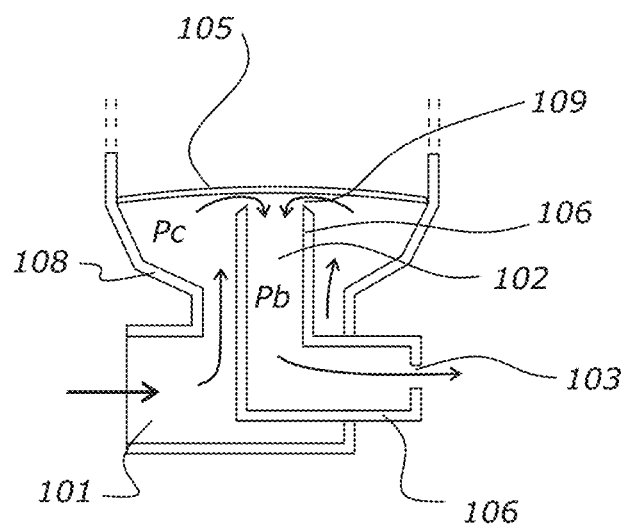
Figure 13C:
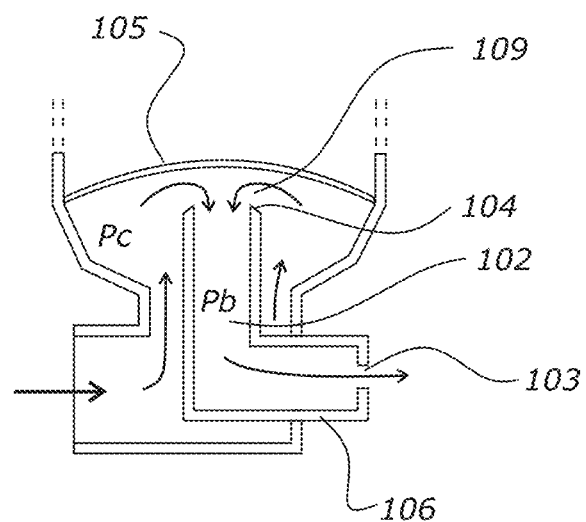

FIGS. 13A to 13C present an alternative embodiment, where the valve seat 104 is at an inlet to the outlet chamber 102. An inlet tube surrounds the outlet chamber. A periphery of the valve member membrane 105 may be supported or held by a wall 108 of the inlet tube with the membrane stretched or tensioned over the valve seat 104. When the valve member 105 is seated against the valve seat 104, the inlet pressure Pc in the inlet 101 acts on the valve member 105 over an area outside of the valve seat 104 (i.e. the valve member area minus the valve seat area). Once the valve member 105 is displaced from the valve seat 104, the inlet pressure continues to act against the valve member 105 over an area outside of the valve seat area, and the back pressure Pb in the outlet chamber created by the outlet vent 103 acts on the valve member over the valve seat area.

wherein the device comprises an inlet tube surrounding the outlet chamber and the valve seat is provided at an opening to the outlet chamber.

Figures 1, 1B:
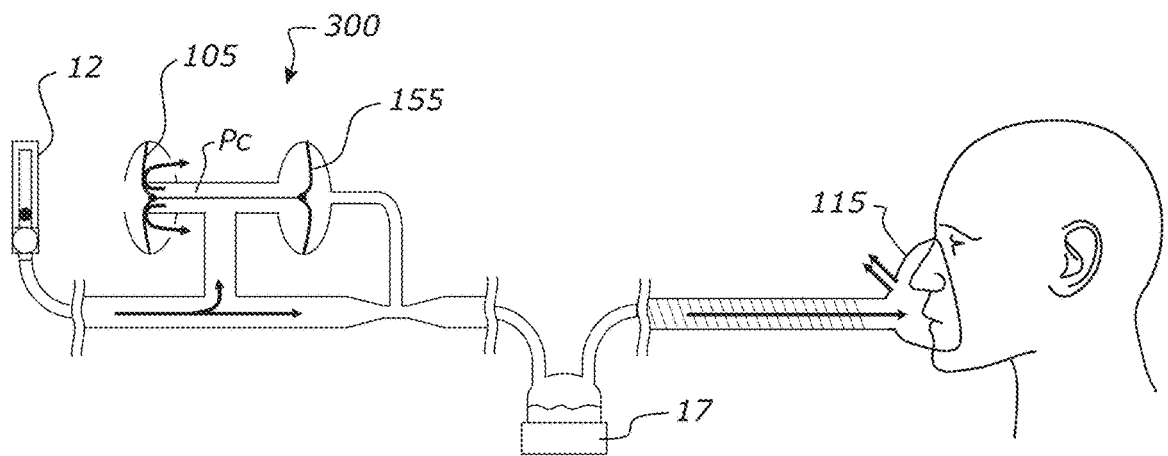
Figures 1, 1B, 2:
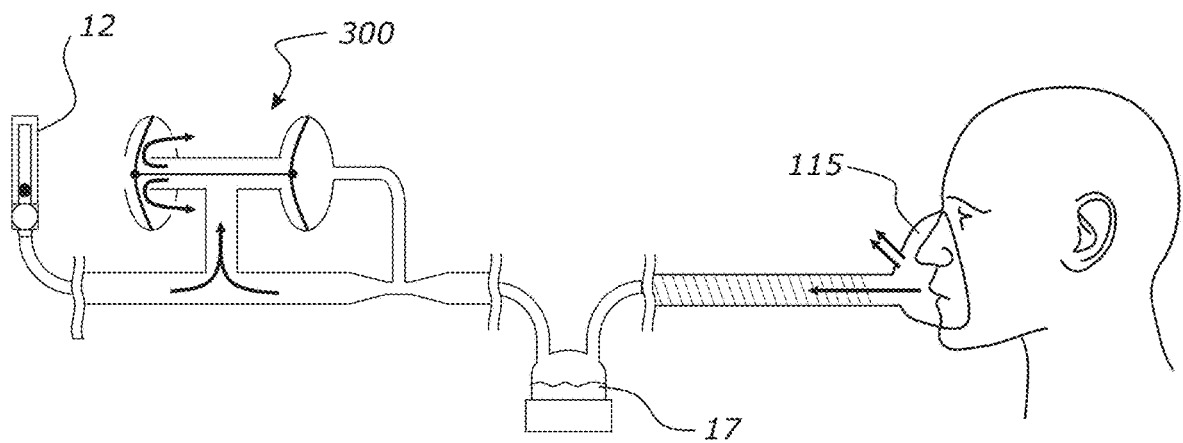
Figures 1, 1B, 2, 3:
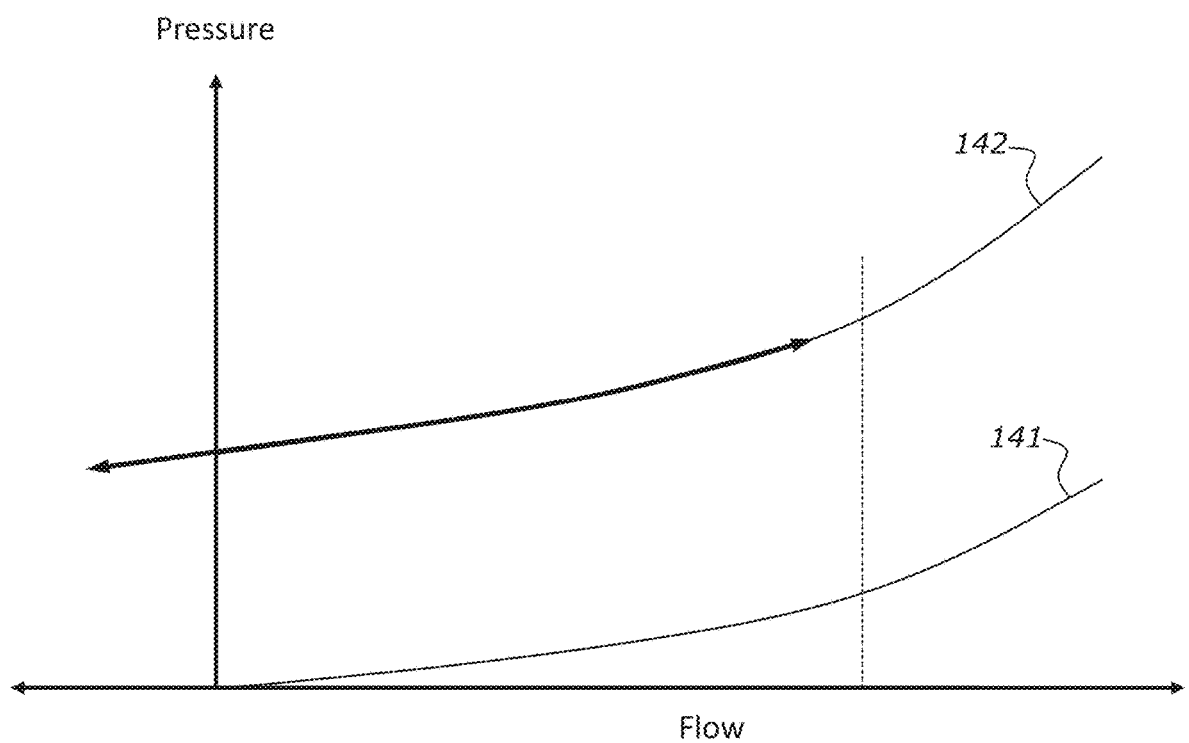

It may be desirable for the PRV to achieve an approximately constant relief pressure (within a pressure band) over a range of operating flow rates. The range of flow rates that the valve is able to regulate a relief pressure within a defined pressure band may be referred to as an effective operating range of the valve. For example, as shown in FIG. 3, in one embodiment a PRV achieves a pressure band of about 18 to 20cmH$_2$O over a flow rate range of about 5 L/min to 35 L/min. A particular valve may be developed to achieve a desired pressure band and flow rate range. A further benefit of a PRV as described is that the PRV results in safe operation even in the event of the system flow being set higher than a desired operating range, by reducing the relief pressure for the higher out of range flow rate. Factors that affect the performance of the valve are discussed in more detail below.

A substantially constant response is desirable because a PRV with a constant relief pressure ensures that the pressure within the system and/or the pressure delivered to user will not rise above a pressure band for a given operating flow range. This improves safety for the user from overpressure if the flow delivered by the system is at the upper end of an operating range. The PRV according to embodiments described herein may also allow for a greater operating flow range since the pressure is kept constant over a flow range, as compared to prior art valves. This is advantageous because a greater range of flow can be used in a respiratory therapy such as high flow therapy.

The operation of a PRV according to embodiments described herein is described with reference to FIGS. 3 to 6. When pressure, Pc, in the inlet 101 is sufficient to overcome the force of the membrane, the membrane 105 is displaced from the valve seat 104, allowing gases to pass from the inlet 101 into the outlet chamber 102 via the gap 109 between the valve seat 104 and the valve member 105. From the outlet chamber, gases may then pass to atmosphere via the outlet 103 or outlets.

As the gases flow through the outlet chamber 102, a pressure, P$_B$, is generated in the outlet chamber which acts on the membrane 105. As the flow rate is increased, this pressure in the outlet chamber may progressively increase according to the 'square rule': pressure is approximately proportionate to flow squared. The rate of increase of pressure in the outlet chamber may increase at a reduced rate compared to the square rule as the volume of the chamber expands due to movement of the valve member.

As the flow rate through the valve 100 increases, the pressure in the outlet chamber 102 increases and the gap 109 between the membrane 105 and the valve seat 104 (e.g. the abutting end of the inlet tube) widens further, which has the effect of progressively decreasing the resistance to flow provided by the gap 109, decreasing the pressure in the inlet tube, Pc, as shown in FIG. 3 from about 35 L/min to about 80 L/min. In other words, the total pressure drop through the PRV from the inlet 101 to the outlet 103 decreases.

As the flow rate is further increased, the gap 109 between the membrane 105 and the valve seat 104 widens even further, eventually to the point at which pressure in the inlet tube 108, Pc, and pressure in the outlet chamber 102, P$_B$, begin to equalise. In other words, the pressure drop across the gap 109 between the valve seat 104 and the valve member 105 approaches zero. The inlet and chamber pressures may not actually achieve equalisation in operation, but tend towards equalisation. In FIG. 3, the inlet pressure and the outlet chamber pressure have approximately equalised at a flow rate of about 120 L/min. This flow rate is outside the effective 'constant' operating range of the PRV.

As the pressure in the outlet chamber Pb and the inlet pressure Pc tend towards equalisation, the pressure drop from the inlet 101 to the outlet chamber 102 decreases, and the pressure drop through the PRV 100 is predominately across the outlet 103, from the outlet chamber 102 to ambient. In other words the pressure drop though the PRV is predominately from the outlet chamber 102 to ambient. Once the pressure drop from the outlet chamber to ambient becomes dominant, the inlet pressure, Pc, increases according to the 'square rule'. In other words, the total pressure drop across the PRV 100 begins to increase according to the 'square rule' once the outlet chamber 102 pressure Pb becomes dominant. In the example valve characteristic presented in FIG. 3, this occurs at about 100 L/min. The pressure drop across the PRV begins to increase according to the square rule outside of the effective operating flow rate range of the valve. The data presented in FIG. 3 is provided for an example valve, other valves according to embodiments described herein will present different flow/pressure characteristics. The performance of a particular valve, including the point at which the pressure begins to increase according to the square rule, depends on various factors. These factors are described in more detail below.

Figure 6:
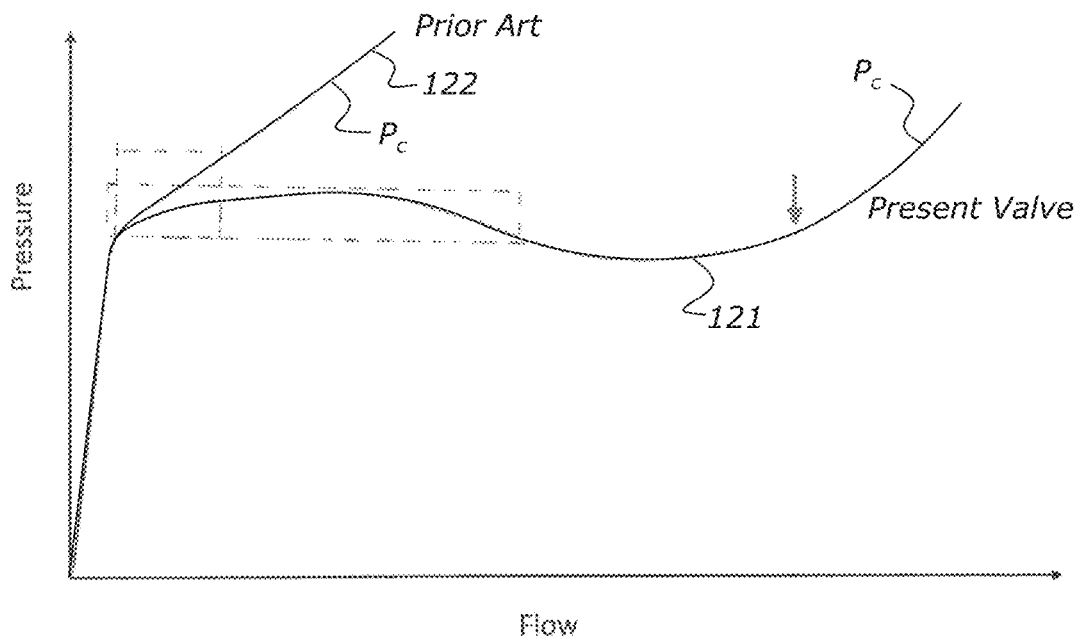
FIG. 6 provides a graphical representation of a comparison between a prior art plunger type valve without an outlet chamber, and a PRV with an outlet chamber according to described embodiments, venting pressure vs venting flow rate.

In a prior art valve, the pressure drop across the valve is predominantly across the gap between the valve seat and the valve member. Once a valve 'cracks' or opens with the valve member moving away from the valve seat, pressure drop across the gap between the valve seat and the valve member will progressively increase in proportion to the flow rate, and may increase linearly. By comparison, a PRV according to embodiments described herein substantially increases proportionate to the square of the flow rate, but offsets the point at which the pressure drop across the PRV will begin to increase. This comparison between a PRV according to embodiments described herein and a prior art valve is displayed schematically in FIG. 6. A valve according to embodiments described herein (pressure curve 121 in FIG. 4) maintains a substantially consistent relief pressure over a large range of flow rates. The approximate point at which the pressure drop across the valve (Pc) begins to increase according to the square rule is indicated by the arrow on the chart. A PRV may be designed so that the point at which the pressure beings to increase according to the square rule is outside of the effective operating flow rate range for the valve, so that the valve presents a relatively constant relief pressure for the intended flow rate range for the valve. The graph in FIG. 6 is illustrative only and the shapes of the pressure curves are exaggerated to emphasise the effect of the PRV according to embodiments described.

Figures 1, 1C:
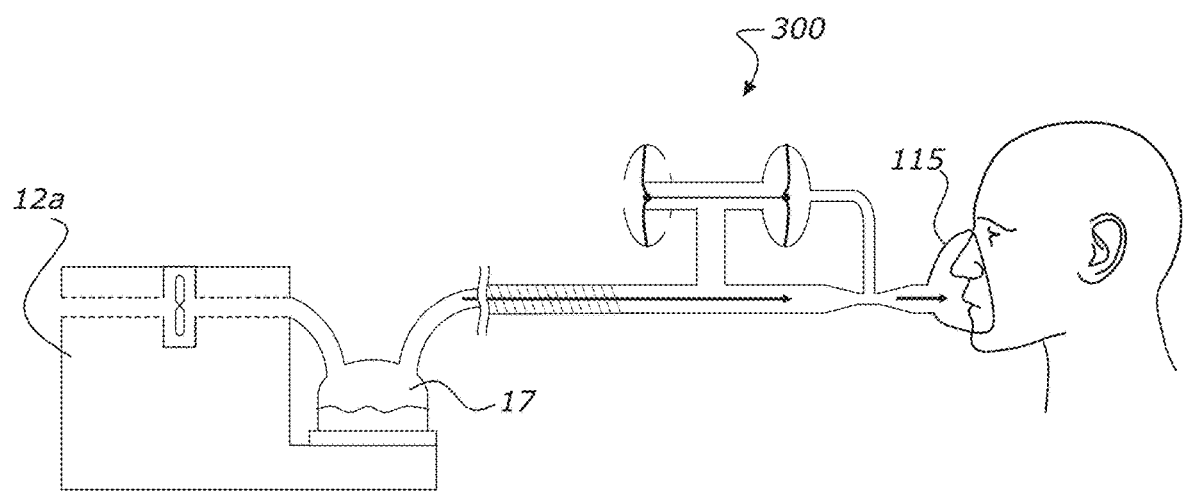
Figures 1, 1C, 2:
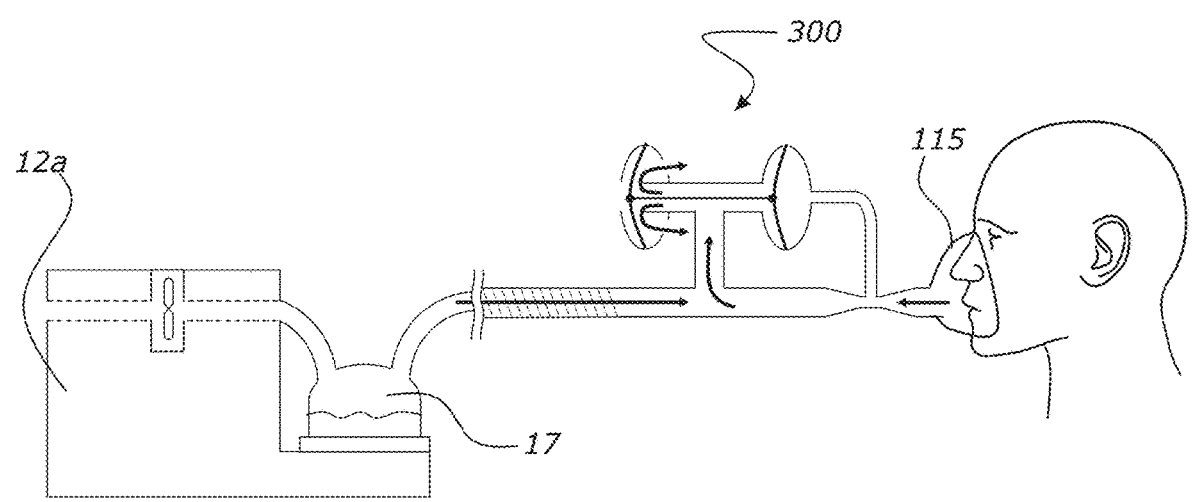
Figures 1, 1C, 2, 3, 4:
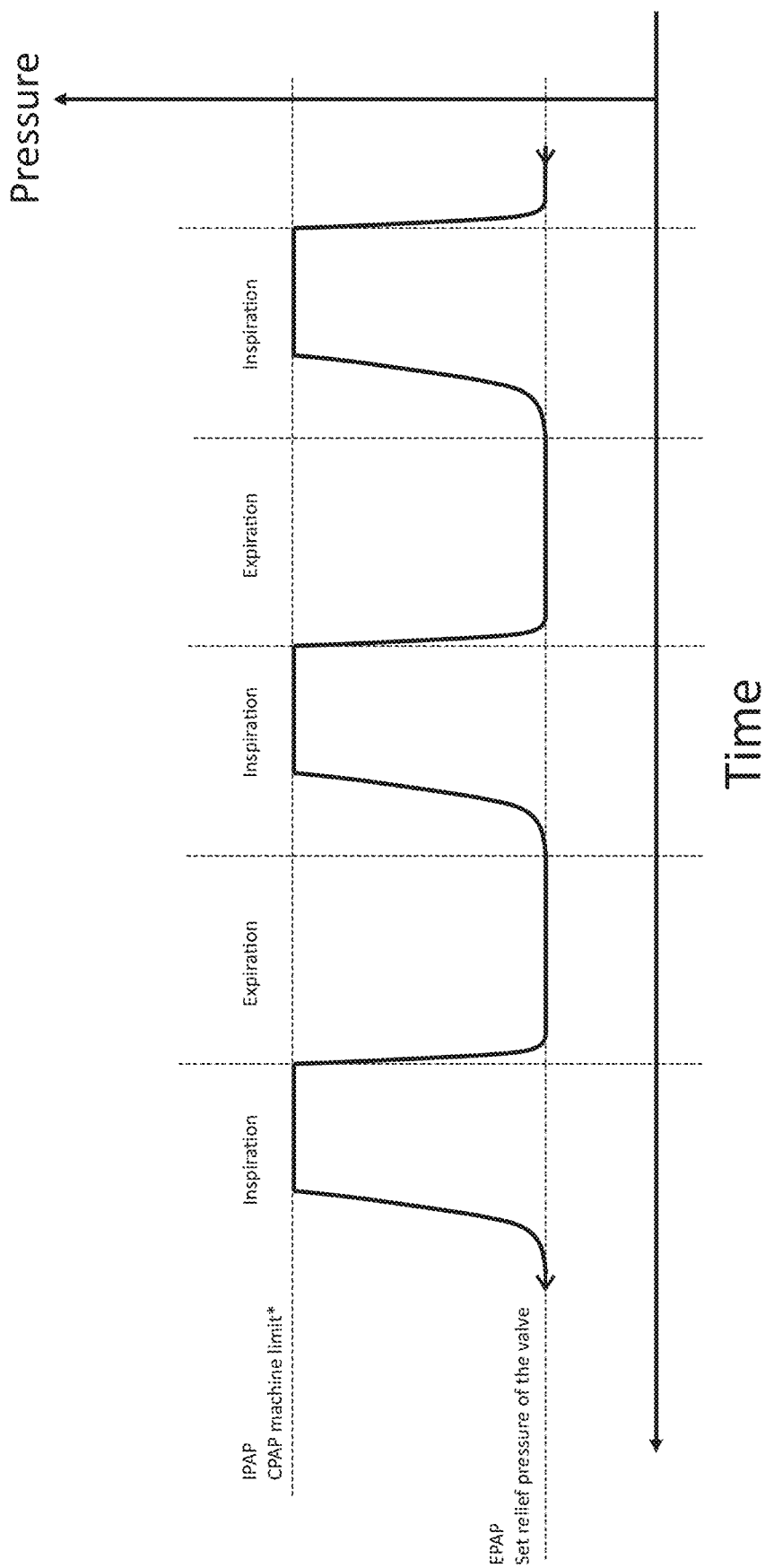
Figures 1, 1C, 2, 3, 4, 5:
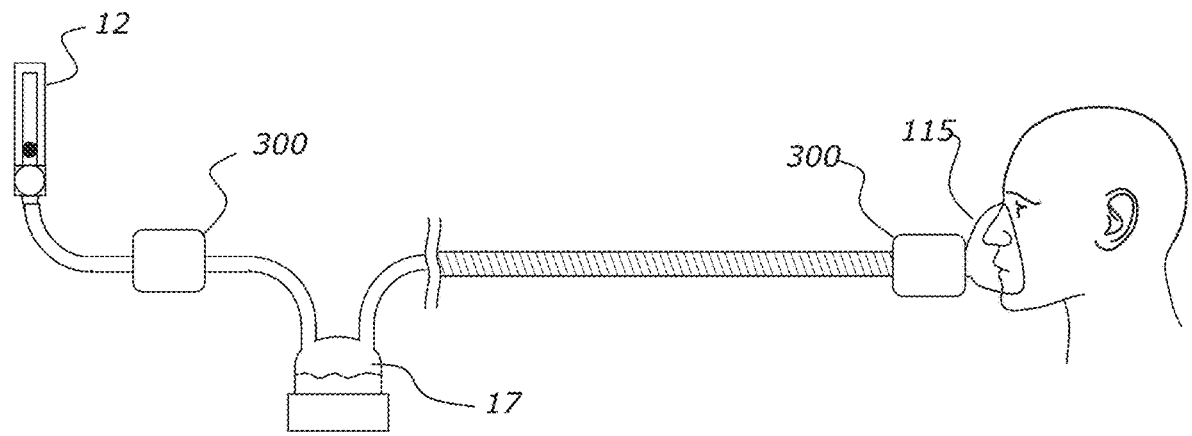

The size and number of outlets (i.e. the overall outlet area) from the outlet chamber has an effect on the pressure, $P_B$ that is generated in the outlet chamber. For example, pressure in the outlet chamber will progressively increase at a greater rate over an increasing flow rate with smaller outlet apertures. Conversely, pressure in the outlet chamber will progressively increase at a lesser rate over an increasing flow rate with larger outlet apertures. Therefore, adjustment of the size and/or number of the outlet apertures (i.e. the overall outlet area) has the resultant effect of adjusting the effective operating range of the valve. This mechanism for altering the characteristic of the PRV is illustrated in FIGS. 3 to 5. In FIG. 3, a test PRV comprised a single outlet aperture from the outlet chamber. In FIG. 4, a test PRV had two outlet apertures of the same size, such that the outlet area of the test PRV for FIG. 4 is twice the outlet area for the test valve for FIG. 3. The greater outlet area resulted in pressure in the outlet chamber progressively increasing at a lesser rate over an increasing flow rate. As a result, the effective flow rate operating range in FIG. 4 is widened, regulating the pressure to an approximately consistent pressure across a larger range of flow rates compared to in FIG. 3. Further, in FIG. 5, a test PRV comprised three outlet apertures, such that the outlet area of the test PRV for FIG. 5 is three times the outlet area for the test valve for FIG. 3. The greater outlet area compared to the valves tested in FIGS. 3 and 4 resulted in a pressure in the outlet chamber progressively increasing at a lesser rate over an increasing flow rate. As a result, the effective flow rate operating range is further widened, regulating the pressure to an approximately consistent pressure across a larger range of flow rates.

In some embodiments, the PRV may be tuned to a particular effective operating range at manufacture—such as by assembly with a predetermined number and/or size of outlet holes. Alternatively, the end user may tune the valve to a particular effective operating range—such as by a means to selectively adjust the outlet area from the outlet chamber. Such means may be, for example, a feature to selectively open/close a number of outlet holes. In one embodiment the outlet chamber may comprise one or more outlet apertures, and a covering member comprising a corresponding one or more apertures may be movable coupled to the chamber. The member may be moved relative to the outlet chamber to align the apertures of the outlet chamber and the apertures of the covering member to maximise the outlet area from the chamber. The covering member may be moved relative to the chamber so that the apertures of the chamber and member are partially aligned, so that the outlet area is less than the maximum outlet area. For example, the covering member may be a ring member with holes that is rotationally coupled to rotate relative to the outlet chamber to move between a position where the holes of the member and the outlet apertures 103 from the chamber 102 and are aligned (maximum outlet area), and a second position wherein the where the holes of the member and the outlet apertures 103 from the chamber 102 and are not aligned so that the outlet apertures are partially covered (minimum outlet area).

Alternatively, there may be a plurality of outlet apertures 103 with removable covers, and the outlet area is variable by removing the cover from one or more outlet apertures 103.

Figure 7:
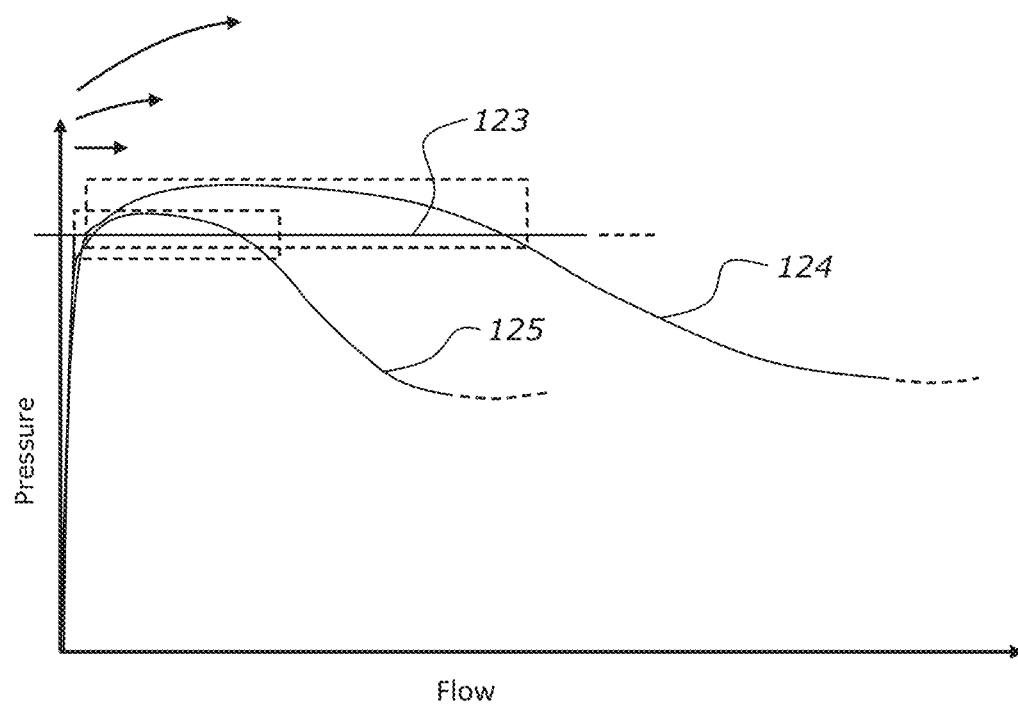
FIG. 7 provides a graphical representation of the effect of different outlet areas on the performance of a PRV according to described embodiments, venting pressure vs venting flow rate.

A small outlet area produces a relatively higher resistance to flow, resulting in a relatively higher backpressure in the outlet chamber 102, which acts on the valve member 105 to further 'push' the member away from the abutting inlet tube or valve seat 104. As a result, the valve will have a short effective operating range with a pressure curve comprising a relatively short, sharp, 'knee' indicative of how rapidly the valve reaches its maximum predetermined relief pressure. Conversely, a large outlet area produces less resistance to flow, resulting in less backpressure acting on the valve member to further 'push' the member away from the abutting inlet tube. The larger outlet area will provide a wide effective operating range with a pressure curve comprising a relatively longer, rounded, 'knee'. This concept is further illustrated in FIG. 7, wherein 123 illustrates an ideal valve pressure curve that has no static leak, a sharp 'knee' and constant relief pressure. Curve 124 illustrates a pressure curve for a valve comprising a relatively larger outlet area, with the pressure curve having a wide effective flow rate operating range and a relatively long rounded 'knee'. For comparison, curve 125 illustrates a pressure curve for a valve comprising a relatively smaller outlet area, with the pressure curve having a shorter effective flow rate operating range and a relatively shorter and less rounded 'knee'.

The outlet or outlets 103 from the outlet chamber 102 provide an amount of resistance to flow from the chamber 102 and therefore affect the amount of pressure in the chamber that acts to move the valve member from the valve seat. Discussed above is the effect of the area of the outlet. Also, a length of the outlet from the outlet chamber may have an effect on the pressure in the outlet chamber. In some embodiments, the outlet may comprise one or more apertures in a wall of the outlet chamber, for example as shown in FIGS. 2A to 2C. In some embodiments, the PRV may comprise an outlet tube (not shown) extending from the outlet chamber. The length of the outlet tube may provide resistance to flow that may affect the pressure level generated in the outlet chamber.

The position of the outlet(s) from the outlet chamber may also affect the gas flow dynamics of the PRV. As such, the position of the outlet(s) may provide some resistance to flow that may subsequently affect the amount of pressure generated in the outlet chamber. The shape of the outlets may also have an effect on the performance of the PRV.

As illustrated in the embodiment of FIGS. 2A to 2C and FIG. 12A, preferably the outlet is located radially between an outer perimeter of the valve member and an outer perimeter of the valve seat and/or inlet and/or an inlet tube. Positioning the outlet in between the outer perimeter of the valve member and the valve seat assists with creating a flow path in the outlet chamber against the valve member. In some embodiments, the inlet, the valve member, the valve seat and the outlet are arranged so that the flow of gases through the outlet chamber is directed against the valve member as the flow of gases enters the chamber to be reflected from the valve member through an angle greater than 90 degrees to exit the chamber via the outlet. In some embodiments, as illustrated, the inlet is arranged to direct the flow of gases into the outlet chamber perpendicular to the valve member. The direction of flow into the chamber may be substantially opposite to the direct of the flow of the gases out of the outlet chamber (e.g. the direction of flow from the outlet is about 180 degrees to the direction of flow from the inlet). In some embodiments, the outlet is located in a wall of the outlet chamber opposite to the valve member. In some embodiments, the outlet vent 103 may be provided with an outlet tube concentric with the inlet tube 101. In some embodiments the outlet vent maybe located adjacent a perimeter of the valve member. Alternatively or additionally, in some embodiments, the outlet vent or vents 103 may be provided through the valve member, for example apertures through the valve member or the valve member may be porous. For example, porous or with one or more apertures through the valve member in an area outside the valve seat area. The whole of the valve member may be porous, resulting in a constant leak flow through the valve member even when the valve member is against the valve seat.

Furthermore, the size of the outlet chamber 102 may affect the performance of the valve. For example, a very large outlet chamber will take longer to pressurise and therefore may result in a valve characteristic with a 'soft' opening characteristic. In contrast, a small volume outlet chamber may pressurise more quickly, resulting in a quicker lifting of the membrane from the valve seat. In some embodiments, the outlet chamber may have a zero volume when the valve member is against the valve seat, and a volume greater than zero once the valve member is moved away from the valve seat. In a zero volume chamber, the valve member may lie against a wall of the chamber 102 when the valve member 105 is against the valve seat 104. The wall may be curved or flat. As the valve member 105 lifts, the valve member may expose outlet holes, such that the outlet area is variable depending on the pressure generated in the outlet chamber. Alternatively or additionally, as the valve member 105 lifts away from the valve seat 104 to allow a flow of gases into the outlet chamber 102, the valve member may vary the resistance to flow of the outlet from the outlet chamber. For example, a gap between the valve member and an outlet from the outlet chamber may vary as the valve member moves away from the valve seat, to vary the resistance to flow through the outlet. In preferred embodiments, the valve chamber has a sufficient volume so that the velocity of the gases flow within the chamber is substantially less that the velocity of the flow of gases through the gap between the valve seat and the valve member. In some embodiments, the velocity of the gases flow within the chamber is substantially less that the velocity of the flow of gases through the outlet from the chamber.

Figure 8:
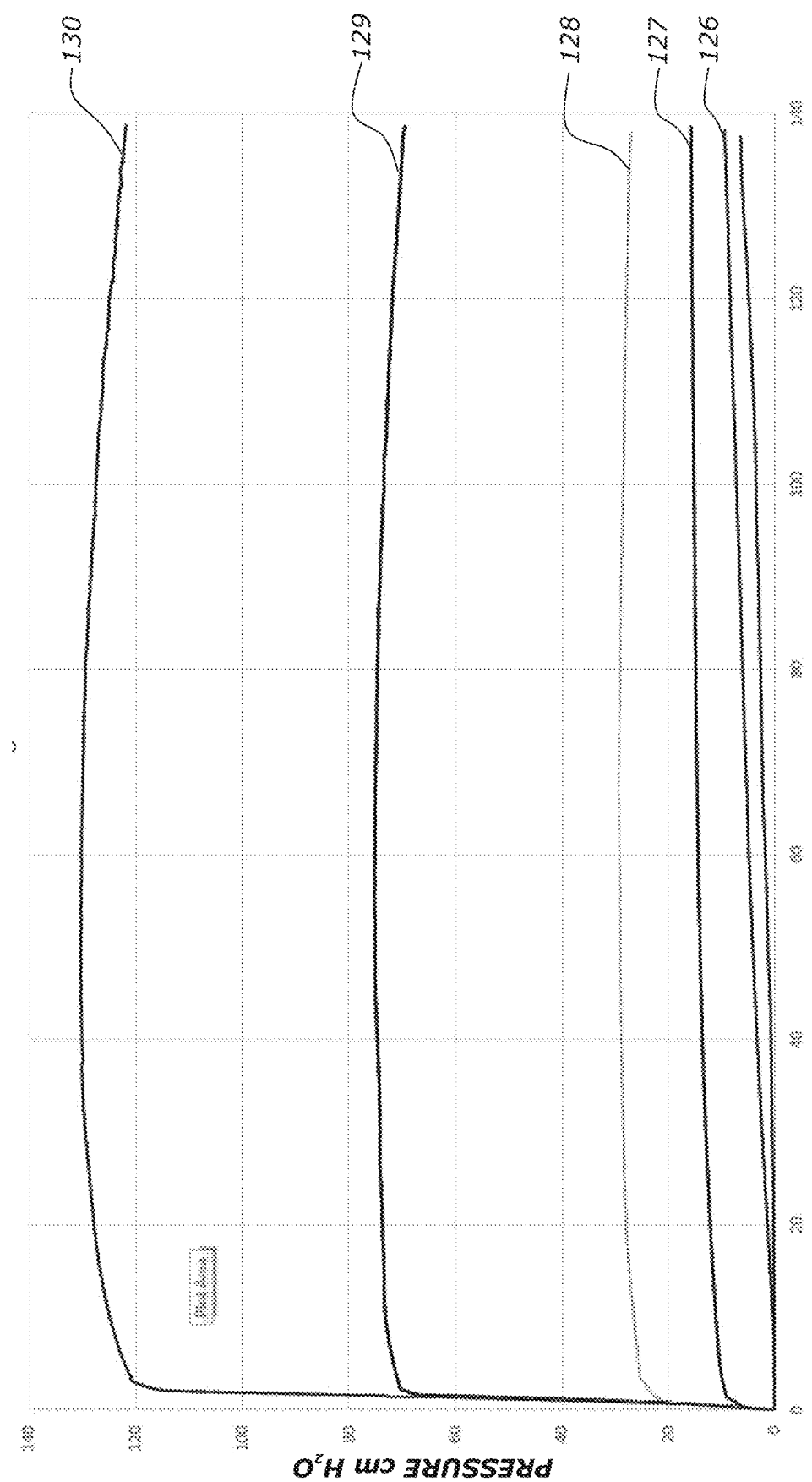
FIG. 8 shows a chart illustrating the effect of different tensions in a membrane valve member on the relief or venting pressure of a PRV vs venting flow rate of the PRV.
Figure 11A:
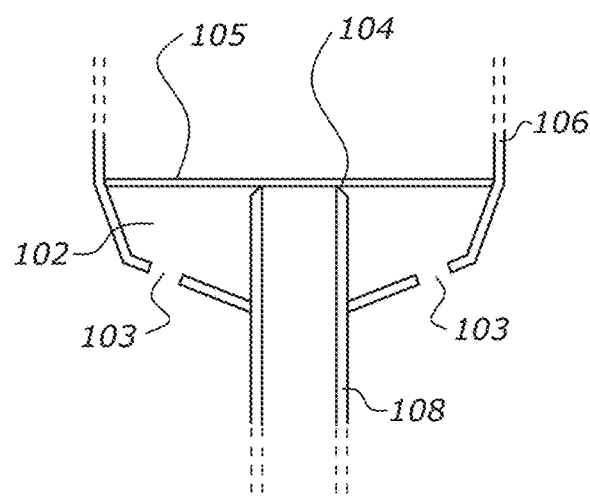
FIGS. 11A and 11B illustrate a PRV each with a different amount of extension of an inlet tube to alter the amount of tension in a membrane valve member.
Figure 11B:
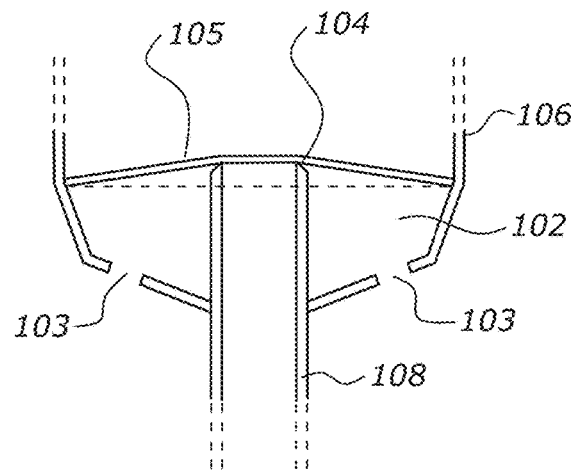

As described above, in some embodiment the inlet tube 108 extends into the outlet chamber 102 so that the membrane abuts the end of the tube providing a valve seat. An alternative or additional means by which the characteristics of the valve may be adjusted is by varying the distance that the inlet tube extends into chamber and thus how much the membrane is stretched or tensioned over the valve seat. The inlet pressure required to lift the membrane away from the valve seat is directly related to the amount the membrane is tensioned over the valve seat. In some embodiments, the inlet tube 108 may be movably coupled to the outlet chamber 102, for example in a sliding engagement, so that the inlet tube and thus valve seat 104 may be moved relative to the membrane 105 and outlet chamber 102 to adjust the tension in the membrane when abutting the valve seat 104. FIG. 11A illustrates the inlet tube positioned in a first less extended position with the membrane 105 in a less tensioned state, and FIG. 11B illustrates the inlet tube positioned in a second extended position with the membrane in a more tensioned state. Experimental data for different tube extension into the outlet chamber is presented in FIG. 8. Pressure curve 126 is the inlet pressure (Pc) for the PRV with the inlet tube in a non-extended position, curve 127 is for the PRV with the inlet tube first extended beyond the first position, curve 128 is for the PRV with the inlet tube extended beyond the first extended position, 129 is for the PRV with the inlet tube extended beyond the second extended position, and curve 130 is for the PRV with the inlet tube extended to a further extended position beyond the second extended position. FIG. 8 illustrates that for a higher tension in the membrane caused by extension of the inlet tube into the outlet chamber, the greater relief pressure that is achieved. In practice, movement of the inlet tube relative to the chamber 102 or valve member 105 may be achieved by moving the chamber 102 and/or valve member relative to the tube, i.e. where the position of the inlet tube is fixed relative to other system or valve components. For example, the valve member may be fitted to the chamber via a screw interface, and adjusting the position of the valve member within the chamber also adjusts the relative position of the valve member to the valve seat. The chamber 102 may include an adjustment mechanism to move the valve member relative to the valve seat, for example as shown in the FCPRV of FIG. 18B.

In some embodiments, the inlet tube may be fixed to the respiratory gas supply system. In order to adjust the relative positions of the membrane and valve seat, the membrane together with the outlet chamber may be moved relative to the tube which remains fitted in place to the gas supply system.

As described above, valve member may be fixed to the chamber 102 and the chamber 102 may be in a sliding engagement with the inlet tube 108, however, other configurations may be possible. For example, in some embodiments, the inlet tube may engage in the outlet chamber by way of a screw thread arrangement or bayonet-type fitting. The user may rotate the outlet chamber relative to the inlet tube to cause the outlet chamber and membrane to travel longitudinally relative to the inlet tube, such that the membrane presses further over the abutting end of the inlet tube.

The adjustment mechanism may provide discrete adjustment steps (e.g. corresponding with known pressure settings) or continuous adjustment range without steps.

The inlet tube cross sectional area and/or valve seat area may affect the performance of the PRV. For example a smaller inlet tube area or valve seat area will result in a smaller area on the membrane against which the inlet pressure acts, a smaller area requiring a greater inlet pressure to lift the membrane away from the valve seat. Also, a ratio of the area of the inlet tube or valve seat to the total area of the membrane may affect the performance of the PRV for a given tension in the membrane; changing the size of the membrane may also result in a change in tension, further altering valve performance.

In the embodiments described herein, the area of the valve member over which the pressure in the outlet chamber acts is greater than the area of the valve seat/inlet (the area that the inlet pressure acts against when the valve member is seated against the valve seat). The larger the area of the valve member, the greater the force exerted on the valve member by the pressure Pb in the outlet chamber, and therefore the more effect the pressure in the outlet chamber has to push the valve member from the valve seat. The shape of the inlet tube cross section or valve seat may also affect the performance of the PRV.

The material and/or geometry of the membrane may be determined to achieve a particular valve characteristic. For example, the membrane geometry, cross sectional shape and area all combine to determine a spring constant or tension of the membrane. Furthermore, the amount of tension in the membrane may be set during manufacture, by setting an amount of stretch of the membrane during assembly of the PRV. Additionally, the amount of tensioning of the membrane against the valve seat, as discussed above in relation to the movable inlet tube, affects the performance of the PRV.

Figure 9A:
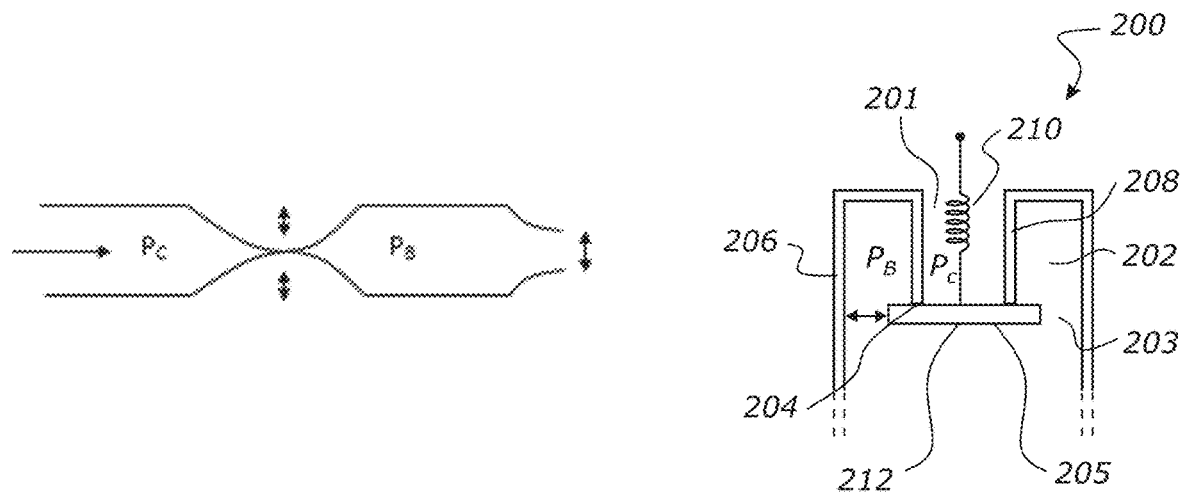
FIGS. 9A to 9C each illustrate a PRV cross section and corresponding schematic representation.
Figure 9B:
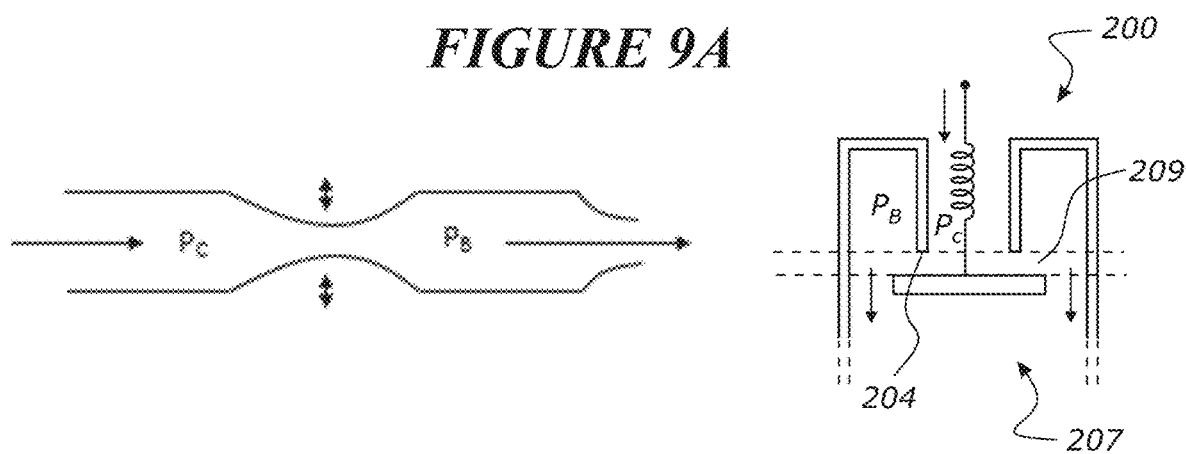
Figure 9C:
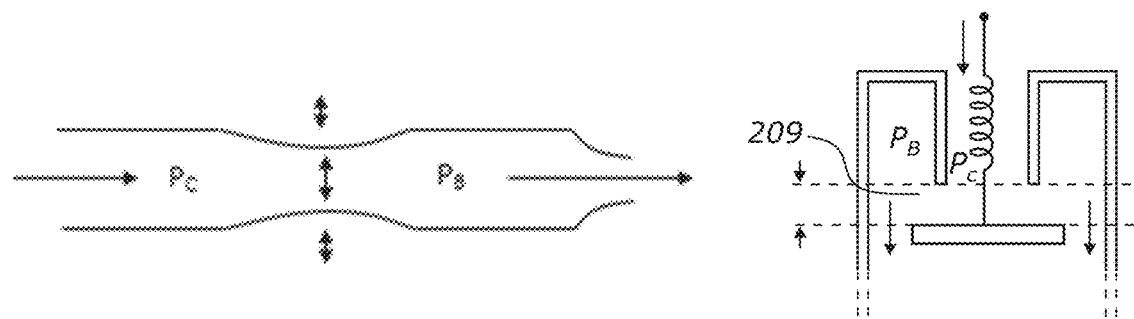

In embodiments described above the valve member is a membrane. In alternative embodiments, the valve member may comprise a plunger type valve member. With reference to FIGS. 9A to 9C, the illustrated PRV 200 comprises an inlet 201, an outlet chamber 202, a valve seat 204 between the inlet and the outlet, a plunger type valve member 205 biased to seal against the valve seat 204. The plunger type valve member is biased by a biasing member 210 (a spring) to seal against the valve seat. An outlet 203 from the outlet chamber is provided between a periphery of the valve member 205 and a wall 206 of the outlet chamber. The outlet 203 is open to ambient or atmospheric pressure, i.e. an open side or displacement side 207 of the chamber towards which the valve member moves may be referred to as a displacement chamber 207, and the displacement chamber is open to atmospheric pressure. The PRV 200 may comprise a housing 206. The outlet chamber may be considered as a pressure side 202 of the housing, and the displacement chamber may be considered as an ambient side 207 of the housing. A boundary between the pressure and ambient sides of the housing shifts as the plunger moves. Ambient (atmospheric) pressure acts on a non-pressure side 212 of the plunger. The non-pressure side is the side of the plunger opposite to a side of the plunger that seals over the valve seat. The inlet 201 may comprise an inlet tube 208 that extends into the outlet chamber, for example as described with reference to earlier embodiments comprising a membrane valve member.

The valve member 205 is adapted to displace from the valve seat by pressure Pc at the inlet increasing above a pressure threshold. The pressure Pc acts on the valve member to force the member away from the valve seat 204 once the pressure Pc reaches the threshold, for example as shown in FIG. 9B. As the member displaces from the valve seat 204, a flow of gases flows from the inlet 201 into the outlet chamber 202, and then from the outlet chamber via the outlet 203 defined between the plunger 205 and the chamber wall 206. The outlet 203 from the chamber 202 is configured so that the flow of gases through the outlet 203 causes a (back) pressure Pb in the outlet chamber 202 that acts on the valve member 205 to further displace the valve member 205 from the valve seat 204, for example as shown in FIG. 9C. As the flow through the PRV increases, the back pressure in the outlet chamber increases and the gap 209 between the valve seat 204 and the valve member 205 increases further. Eventually pressure in the inlet tube 208, Pc, and pressure in the outlet chamber 202, $P_B$, tend towards being equal. As the pressure in the outlet chamber Pb and the inlet pressure Pc tend towards equalisation, the pressure drop from the inlet 201 to the outlet chamber decreases, and the pressure drop through the PRV is predominately across the outlet 203 from the outlet chamber 202. In other words the pressure drop though the PRV is predominately from the outlet chamber 202 to ambient. Once the pressure drop from the outlet chamber to ambient becomes dominant, the pressure Pc at the inlet of the PRV (i.e. the pressure drop across the PRV) then progressively increases according to the 'square rule'. The embodiment of FIGS. 9A to 9C therefore able to achieve characteristics described above with reference to FIGS. 3 to 5.

Figure 10A:
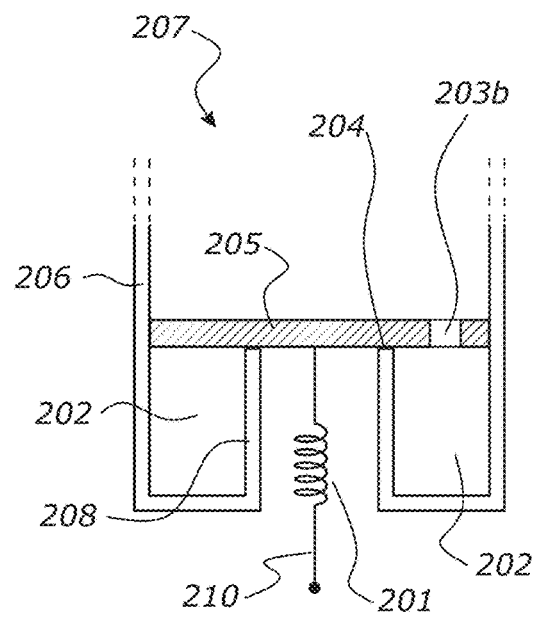
FIGS. 10A and 10B are cross sections of alternative PRV's each with a piston type valve member.
Figure 10B:
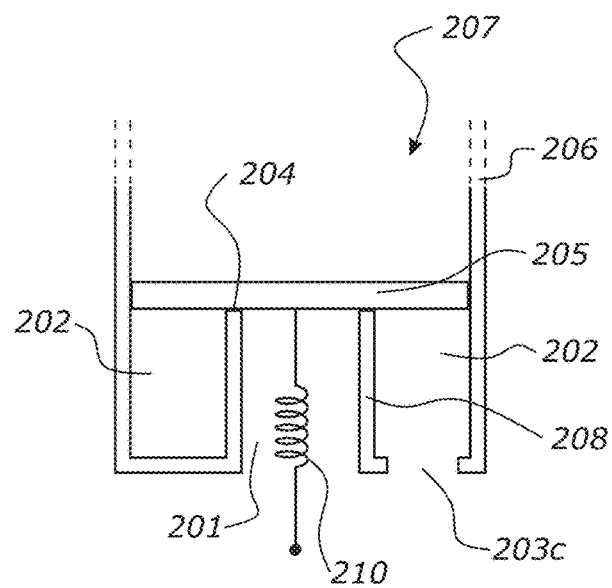

With reference to FIGS. 10A and 10B, in an alternative plunger style pressure relief valve, the outlet from the PRV may be provided by one or more apertures 203b through the valve member 205 (FIG. 10A), or the PRV may comprise an outlet 203c from the outlet chamber 202. In the embodiments of FIGS. 10A and 11B, the plunger valve member 205 is a piston forming a sliding seal with the wall 206 of the outlet chamber 202. However, in an embodiment comprising a piston in sliding relationship with a cylinder housing, there may be flow paths between the piston and cylinder, for example via channels in the cylinder wall, or via cut-outs or notches in a perimeter of the piston. Such flow paths between the piston and cylinder may be in addition to apertures through the piston.

Other features of the membrane valves described above may equally be applied in a plunger style valve such as the PRV's described with reference to FIGS. 9A to 10B. For example, one end of the spring may be fixed relative to the chamber 202, and the inlet tube 208 may be adjustable relative to the chamber 202 to alter the tension applied by the spring 210 to the plunger 205. With reference to the embodiment of FIGS. 10A and 10B, the area of the outlet apertures 203b, 203c through the plunger or through the chamber wall may be adjustable. Additionally or alternatively, the tension or compression of the biasing member (e.g. a spring) may be adjustable. In the figures the spring 210 is illustrated as a spring in tension (this could be a coil spring or a diaphragm member connected to the valve member or any other spring element), however, in an alternative embodiment the spring in compression may act on an opposite side on the valve member (a coil spring in compression, a rubber block or leaf spring or any other spring element).

FIG. 12A illustrates a cross section of a prototype valve. As an example of a valve according to some embodiments described, this valve has the following dimensions.

Valve seat diameter and/or inlet diameter 20 mm. In some embodiments, the valve seat diameter and/or inlet diameter may be in the range of 5 mm to 100 mm. Note that the valve seat area is considered to be the area defined by the valve seat diameter (D in FIG. 13A). So for valve seat diameter of 20 mm, the valve seat area is about 315 mm².

Thus for a valve seat diameter of 20 mm and a valve member diameter of 60 mm, the ratio of valve member area to valve seat area is about 9.

Membrane outer diameter 60 mm. In some embodiments, the membrane diameter may be in the range of 10 mm to 200 mm.

Outlet area for outlets from chamber 54 mm2, 108 mm² and 162 mm² (8.3 mm diameter apertures). The apertures need not be round/circular. These areas correspond with the valves providing the data presented in FIGS. 3, 4 and 5 respectively. In some embodiments, the outlet area may be in the range of 12 mm² to 200 mm².

For a silicone membrane or material with comparable properties, membrane thickness 0.3 mm. In some embodiments, the membrane thickness may be in the range of 0.05 mm to 1 mm.

Volume of outlet chamber 32 mL.

Volume of displacement chamber 55 mL (should be sufficient to not limit valve member unless this is desirable).

In some embodiments, a ratio of the membrane diameter to the membrane thickness may be in the range of 20 to 2000 (for example, a membrane diameter of 20 mm and thickness of 1 mm, to a membrane diameter of 200 mm and thickness of 0.1 mm). Another indicative ratio of the membrane diameter to the membrane thickness is 50, for a diameter of 10 mm and thickness of 0.5 mm.

In some embodiments, a ratio of the valve member 105, 205 area to the inlet or valve seat 104, 204 area may be in the range of 1.2 to 1600 (for example a membrane diameter of 20 mm and inlet diameter of 18 mm, to a membrane diameter of 200 mm and an inlet diameter of 5 mm).

In some embodiments, the PRV is adapted to maintain a relief pressure range of less than 5 cmH$_2$O over a flow rate range of 100 L/min through the PRV.

In some embodiments, the PRV may comprise at least two outlet chambers in series. For example, in some embodiments, the PRV may comprise a first outlet chamber with a first outlet and a second outlet chamber with a second outlet. The second outlet chamber receives the flow of gases from the first outlet.

The valve member displaces from the valve seat by the inlet pressure at the inlet increasing above a pressure threshold to allow the flow of gases from the inlet to the first outlet chamber. The flow of gases then pass from the first outlet chamber via the first outlet to the second outlet chamber and then exit the second outlet chamber via the second outlet. The first and second outlets may each comprise a plurality of apertures in a wall of the respective first or second outlet chamber. The flow of gases through the first outlet and the second outlet causes an outlet pressure (back pressure) in the first outlet chamber to act on the valve member together with the inlet pressure to further displace the valve member from the valve seat. Having two or more outlet chambers in series may provide further benefits in the tuning of the PRV to achieve a desired pressure relief profile. The outlet resistance provided by each of the first and second outlets may in some embodiments be adjustable, as described above with reference to single outlet chamber embodiments.

Figure 2D:
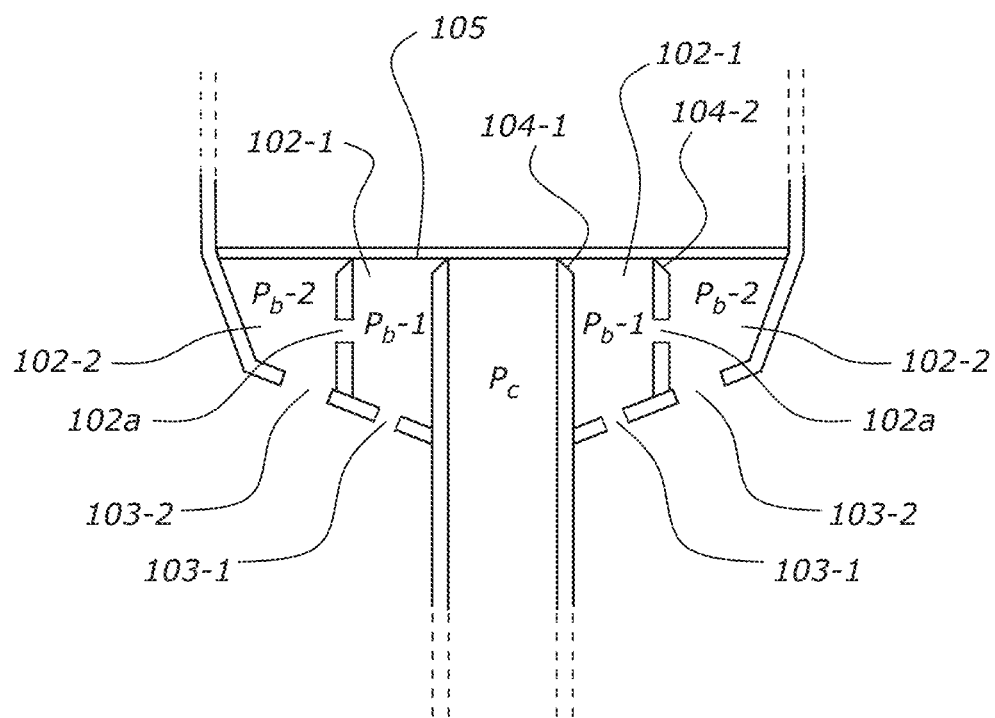
FIG. 2D illustrates a cross section of a PRV with two output chambers in parallel.
Figure 3:
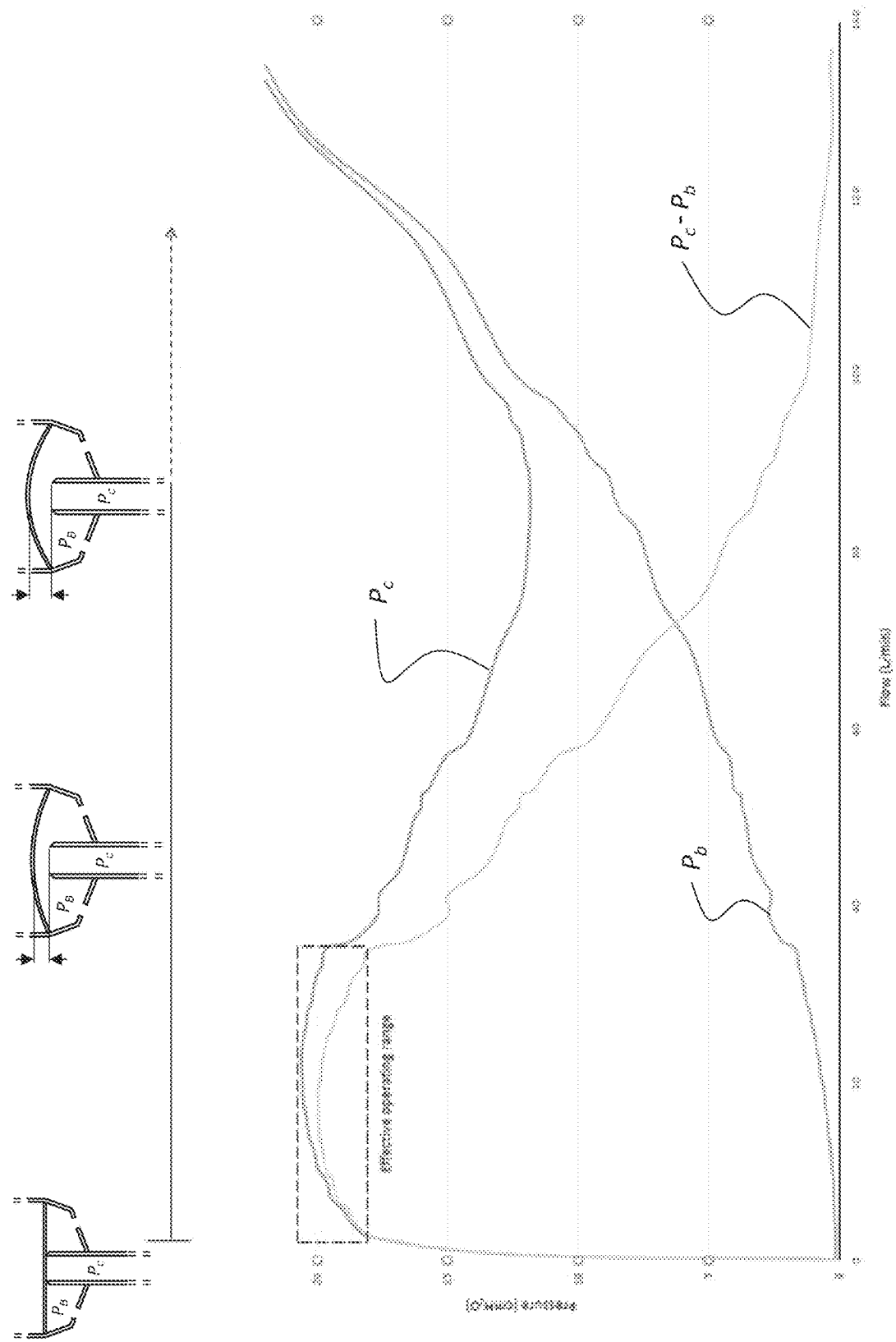
Figure 4:
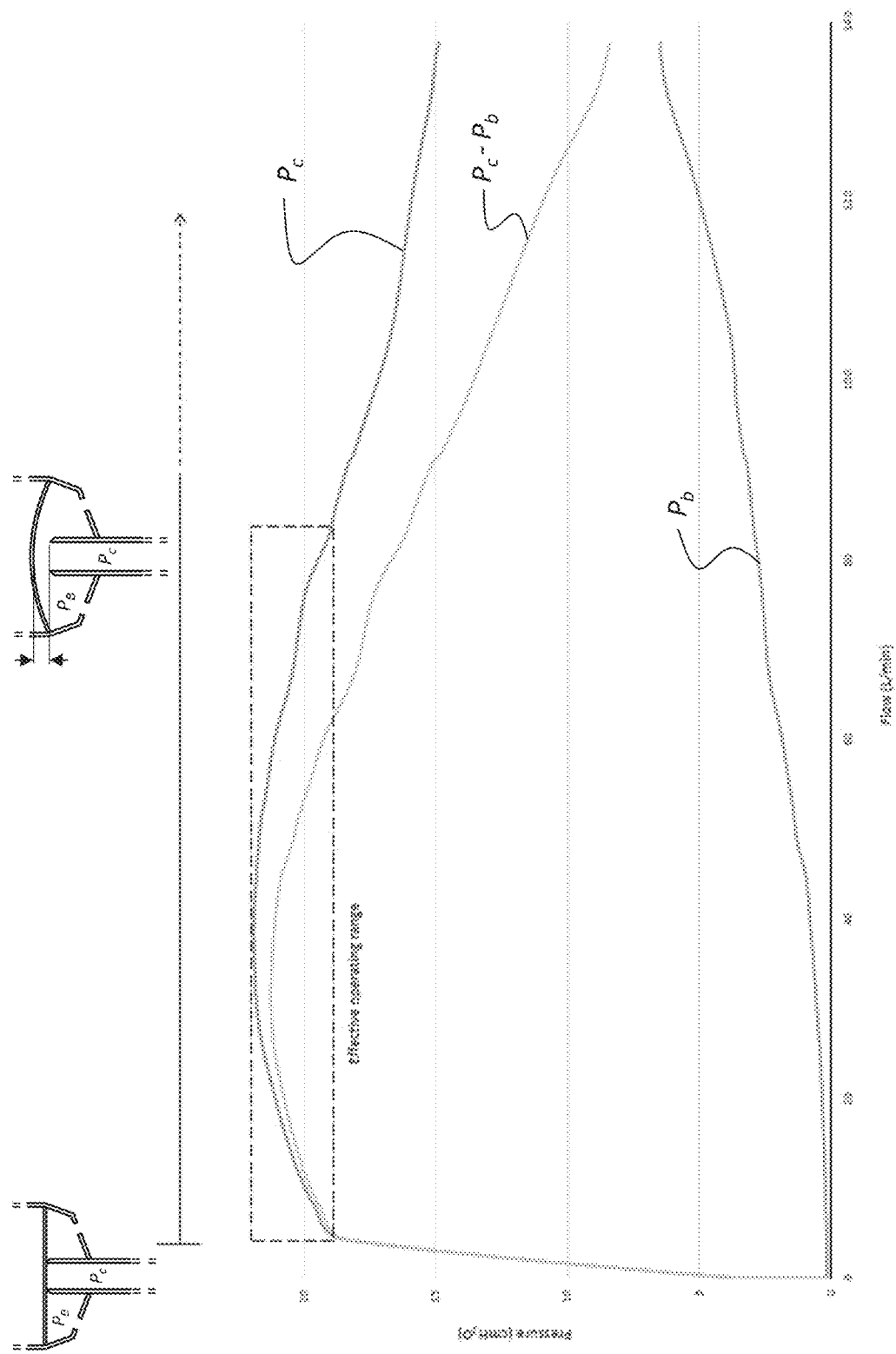
Figure 5:
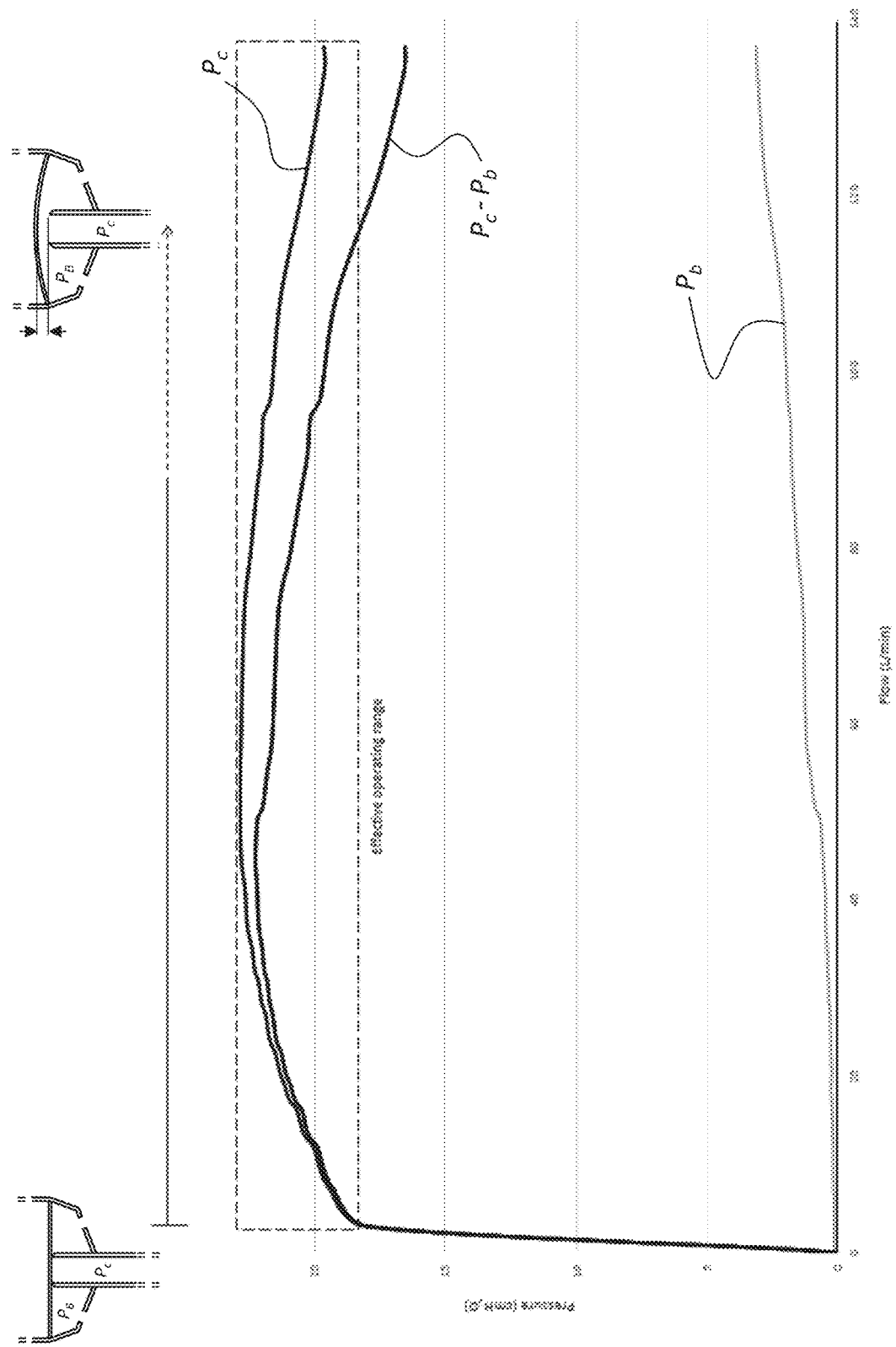

In some embodiments, the PRV may comprise at least two outlet chambers in parallel, for example as illustrated in FIG. 2D. When the valve member 105 lifts off a first valve seat 104-1, the venting flow may initially flow through a vent outlet or outlets 103-1 of a first chamber 102-1. When the pressure Pb-1 in the first chamber builds to a threshold the valve member may then lift off a second valve seat 104-2, to flow into a second outlet chamber 102-2 and vent via at least one vent outlet 103-2 of the second outlet chamber 102-2. Alternatively or additionally the valve may comprise apertures or flow paths 102a between the first outlet chamber and the second outlet chamber. Flow through the first vent outlets 103-1 creates a back pressure Pb-1 in the first chamber 102-1 acting on the valve member. Flow through the second vent outlets 103-1 creates a back pressure Pb-2 in the second chamber 102-2 acting on the valve member.

A PRV according to embodiments described above may have some benefits over prior art valves. In prior art valves, beyond the pressure relief threshold, and as the flow rate is increased, the pressure in the system will progressively increase proportionate to flow. As a result, the patient and components in the system may be exposed to increasingly greater pressures as the flow rate is increased. In a PRV according to embodiments described herein, once the valve member is lifted away from the valve seat, the pressure, $P_B$, in the outlet chamber is generated and acts on the valve member to further decrease a restriction to flow across the valve seat. This may have an advantageous effect of offsetting a point at which the pressure drop across the PRV begins to increase. As such, the 'effective operating range' of the valve may be extended over a larger range of flow rates than that of a prior art valve.

In embodiments comprising a membrane valve member, the membrane has a low spring constant that performs in a way similar to a very long soft spring. A low spring constant may be desirable to substantially reduce the resistance to flow through the valve. Furthermore, the membrane provides flexibility in design, for example allows for a shorter length valve compared to a valve using a long spring to achieve a low spring constant.

Additionally, the membrane advantageously simultaneously serves as a valve member, a valve actuating or biasing member (e.g. replaces the need for a spring in addition to a valve member, and a sealing member. As a result, the cost of manufacture may be substantially reduced, no lubrication of moving parts is required, which is useful to prevent contamination, and the membrane provides a firm seal under tension (even at low tension).

In use, oscillations of the membrane are minimal due to the low membrane mass (i.e. the membrane is lightweight). In particular, the low mass of the membrane provides low inertia in the movement of the membrane by comparison to prior art valves having plunger type valve members that may oscillate or chatter/flutter. Also, low inertia means gravity and therefore orientation has a minimal effect on the operation of the valve.

In some embodiments described herein, the characteristics of the PRV may be adjusted or tuned. For example, the outlet area from the outlet chamber and/or tension in the membrane or biasing member (by for example adjusting the relative positions of the inlet tube/valve seat and the valve member) may be adjusted to tune the performance of the valve. It may be desirable to tune the valve such that the pressure relief characteristic of the valve is approximately constant over a range of flow rates. Adjustability provides a user of a system greater flexibility. In some embodiments, two or more features of the valve may be adjusted simultaneously. For example, adjustment of the membrane tension by screwing a portion of a valve body relative to the valve seat may simultaneously alter the size of vent outlets from the valve body. For example, when setting higher pressures the operating flow range may also be extended by increasing outlet area. In a further example, altering membrane tension by altering the position of the valve seat by moving the inlet tube 101 may simultaneously alter the size of the flow restriction 152.

In embodiments described above a back pressure Pb acts on the valve member. The back pressure is generated by a flow restriction provided by the vent outlet or outlets 103. In some embodiments, the vent outlets may be sufficiently large so that little or no back pressure is generated on the valve member, in which case ambient pressure acts on the valve member outside of the valve seat area (FIG. 2A) or over the valve seat area (FIG. 13A). In such a valve, the pressure required to lift the valve member is determined by the biasing of the valve member against the valve seat. In a preferred embodiment comprising a membrane valve member, the membrane presents a low spring constant, such that a relatively 'flat' or 'constant' venting pressure may be achieved. Furthermore, a low spring constant is achieved in a small valve height. In some embodiments, a valve member may be biased against a valve seat by a diaphragm membrane, or the valve member is or comprises a diaphragm/membrane. Such a valve may be configured as shown in FIG. 12A but with large outlet vent apertures 103 such that flow from the vent outlets 103 does not generate a back pressure Pb.

The valve may be adjusted or set to a 'safe' pressure for different patient groups (i.e. adults, neonates, etc) which may present different airway flow restrictions. This may be set during manufacture or by the medical practitioner, before use. Further, adjustment of the valve characteristics may enable the valve to be employed in other (non-respiratory) systems.

In some embodiments, the PRV may be adapted for use as a pressure regulating device to provide peak end expiratory pressure (PEEP) and peak inspiratory pressure (PIP), for example for use in infant resuscitation. FIG. 1A illustrates a system comprising a flow source 12, an optional PRV 100-1 providing a patient safety pressure limit, a pressure gauge to indicate a pressure to a medical professional (e.g. a nurse) and a PRV 100-2 configured to provide PEEP and PIP provided at or near to the mask 115. The PRV 100 configured to provide PEEP and PIP comprises at least one outlet vent 103*a* that is occludable by a professional, i.e. by a finger, and at least one outlet vent 103*b* that is not occludable. There may be a cover or baffle 103*c* over the vent 103*b* so that vent 103*b* cannot be blocked/occluded by a professional. The flow chart provided in FIG. 1A sets out a method for tuning or configuring the valve to provide PEEP and PIP. At step 41 a mask seal is created with the mask 115 and at step 42 an input flow rate is set for the flow source to provide a flow of gases to the mask 115. At step 43 the professional blocks the accessible/occludable outlet vent 103*a* with a finger which acts to reduce the relief pressure of the valve due to a back pressure on the valve member. The valve is then adjusted at step 44 to achieve a desired PEEP, for example by adjusting valve member bias and/or adjusting the size of the outlet vent 103*b* that is not occludable. At step 45 the outlet vent 103*a* is unblocked, and at step 46 the occludable outlet vent 103*a* is adjusted to achieve the desired PIP pressure. Thus, in use, the medical professional blocks the occludable vent outlet to provide PEEP, and unblocks the occludable vent to provide PIP. The PRV adapted for use to provide PEEP and PIP may replace a prior art device used for this purpose, for example a device as described in international patent publication WO03/066146.

In the present valve, leaks from the valve may have little effect on the operation of the valve, as leaks will only provide the equivalent of additional outlet area. As such, a leak would further contribute to the effect of the outlet holes—that is, a leak from the outlet chamber would provide less resistance to flow out of the outlet chamber and reduce the amount of backpressure that acts on the valve membrane to further 'push' the membrane away from the abutting inlet tube. An example of a 'leak', although unlikely, may include a small fluid passage around the edges of the membrane (i.e. where the membrane is sandwiched between halves of the valve chamber) inadvertently formed during assembly, or leak through the valve member, or leak through a bayonet/screw feature to provide pressure adjustment.

Flow Compensating Pressure Relief Valve (FCPRV) 300

The maximum pressure and therefore flow rate that can be delivered to a patient is limited by the set relief pressure of the pressure relief valve. The pressure drop through a system may vary in use for a given flow rate. For example, tubes may curve, bend, fold or crush, in use, or different patients may present different airway restriction characteristics. Where a tube is folded or crushed or otherwise partially occluded, the partial occlusion presents an additional flow restriction in the system. An additional pressure drop is created across the partial occlusion and the flow rate through the system is decreased. In a system configured to deliver a particular flow rate (rather than a particular pressure), for example a high flow system, the flow source may increase the system pressure to account for the additional pressure drop caused by the partial occlusion, to maintain the set or desired flow rate. The amount the system or driving pressure may be increased to maintain a desired flow rate is limited by the relief pressure provided by the PRV. It may be desirable to provide a pressure relief valve that compensates for the pressure drop in a system, so that the maximum flow rate through the system is not limited by the relief pressure of the PRV. Such a valve would extend the range of flows deliverable to a patient. Therefore, in some embodiments, it may be desirable to have a PRV with a relief pressure that is dependent on the flow rate in the system; as the flow rate is increased, the relief pressure is increased to account for an additional or variable pressure drop in the respiratory system. In some embodiments, the pressure relief valve compensates for the pressure drop in a system, so that the maximum flow rate through the system is not limited by the relief pressure of the PRV, while also ensuring the patient is protected from over pressure.

Figure 14A:
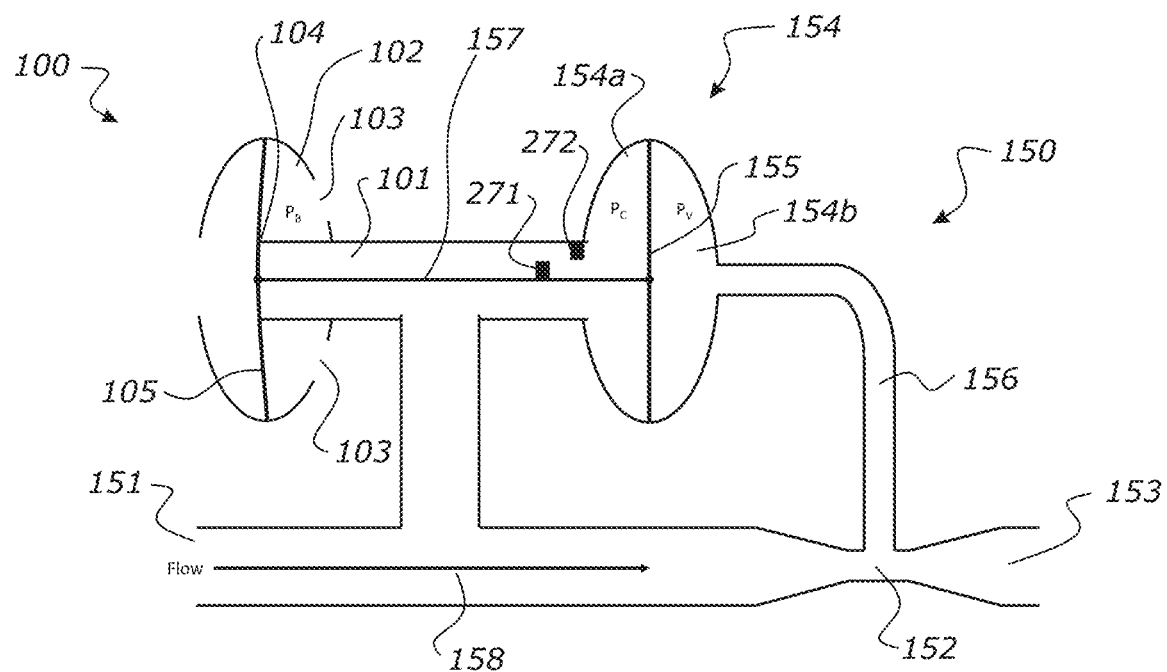
FIGS. 14A and 14B are schematic representations of a flow compensated pressure relief valve.
Figure 14B:
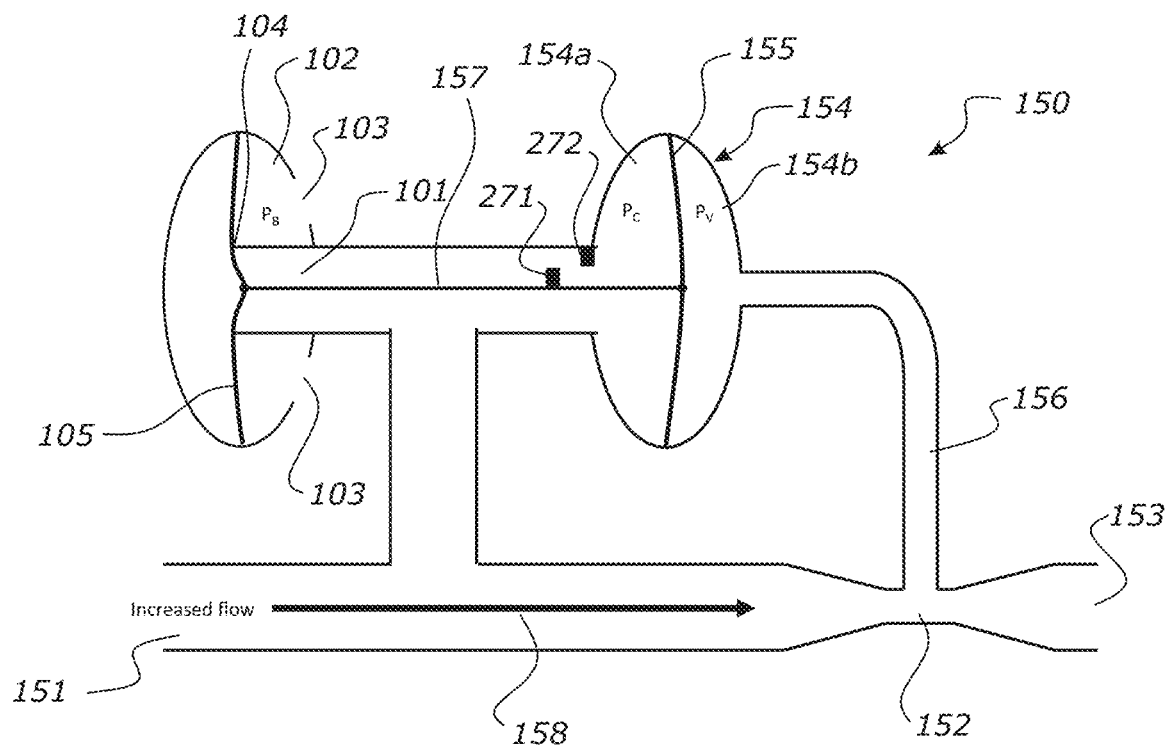
Figure 15A:
FIG. 15A shows system pressure (drop) vs flow rate curve and a relief pressure vs flow rate curve for a FCPRV, wherein the flow rate is the flow rate of gases provided to a patient or from a main outlet of the FCPRV.

FIGS. 14A and 14B illustrate a flow compensated pressure relief valve or device 300 (FCPRV) that dynamically adjusts its relief pressure proportionally with the flow rate through the system. An example characteristic of the FCPRV 300 is illustrated in FIG. 15A. With reference to FIG. 15A, an ideal relief valve relief pressure may be 20cmH$_2$O, indicated by line 140. The respiratory system, for example system 10 of FIG. 1, has a system pressure drop versus flow rate characteristic illustrated by curve 141 in FIG. 15A; as the flow rate through the system (e.g. from the flow source to the patient and ambient) is increased the pressure drop through the system increases. Pressure drop curve 141 illustrates the system pressure drop from the FCPRV to the nasal cannula (without any occlusion), or in other words indicates the pressure at the FCPRV (Pc). For a relief pressure of 20cmH$_2$O, the maximum flow rate the system can deliver to a patient is about 75 L/min, indicated by the point at which the system pressure v flow curve 141 intersects the 20cmH$_2$O relief pressure line 140. If there was an additional occlusion in the system, the pressure drop through the system would increase above the curve 141 and the maximum flow rate deliverable to the patient would be reduced for the given maximum relief pressure of 20cmH₂O.

In FIG. 15A, the pressure v flow curve 142 illustrates an example pressure relief v flow curve of a FCPRV configured as shown in FIGS. 14A and 14B. As shown, for the configuration illustrated in FIGS. 14A and 14B, the relief pressure (curve 142) increases with increasing flow rate. In FIG. 15A, the relief pressure 142 follows that of the system pressure v flow curve 141. This indicates that the valve is matched to the system pressure drop due to resistance to flow. In the illustrated embodiment, the pressure relief level is consistently above the system pressure drop by 20cmH₂O. The offset between curves 141 and 142 (20cmH₂O in FIG. 15A) is the maximum pressure the patient can be exposed to, as explained in more detail below with reference to FIG. 15B.

The FCPRV 300 illustrated in FIGS. 14A and 14B comprises a PRV 100 as described earlier. The FCPRV 300 further comprises a pressure sensing mechanism 150 to dynamically adjust the pressure threshold at which the PRV 100 vents pressure based on the flow rate of the gases passing through the FCPRV 300. In the illustrated embodiment, the sensing mechanism 150 includes a flow restriction or flow constriction 152 between a main inlet 151 and a main outlet 153 of the FCPRV. For ease of reference, the term 'flow restriction' may be used herein to describe both a flow restriction such as an orifice plate and a flow constriction such as used in a venturi. In operation, the flow of gases in a respiratory system flow through the device 300 from the main inlet 151 to the main outlet 153. The flow restriction 152 is downstream of the valve inlet 101 of the pressure relief valve 100, and therefore senses flow to the patient or through the main outlet of the valve. The sensing mechanism 150 also includes a sensing chamber 154, and a sensing member 155 located in the sensing chamber 154. The sensing member 155 divides the sensing chamber 154 into a first chamber 154*a* and a second chamber 154*b*. The first chamber 154*a* is in fluid communication with the flow of gases upstream of the flow restriction 152, e.g. the first chamber 154*a* is in fluid communication with the main inlet 151 and the valve inlet 101 upstream of the restriction 152. The second chamber 154 is in fluid communication with the flow of gases at the flow constriction 152 or downstream of the flow restriction 152. In the illustrated embodiment the device comprises a flow constriction configured as a venturi, with the second chamber 154*b* in fluid communication with the constriction via a pressure 'tap' or communication line 156. However in an alternative configuration the device may comprise a flow restriction 152, e.g. an orifice plate, and the first and second chambers may tap off either side of the orifice plate. A pressure differential may be generated in any other suitable way, for example by a permeable membrane or a filter with a known pressure drop (a flow restriction).

A resulting pressure drop caused by the flow of gases that pass from the main inlet 151 to the main outlet 153 of the device and passing through the restriction 152 is therefore sensed by the sensing member 155 located within the sensing chamber 154. In order to increase the flow rate through the respiratory system, the pressure provided by the flow source 12 is increased, increasing the pressure at the PRV inlet 101 and also in the first chamber 154*a* of the sensing chamber 154, this pressure is indicated as Pc in FIG. 14A. Further, as the flow rate increases, a larger pressure drop is created by the restriction 152 due to an increase velocity of the gases passing through the restriction 152, and the pressure Pv in the second chamber 154*b* of the sensing chamber 154 decreases. Thus an increasing flow rate through the device 300 from the main inlet 151 to the main outlet 153 results in an increasing differential pressure across the sensing member 155, with the first chamber 154*a* being a high (higher) pressure side of the sensing chamber 154 and the second chamber 154*b* being a low (lower) pressure side of the sensing chamber 154. This causes the sensing member 155 to move towards the low pressure side of the sensing chamber 154, away from the pressure relief valve 100.

The sensing member 155 is mechanically coupled to the valve member of the pressure relief valve, so that as the sensing member 155 moves towards the lower pressure side of the sensing chamber 154, the sensing member 155 pulls or biases the valve member 105 of the PRV 100 against the valve seat 104. Thus the sensing member 155 biases the valve member 105 against the valve seat 104 in response to the flow rate of the flow of gases through the device 300 from the main inlet 151 to the main outlet 153. In some embodiments the sensing member 155 is coupled to the valve member 105 by a mechanical link 157, for example a flexible member such as a cord or wire (e.g. a Nylon line), or a rigid member such as a rod or shaft. In some embodiment the mechanical link is capable of transmitting only tension (e.g. a wire or decoupled shaft), or both tension and compression (e.g. a shaft).

In a preferred embodiment, the sensing member is a membrane 155, which may be configured in a similar way to the valve member 105 of the pressure relief valve described earlier, however with no valve seat or inlet tube in the sensing chamber 154. Alternatively, the sensing member 105 may be a plunger or piston that pneumatically separates the first and second chambers and moves within the sensing chamber 154 according to the differential pressure provided by the flow constriction or restriction.

In the preferred embodiment comprising a membrane sensing member, an increasing differential pressure between the first and second chambers 154*a*, 154*b* causes the sensing membrane 155 to inflate or expand towards the low pressure side of the sensing chamber and via the mechanical link 157 with the valve member 105, provides tension to the PRV valve member 105 as shown in FIG. 14B, such that the relief pressure provided by the PRV 100 increases proportionally with the flow rate through the FCPRV from the main inlet 151 through the restriction 152 to the main outlet 153.

Four stages of operation of the FCPRV 300 is described with reference to FIG. 15B. In stage 1, indicated by point 1 on the system pressure drop line 141, the respiratory system is providing a flow of gases to a patient and all (or substantially all) of the flow provided from the flow source 12 to the main inlet 151 of the FCPRV 300 is delivered to the system from the main outlet 153 of the FCPRV 300. At point 1 a very low or ambient pressure is being delivered to the patient since all pressure is being dropped through the system. As the flow rate delivered to the patient is adjusted up and down, for example by a user, the pressure relief threshold of the PRV 100 varies along the relief pressure v flow curve 142—as the flow rate to the patient increases, the increasing differential pressure sensed by the sensing member 155 acts on the valve member 105 to increase the PRV vent threshold pressure 142.

For a given flow rate setting (90 L/min in FIG. 15B), in stage 2, in a situation where a flow restriction is introduced to the system 12, for example by the partial occlusion of a patient inspiratory conduit 14, or a squashed nasal prong of a nasal cannula patient interface 15, or more importantly a blockage at the patient, for example between a nasal prong and the patient's nares, the flow rate may instantaneously decrease. However, in a set flow system, the flow source 12 (rapidly) adjusts to increase pressure in the system to maintain the flow rate at a desired level. The drop in flow rate and then increase in pressure by the flow source response to maintain a set flow rate to the FCPRV may occur essentially instantaneously, i.e. very quickly, and is therefore negligible. As the flow is maintained, the differential pressure caused by the flow constriction or restriction 152 of the FCPRV 300 remains constant, the bias provided to the valve member 105 by the sensing member 155 remains constant, and therefore the relief pressure threshold for the PRV 100 remains constant. However, as the system pressure has increased (for example due to an increased pressure in the patient's airway/nares), the pressure Pc acting on the valve member 105 (and the sensing member 155 on the high pressure side of the sensing chamber 154) is increased towards the relief pressure of the PRV 100. This situation is represented by the vertical arrow 2 in FIG. 15B. If a partial occlusion was held and an equilibrium condition reached, a higher system pressure v flow curve indicated by curve 141b in FIG. 15B would result, with a smaller offset between the higher system pressure v flow curve 141b and the PRV relief pressure v flow curve 142. For example, for a partial blockage between a nasal prong and a patient's nare that results in an increased system pressure 141b, the pressure generated in the patient's nare is the offset between curve 141b and curve 141.

Figure 15B:
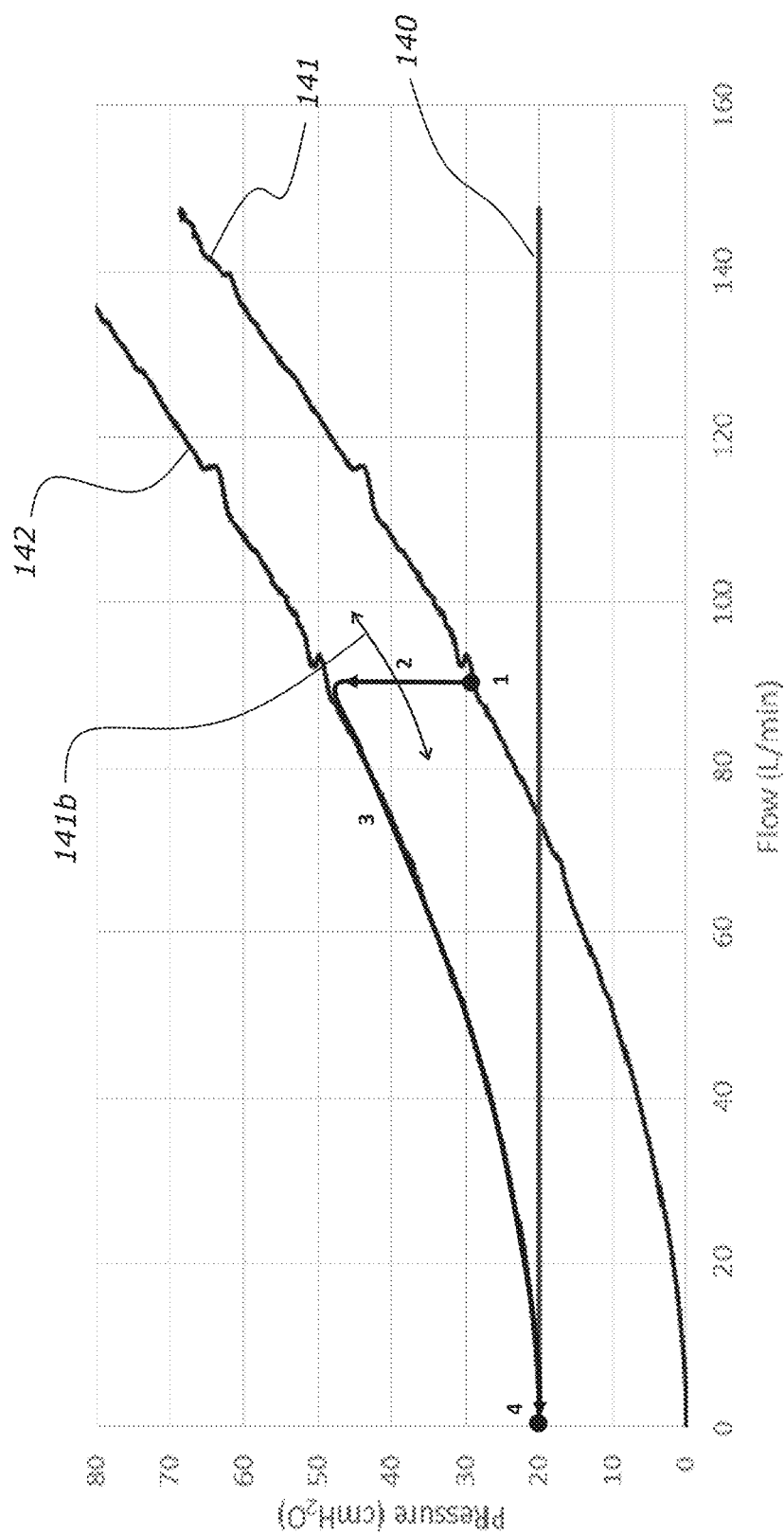
FIG. 15B shows system pressure (drop) vs flow rate curve and a relief pressure vs flow rate curve for a FCPRV, and a representation of various stages of operation of the FCPRV, wherein the flow rate is the flow rate of gases provided to a patient or from a main outlet of the FCPRV.

In stage 3, the introduced flow restriction (e.g. squashed conduit 14 or blockage in patient's nare) is increased to a level whereby the system pressure required to maintain the desired flow rate is above the relief pressure 142 of the flow compensated relief valve for the given flow rate (about 90 L/min in FIG. 15B). As the system pressure at the FCPRV 300 (e.g. Pc) exceeds the flow compensated relief pressure 142, the PRV 100 begins to vent, with a portion of the flow provided to the main inlet 151 venting via the PRV 100 and a portion of the flow passing through the restriction 152 and from the main outlet 153. The flow source maintains a set flow rate to the main inlet of the FCPRV. Thus as the PRV 100 begins to vent, the flow rate through the constriction or restriction 152 decreases, and the pressure differential acting on the sensing member 155 decreases. This causes the bias provided by the sensing member 155 to the valve member 105 via the mechanical link 157 to decrease, and therefore the pressure relief threshold for the PRV 100 to decrease. This situation is represented by arrow 3 on the pressure relief v flow curve 142 in FIG. 15B. In an ideal situation, an equilibrium state will be reached, whereby the patient receives as much flow as possible without exceeding the pressure relief threshold, or without exceeding a maximum delivered pressure at the patient interface.

In stage 4, indicated by point 4 in FIG. 15B, the flow restriction introduced to the system may completely (or substantially completely) block the system, for example a conduit 14 is completely occluded (complete crushed or pinched closed) or a patient's nare is completely blocked. All flow delivered to the main inlet 151 of the FCPRV 300 is vented via the PRV 100. As there is no flow through the device 300 from the inlet 151 to the outlet 153, and therefore no flow through the constriction/restriction 152, the pressures in the first and second chambers 154a, 154b are equal and the sensing member 155 provides a minimum bias to the valve member 105. Changes in pressure Pc does not change the pressure differential across the sensing membrane 155. The PRV 100 operates as described above in relation to earlier embodiments (for example with reference to FIGS. 2A to 2C) without a sensing mechanism 150, although possibly with a higher pressure threshold due to the coupling to the sensing member 155. In this state, the two membranes act as two springs in series.

Thus, in a situation whereby a patient's nares are blocked, the maximum pressure that the patient can receive is the offset between the relief pressure curve 142 and the system pressure drop curve 141, protecting the patient against overpressure. For example, in FIG. 15B this maximum patient pressure is 20cmH$_2$O. Thus, the FCPRV provides a venting pressure threshold that is dependent on flowrate yet simultaneously sets an upper pressure limit that the patient will receive. The FCPRV 300 must be capable of venting the maximum flow rate provided by the flow source 12, to ensure the FCPRV can vent the system along curve 142 back to zero flow to the patient, otherwise a higher patient pressure than the indicated offset pressure may eventuate.

The above described operation of the FCPRV is for a system providing a flow of gases to a user via an unsealed patient interface, such as a nasal cannula that does not seal with the patient's nares. The gases source in such a system may be a compressed gas tank or a hospital wall flow meter supply, or a blower capable of providing sufficient flow rate, or other suitable source that has the ability to provide a rapid response to variation in system resistance to maintain a set flow to the system. A system including a flow meter 12 providing a set flow rate of gases to a patient via a FCPRV 300, humidifier 17, filter 5 and an unsealed nasal cannula 15 is illustrated in FIG. 1AA. Such a system is particularly adapted for providing nasal high flow therapy.

A FCPRV may also be used in a respiratory system together with a flow source for providing continuous positive airway pressure. A CPAP system comprising a FCPRV is illustrated in FIGS. 1B-1 and 1B-2, and a characteristic of FCPRV in such a system is represented by the chart of FIG. 1B-3. The system comprises a flow source 12 such as a compressed gas tank or a hospital wall flow meter supply, a FCPRV 300, a humidifier and a sealed patient interface, such as a face mask that seals over the mouth and nose of a patient, and interconnecting hoses or conduits. The sealed mask has bias flow holes to allow a bias flow of gases from the mask, to flush CO2/exhaled gases. In a CPAP system, the input flow is set to exceed peak inspiratory demand and mask leak and bias flow and the FCPRV is configured to continuously vent a portion of the gases provided by the flow source. The flow rate provided by the flow source 12 results in a pressure Pc at the PRV that is sufficient to lift the valve member 105 off the valve seat to allow for venting of a portion of the gases during normal CPAP therapy. Thus, the pressure (Pc) at the FCPRV during CPAP therapy is the FCPRV venting pressure, indicated by line 142 in FIG. 1B-3. As the patient inhales, as represented in FIG. 1B-1, the flow through the main flow path of the FCPRV and to the patient is at its highest, resulting in a relatively high differential pressure sensed by the sensing member 155, which causes a corresponding higher relief pressure of the FCPRV. As the FCPRV is tuned so that there is approximately a constant offset pressure between the system resistance to flow and the venting pressure of the FCPRV, the pressure at the patient remains constant, indicted by the pressure difference between lines 141 and 142 in FIG. 1-B3. In FIG. 1-B3, curve 141 illustrates the pressure drop from the FCPRV to the patient interface. During inhalation, a comparatively low flow is vented at the FCPRV and the pressure FCPRV is towards the right hand end of the arrow on line 142 in FIG. 1B-3.

As the patient ends inhalation, flow through the valve reduces to a low level equal to a bias flow and/or leak flow at the patient interface. The venting pressure at the FCPRV decreases due to a reduced differential pressure at the sensing member caused by the low flow. The system pressure drop also decreases due to the reduced flow. A comparatively high flow is therefore vented at the FCPRV and the pressure at the FCPRV is towards the left hand end of the arrow on line 142 in FIG. 1B-3. Towards the left hand end of the arrow on line 142, almost all flow received by the main inlet of the FCPRV is vented at the FCPRV, with only a small flow exiting the FCPRV main outlet due to bias flow and/or system leak.

As the patient exhales, flow reverses through the FCPRV as well as exiting through the bias holes/mask leak if applicable. The exhaling reverse flow at the FCPRV results can cause a pressure increase at the main outlet which counteracts any reduction in pressure due to the FCPRV venturi and results in a low differential pressure at the sensing member, resulting in a comparatively high flow venting at the FCPRV, such that the pressure at the FCPRV is towards the left hand end of the of the arrow on line 142.

Thus, a set flow gases source can be used together with a FCPRV as described herein tuned to continuously vent to provide a constant pressure to the patient. The pressure to the patient, indicated as the difference between lines 141 and 142 in FIG. 1B-3 is maintained as the pressure at the valve cycles along line 142 as indicated by the arrow. The variation in venting flow at the FCPRV results in a varying flow to the patient to achieve a constant patient pressure during a breathing cycle.

In a CPAP system the flow source must be capable of providing more than the maximum inspiratory flow, otherwise the pressure at the FCPRV will drop below the set venting pressure and the pressure to the patient will be reduced. The vertical dotted lines in FIG. 1B-3 indicate the boundaries of the FCPRV dictated by the maximum flow provided by the flow source and the minimum flow being the bias flow and/or leak from the system, i.e. leak at the patient interface. The FCPRV relief pressure cycles between these boundaries A FCPRV may also be used in a respiratory system for providing a bi-level continuous positive airway pressure. A bi-level pressure system comprising a FCPRV is illustrated in FIGS. 1C-1 and 1C-2, and a characteristic of FCPRV in such a system is represented by the chart of FIG. 1C-3. The system comprises a CPAP source gases source 12a (i.e. a constant pressure source CPAP blower), a FCPRV 300, a humidifier and a sealed patient interface, such as a face mask that seals over the mouth and nose of a patient, and interconnecting hoses or conduits. The sealed mask may have bias flow holes to allow a bias flow of gases from the mask, to flush CO2/exhaled gases. The FCPRV is located close to the patient interface so that a low resistance to flow exists between the FCPRV and the patient.

Unlike the system of FIGS. 1B-1 and 1B-2 wherein the FCPRV is tuned to achieve a constant offset between the FCPRV relief pressure 142 and the system pressure drop 141 from the FCPRV to the patient, in the system of FIGS. 1C-1 and 1C-2, the FCPRV is tuned so that the relief pressure curve 142 diverges from the system pressure drop curve 141 for increasing flow rate, as illustrated in FIG. 1C-3

As the patient inhales, flow through the FCPRV causes the sensing member to maintain the valve member sealed against the valve seat so that the FCPRV does not vent, and the patient is provided with an inspiratory positive airway pressure equal to the CPAP pressure provided by the gases source. This pressure level is indicated by the uppermost horizontal pressure line in FIG. 1C-3.

As the patient inhales, initially a maximum inhalation flow is experienced and the IPAP is achieved at the patient. As the patient continues to inhale, the flow rate of the patient naturally drops and the flow through the valve therefore decreases. The venting pressure at the FCPRV decreases due to a reduced differential pressure at the sensing member caused by the reduced flow through the FCPRV flow restriction, and the FCPRV vents flow. The pressure at the FCPRV is therefore the venting pressure, which is the curve in FIG. 1C-3 between the vertical pressure axis and the horizontal IPAP line.

Towards the end of inhalation, flow through the FCPRV to the patient reduces even further to a low level equal to a bias flow and/or leak flow at the patient interface, and the pressure at the FCPRV and therefore at the patient continues to move to the left in FIG. 1C-3 towards the vertical pressure axis, and the FCPRV vents more flow from the pressure gases source. As expiration begins, there is no flow through the FCPRV as exhalation cancels bias flow and the pressure at the FCPRV is presented by the crossing at the vertical pressure axis in FIG. 1C-3, and the FCPRV continues to vent flow from the system. As the patient continues to exhale the pressure at the FCPRV and therefore essentially at the patient since the FCPRV is close to the patient is the venting pressure of the FCPRV. Therefore the venting pressure of the FCPRV sets the expiration positive airway pressure level for the bi-pressure system. Such a system may be used for patient resuscitation, for example infant resuscitation.

A breath beginning with inhalation and ending with exhalation moves from right to left in FIG. 1C-3. A representation of the pressure at the patient interface for multiple breaths is indicted in FIG. 1C-4 where the time axis extends from right to left.

A further system configured for bi-level pressure therapy is illustrated in FIG. 1C-5, where the CPAP constant pressure source in the system of FIGS. 1C-1 and 1C-2 has been replaced with a flow source 12 combined with a FCPRV 300, to achieve a constant pressure source as described above with reference to FIGS. 1B-1 and 1B-2 for a CPAP system.

A FCPRV tuned or configured for use in a bi-level pressure system may also be configured to operate as an anti-asphyxiation valve when flow to the patient fails, for example in the event the flow or pressure source becomes inoperable. The EPAP pressure level may be set for a particular flow through the FCPRV to the patient (ie passed on a bias flow level) and also to allow the patient to exhale in the event of no flow through the FCPRV to the patient.

Figure 1D:
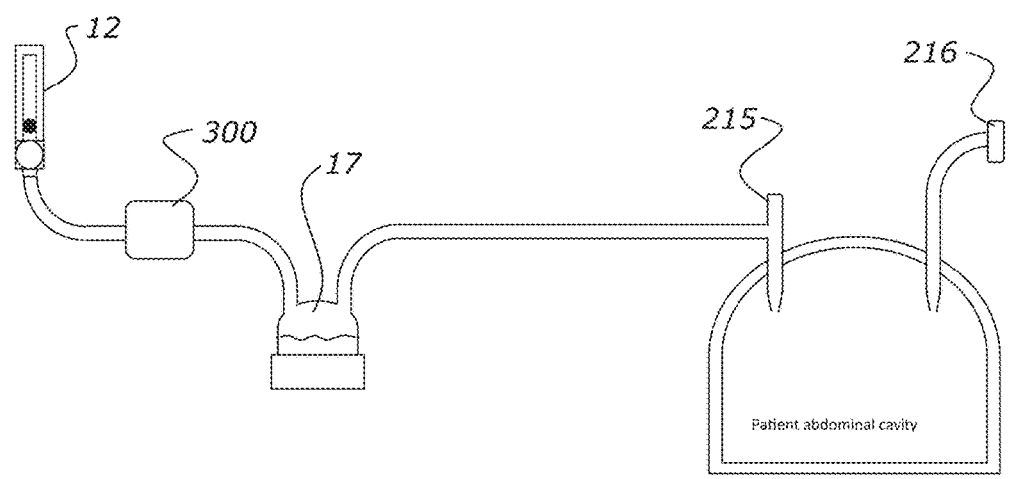
FIG. 1D illustrates a surgical insufflation system comprising a flow controlled pressure relief valve.

A FCPRV may also be used together with a flow source for providing continuous positive pressure in surgical insufflation. A surgical insufflation system is illustrated in FIG. 1D. The system comprises a flow source 12 such as a compressed gas tank or a hospital wall flow meter supply, a FCPRV 300, a humidifier 17, a trocar 215 to provide the humidified gases flow from the system to a patient's abdominal cavity, and a filter 216 for the flow of gases to exit the abdominal cavity. The combination of a set flow source and a FCPRV provides a constant pressure as described above for a CPAP system and a sealed patient interface with reference to FIG. 1B-1 with a flow characteristic as illustrated in FIG. 1B-3.

Figures 1, 1E:
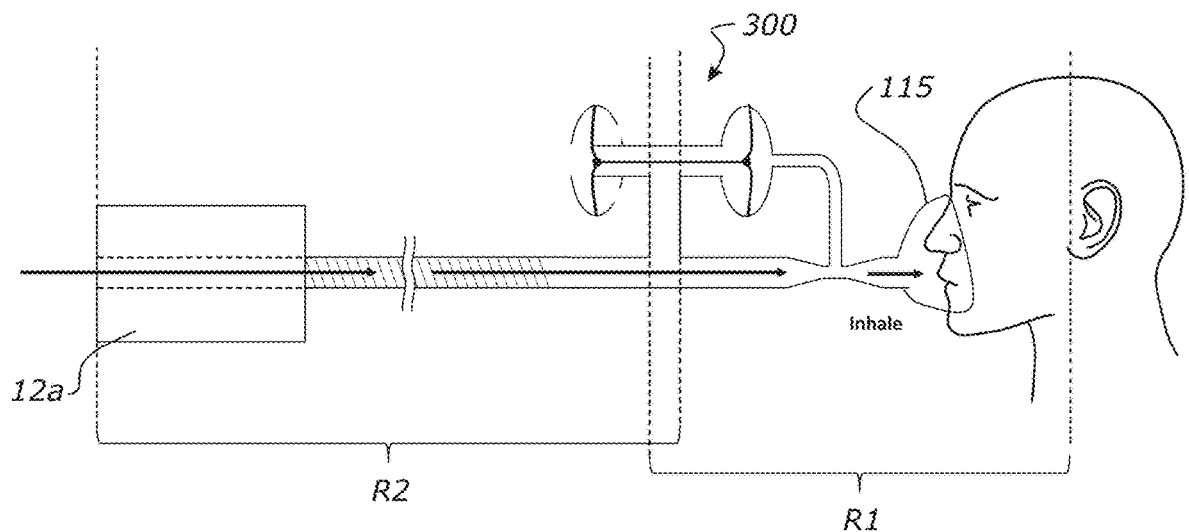
Figures 1, 1E, 2:
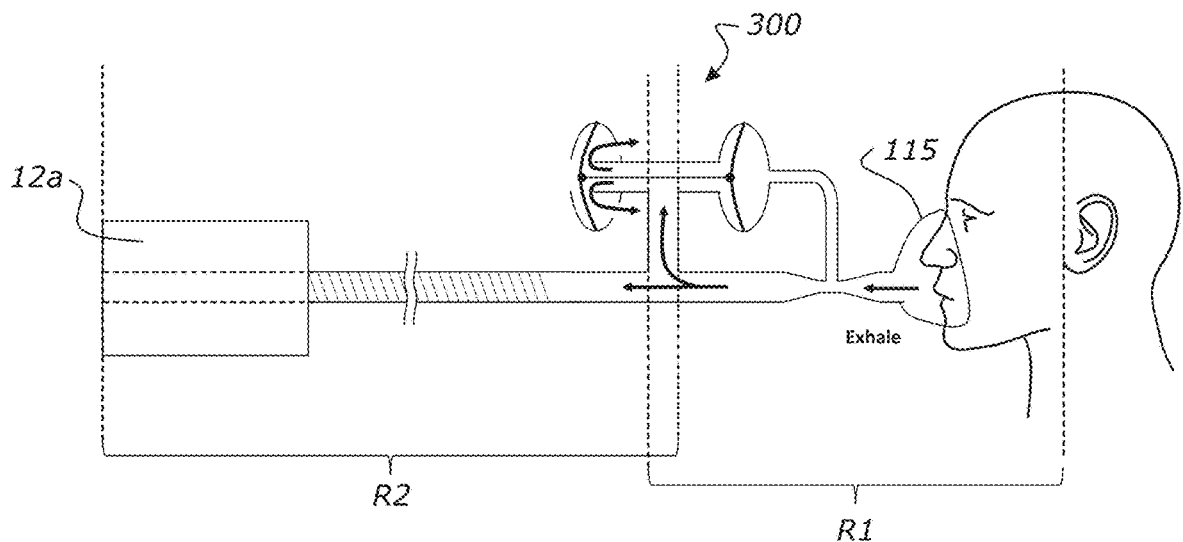

A FCPRV may also be used in a respiratory system as an anti-asphyxiation valve. A ventilation or CPAP system comprising a FCPRV as an anti-asphyxiation valve is illustrated in FIGS. 1E-1 and 1E-2. The system comprises a CPAP source gases source (i.e. a constant pressure source CPAP blower) or a ventilator to provide a flow of gases to the user via a patient interface, such as a face mask that seals over the mouth and nose of a patient. The sealed mask has bias flow holes to allow a bias flow of gases from the mask, to flush $CO_2$/exhaled gases. A FCPRV 300 is preferably located close to the patient interface so that a low resistance to flow exists between the FCPRV and the patient. During treatment the ventilator or CPAP gases source provides a continuous positive pressure or alternating bi-level pressure. The valve is tuned to remain closed during at least a portion of a normal inspiration period. When the patient exhales, the valve operates as described above with reference to FIG. 1C-2 for a bi-level system. Alternatively or additionally an expiratory limb may be provided. In the event that the ventilator or CPAP source fails or stops functioning, the CPAP source or ventilator flow path opens to allow the patient to 'pull' inspiration air through the ventilator/CPAP source, delivery conduit and patient interface, as shown in FIG. 1E-1. As the FCPRV is located close to the patient interface, the resistance to flow from the patient to the FCPRV (R1) is low compared to the resistance to flow from the FCPRV to the CPAP source or ventilator (R2). Therefore, when the patient exhales a substantial portion of the patient's exhaled breath vents from the FCPRV, as shown in FIG. 1E-2. Prior art respiratory systems may include an anti-asphyxiation valve, for example a valve at the patient interface. A prior art anti-asphyxiation valve may comprise a flap valve arrangement which opens in the absence of pressure, and such a valve can be affected by gravity depending on the orientation of the mask. A FCPRV according to the present invention is not affected by gravity or orientation.

Figures 1, 1F:
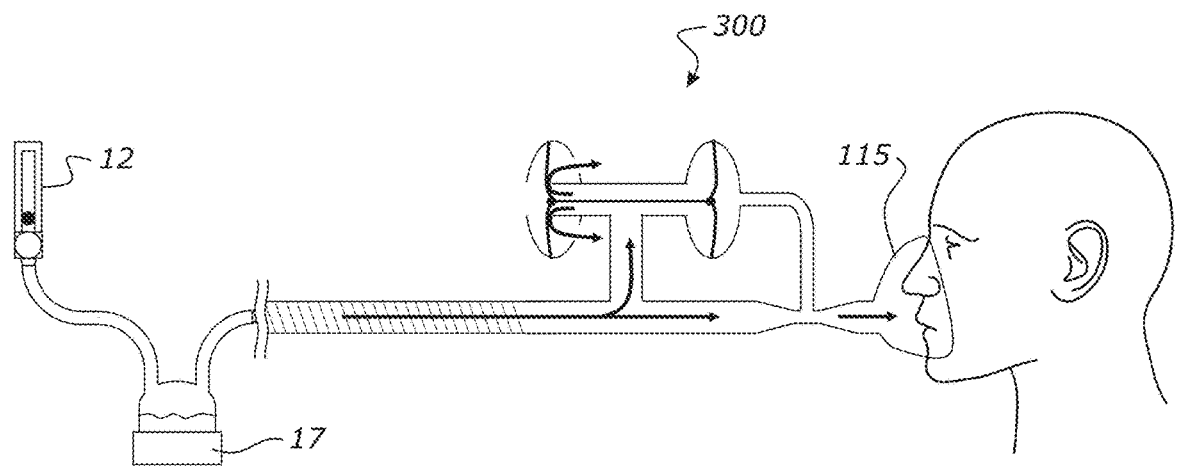
Figures 1, 1F, 2:
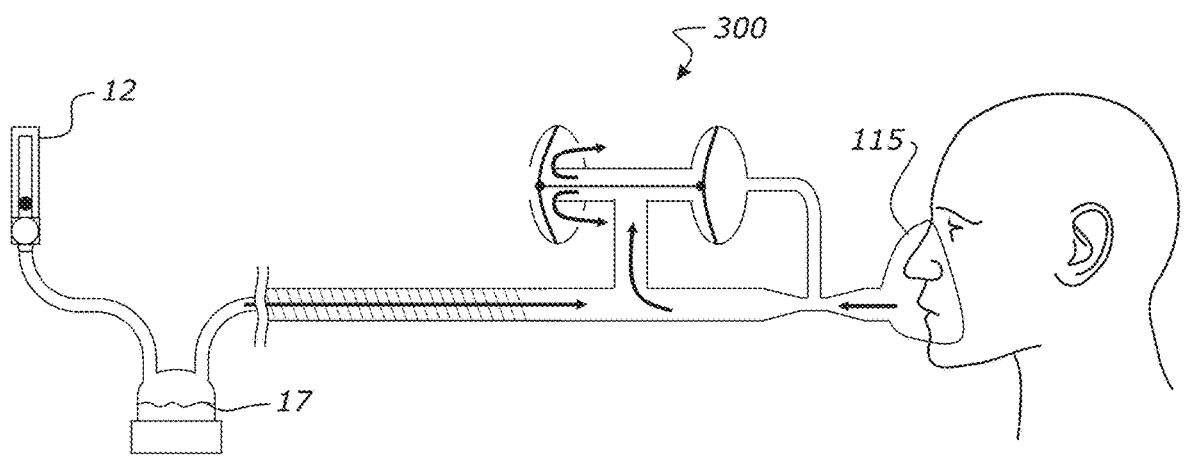
Figures 1, 1F, 2, 3:
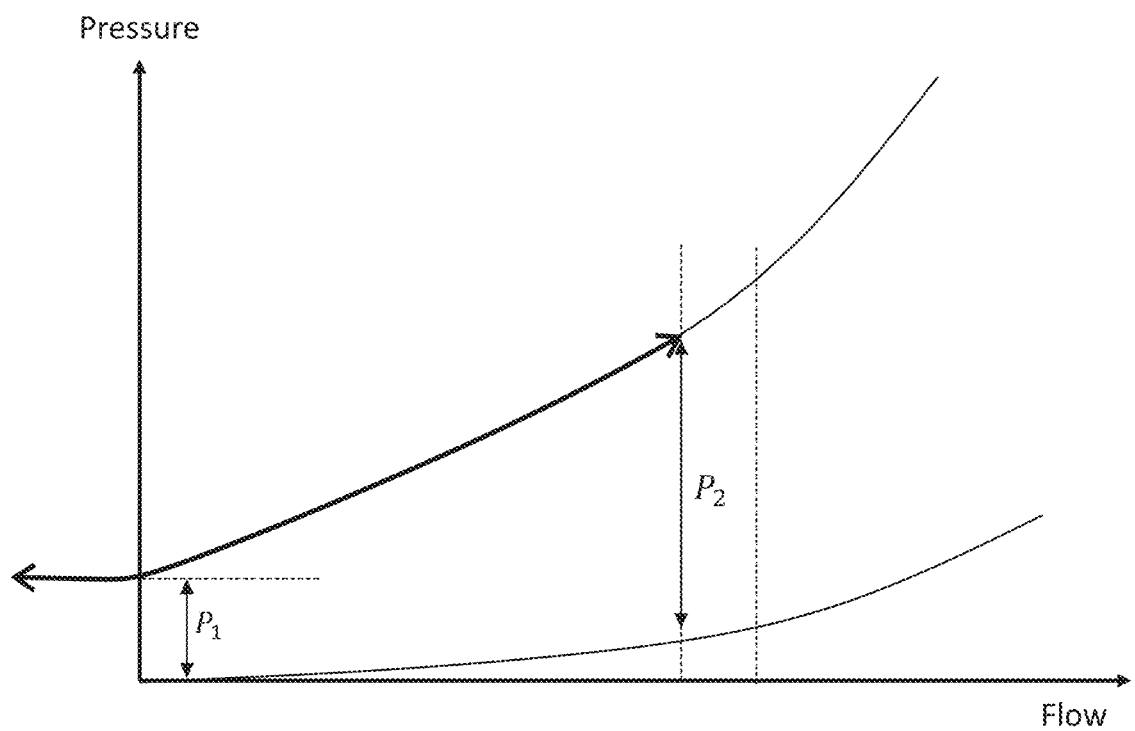

Another system configuration for providing a bi-level pressure or to operate as a ventilator system for a patient that is apnoeic (ie not self-breathing) is illustrated in FIGS. 1F-1 and 1F-2, and a characteristic of an FCPRV in such a system is represented by the chart of FIG. 1F-3. The system comprises a flow source 12 such as a compressed gas tank or a hospital wall flow meter supply, a FCPRV 300, a humidifier 17 and a sealed patient interface 115 such as a face mask that seals over the mouth and nose of a patient, or laryngeal mask airway (LMA) or endotracheal intubation, and interconnecting hoses or conduits. The sealed mask 115 may have bias flow holes to allow a bias flow of gases from the mask, to flush $CO_2$/exhaled gases. The FCPRV is located close to the patient interface so that a low resistance to flow exists between the FCPRV and the patient. However, the FCPRV may be located upstream of the humidifier or anywhere in the system.

In the system of FIGS. 1F-1 and 1F-2, the FCPRV functions in much the same way as the FCPRV used in a system for providing a constant pressure, as described above for the CPAP system of FIGS. 1B-1, 1B-2 and 1B-3. In the system of FIGS. 1F-1 and 1F-2, the FCPRV is tuned to continuously vent, so that the pressure at the FCPRV is the venting pressure, and the patient pressure is equal to the FCPRV venting pressure minus the system pressure drop from the FCPRV to the patient, i.e. the difference between curves 142 and 141 in FIG. 1F-3. However, unlike the system of 1B-1 and 1B-2 where the FCPRV is tuned to achieve a constant offset between the FCPRV relief pressure 142 and the system pressure drop 141, in the system of FIGS. 1F-1 and 1F-2, the FCPRV is tuned so that the relief pressure curve 142 diverges from the system pressure drop curve 141 for increasing flow rate, as illustrated in FIG. 1F-3. Therefore, as the system pressure at the FCPRV cycles back and forth along the pressure flow curve 142 in FIG. 1F-1, the pressure to the patient cycles between a relatively low pressure P1 and a relatively high pressure P2. As described with reference to FIG. 1B-3, as the patient breathes in, the flow to the patient is at its highest resulting in a relatively high differential pressure sensed by the sensing member 155, which causes a corresponding higher relief pressure of the FCPRV. A comparatively low flow is vented at the FCPRV and the pressure at the FCPRV is towards the right hand end of the arrow on line 142 in FIG. 1F-3. The FCPRV pressure moves towards the left hand end of the arrow on the relief valve pressure curve 142 in FIG. 1F-3 as the patient ends inspiration and begins to exhale. Due to the diverging FCPRV pressure curve the patient receives a higher pressure during inspiration and a lower pressure during expiration, to assist with ventilation. The inventors have also discovered that by providing a significant pneumatic coupling between the sensing member 155 and the main gases flow path 158, the FCPRV can be made to operate in a relatively fast response configuration, so that the pressure at the FCPRV rapidly jumps from the inspiration pressure P2 and the expiration pressure P1, which is particularly useful for ventilating an apnoeic patient. Pneumatic coupling of the sensing member and the main gases flow path is discussed below in more detail with reference to FIGS. 27E and 27F.

A FCPRV configured for bi-level pressure as described with reference to FIGS. 1F-1 to 1F-3 may also be used together with an infant resuscitation PEEP/PIP device, for example a device as described in international patent publication WO03/066146. The FCPRV 300 is tuned to continuously vent, as described above. To provide peak end expiratory pressure a medical professional blocks a vent outlet on a resuscitation device (e.g. Fisher and Paykel Healthcare's Neopuff® device) at the patient interface (face mask). This acts to increase the resistance to flow which causes the FCPRV relief pressure to reduce so that the FCPRV vents to reduce the flow to the infant to achieve peak end expiratory pressure (e.g. P1 in FIG. 1F-3).

To provide peak inspiratory pressure the medical professional unblocks the vent outlet on the Neopuff® device, reducing the relief pressure at the FCPRV, e.g. to achieve pressure P2 in FIG. 1F-3. To tune the FCPRV for this use, the patient interface face mask is sealed and an input flow rate from a flow source is set. The Neopuff® vent is occluded and the FCPRV is adjusted, for example by adjusting valve member bias, to achieve a desired PEEP. The Neopuff® vent is then unoccluded and adjusted to achieve a desired PIP pressure.

In some embodiments, the flow compensated pressure relief valve 300 may be matched to the pressure drop of the system under normal operating conditions, e.g. without any additional resistance to flow added to the system such as an occlusion of a conduit. Such an arrangement is illustrated by the characteristics presented in FIGS. 15B and 1B-3. This ensures that the valve relief pressure is consistently offset from the pressure drop across the system, for example as shown in FIG. 15B whereby the pressure relief line 142 is a constant 20cm$H_2O$ above the system pressure drop line 141.

In some applications, a constant offset may not exist between the system pressure v flow curve 141 and the relief pressure v flow curve 142, for example as described above with reference to FIG. 1C-3 for a bi-level pressure system, and FIG. 1F-3 for a ventilator system.

Figure 17:
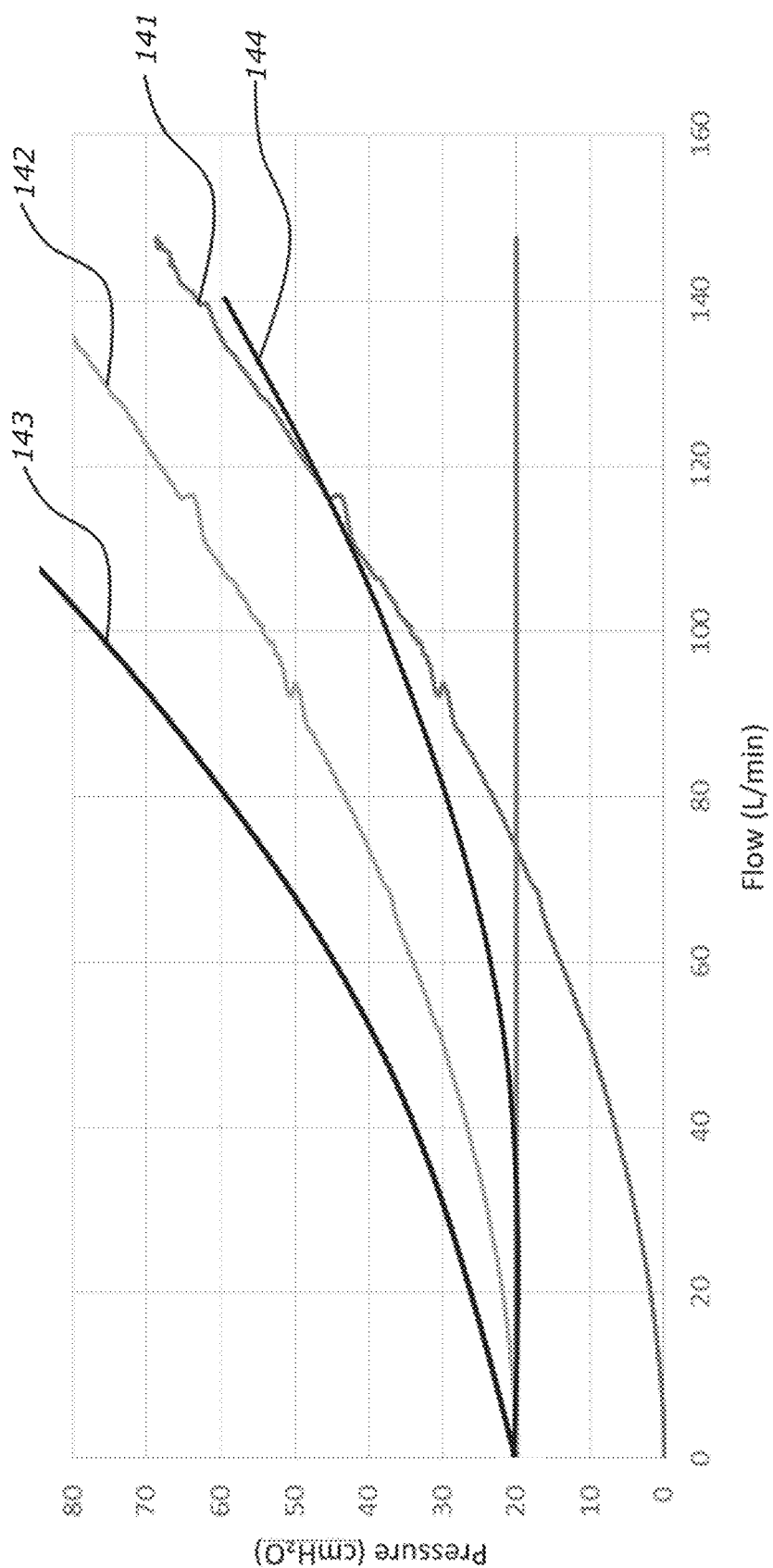
FIG. 17 shows the same chart as FIG. 15B but with an additional two flow compensated relief pressure vs flow rate curves.

FIG. 17 provides a further example of a FCPRV characteristic for a set flow unsealed patient interface system without a constant offset between the system pressure drop 141 and the FCPRV relief pressure 142. In FIG. 17, curves 143 and 144 are indicative of FCPRV relief pressures that are not matched to the system pressure drop. The upper line 143 illustrates a progressively increasing dynamically adjusting relief pressure as flow increases. Such a characteristic may be desirable to compensate for expected partial circuit occlusions such as bending. The lower line 144 illustrates a progressively decreasing dynamically adjusting relief pressure as flow increases, which eventually intersects the system pressure drop (Pc) sensed by the FCPRV 300. In this instance, the system is limited to delivery of approximately 105 L/min flow, higher flows will result in the FCPRV venting flow via the outlet vent. This is a practical option if the system resistance to flow cannot be matched. For example, where a single valve configuration is provided for use in a range of different systems each with a different resistance to flow, it may not be feasible to match the valve to the resistance to flow of these systems. Therefore a low curve maintains safe pressures, but limits flow, which is acceptable where the flow limit is greater than a desired therapeutic flow rate. In either case, the non-matched relief pressure v flow curves 143 and 144 may be less desirable than the matched curve 142. In some embodiments, a progressively decreasing dynamically adjusting relief pressure as flow increases from the inlet to the outlet of the FCPRV may be desirable. As the delivered flow increases, the pressure in the system increases (i.e. pressure flow curve 141). If the pressure in the system keeps increasing, a system component may eventually fail due to overpressure (such as seals, humidifier chamber, tubes or circuits connections, etc). Therefore, it is desirable to provide some upper limit to protect the system. More importantly, the point at which curve 144 intersects pressure flow curve 141 provides an upper pressure limit, to limit flow to the patient and therefore limit patient pressure to safe levels. The pressure flow curve 141 will vary for different systems. For example, a system with an adult cannula will have less resistance to flow than an infant cannula. As such, the pressure flow curve for the system with the infant cannula would be 'steeper' than the pressure flow curve for the system with an adult cannula. As such, the system pressure drop characteristics for a particular system must be determined to determine a suitable upper limit for the FCPRV (i.e. the shape of the pressure relief v flow threshold curve 142 needs to be tuned so that the pressure relief v flow curve 142 intersects the system pressure v flow curve 141 for a particular system at a desired upper pressure limit).

A number of factors relating to the configuration of the FCPRV affect the FCPRV's operational characteristic. For example, as the flow restriction 152 venturi or orifice is responsible for the pressure differential sensed by the sensing member 155, the shape of the relief pressure v flow curve 142 may be determined by the size of the venturi throat or orifice diameter.

In order to tune the relief pressure characteristic a FCPRV 300 may be provided with any one or more of the following described variable features.

The flow compensated pressure relief valve device 300 may be employed in a system of known resistance to flow. In such a situation the venturi or orifice may be of a fixed size and determined for use with a system of a known resistance to flow of a particular system.

Alternatively, where the system that the FCPRV will be employed in is unknown, a FCPRV may be provided with an adjustable venturi or orifice (e.g. adjustable area and/or length), in order to allow a user to 'tune' the FCPRV to the particular application. For example, the FCPRV 300 may be provided with a range of different orifice plates, each with an orifice of a different size. The orifice plates are interchangeable, each with a known resistance. For example, a nasal high flow system may interchange between an 'adult' and a 'paediatric' cannula. Each cannula presents a different known resistance to flow. One orifice may, for example, 'tune' the flow compensated pressure relief valve to the system configured for the 'adult' cannula, and another orifice 'tune' the flow compensated pressure relief valve to the system configured for the 'paediatric' cannula. The different orifices may be located on a slidable plate, where the slidable plate may slide a respective orifice into the flow path of the flow compensated pressure relief valve. Other means for adjusting the size of a venturi throat, or orifice/flow restriction, may be employed. For example, an orifice may be provided that is sized to be a maximum flow restriction (i.e. minimum orifice size) and this may be drilled out to achieve a larger orifice size/smaller flow restriction. Alternatively a large orifice size may be provided, and an insert or inserts each with a smaller orifice size may be provided to fit into or adjacent to the large orifice. The flow restriction may be provided by a valve arrangement, for example a gate valve type arrangement. For a gate valve type arrangement, the valve may have a screw thread adjustment to move the gate of the valve to adjust the size of the flow restriction. The screw thread may provide many turns to provide a relatively fine adjustment to achieve precise tuning of the FCPRV. Alternatively or additionally, a range of different patient interfaces may be provided, each with the same resistance to flow, such that all patient interfaces in the range of interfaces may be used with the same FCPRV setup. For example a flow restriction may be provided to each patient interface in the range so that each patient interface has the same total restriction to flow. The flow restriction may be provided by a filter, an orifice, a narrow section of tube or any other suitable arrangement.

In some embodiments the FCPRV may comprise more than one flow restriction in series and/or in parallel. In some embodiments the flow restriction may be configured to provide a first resistance to flow in a first direction of flow through the restriction and a second resistance to flow in a second opposite direction of flow through the flow restriction. For example, the flow restriction may comprise an angled lead in to channel or funnel flow into the orifice, which has the effect of making the orifice larger. An angled lead in provides a benefit of flattening a negative flow response. In some embodiments the flow restriction 152 may comprise an angled lead out, which also has the making the orifice larger, by gently directing flow from the orifice. This has the benefit of flattening the positive flow response. Generally a lead out has a greater effect than a lead in on the flow response. A lead in may be particularly beneficial for bi-level PAP, as a lead in becomes a lead out when the patient exhales (negative flow).

The effect of the resistance to flow in the system on the FCPRV may also be dependent on the position of the FCPRV in the system. Therefore the FCPRV is preferably tuned for a particular position within the system. In humidified systems the FCPRV is preferably located in the system upstream of the humidifier to avoid the possibility of condensate in the FCPRV. However, the FCPRV could be located elsewhere in the system, for example downstream of a humidifier.

Figure 18:
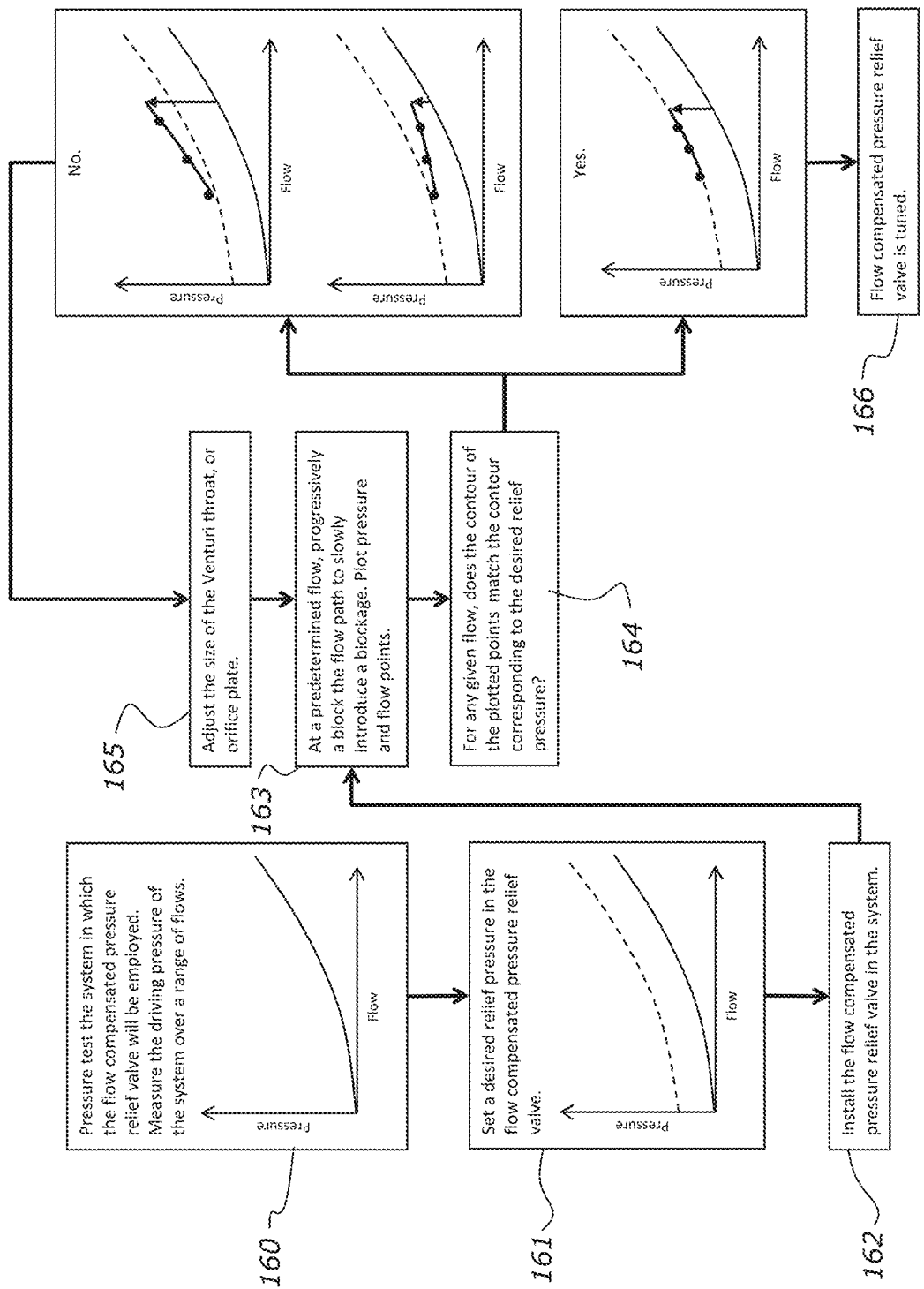
FIG. 18 illustrated a tuning routine for a FCPRV.

FIG. 18 illustrates a tuning method for a flow compensated pressure relief valve as described herein. At step 160 a system is pressure tested to determine a system flow (e.g. flow delivered to the patient) versus pressure drop response curve for the system. In step 161 a desired relief pressure v flow curve is determined, for example by adding an offset pressure to the system pressure v flow curve. At step 162, a FCPRV according to an embodiment described herein is installed in the system. At step 163, a flow restriction is progressively added to the system downstream of the FCPRV 300, and the resulting relief pressure for a range of flow rates is determined. At step 164, the actual pressure relief v flow curve is compared to the desired curve. At step 165, if the actual curve does not match the desired curve the, then the size of the flow restriction is adjusted and steps 163 and 164 are repeated again, until the desired pressure relief characteristic is achieved, at which point at step 166 the FCPRV has been successfully tuned. The flow restriction could be dynamically adjusted in a continuous state, i.e. a tapered plug in a hole which can move back and forward to continuously vary the restriction, or altering the position of a valve, for example a gate valve with a gate driven by a screw thread adjustment, as described above.

Alternatively or additionally the vent pressure threshold may be adjusted by adjusting any one or more of the features described above in relation to the PRV 100, 200. For example, the tension in the valve membrane 105 may be adjusted by for example adjusting the relative position of the valve inlet tube 108 to the valve member 105, or the size of the vent outlet 103. In the PRV 100, the size of the vent outlets determine the shape of the pressure relief valve relief pressure v flow curve as illustrated in FIGS. 3 to 5 and 7 and therefore the vent pressure threshold over a range of flow rates. When the system is completely blocked/occluded, the FCPRV operates as the PRV 100 described earlier, except that the sensing member may provide some additional bias to the valve member 105. Also, the biasing force provided to the valve member 105 by the sensing member 155 may be adjustable. For example the length of the mechanical link 157 between the sensing and valve members may be adjustable, a shorter length link increasing the biasing force and therefore the vent pressure.

Figure 18A:
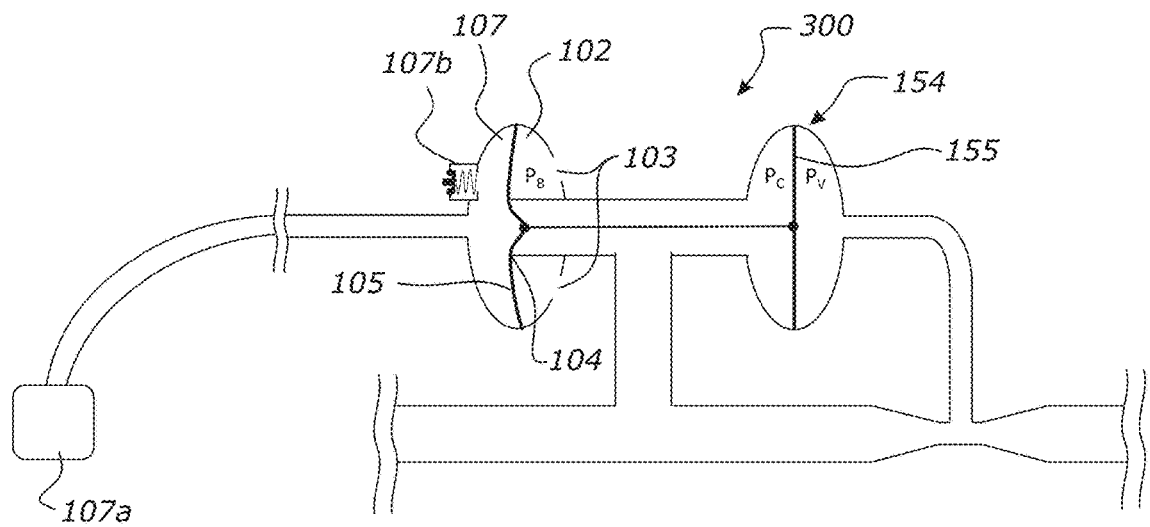
FIGS. 18A to 18C are schematic representations of flow compensated pressure relief valves each comprising an adjustment mechanisms for adjusting a relief valve venting pressure characteristic of the FCPRV.
Figure 18B:
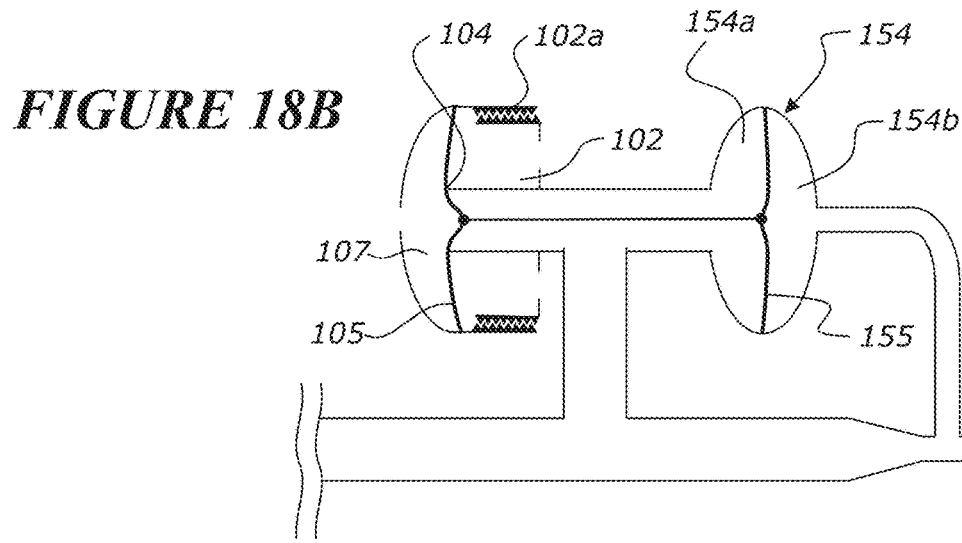
Figure 18C:
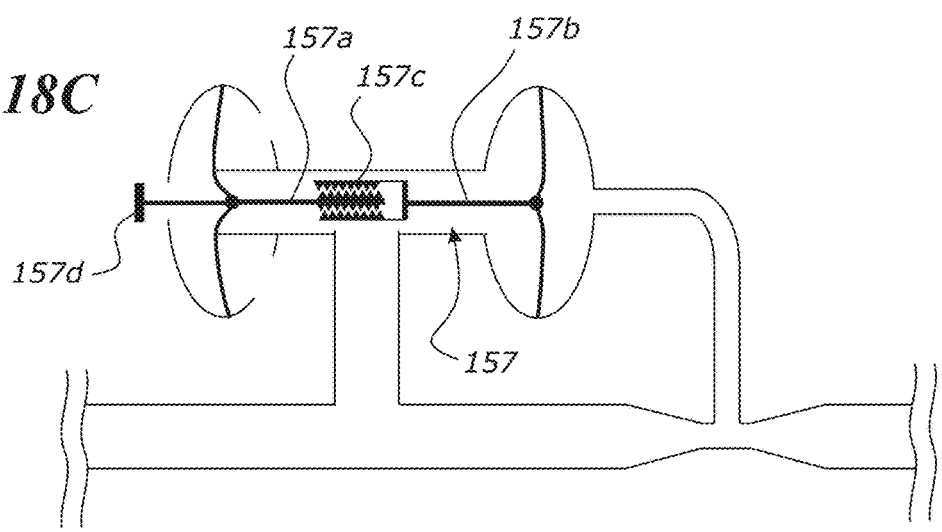

Further adjustment mechanisms for adjusting the relief valve venting pressure are illustrated in FIGS. 18A to 18C. In some embodiments, as shown in FIG. 18A, the displacement chamber 107 may be sealed or sealable from the ambient environment. In the illustrated embodiment, the FCPRV is provided with a device 107a to alter the pressure within the displacement chamber. Such a device may also be provided with a PRV 100 (i.e. one that is not flow controlled). For example, the device 107a may be a foot or hand operable pump to increase or decrease the pressure in the displacement chamber. An effective volume of the displacement chamber may comprise the volume of the displacement chamber 107 and the volume of the device 107a. For example the device 107a may be an air filled syringe or other cylinder and plunger arrangement, or an air filled bag/balloon. By reducing the volume of the device, the effect volume of the displacement chamber is reduced, resulting in an increase in the pressure in the displacement chamber 107. The altered pressure in the displacement chamber alters the relief pressure for the PRV of the FCPRV, an increasing displacement chamber pressure increasing the relief pressure and a decreased displacement chamber pressure decreasing the relief pressure. The device 107a should be adapted to not lift the valve member off the valve seat 104 unless this is desirable. The pressure adjustment device 107a may be located at the displacement chamber, i.e. on the FCPRV, or may be remote, connected to the displacement chamber via a hose or conduit. The device 107a may be adjustable by hand or foot, or may be driven by an electromechanical means, such as a solenoid or may be an electrically driven mechanical pump. The PRV 100 may also be provided with a reset device 107b to reset the displacement chamber pressure to ambient pressure. The reset device may be a manually or electrically operated relief valve, such as a poppet valve or other similar device. In FIG. 18A the FCPRV 300 is illustrated in a no flow condition, with the valve member 105 biased against the valve seat 104 by the pressure of the displacement chamber.

In some embodiments, the relative position of the valve member 104 and valve seat may be adjustable, to adjust the relief pressure. As described previously, the position of the valve inlet to the valve seat may be adjustable. Alternatively or additionally, in some embodiments the position of the valve member to the valve seat is adjustable. As shown in FIG. 18B, the valve member may be supported by a housing part, and the position of the housing part relative to the inlet is adjustable, for example via a screw thread arrangement 102a between the displacement chamber 107 housing and the outlet chamber 102 housing. Alternatively or additionally the sensing member 155 may be adjustable relative to the valve inlet, to adjust the bias provided by the sensing member to the valve member against the valve seat. For example, the sensing chamber housing may comprise screw thread arrangement to move the relative position of the sensing member to the valve seat 104. A user may manipulate the threaded arrangement, for example by turning a housing part by hand, to adjust the relieve pressure. The housing may provide an indication of housing position relating to relief pressure setting.

As described previous, the mechanical link 157 connecting between the sensing member and the valve member may be length adjustable. In some embodiments, the length of the mechanical link may be adjusted during use of the FCPRV. For example, as shown in FIG. 18C in some embodiments the mechanical link may comprise a first part 157a and a second part 157b and a threaded engagement 157c between the first and second parts 157a, 157b, to adjust the total length of the link 157. A control handle or knob 157d may be provided to allow a user to rotate one part 157a relative to the other link part 157b to adjust the total length of the link 157 via the threaded engagement 157c.

In some embodiments, the FCPRV may comprise or provide an upper pressure limit. The upper pressure limit may correspond to an upper safety pressure limit for a system, to protect system components. The upper pressure limit may be set by limiting an amount of travel of the sensing member, e.g. limiting the deformation of the sensing membrane or limiting the amount of travel of a sensing plunger or piston. Limiting the amount of travel of the sensing member limits the amount of tension that the sensing member can provide to the valve member, which in turn provides an upper limit on the effect the flow rate through the flow restriction of the FCPRV has on the valve member. In some embodiments the second chamber may limit the deformation of sensing membrane or limit the travel of a sensing plunger or piston. For example, a sensing membrane may be limited to a maximum inflated configuration once the membrane is inflated against a wall of the second chamber. Or a maximum travel for a sensing piston or plunger may be set by the piston or plunger hitting a wall of the second chamber, or a mechanical stop in the second chamber (e.g. a shoulder or projection extending from a wall of the second chamber as represented by item 271 in FIG. 21). Alternatively, a mechanical stop may be provided to engage the mechanical link 157, 257 between the sensing member and the valve member. A representation of this embodiment is provided in FIGS. 14A and B, wherein a shoulder 272 projecting from a wall of the FCPRV is adapted to engage a shoulder provided by a flange or projection 273 on the mechanical link to limit the movement of the sensing member.

Figure 19:
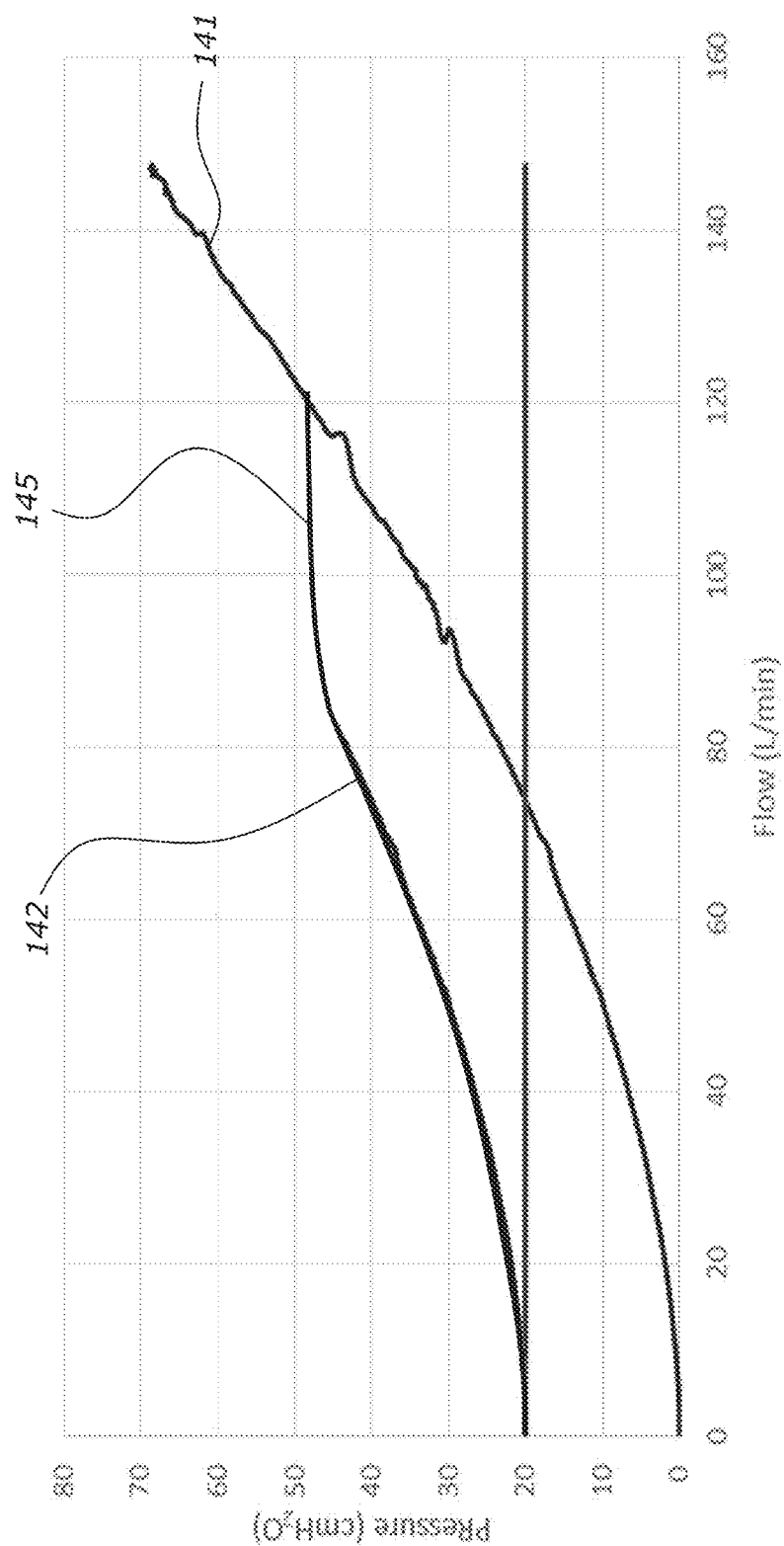
FIG. 19 shows a system pressure (drop) vs flow rate curve and a relief pressure vs flow rate curve for a FCPRV, where the relief pressure is limited to a maximum relief pressure.

The effect of limiting the travel of the sensing member or the mechanical link is represented in FIG. 19. As the flow rate delivered to the patient increases the pressure drop through the system 141 increases, and the pressure differential across the sensing member increases so that the relief pressure 142 of the FCPRV increases. However, once the travel of the sensing member reaches a maximum travel, the effect of any further increase in flow rate and resulting increasing pressure differential across the sensing member is not transmitted to the valve member, and therefore the relief pressure reaches a maximum pressure. In FIG. 19, the maximum relief pressure is indicated by line 145, and is less than 50cmH$_2$O.

The concept illustrated in FIG. 19 i.e. limiting the travel or deformation of the sensing member is a maximum level may be advantageous because a maximum system pressure limit can be achieved regardless of or independent of the type of system that the FCPRV is used with. Manually setting a maximum system pressure would require knowledge of the resistance to flow through the system, however, the configuration as described allows limiting a system pressure independent of the type of system with which the FCPRV is used.

In some embodiments the mechanical link operates in compression only, by being uncoupled from the valve member or the sensing member or both the valve member and the sensing member. Such an embodiment is illustrated by the schematic representations presented in FIGS. 16A to 16C, in which the ends of the mechanical link 157 are not coupled to the valve member 105 and the sensing member 155. With no gases flow through the main flow path of the valve 158 (i.e. zero flow into the FCPRV inlet 151) one end of the mechanical link 157 bears against the valve member 105 and the other end of the mechanical link 157 bears against the sensing member. The length of the mechanical link is greater than the distance between the valve member and the sensing member when in their un-deflected state. The valve member has a higher bias than the sensing member such that the valve member bears against the valve seat 104. For example, in an embodiment comprising a membrane valve member and a membrane sensing member, the valve member membrane has a higher tension than the sensing member membrane so that the valve member is biased against the valve seat against the bias of the sensing member. As flow through the FCPRV from the inlet 151 to the outlet 153 increases, the differential pressure across the sensing member increases, which acts against the bias of the sensing member to reduce a force applied by the mechanical link 157 to the valve member. As the flow continues to increase, the force provided by the mechanical link to the valve member progressively reduces, and therefore the relief pressure progressively increases. FIG. 16B illustrates a valve state in which flow through the main flow path and flow restriction 152 has reduced the force applied to the valve member 105 by the mechanical link 157, with the mechanical link bearing against both the valve member 105 and the sensing member 155. As the flow continues to increase, the sensing member is deflected such that the mechanical link loses contact with either the sensing member 155, the valve member 105 or both. FIG. 16C illustrates a high flow condition where the link is no longer in contact with the valve member and the sensing member. At this stage, the bias of the sensing member no longer provides any force via the mechanical link to the valve member 105. Thus, above a predetermined flow threshold, the relief pressure is determined by the bias of the valve member against the valve seat 104 only, with the FCPRV acting as PRV without flow compensation. The bias of the valve member against the valve seat sets a pressure limit for the system that is irrespective of flow rate, indicated by the horizontal dashed line in the flow vs pressure curve of FIG. 16D. As shown in FIG. 16D, the relief pressure progressively increases for increasing flow until contact between the mechanical link and one or both the valve and sensing members is lost (as shown in FIG. 16C), at which point the pressure limit is reached as set by the bias of the valve member.

In the event a flow restriction is introduced to the system downstream of the FCPRV (for example a partially collapsed conduit), the flow source (12 in FIG. 1AA) maintains a set flow to the FCPRV and the pressure Pc at the FCPRV increases without a corresponding increase in differential pressure across the sensing member. In this situation, the pressure Pc increases until the relief pressure is reached, indicated by the vertical line in FIG. 16D, with the sensing member, mechanical link and valve member moving in a direction whereby the valve member lifts off the valve seat to vent flow via the outlet chamber and outlet vent openings 103.

Figure 16A:
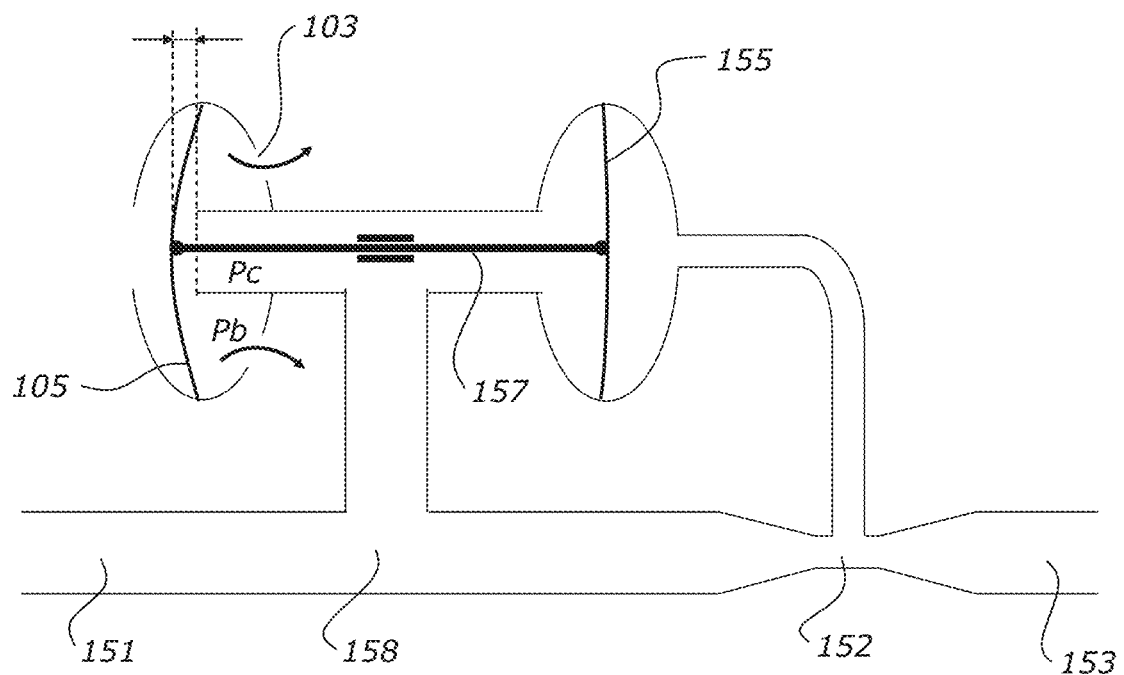
FIGS. 16A to 16C are schematic representations of a flow compensated pressure relief valve.
Figure 16B:
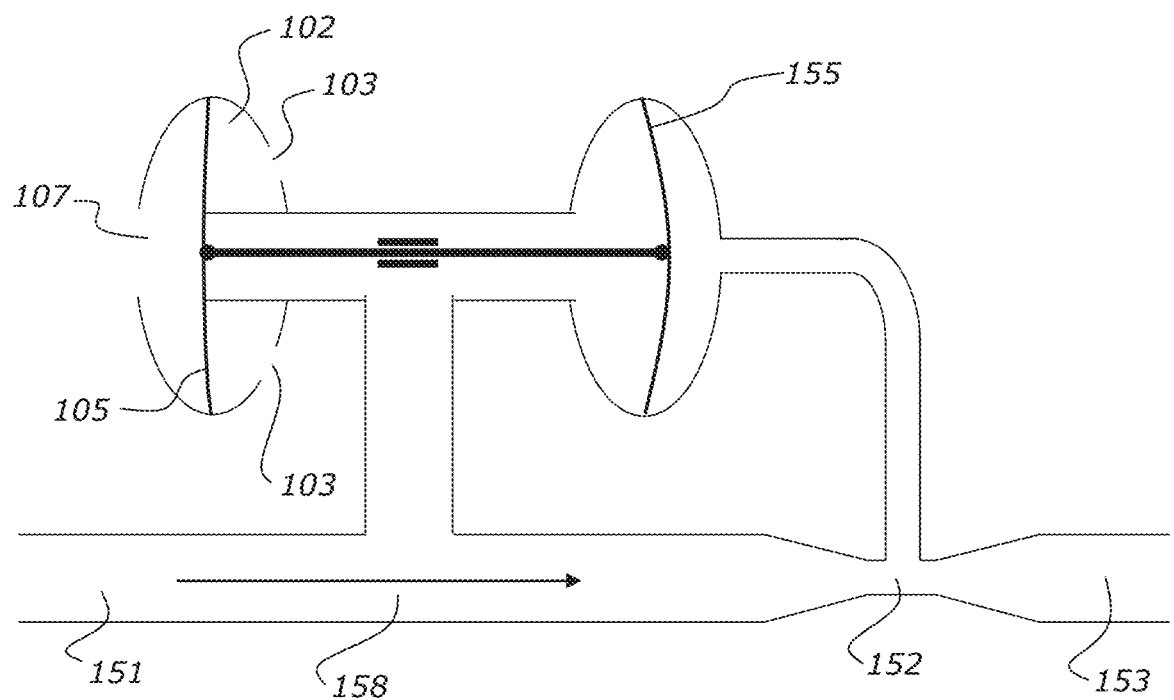
Figure 16C:
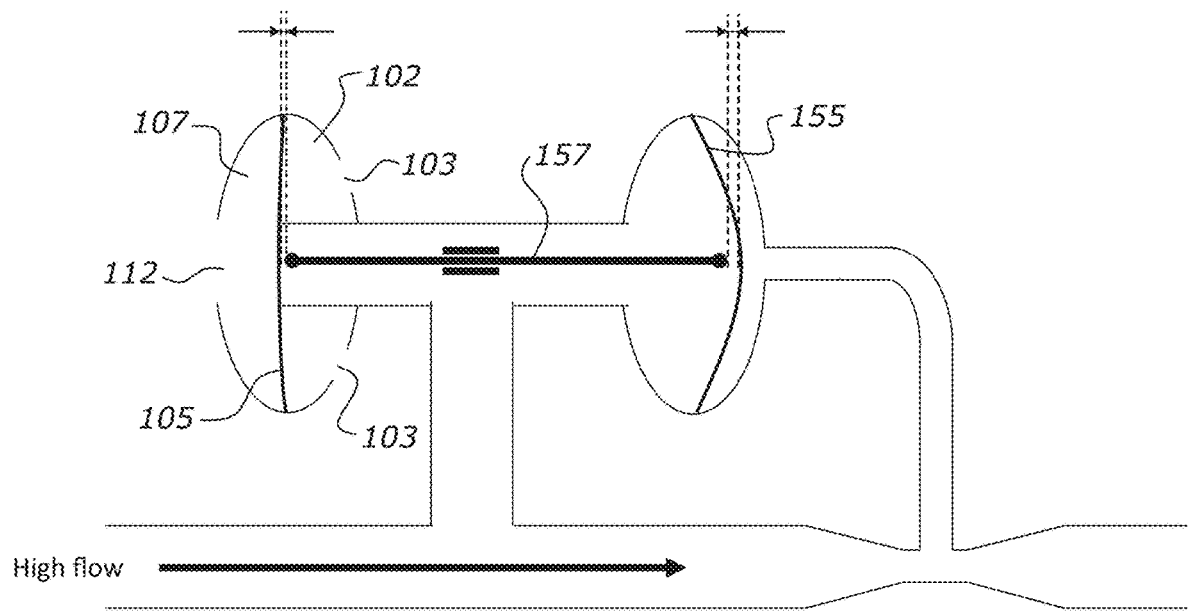
Figure 16D:
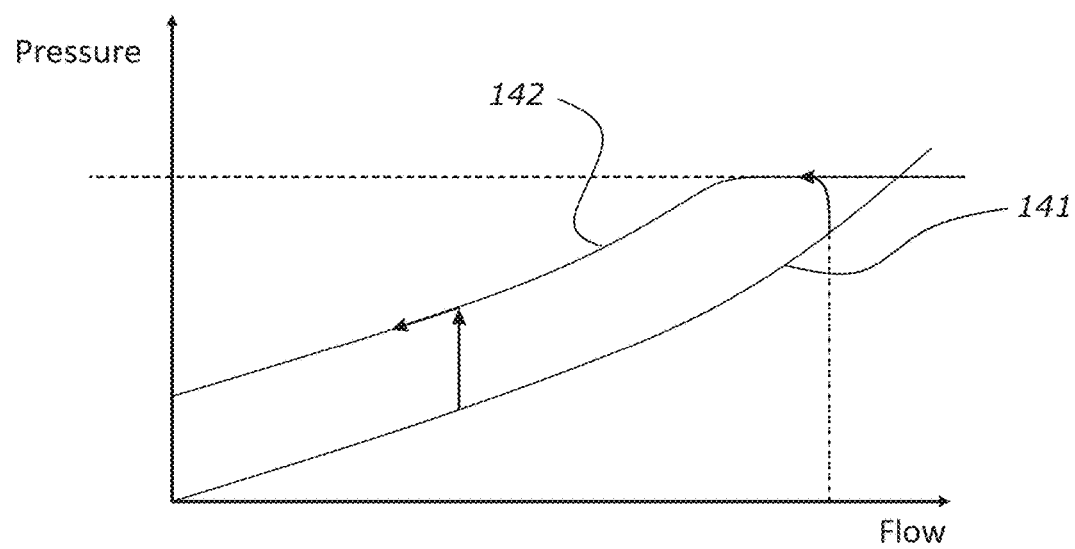
FIG. 16D shows a system pressure (drop) vs flow rate curve and a relief pressure vs flow rate curve for the FCPRV, wherein the flow rate is the flow rate of gases provided to a patient or from a main outlet of the FCPRV.

FIG. 16A illustrates a condition whereby a complete blockage downstream of the FCPRV has results in all flow provided to the FCPRV inlet 151 is vented via the PRV vent outlets 103.

Figure 23A:
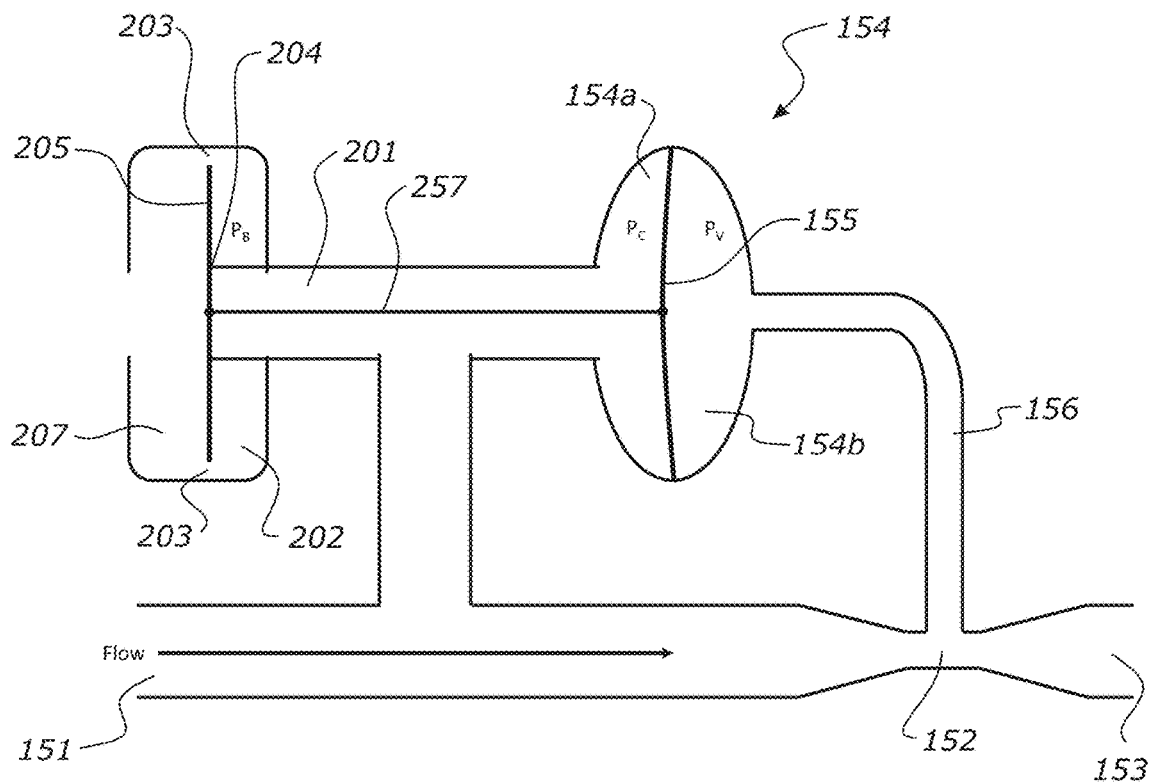
FIGS. 23A and 23B are schematic representations of the FCPRV of FIG. 22.

In some embodiments, the valve member is biased against the valve seat by tension in the membrane valve member or a biasing spring member, for example as described with reference to FIGS. 9A and 10A. A further amount of bias (positive or negative) is provided by the sensing member via the mechanical link, to alter a pressure required to lift the valve member away from the valve seat. In some embodiments, the valve member is not biased against the valve seat other than by a bias provided by the sensing member, for example, as shown in FIG. 23A. A membrane valve member may not be stretched over the valve seat such that the membrane is not biased against the valve seat until it is pulled into contact with the valve seat by the sensing member. In some embodiments, the sensing member provides a positive bias to the valve member, i.e. the sensing member pulls the valve member against the valve seat. In some embodiments, as described with reference to FIGS. 16A to 16D, the sensing member provides a negative bias to the valve member, i.e. the sensing member pushes the valve member away from the valve seat. Unless the context suggests otherwise, a bias or biasing of the valve member against the valve seat is intended to mean a total biasing of the valve member against the valve seat provided by tension in the valve member membrane or by a spring element or by the sensing member via the mechanical link.

The representation of FIGS. 14A and 14B illustrate one possible configuration for a FCPRV. In this arrangement, the valve inlet 101 and first chamber 154a of the sensing chamber 154 are connected to a main flow path 158 comprising the main inlet 151, main outlet 153 and flow resistance 152 via a 'T' piece, with a foot of the T piece connected to the main flow path and the PRV 100 and sensing chamber 154 arrangement oppositely at each side of the top of the 'T' piece.

Figure 20:
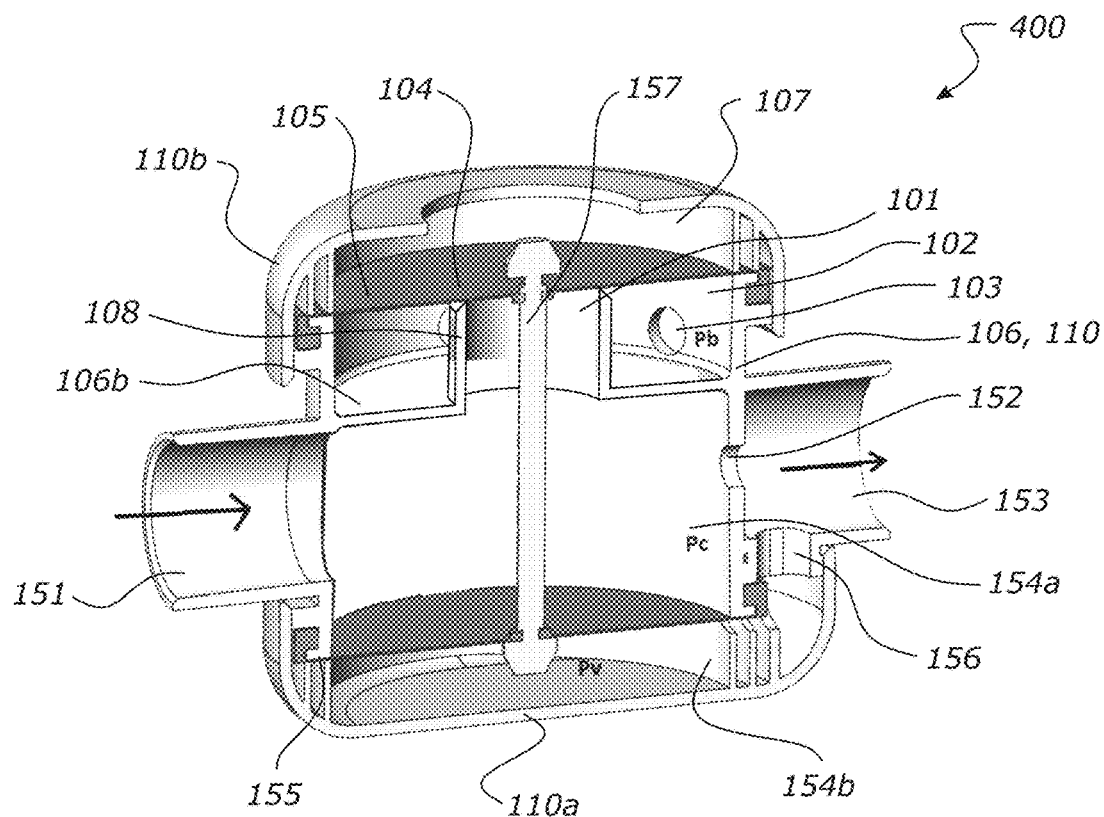
FIG. 20 shows a cross sectional view of a FCPRV.

An alternative embodiment for a flow compensated pressure relief valve is illustrated in FIG. 20. In comparison to the configuration of FIGS. 14A and 14B, the embodiment of FIG. 20 is configured to a single valve unit 400 that occupies less space and is more aesthetically pleasing in appearance.

In FIG. 20, a valve body 110 forms the first chamber 154a of the sensing chamber 154 and the outlet chamber 102. The first chamber 154a and the outlet chamber 102 are divided by a wall 106b. The main inlet 151 and main outlet 153 are formed in or with the body 110 to communicate directly with the first chamber 154a, such that the flow of gases passing from the main inlet 151 to the main outlet 153 pass through the first chamber 154a. An orifice 152 is provided in a wall 106 of the body 110 at the main outlet 153, and a pressure tap 156 is provided in the outlet and/or downstream of the orifice to communicate with the second chamber 154b which is provided by a cap 110a attached to an end of the body 110. The first and second chambers 154a, 154b form the sensing chamber 154 with the sensing member 155 therein. In the illustrated embodiment the sensing member 155 is a membrane that is secured between the cap 110a forming the second chamber 154b and the body 110 forming the first chamber 154a. A valve inlet tube 108 extends from the first chamber 154a into the outlet chamber 102, and an end 104 of the inlet tube provides a valve seat 104 against which the valve member 105 seals. The valve member 105 is secured to the body 110 with a second cap 110b attached to the body 110. Outlet apertures 103 are provided in a wall 106 of the body 110 forming the outlet chamber 102. The valve member 105 and the sensing member 155 are coupled by a rigid rod 157.

Figure 21:
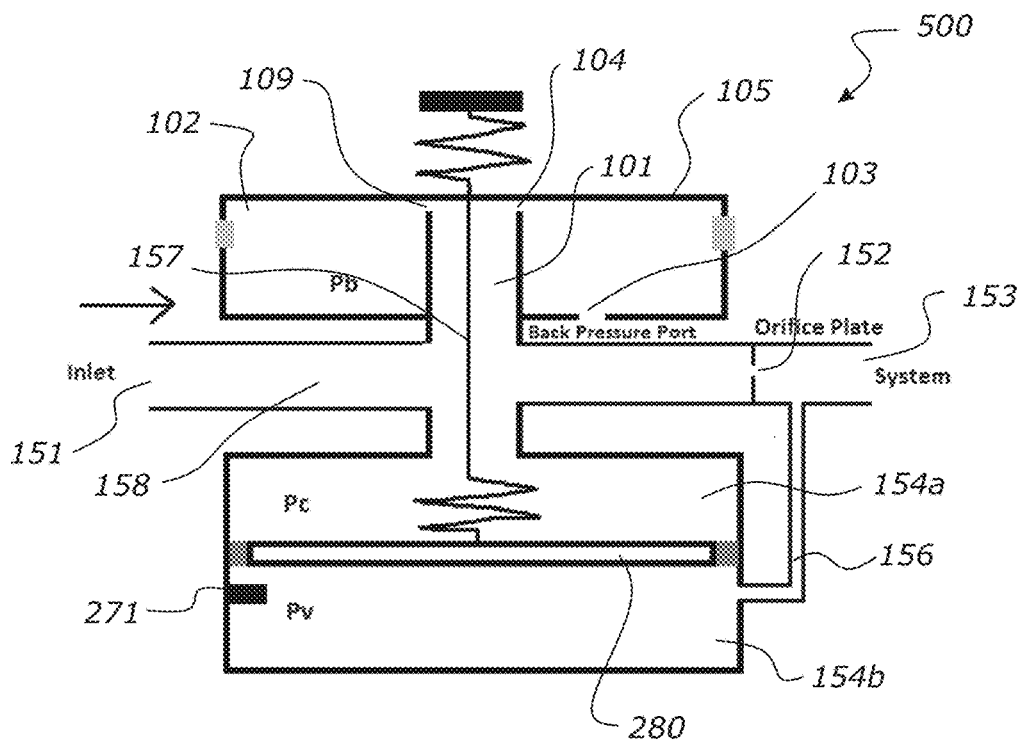
FIG. 21 shows a free-body diagram of another FCPRV.

FIG. 21 is a free body diagram of an embodiment of a FCPRV 500 similar to that of FIG. 20, however, the sensing member 155 is a piston 280 that moves within a cylinder forming the sensing chamber 154. In this embodiment the valve member 105 is a membrane.

Figure 22:
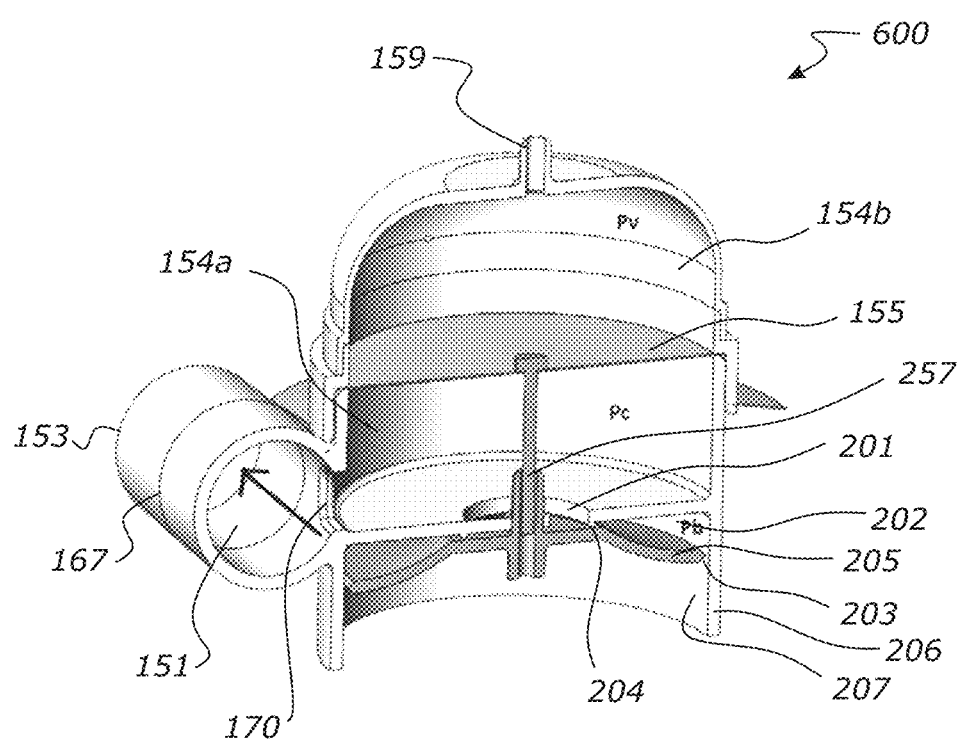
FIG. 22 shows a cross sectional view of another FCPRV.

FIG. 22 illustrates a further alternative embodiment for a FCPRV 600. The embodiment of FIG. 22 is similar to the embodiment of FIG. 20, however in FIG. 22 the valve member 205 is not a membrane but is an unsealed plunger 205, meaning the plunger does not form a seal with a wall 206 of the outlet chamber 202. In this embodiment the valve member 205 is similar to the valve member described with reference to FIGS. 9A to 9C. In FIG. 22, the mechanical link 257 between the valve member 205 and the sensing member 155 is of an adjustable length, for example may comprise telescoping parts. Adjustment of the length of the link adjusts an amount of force that the sensing member 155 provides to the valve member 205 in addition to a force resulting from a pressure differential between the first and second chambers 154a, 154b. The flow from the main inlet 151 to the main outlet 153 is via a conduit 167. The conduit 167 intersects the first chamber 154a (e.g. the conduit may be tangential to the first chamber) so that the flow of gases from the main inlet to the main outlet communicate with the first chamber 154a via an opening 170 in a wall of the first chamber 154a. A communication line (not shown) may be connected from a downstream side of a flow restriction (the flow restriction, such as an orifice or venturi, is downstream from the opening 170) to the second chamber 154b via a nipple 159 or other suitable connection.

Figure 23B:
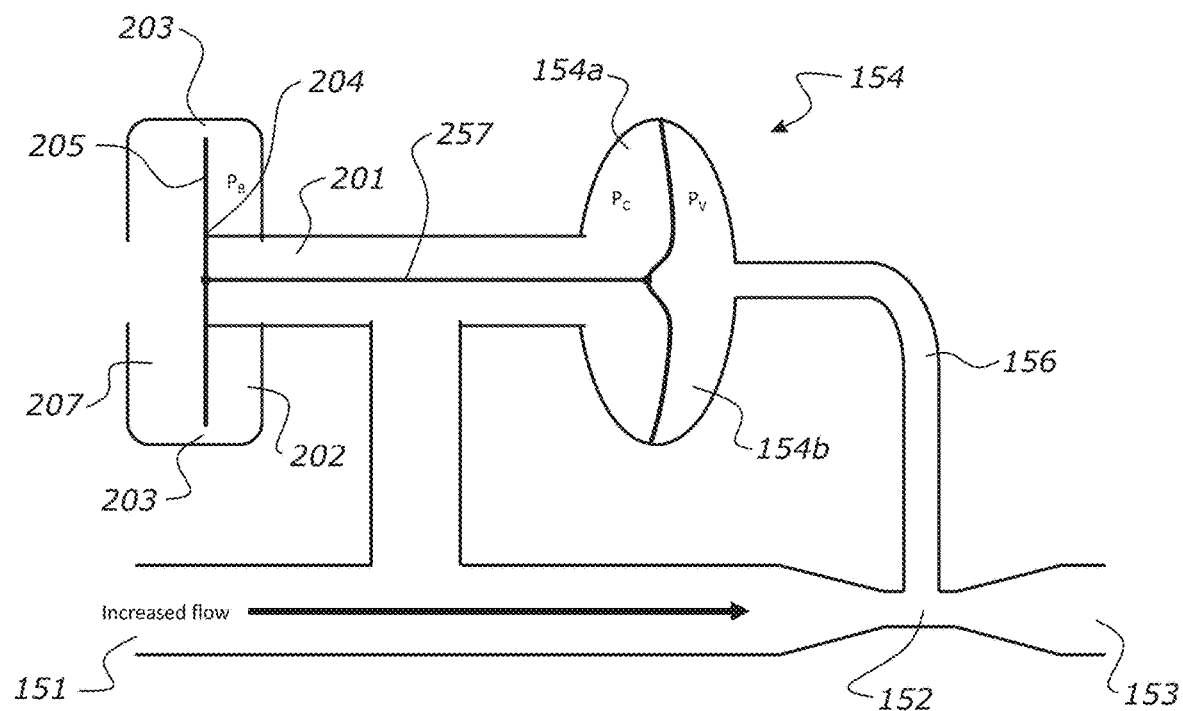

Schematic representations of the FCPRV of FIG. 22 are provided in FIGS. 23A and 23B. FIG. 23A shows a no flow or low flow configuration, with no differential pressure or a small differential pressure across the sensing membrane. FIG. 23B shows an increased flow or high flow configuration, where there is a pressure differential across the sensing member such that the sensing member 155 is deformed towards the second chamber 154b of the sensing chamber. The deformation of the sensing member causes the sensing member to bias the sealing member 205 against the valve seat 204 via the mechanical link 257. FIG. 23A illustrates the sensing membrane 155 being deformed from a neutral (undeformed or un-stretched) when in a no-flow or low flow configuration. This deformation is an initial deformation or preloading, which provides an initial or minimum bias force to the valve member 205 against the valve seat 204, for example as described above for a PRV 100 according to some embodiments.

Figure 24:
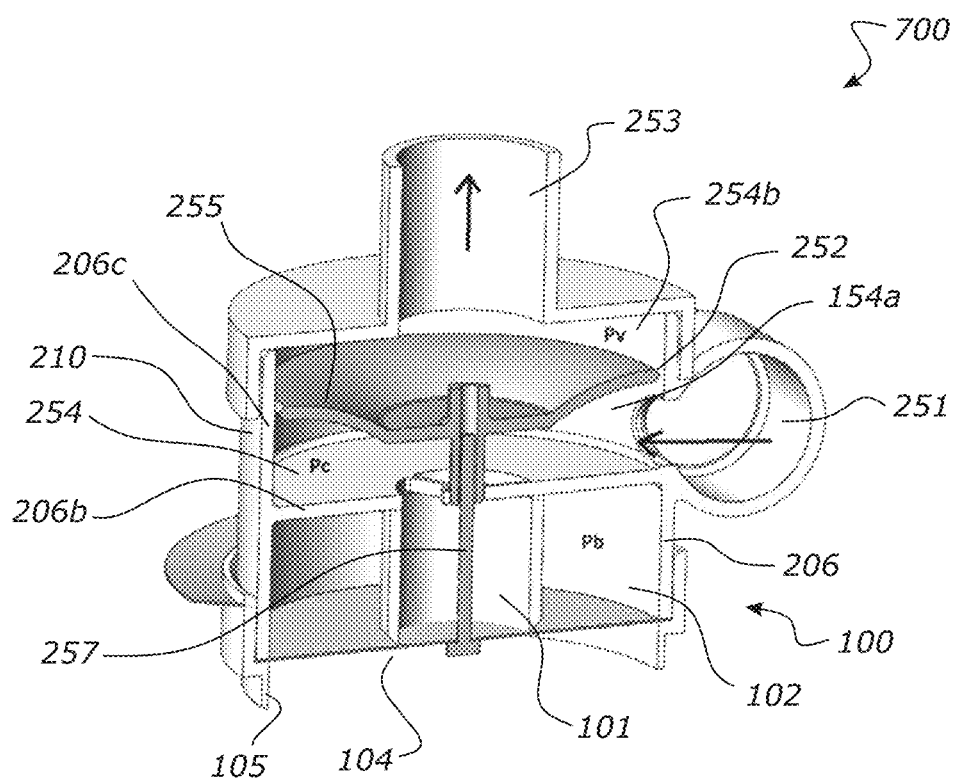
FIG. 24 shows a cross sectional view of another FCPRV.

FIG. 24 illustrates a further alternative embodiment for a FCPRV 700. The FCPRV has a main inlet 251 and a main outlet 253, for receiving a flow of gases from a gases source and delivering the flow of gases to a system for example the respiratory system 12 of FIG. 1. A PRV 100 is provided to relieve pressure above a pressure threshold, and in the illustrated embodiment includes a membrane valve member 105 and other features as described with reference to earlier embodiments, including a valve inlet 101, an outlet chamber 102 and a valve seat 104. Vent outlets (e.g. vent outlets 103 in FIG. 2A) from the outlet chamber 102 are obscured from view in FIG. 24 but are provided in the wall 206 of the outlet chamber 102. The FCPRV 700 comprises a sensing mechanism to dynamically adjust the pressure threshold of the PRV 100 based on a flow rate of the flow of gases passing from the main inlet 251 to the main outlet 253. The sensing mechanism includes a sensing chamber 254 with a sensing member 255 located in the sensing chamber 254. A body 210 of the FCPRV 700 forms both the sensing chamber 254 and the outlet chamber 102, with a dividing wall 206b separating the two.

Unlike the previously described embodiments, in the embodiment of FIG. 24, the flow of gases from the main inlet 251 to the main outlet 253 flow through the sensing chamber 254 from the first chamber 254a to the second chamber 254b, with the main outlet 253 being from the second chamber 254b. The sensing member 255 is an unsealed plunger, meaning the plunger does not form a seal with a wall 206c of the sensing chamber. The sensing plunger 255 is mechanically coupled to the valve member 105 by a mechanical link 257. In the illustrated embodiment the link 257 comprises two telescoping members to be length adjustable. An annular gap 252 between an outer perimeter of the plunger 255 and a wall 206c of the sensing chamber provides a restriction to flow of gases from the main inlet to the main outlet. Additionally, in some embodiments, the plunger may include apertures (not shown) through the plunger, so that the apertures through the plunger and the annular gap 252 between the plunger and the chamber wall provide a desired resistance to flow. In an alternative embodiment, the plunger may be a piston, e.g. forming a seal with a wall of the sensing chamber, but with one or more apertures through the piston providing the flow restriction 252. The gap or flow restriction 252 is downstream of the valve inlet 101 since the valve inlet 101 receives the flow of gases from the main inlet 251 prior to the flow of gases passing through the flow restriction 252, or in other words the valve inlet 101 is upstream of the flow restriction 252 since the valve inlet 101 does not see the pressure drop created by the restriction 252. As the flow passes through the annular gap 252, a pressure drop is created such that the pressure in the sensing chamber on a downstream side 254b of the plunger 255 is lower than the pressure in the sensing chamber 254 on an upstream side 254b of the plunger 255. The upstream side of the sensing member 255 may be referred to as the first chamber 254a of the sensing chamber 254, and the downstream side of the sensing member 255 may be referred to as the second chamber 254*b*; the sensing plunger 255 divides the first and second chambers 254*a*, 254*b* although does not pneumatically separate the two chambers since a flow of gases passes from the first chamber to the second chamber. The first chamber 254*a* is in fluid communication with the flow of gases upstream of the flow restriction 252 provided by the gap between the sensing member 255 and the sensing chamber wall 206*c*, and the second chamber 254*b* is in fluid communication with the flow of gases downstream of the flow restriction 252 provided by the gap 252 between the sensing member 255 and the chamber wall 206*c*. The pressure differential across the sensing member 255 causes the sensing member 255 to move away from the valve inlet 101 dependent on the flow rate of the gases passing from the main inlet to the main outlet via the sensing chamber 254, and bias the valve member 101 via the link 257 towards the valve seat 104.

Figure 25A:
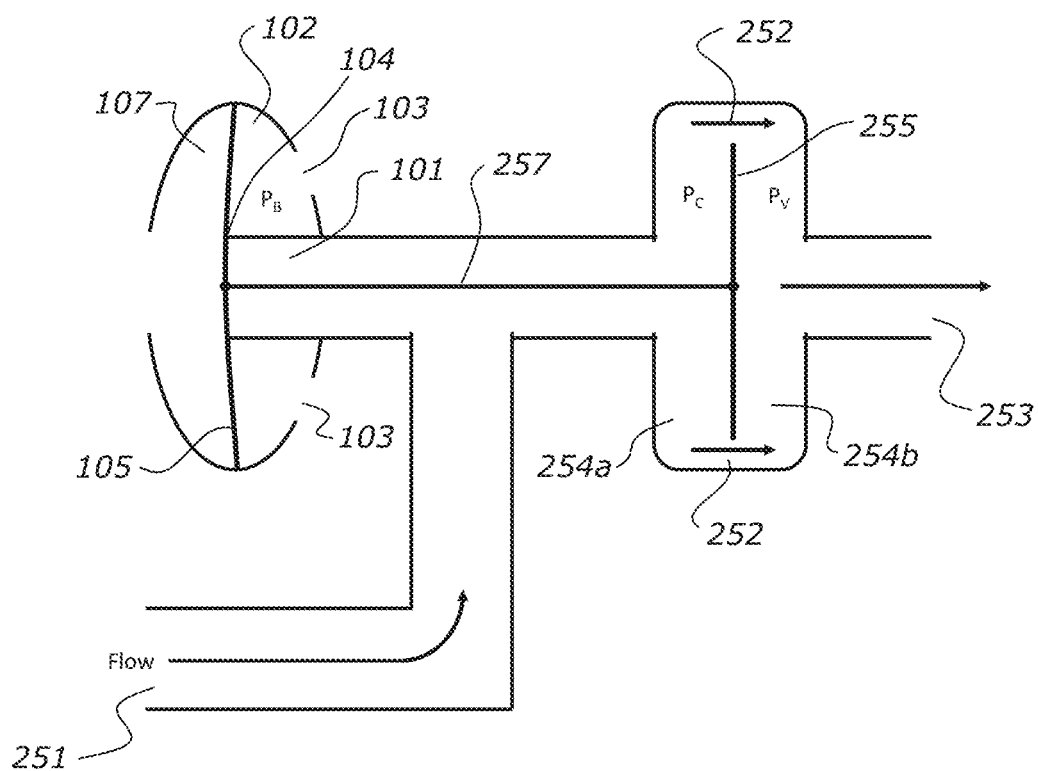
FIGS. 25A and 25B are schematic representations of the FCPRV of FIG. 24.
Figure 25B:
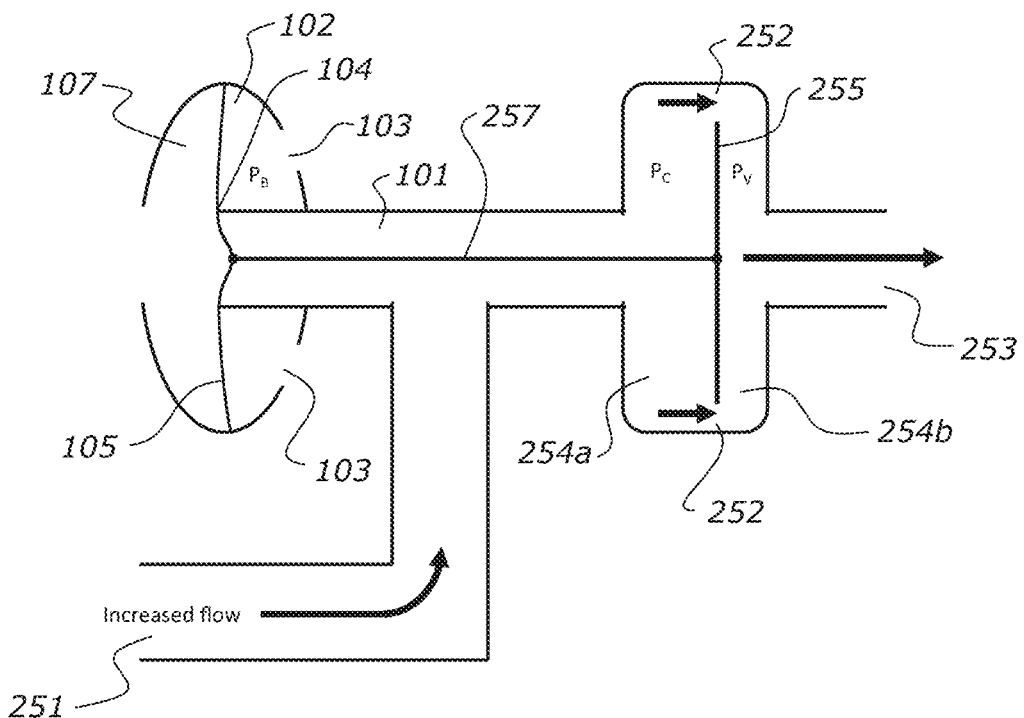

Schematic representations of the FCPRV of FIG. 24 are provided in FIGS. 25A and 25B. FIG. 25A shows a no flow or low flow configuration, with no differential pressure or a small differential pressure across the sensing plunger 255. FIG. 25B shows an increased flow or high flow configuration, where there is a pressure differential across the sensing plunger such that the sensing plunger 255 is forced towards the second chamber 254*b* of the sensing chamber. The movement of the sensing plunger causes the sensing plunger to bias the sealing member 105 against the valve seat 104 via the mechanical link 257, with the flow through the FCPRV from the main inlet 251 to the main outlet 253 passing through the flow restriction provided by the annular gap 252 between the plunger 255 and a wall of the sensing chamber 254.

Figure 26A:
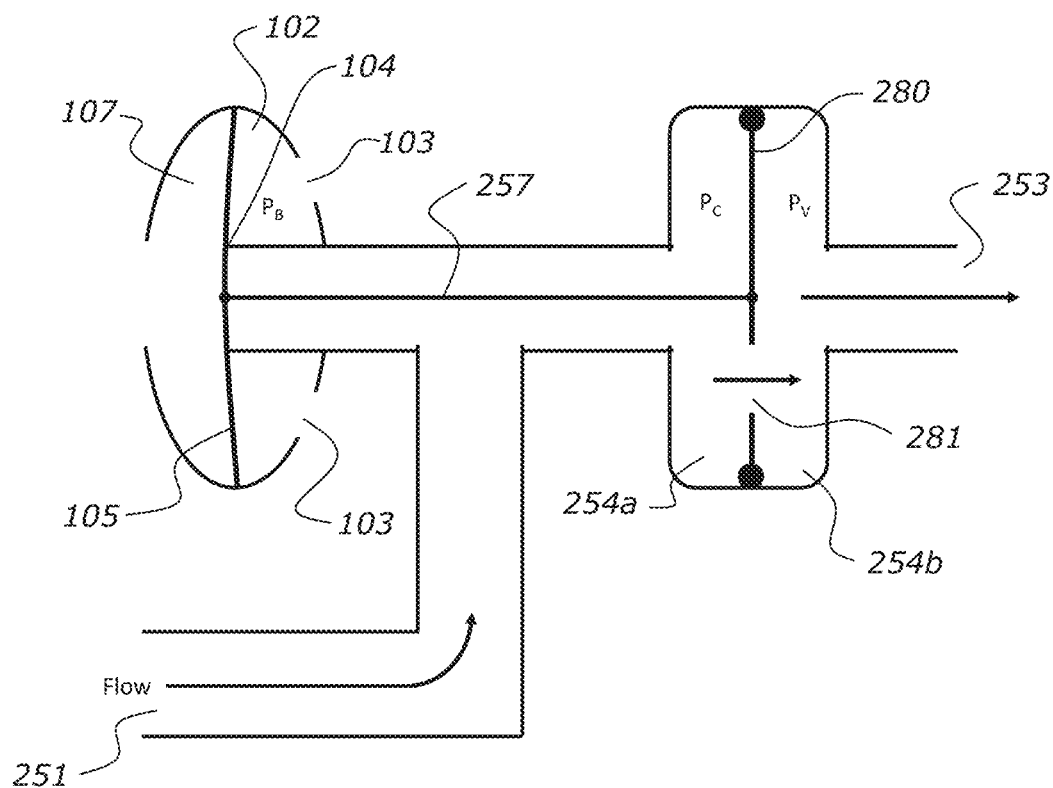
FIGS. 26A and 26B are schematic representations of a FCPRV similar to that of FIG. 24, comprising a sensing piston with apertures.
Figure 26B:
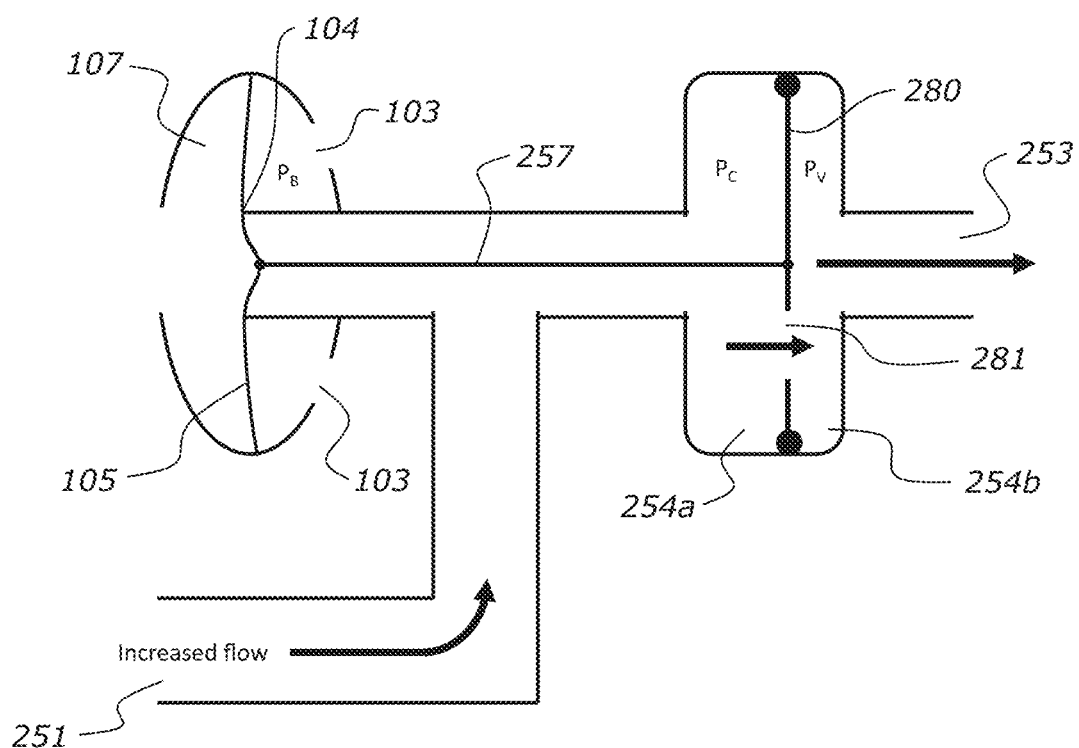

Schematic representations of FCPRV similar to that of FIG. 24 are provided in FIGS. 26A and 26B. In this embodiment, the sensing member is a piston 280 that forms a seal with a wall of the sensing chamber. The piston includes an aperture 281. The aperture 281 provides a restriction to flow through the sensing chamber. FIG. 26A shows a no flow or low flow configuration, with no differential pressure or a small differential pressure across the sensing piston 280. FIG. 26B shows an increased flow or high flow configuration, where there is a pressure differential across the sensing piston such that the sensing piston 255 is forced towards the second chamber 254*b* of the sensing chamber. The movement of the sensing piston causes the sensing piston to bias the sealing member 105 against the valve seat 104 via the mechanical link 257, with the flow through the FCPRV from the main inlet 251 to the main outlet 253 passing through the flow restriction provided by the aperture 281 through the piston 280. Furthermore, in an embodiment comprising a piston sensing member 255 in sliding relationship with a cylinder housing 254, there may be flow paths between the piston 255 and cylinder 254, for example via channels in the cylinder wall, or via cut-outs or notches in a perimeter of the piston. Such flow paths between the piston and cylinder may be in addition to apertures through the piston. In a further embodiment, the arrangement of FIGS. 26A and B may be implemented with a membrane sensing member, with apertures through the membrane, or by using a porous membrane. A flow path may be provided through a mechanical link and an aperture though the sensing member, for example a hollow mechanical link with an end extending through the sensing member.

Figure 27A:
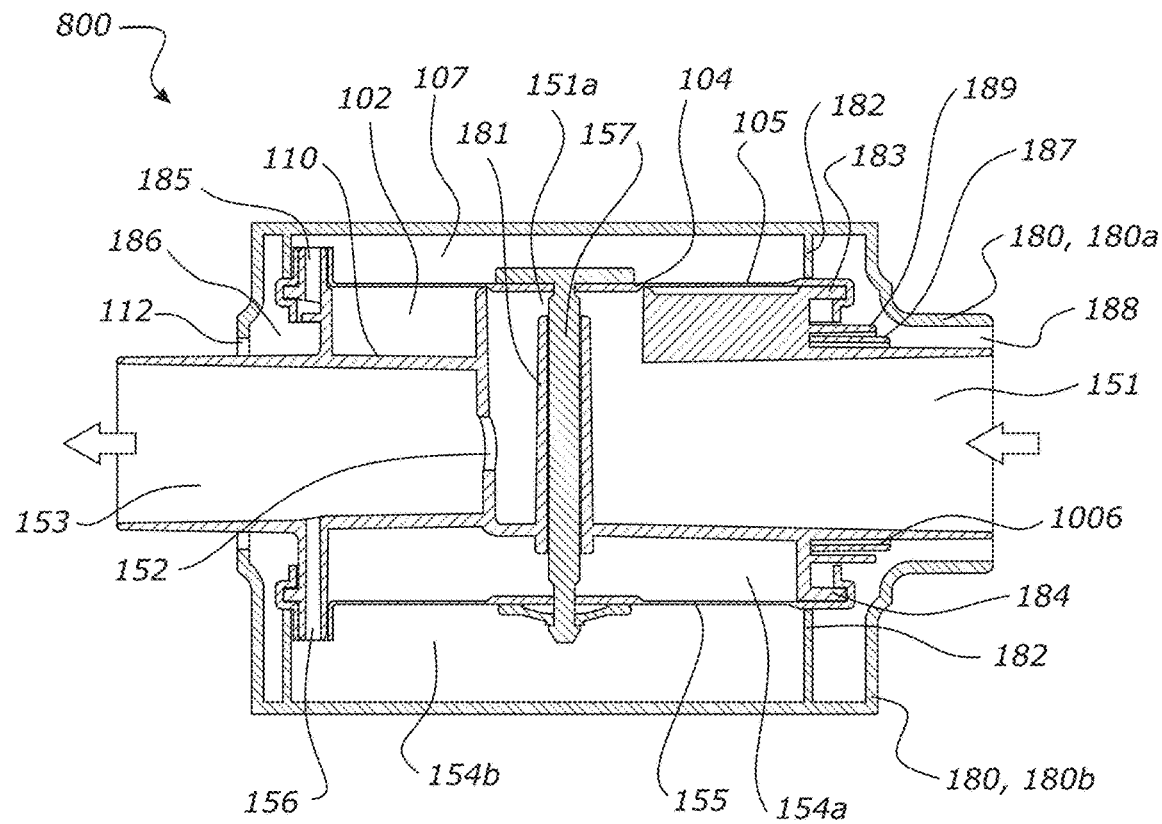
FIGS. 27A and 27B show cross sectional views of another FCPRV. The views are section on an axis through a central axis of a valve member and sensing member of the valve. The cross sectional plane in FIG. 27A is at a right angle to the cross sectional plane in FIG. 27B.
Figure 27B:
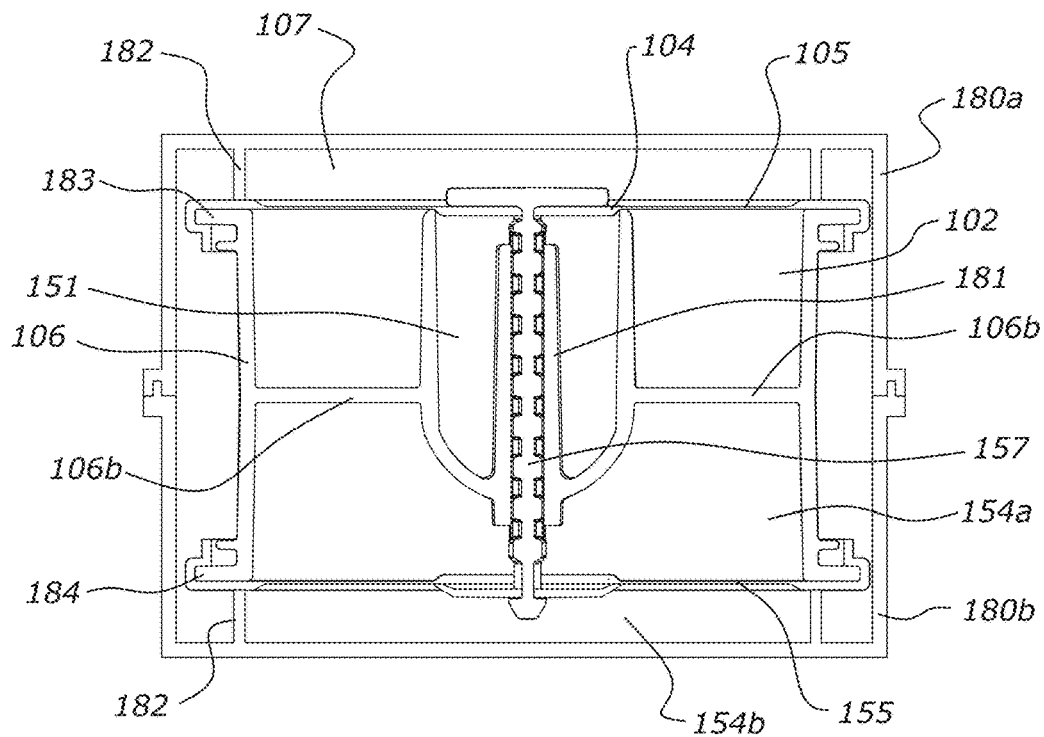
Figure 28A:
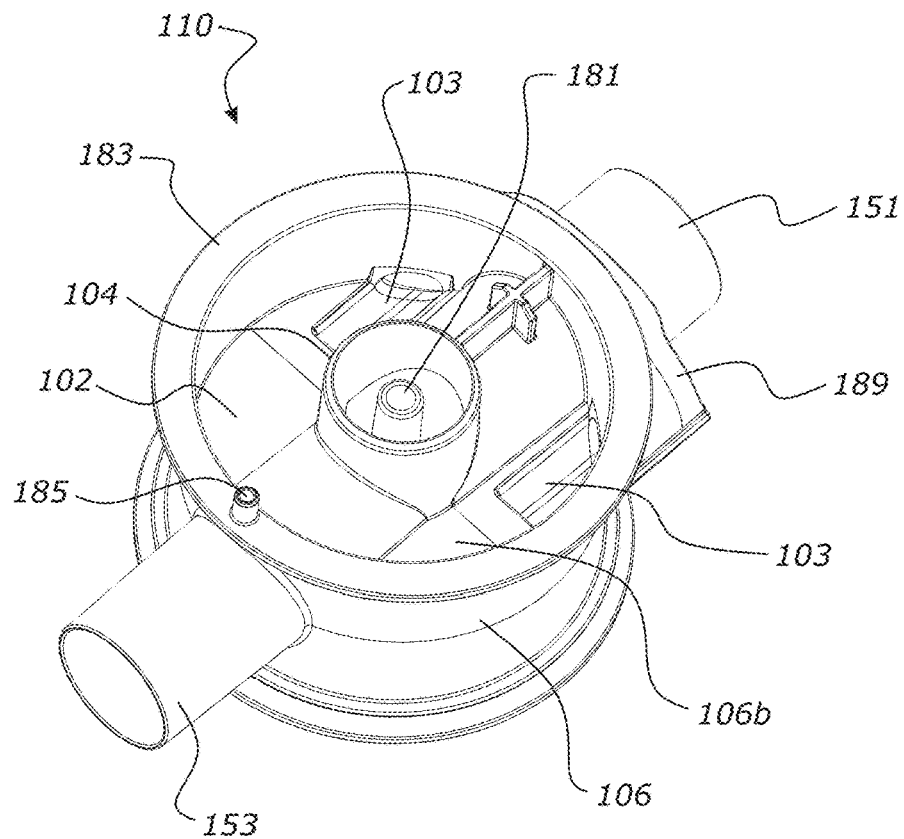
FIG. 28A to 28C are views of a valve body of the FCPRV of FIGS. 27A and 27B.
Figure 28B:
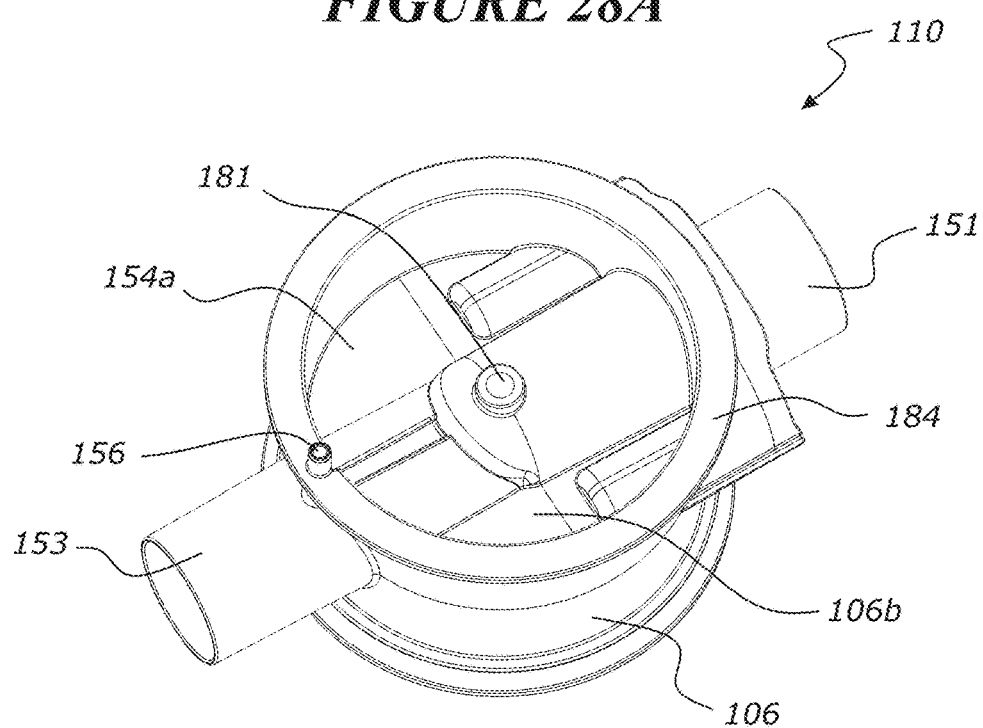
Figure 28C:
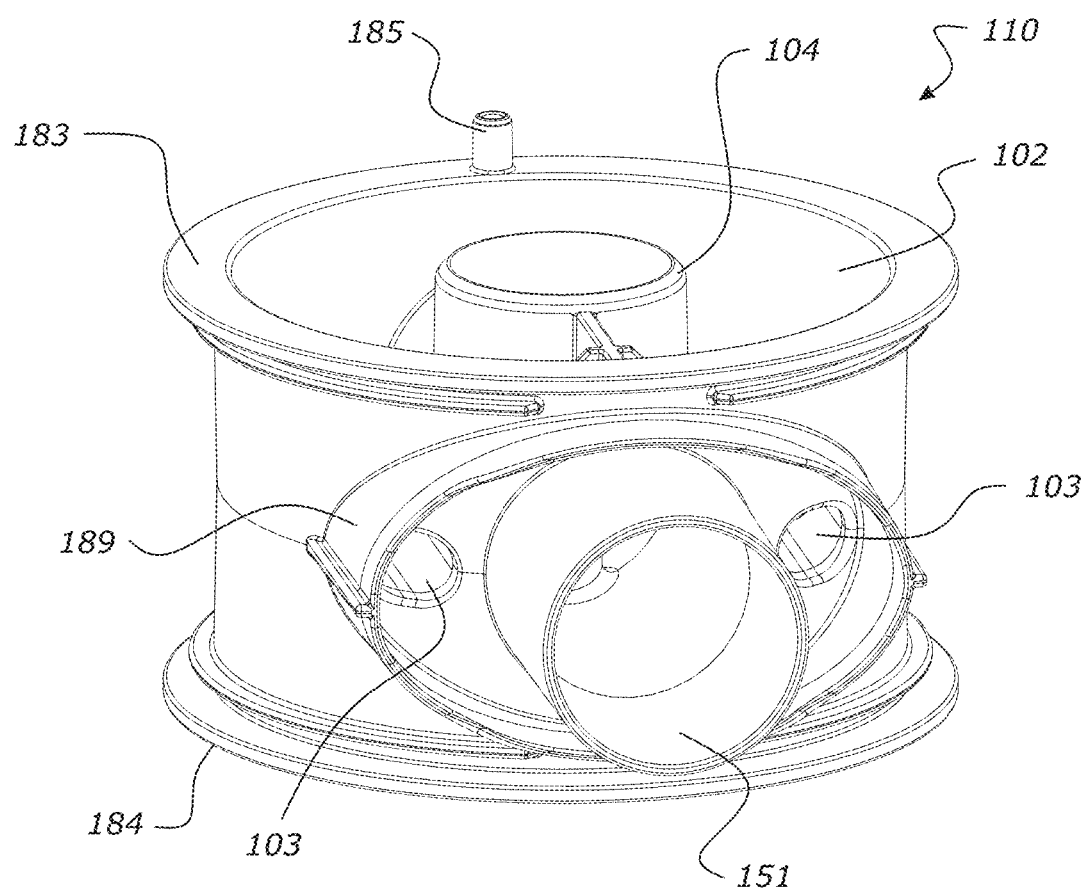

In some embodiments the FCPRV comprises an outer housing or housing enclosure to enclose components of the FCPRV such as the membranes 105, 155. FIGS. 27A and 27B show an FCPRV 800 comprising a housing 180. The housing encloses the valve member 105 and the sensing member 155. The FCPRV has a body 110. In some embodiments the body provides or forms the outlet chamber 102 and the first chamber 154*a* of the sensing chamber 154. In some embodiments, the body also comprises the main inlet 151 and the main outlet 153, for example in an integrally formed body 110. The body 110 of the embodiment shown in FIG. 27*a* is shown in FIGS. 28A and 28B. In some embodiments, the housing 180 comprises two parts 180*a*, 180*b* (e.g. two halves) that assemble together. The two housing parts may be secured together with a complementary tongue and groove arrangement or using a screwed or bolted arrangement, or may be welded together, e.g. ultrasonic welding or any other suitable method. A seal member e.g. gasket may be provided between the two housing parts, however a seal is likely unnecessary since ambient pressure is present on the inside and outside of the housing. The body 110 and valve and sensing members are received within and enclosed by the two housing parts. In some embodiments, one of the housing parts 180*a* (a first housing part) provides the displacement chamber 107 into which the valve member displaces from the valve seat 104. In some embodiments one of the housing parts 180*b* (a second housing part) provides the second chamber 154*b* of the sensing chamber 154. In some embodiments, the valve member and/or the sensing member also provides or acts as a sealing member to seal the outlet chamber 102 or the first chamber 154*a* of the sensing chamber. For example, the housing (e.g. the first housing part 180*a*) comprises an annular member 182 extending inwardly from a side wall of the housing. The annular member 182 bears against a perimeter portion of the valve member 105 (diaphragm) so that the valve member is sandwiched between the housing and the body 110, to seal the outlet chamber 102 from ambient or the displacement chamber 107 (but for any flow path that may be provided through the valve member). The body may comprise an annular shoulder or flange 183, and the valve member sandwiched between the body annular flange and the housing annular member. In some embodiments the valve member may comprise a radially inwardly facing channel or groove that receives an outer edge of the annular flange 183. The housing annular member 182 and housing wall radially inward of the annular member 182 forms the displacement chamber. The annular member 182 and body flange 183 may be circular or other shape. The second chamber 154*b* of the sensing chamber may be similarly formed, with the body 110 comprising an annular flange 184 and the housing an annular member 182 extending from a side wall of the housing 180, and with the sensing member captured/sandwiched between.

In some embodiments the body 110 is clamped between the two housing parts. As best shown in FIG. 27B, the body 110 is clamped between the annular walls 182 of the housing parts 180*a*, 180*b*. The valve member and the sensing member are also clamped between a respective housing part 180*a*, 180*b* and the body 110.

Figure 27C:
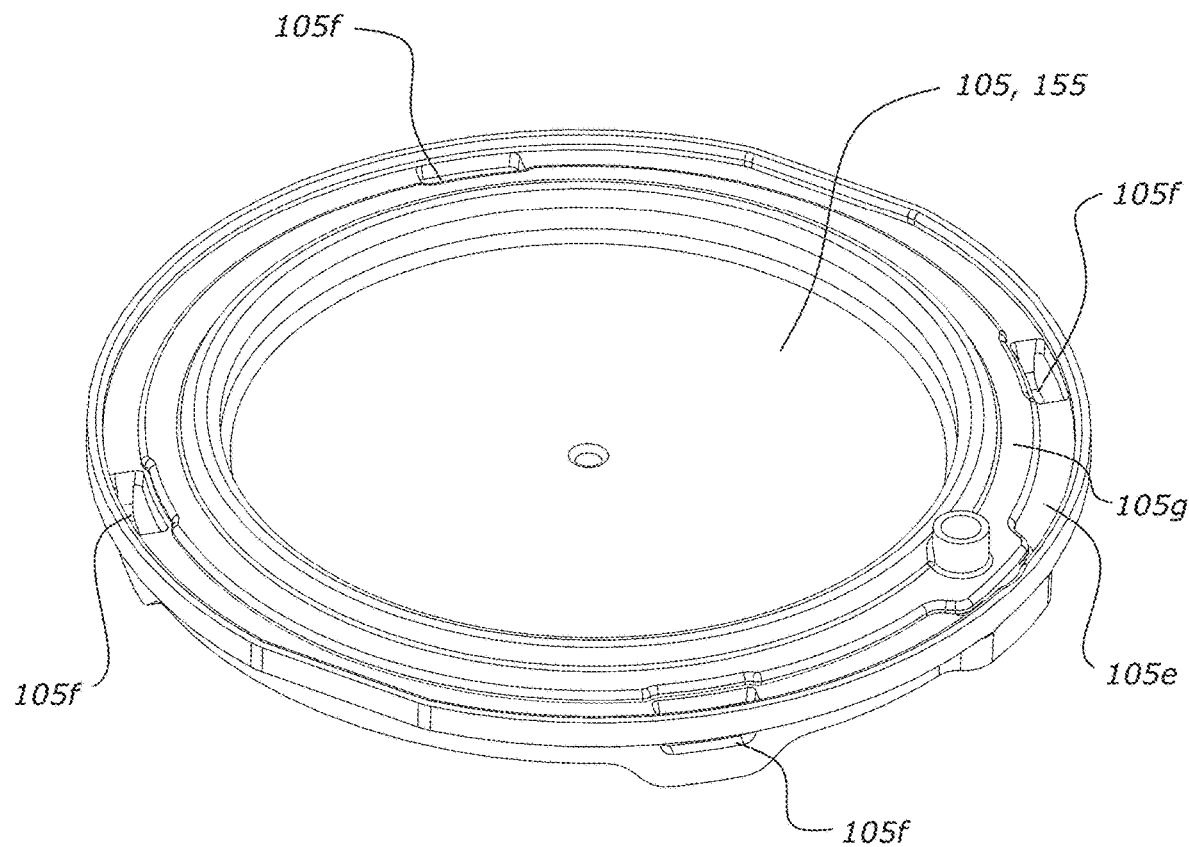
FIGS. 27C and 27D illustrate a valve member or sensing member comprising a resilient diaphragm or membrane and a rigid frame.
Figure 27D:
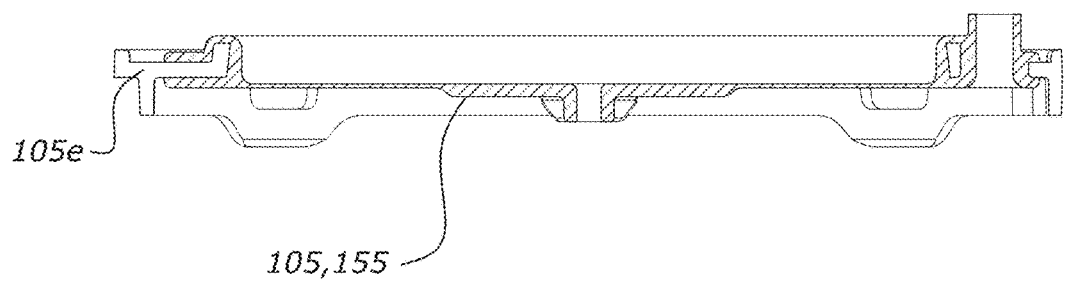
Figure 27E:
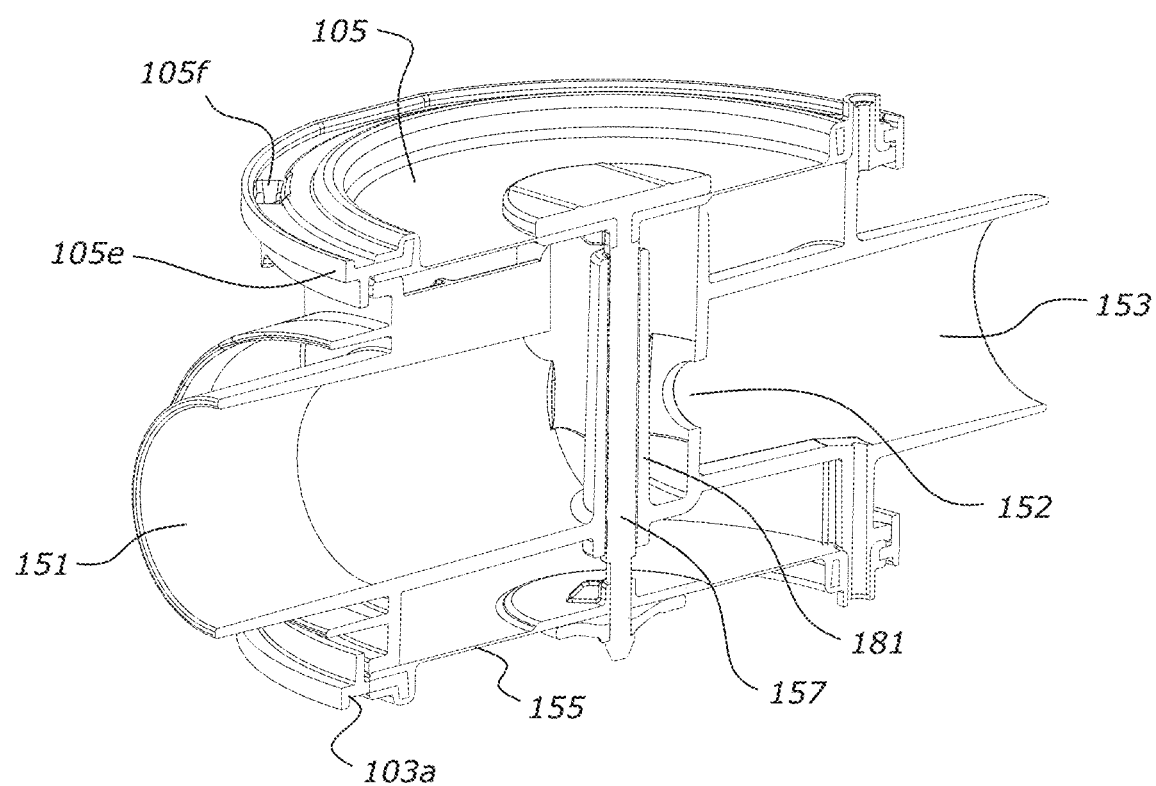
FIG. 27E is a cross sectional view of a valve body, valve member and sensing member assembly for a flow controlled pressure relief valve.

In some embodiments, the valve member and/or the sensing member comprises a rigid frame and a diaphragm or membrane. The rigid frame supports or holds or is coupled to a perimeter of the diaphragm or membrane. As described earlier, in some embodiments, the membrane 105, 155 is an elastomeric membrane. With reference to FIGS. 27C to 27E, the membrane 105 may be held by the frame 105*e* in a tensioned state so that the membrane has a predetermined tension. The rigid frame 105*e* may be overmolded to the membrane 105, or in a preferred embodiment the membrane is overmolded to the frame. In the overmolding process the rigid frame may be held in a mold cavity, and an uncured material injected into the cavity to form the membrane overmolded to the frame. As the membrane material cures, the material of the membrane shrinks, for example by 2-3%, resulting in pre-tensioning of the membrane within the frame. The frame 105e engages the valve body 110 to assemble the membrane to the body. The frame may include a clipping interface 105f to clip the frame to the body. The frame results in a correct tension to be achieved and maintained in the membrane during assembly of the FCPRV. Additional pre-tensioning may be added using features on the body 110 which result in deflection of the membrane 105 and 155. The coupling of the frame 105e to the valve body ensures the correct tension is maintained, as the membrane need not be stretched to assemble to the valve body. In an embodiment without a frame (for example as shown in FIG. 27B), a membrane may need to be stretched or otherwise deformed to be fitted to the valve body, which can result in a variation in the tension in the membrane once assembled to the valve body, resulting in a variation in performance between different valves. Where ports are provided through the valve member, for example pressure ports 156 and 185 shown in FIG. 27A, the ports may extend through the rigid frame, or through the frame and membrane material overmolded to the frame. Such an arrangement for the ports means the ports do not interfere with the tension of the membrane. An area 105g of the membrane material overmoulded over the frame may form a seal with a chamber wall of the valve, e.g. the sensing chamber or the outlet chamber or displacement chamber.

The relatively rigid frame 105e of the valve member 105 and the sensing member 155 may be formed from any suitably rigid material, such as a metal or a plastic material, such as polycarbonate or other plastics material known in the art. The body 110 is also constructed from a relatively rigid material and may be made from the same material as the frames of the valve and sensing members or other rigid material known in the art. Preferably the housing is also constructed from a relatively rigid material, and may be made from the same material as the valve body or other material known in the art. Parts of the valve, such as the valve membrane or valve body may be formed from a vapour permeable material.

The housing 180 extends outside of a perimeter of the valve member 105 and the annular wall 182 to create a cavity or space 186 (a first space) within the housing and outside of the displacement chamber. In some embodiments, the housing space 186 within the housing 180 surrounds the displacement chamber and the outlet chamber 102. In some embodiments, the housing space 186 within the housing 180 surrounds the displacement chamber 107, outlet chamber 102 and sensing chamber 154. A communication conduit or line 185 may be provided between the displacement chamber 107 and the housing space 186. The space 186 is open to the ambient environment via an aperture 112 and 188. In some embodiments the communication conduit is in direct fluid communication with the ambient environment. In some embodiments, the aperture 112 is coaxial with one of the main inlets and the main outlets. In the illustrated embodiment of FIG. 27a, the aperture in fluid communication with the displacement chamber 107 is coaxial with the main outlet 153, such that the aperture 112 is an annular aperture. In some embodiments the port 185 fluidly connecting the displacement chamber 107 with the housing space 186 extends through the valve member 105 adjacent a perimeter of the valve member 105 and radially inside of the annular wall 182 of the housing 180.

In some embodiments, a communication port or line 156 is provided between the main outlet 153 and the second chamber 154b of the sensing chamber 154. In some embodiments the port 156 fluidly extends through the sensing member 155 adjacent a perimeter of the sensing member 155 and radially inside of the annular wall 182 of the housing 180. The pressure at the main outlet or downstream of the flow restriction or orifice 152 is sensed at position 156a (FIG. 27A). This could equally be at a flow constriction. As this pressure sampling point is in the main gases flow, the pressure sensed by the sensing member 155 in the second chamber of the sensing chamber 154 may experience turbulent/dynamic pressures. The FCPRV may optionally include a baffle to shield port 156 from the main stream of gases to stabilise pressure fluctuations sensed by the sensing member. The FCPRV may optionally include a baffle to shield a flow path from the main gases flow path and the sensing chamber to stabilise pressure fluctuations sensed by the sensing member.

In some embodiments the housing 180 provides a cavity or space 187 (a second space) outside of the outlet chamber 102. Vent outlets 103 may be provided through the wall 106 (shown in FIG. 27A) of the body 110 so that gases passing through the pressure relief valve 100 when the valve member lifts away from the valve seat 104 can vent from the outlet chamber 102 into the housing space 187. The outlet chamber 102 may be a first outlet chamber and the housing space 187 a second outlet chamber, the first and second outlet chambers arranged in series, the venting gases passing through the first outlet chamber and through the second outlet chamber to vent to the surrounding environment. An outlet 188 or outlets from the vent or housing space 187 to the surrounding ambient environment may also be described as vent outlets. The vent outlets 103 and 188 may be tuned to achieve a particular valve characteristic. In some embodiments vent outlets 103 may be sufficiently large compared to the vent outlet 188 so that a substantial pressure drop is achieved at the vent outlet 188, or alternatively, in some embodiments vent outlets 103 may be sufficiently small so that a substantial pressure drop is achieved at the vent outlets 103 from the outlet chamber 102. In some embodiments, the housing spaces 186, 187 described above are joined as a single housing space surrounding the sensing chamber 154, the outlet chamber 102 and the displacement chamber 103. In some embodiments, the housing provides two separate housing spaces 186, 187. In some embodiments the body or housing comprises a shroud or duct 189 extending between the vent outlets 103 and the housing vent outlet 188, to channel gases venting from the outlet chamber to the housing vent outlet 188. The duct may be located with the housing space 186 that is in fluid communication with the displacement chamber. An interior of the duct 189 may provide the housing space 187 into which the gases vent from the outlet chamber. The duct may substantially separate the gases venting from the outlet chamber from the housing space 186 in communication with the displacement chamber. In the illustrated embodiment the duct 189 extends from the body.

In some embodiments, the housing vent outlet 188 from the housing space 187 to ambient is coaxial with one of the main inlets and the main outlets. In the illustrated embodiment of FIG. 27A, the vent outlet 188 is coaxial with the main inlet 151, such that the vent outlet 188 is annular.

In some embodiments, the main inlet and the main outlet are aligned, as best shown in FIG. 27A. As described above, in some embodiments, the displacement chamber outlet 112

(a first housing outlet) and the vent outlet 188 (a second housing outlet) are coaxial with a respective one of the main inlet and the main outlet.

As shown in FIG. 27A, in some embodiments valve includes a bend in the flow path between the main inlet 151 and the valve seat 104. In the embodiment of FIG. 27A the bend is a 90 degree bend. The pressure sensed by the valve member 105 is sampled at a downstream side of the bend, at location 151*a* in FIG. 27A. The bend may reduce turbulent dynamic pressure at the sampling point 151*a* acting on the valve member 105. The sample point 151*a* is out of the main gases flow path 158 which is the straight-through flow path from the main inlet 151 to the main outlet 153.

As described earlier with reference to previous embodiments, the valve member and the sensing member may be coupled by a mechanical link 157. The mechanical link 157 may be a rigid rod or shaft, or a flexible member such as a line or cord. The mechanical link is received in a guide, e.g. tubular guide 181. In the embodiment of FIG. 27A the link is a rigid rod or shaft that slides within the tubular guide 181. In some embodiments, the first chamber 154*a* of the sensing chamber 154 is in fluid communication with the main inlet via the mechanical link guide 181, such that the sensing member can sense the pressure within the main inlet via the mechanical link guide. The guide 181 locates the link 157 and provides fluid communication between the main inlet 151 and the sensing chamber 154*a*. The main inlet or main flow path is in fluid communication with the sensing chamber via an annular space between the link 157 and the link guide 181. The space has a relatively small cross sectional area and also may have a relatively long path, from the main gases flow path to the sensing chamber 154. The small area of the space between the link and the link guide provides a deliberate resistance to flow that impedes the time it takes for pressure fluctuations in the main gases flow path 158 to reach the sensing chamber and sensing member 155. As a result a time constant of the valve response is lengthened, making the valve less responsive to pressure fluctuations which is beneficial in some applications such as CPAP. In some embodiments the link 157 comprises a ribbed outer surface. The ribs create a turbulent flow path to create additional resistance to flow between the inlet and the sensing chamber. The ribs can create resistance to flow due to turbulence while maintaining a reasonable space between the link and link guide, i.e. without requiring a close tolerance fit between the shaft and the shaft guide to create the desired resistance to flow.

Figure 29A:
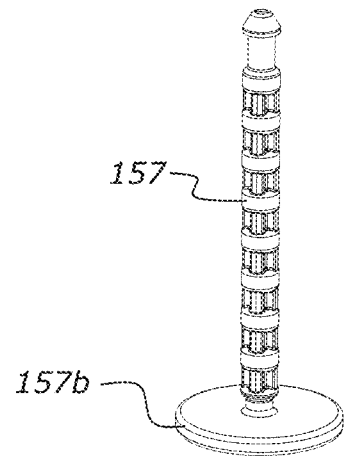
FIGS. 29A and 29B show a mechanical link of the FCPRV of FIGS. 27A and 27B.
Figure 29B:
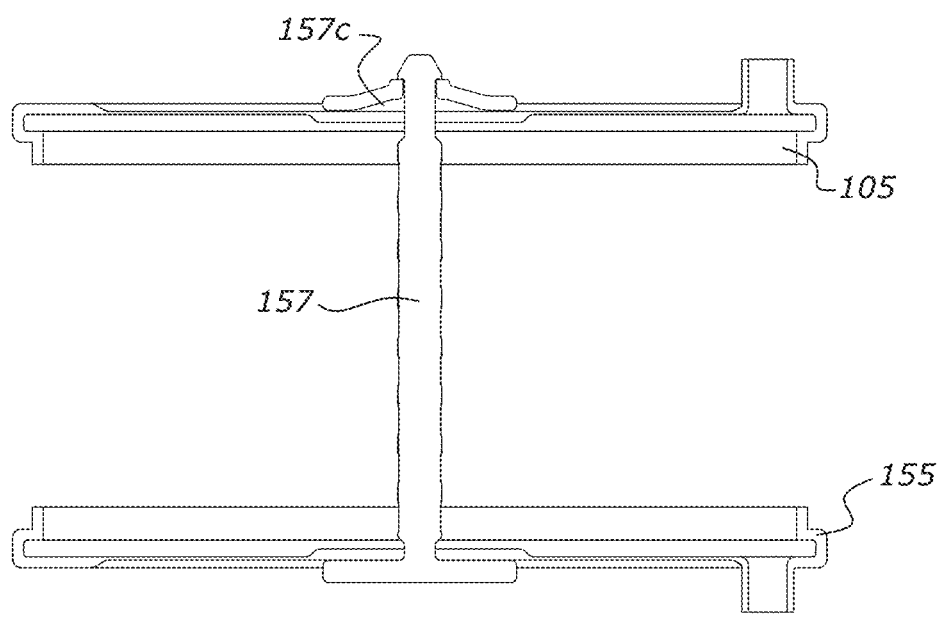

In some embodiments, the mechanical link is a rigid shaft or rod comprising a ribbed structure as shown in FIGS. 29A and 29B. The ribs provide sufficient rigidity to the shaft for a reduced amount of material. A flange 157*b* is provided at one end of the shaft. A locking washer 157*c* or other means to couple the link to the sensing member is provided to the opposite end. The locking washer comprise a number of projections extending inwardly from an outer perimeter portion. A radial inward end of the projections engage an end of the shaft. The washer is retained on the end of the shaft by a shoulder or washer receiving portion. The washer and the flange bear against a respective one of the valve member 105 and the sensing member 155, to couple the two members together, as shown in FIG. 29B. In some embodiments the washer could be overmoulded into the valve member or sensing member, so that the member is clipped to the link. In some embodiments a washer or locking washer may be provided at both ends of the shaft. The washer may provide a flange 157*b* as described below.

Figure 27F:
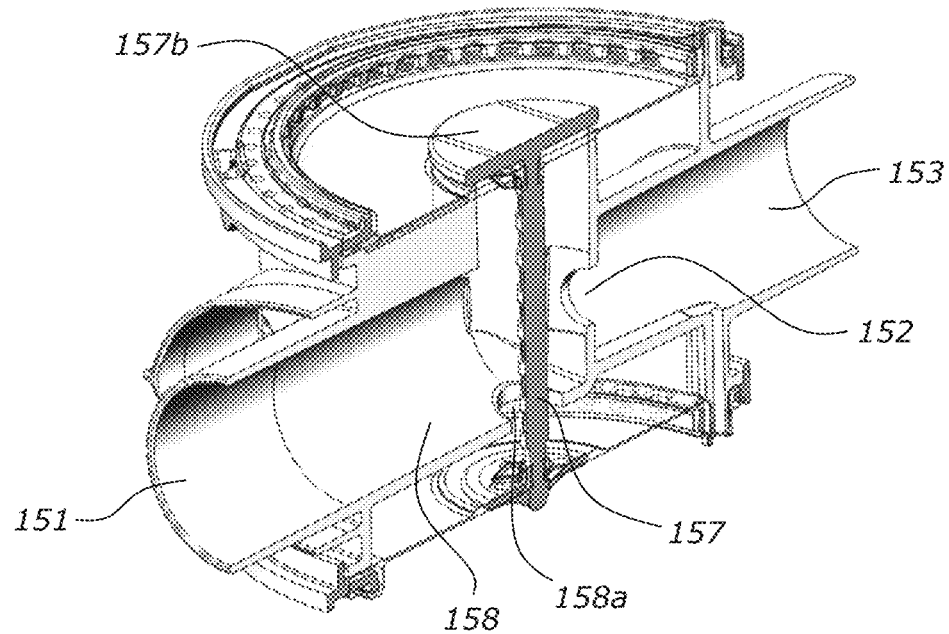
FIG. 27F is a cross sectional view of a valve body, valve member and sensing member assembly for a flow controlled pressure relief valve. The assembly of FIG. 27F has an increased pneumatic coupling between a main flow path and a sensing chamber compared to the assembly of FIG. 27E.

In some embodiments the mechanical link comprises a flange 157*b*, to support the valve member 105 against the valve seat. In some embodiments, as shown in FIGS. 27E and 27F, the flange 157*b* has a diameter that is larger than the diameter of the valve seat so that when the valve member is seated against the valve seat the valve member is supported against the valve seat between the flange and the valve seat. Where the sensing member pulls the valve member against the valve seat the flange supports and pulls the valve member over an area greater than an area defined by the outside diameter of the valve seat, as shown in FIGS. 27E and 27F. The flange acts to maintain a flat area of the valve member over the valve seat. In some embodiments the flange supports the valve member on a side of the valve member opposite to the side that contacts the valve seat 104. In some embodiments the flange may be overmoulded within the valve member. The diameter of the flange may be less than (FIGS. 27A and B), or greater than (FIGS. 27E and F) or equal to the diameter valve seat. In some embodiments, the flange may seat against the valve seat, in which case the flange is part of the valve member.

The embodiment of FIG. 27E comprises a relatively restricted pneumatic coupling between the main gases flow path 158 and the sensing member 155. As described above with reference to FIG. 27A, this provides a damping effect on pressure fluctuations in the main gases flow path 158 reaching the sensing member 155 and therefore provides a stable valve operation. However, in some applications, desirable smaller time constant/faster responding valve may be desirable. A faster response characteristic can be achieved by providing an increased or significant pneumatic coupling between the main gases flow path upstream of the flow restriction (ie the main inlet) and the sensing member 155. FIG. 27E illustrates an embodiment comprising an increased pneumatic coupling between the main gases flow path 158 and the sensing member 155. The FCPRV of FIG. 27F is identical to the embodiment of FIG. 27E but is without the mechanical link guide tube 181. An opening 158*a* is provided between the main inlet or main gases flow path 158 and the sensing chamber through which the mechanical link extends. Thus with the link received through the opening the opening 158 provides an annular space between the main gases flow and the sensing chamber and therefore sensing member. The increased area of the annular space of opening 158*a* compared to the annular space between the link guide 181 and the link in FIG. 27E results in a faster response such that the valve of FIG. 27F responds more rapidly to pressure changes in the main gases flow path 158. Alternatively a guide tube can be provided with a greater clearance between the guide tube 181 and the kink 157. The increased area of the opening 158*a* results in a reduced flow restriction between the main gases flow and the sensing chamber. The resulting faster response valve is particularly useful for use together with a set flow source such as a compressed gas tank or a hospital wall flow meter supply to act as a ventilator, for example the system described above with reference to FIGS. 1F-1, 1F-2 and 1F-3. In faster response valve the system pressure at the FCPRV and therefore also at the patient tends to rapidly change between bi-level pressures P1 and P2 illustrated in FIG. 1F-3. The valve thus configured advantageously provides a very low cost, portable ventilator that may be useful in circumstances where a conventional ventilator is not available, for example in ambulance transit, mass patient events where a limited number of conventional ventilators may be available, in field hospitals, and in developing countries.

In the embodiment of FIG. 27F, the flow restriction between the main gases flow 158 and the first chamber 154a of the sensing chamber 154 is reduced, to increase the pneumatic coupling between the main gases flow and the first chamber. Alternatively or in additionally, pneumatic coupling between the main gases flow 158 and the sensing chamber 154 may be increased to achieve a faster response valve by increasing the pneumatic coupling between the main gases flow 158 and the second chamber 154b of the sensing chamber 154. For example, the area of the pressure port 156 between the main flow path 158 and the second chamber 154b may be increased and/or the length of the pressure port 156 may be reduced. An faster response valve may also be achieved by increasing the area of the pressure port 185 from the displacement chamber 107 or by reducing the volume of the first and/or second chambers of the sensing chamber.

Various FCPRV embodiments have been described above. A valve body 110, valve member 105 and sensing member 155 for two preferred embodiments are illustrated in FIGS. 27E and 27F. For these embodiments some exemplary approximate valve dimensions are provided below.

Valve seat diameter 20 mm/PRV inlet tube 101 area 315 mm2 (i.e. the area of the valve member 105 exposed to the inlet pressure Pc when the valve member is seated against the valve seat 104).

Valve member and sensing member 0.3 mm thick rubber material, e.g. elastic modulus of about 0.1 GPa (e.g. silicone rubber).

Valve member and sensing member diameter of about 60 mm.

Valve member bias against valve seat of about 1 mm.

Sensing member bias of about 1 mm, i.e. with valve member against valve seat, sensing member will be displaced by about 1 mm.

Flow restriction orifice 152 area 37 mm2.

Outlet vent aperture 103 80 mm2 (for example two holes, each 40 mm2) in flow direction.

Figure 30:
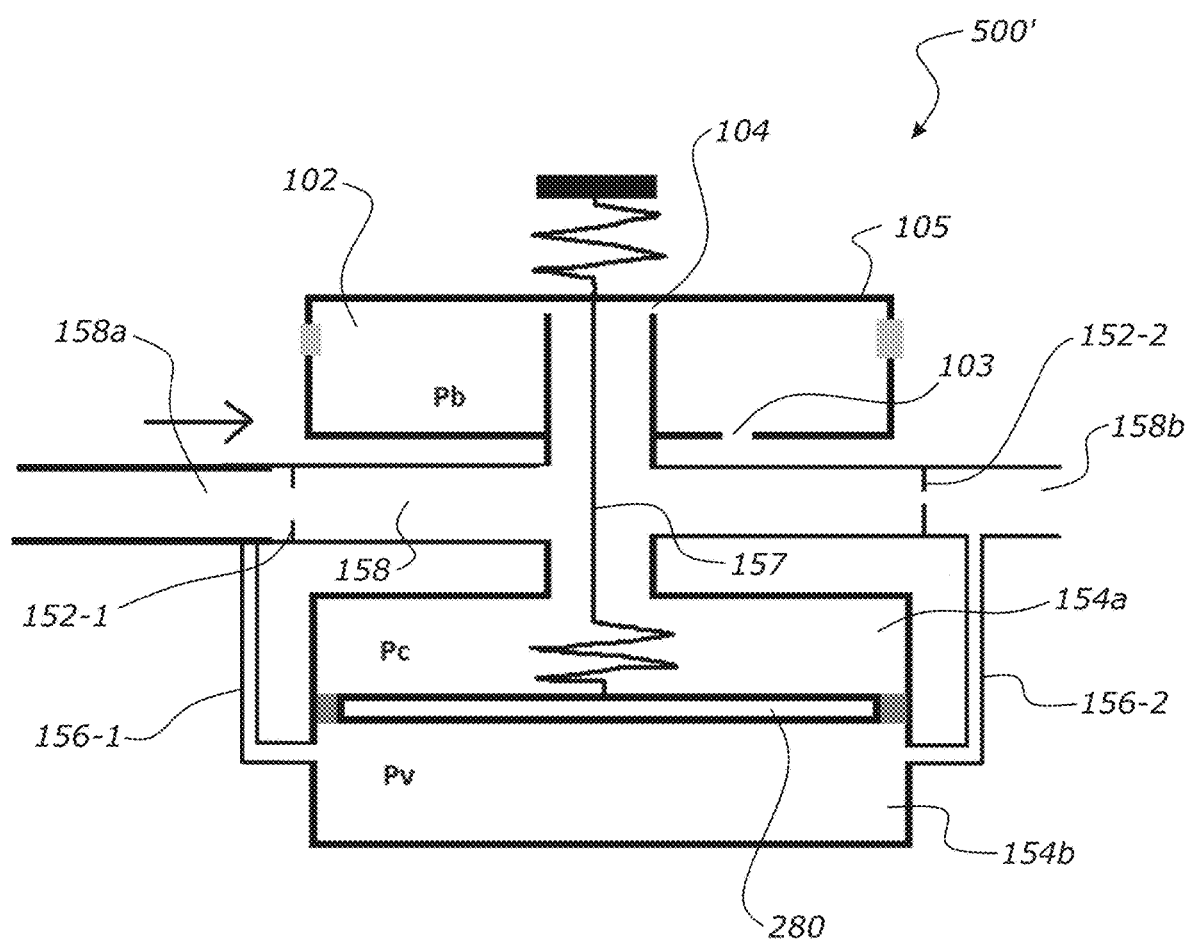
FIG. 30 shows a free-body diagram of another FCPRV that is adapted to be reversible.

In some embodiment the FCPRV may be configured to be reversible, so that the FCPRV may be connected in a system in a first configuration with a first connection of the main flow path 158 as the inlet 151 and a second connection of the main flow path 158 as the outlet 153, and in a second configuration with the first connection of the main flow path 158 as the outlet 153 and the second connection of the main flow path 158 as the inlet 151. As shown in FIG. 30, the FCPRV is connected with a first connection 158a of the main flow path 158 connected in a system as the main inlet 151. A second connection 158b of the main flow path 158 is connect as the main outlet 153. The reversible valve 500' is provided with a first pressure port or communication line 156-1 between the first connection 158a of the main flow path and the sensing chamber 154b and a second pressure port or communication line 156-2 between the second connection 158b of the main flow path 158 and the sensing chamber 154b. The reversible FCPRV is also provided with a first flow restriction 152-1 (e.g. orifice or venturi) adjacent the first connection 158a of the main flow path 158 and a second flow restriction 152-2 (e.g. orifice or venturi) adjacent the second connection 158b of the main flow path 158. An inlet conduit and an outlet conduit of the system are adapted so that when the inlet conduit is attached to the main flow first connection 158a or the main flow second connection 158b, the first pressure port 156-1 or the second pressure port 156-2 is blocked by the inlet conduit. Alternatively, the FCPRV may be provided with a connector 168 to be optionally fitted to either the main flow path first connection 158a or the main flow path second connection 158b to block the respective pressure port 156-1 or 156-2 and configure the first connection 158a or second connection 158b as the inlet 151 to the main flow path. The other one of the first and second main flow connections 158a, 158b is configured as the main outlet 153, with the respective first or second pressure port 156-1, 156-2 unblocked. For example, when the inlet conduit or connector 168 is connected to the first main flow connection 168a as shown in FIG. 30, the first pressure port 156-1 is blocked, a pressure drop at the first restriction 152-1 is not sensed by the sensing member 280. The sensing member 280 senses a pressure differential via the second pressure portion 156-2 adjacent the main flow connection 158b configured as the main outlet 153. Where the system conduits are configured as inlet and outlet conduits such that the inlet conduit blocks the pressure ports 156-1, 156-2 and the outlet conduit does not block the pressure ports 156-1, 156-2, the FCPRV may be fitted either way round in the system and achieve the same performance characteristics, where the FCPRV is configured to have the same flow path from the first connection 158a to the valve seat 104 and from the second connection 158b to the valve seat 104 (i.e. with the first and second flow restrictions 156-1, 156-2 identical). Such an arrangement avoids inadvertently connecting the FCPRV in a system the wrong way around. Alternatively, the FCPRV may be configured to provide different characteristics depending on the direction of main flow through the valve. For example, in the embodiment of FIG. 30, the first flow restriction 156-1 may be different to the second flow restriction 156-2, such that the direction of connection of the valve optionally selects the first or second flow restriction to be sensed by the sensing member. The reversible valve illustrated in FIG. 30 reflects the embodiment of FIG. 21 comprising a piston sensing member 280. However, the reversible configuration comprising first and second restrictions 152-1, 152-2 and first and second pressure ports 156-1, 156-2 described with reference to FIG. 30 may be implemented any in a FCPRV according to any of the embodiments described herein, for example a FCPRV comprising a membrane sensing member 155.

In some embodiments, the FCPRV is provided with a tube or conduit, for example a conduit to provide a flow of gases from the FCPRV to the patient. The conduit may be permanently attached to the FCPRV. By providing the FCPRV together with a conduit, the risk of inadvertently connecting the FCPRV the wrong way around in a system is reduced.

In some embodiments a PRV or FCPRV as described herein may be adapted for use in a system comprising a humidifier, and/or may be located in a system near to a patient. Thus in some applications, condensate from humidified gases or a patient's breath may accumulate in the PRV or FCPRV. In order to reduce or prevent the accumulation of condensate, in some embodiments the PRV or FCPRV may comprise a heater to heat the device or parts of the device to reduce or eliminate condensate forming in the PRV or FCPRV. For example, the valve body 110 may be heated by an electrical heater, such as a wire or other resistive element provided to or in the body. The valve may comprise a water trap or other mean to remove condensate. In some embodiments the PRV or FCPRV may be used in a system without a humidifier.

In a further alternative embodiment, a FCPRV may comprise a sensing mechanism that is an electrical sensing device, comprising one or more electronic sensors to detect the flow rate (e.g. a pressure drop across a flow restriction or flow through the restriction) of gases flowing from the main inlet to the main outlet of the FCPRV. Some examples of sensors that may be suitable are hot film sensors or ultrasonic sensors, or any other suitable sensor, including the use of pressure sensors or a differential sensor to measure flow via an orifice or venturi. An electrical controller/processor that receives a signal from the sensor(s) may provide an output to drive an actuator to control a PRV of the FCPRV to adjust the relief pressure threshold of the PRV of the FCPRV. For example, the actuator may compromise a servo that drives a member such as the link 157, 257 attached to a valve member 105, 205 of the PRV to adjust an amount of bias of the member 105, 205 towards a valve seat 104, 204 of the PRV. A solenoid may be controlled to move the valve member.

Various PRV and FCPRV embodiments have been illustrated with circular valve and sensing members. However, other shapes may be desirable to achieve desired characteristics.

Figure 31A:
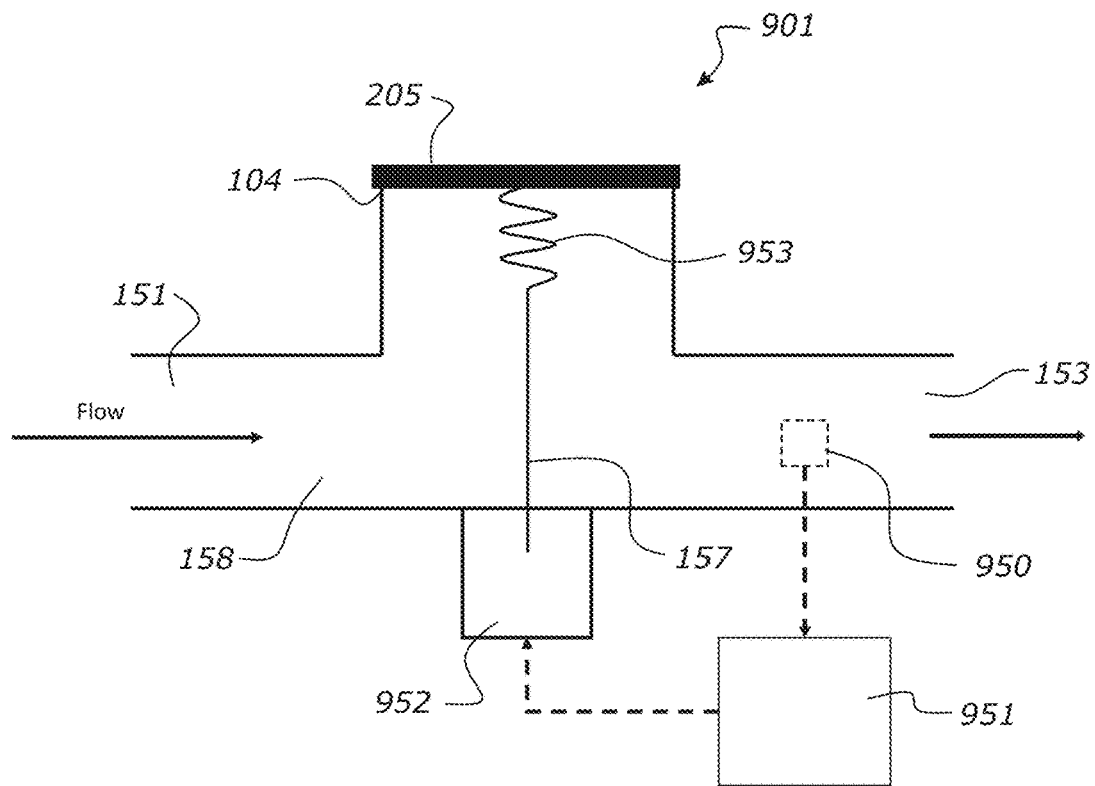
FIGS. 31A and 31B are schematic representations of an electro-mechanical FCPRV.
Figure 31B:
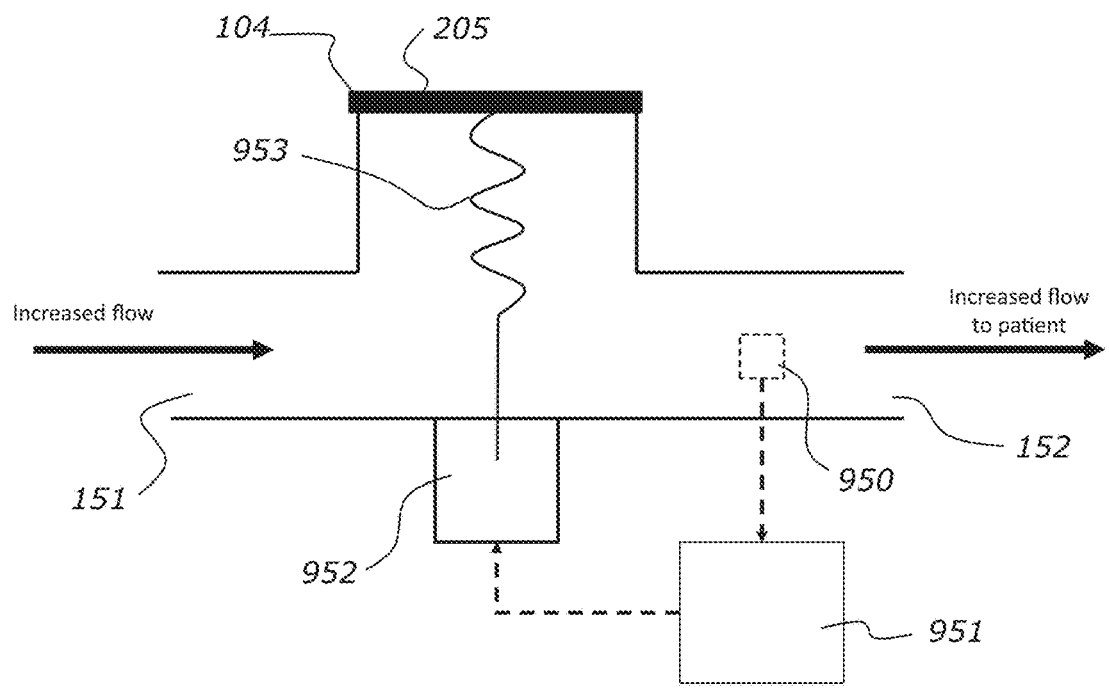

FIGS. 31A and 31B illustrate a FCPRV 901 comprising an electrical sensing device. The electrical sensing device comprises a flow and/or pressure sensing arrangement 950, a processor or controller 951 (e.g. digital and/or analogue electronics and/or electro-mechanical devices) and an actuator 952. The sensing arrangement may comprise a venturi and first and second pressure sensors to measure the flow at the venturi throat and adjacent the venturi throat, or may comprises an orifice with an upstream and a downstream pressure sensor, or any other flow sensing arrangement known in the art. The controller 951 receives a signal from the sensor 950 and controls the actuator 952 to vary an amount of force or load applied to the valve member 205 (ie a plunger) against the valve seat 104, for example via a mechanical link 157 based on the flow rate of gases flowing through the main outlet 153. In the embodiment of FIGS. 31A and 31B, the valve member is a plunger adapted to bear against the valve seat 104. The actuator may be connected to the valve member 205 via a biasing member or element 953, for example a spring 953. The actuator may be driven by the controller to adjust the amount of bias provided by the biasing member 953 to adjust the pressure required to lift the valve member 205 off the valve seat 104 depending on the flow rate determined by the controller from the signal provided by the sensor 950. FIG. 31B illustrates the actuator driven to increase bias by elongating the biasing member 953, to increase the relief pressure of the PRV. The coupling member 157 may also be rigid, whereby the actuator directly opens and closes the valve member. In such an embodiment, the sensor measures both pressure and flowrate and opens the vent valve based on a relationship between pressure and flow rate; for a measured flow rate and measured pressure, the valve will open a predetermined amount, to control the pressure at the patient to achieve a characteristic illustrated in FIG. 15B.

Figure 32A:
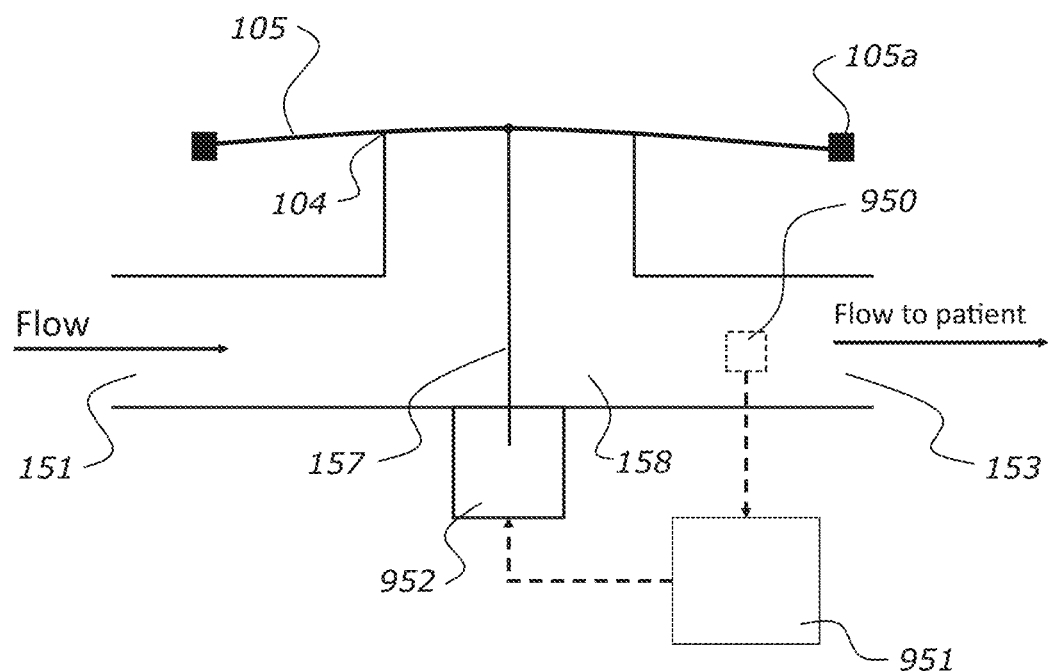
FIGS. 32A and 32B are schematic representations of another electro-mechanical FCPRV.
Figure 32B:
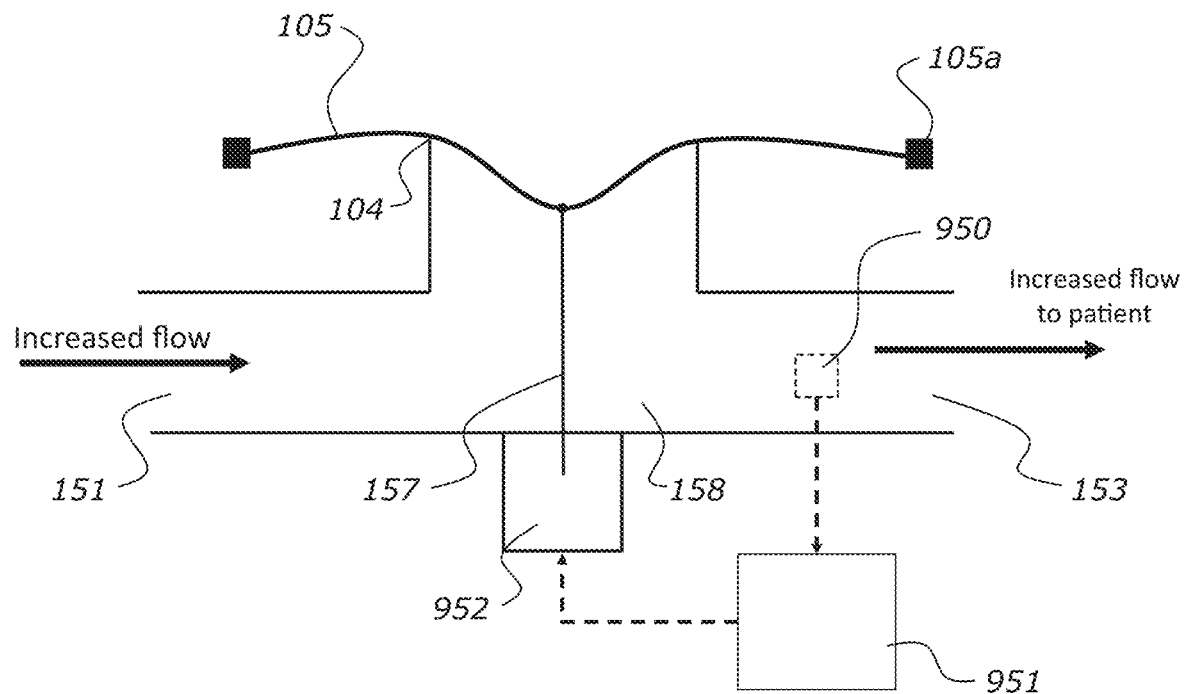

FIGS. 32A and 32B illustrate a FCPRV comprising an electrical sensing device. The electrical sensing device comprises a flow and/or pressure sensor 950, a processor or controller 951 (e.g. digital and/or analogue electronics) and an actuator 952. The controller 951 receives a signal from the sensor 950 and controls the actuator 952 to vary an amount of force or load applied to the valve member 105 against the valve seat 104, for example via a mechanical link 157. In the embodiment of FIGS. 32A and 32B, the valve member 104 is flexible diaphragm adapted to bear against the valve seat 104. The actuator may be driven to adjust the amount of force or load applied to the valve member to vary an amount of flex in the flexible diaphragm as it is pulled against the valve seat, to adjust the pressure required to lift the valve member 105 off the valve seat 104 depending on the flow rate determined by the controller from the signal provided by the sensor 950. Bias against the valve seat is provided by the resiliency of the flexible diaphragm. FIG. 32B illustrates the actuator driven to increase bias by pulling the diaphragm against the valve seat 104.

Figure 33A:
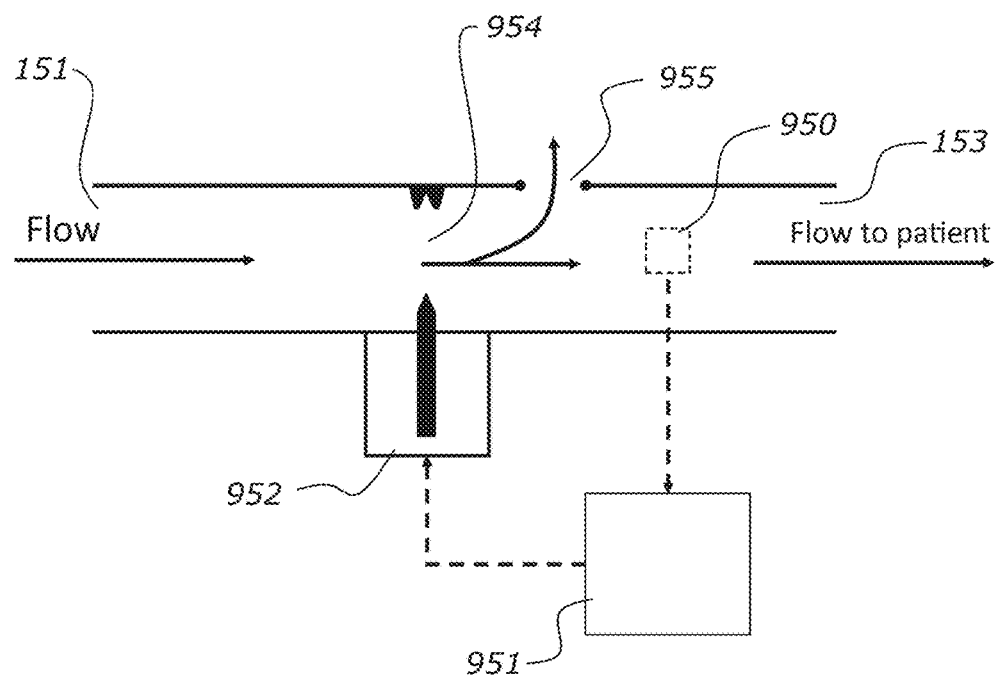
FIGS. 33A and 33B are schematic representations of another electro-mechanical FCPRV.
Figure 33B:
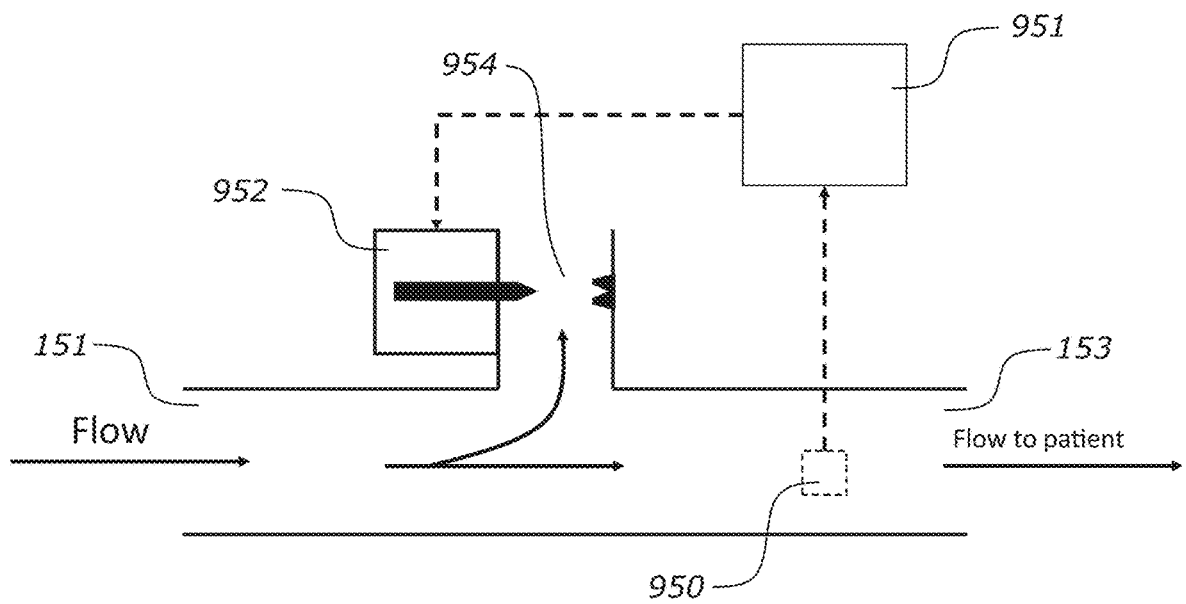

FIGS. 33A and 33B illustrate flow controlled pressure regulating devices that control the pressure at the patient to a safe level based on a relationship between pressure and flow rate provided to the patient. The devices each comprises an electrical sensing device. The electrical sensing device comprises a flow and pressure sensor(s) 950, a processor or controller 951 (e.g. digital and/or analogue electronics) and an actuator 952. The controller 951 receives a signal from the sensor 950 and controls the actuator 952 to vary the size of a restriction or opening/orifice to adjust the amount of flow to the patient. The sensor 950 is located downstream (ie on a patient side) of the variable flow restriction 954 (e.g. a valve), to provide an indication of pressure relative to the patient. Turbulent may occur after the variable restriction or valve 954. To reduce the effect of turbulence on the sensing device 950 baffles or vanes may be provided and/or the sensor may be located sufficiently downstream of the variable flow restriction/valve. In FIG. 33A the variable flow restriction 954 is in the main flow path from the main inlet 151 to the main outlet 153. If a flow restriction is introduced to the system downstream of the variable restriction 954 (or in the patient's nares for example), the controller senses an increased pressure for a given flow rate and may reduce the flow restriction 954 by moving the actuator 952 to increase the size of the orifice or opening 954 to maintain a set flow rate through the system (e.g. as indicated by the vertical line in the chart of FIG. 15B). If a restriction to flow results in a pressure at the device reaching a pressure limit based on a pressure vs flow relationship (i.e. curve 142 in FIG. 15B), the controller may then begin to increase the flow restriction 954 by moving the actuator 952 to decrease the size of the orifice or opening, to limit the pressure at the device and therefore the flow rate and pressure at the patient (i.e. the flow restriction controlled so that the pressure and flow at the device is at point 3 in FIG. 15B). Thus the valve or variable flow restriction 954 is controlled based on a relationship between pressure and flow rate. An additional vent 955 may be used to reduce the pressure in the outlet tube in the case of a fast blockage which the actuator cannot respond fast enough.

In FIG. 33B, the variable flow restriction 954 is in a vent path to vent a portion of flow from the system. If a flow restriction is introduced to the system downstream of the valve or variable restriction 954, the controller senses an increased pressure and reduces the flow restriction 954 by moving the actuator 952 to increase the size of the orifice or opening 954, to vent flow from the system, to maintain a maximum set pressure at the pressure regulating device and therefore the patient. Thus, the valve or variable flow restriction 954 is controlled based on a relationship between pressure and flow rate. In some embodiments, the device of FIG. 33A may comprise a second actuator and valve 954 to control a flow rate of gases venting from the aperture 955. For example, the vent aperture 955 in FIG. 33A may be controlled by a valve arrangement as shown in FIG. 33B. A controller may control the (first) actuator and valve to occlude the flow from the main inlet to the main outlet as shown in FIG. 33A, and the second actuator and valve to control a vent flow from the aperture 955 downstream of the first valve, as shown in FIG. 33B. The first valve may be controlled as described above, however, in an event the first valve is unable to respond to a quick pressure increase, the second valve can operate to vent flow and pressure.

Figure 34A:
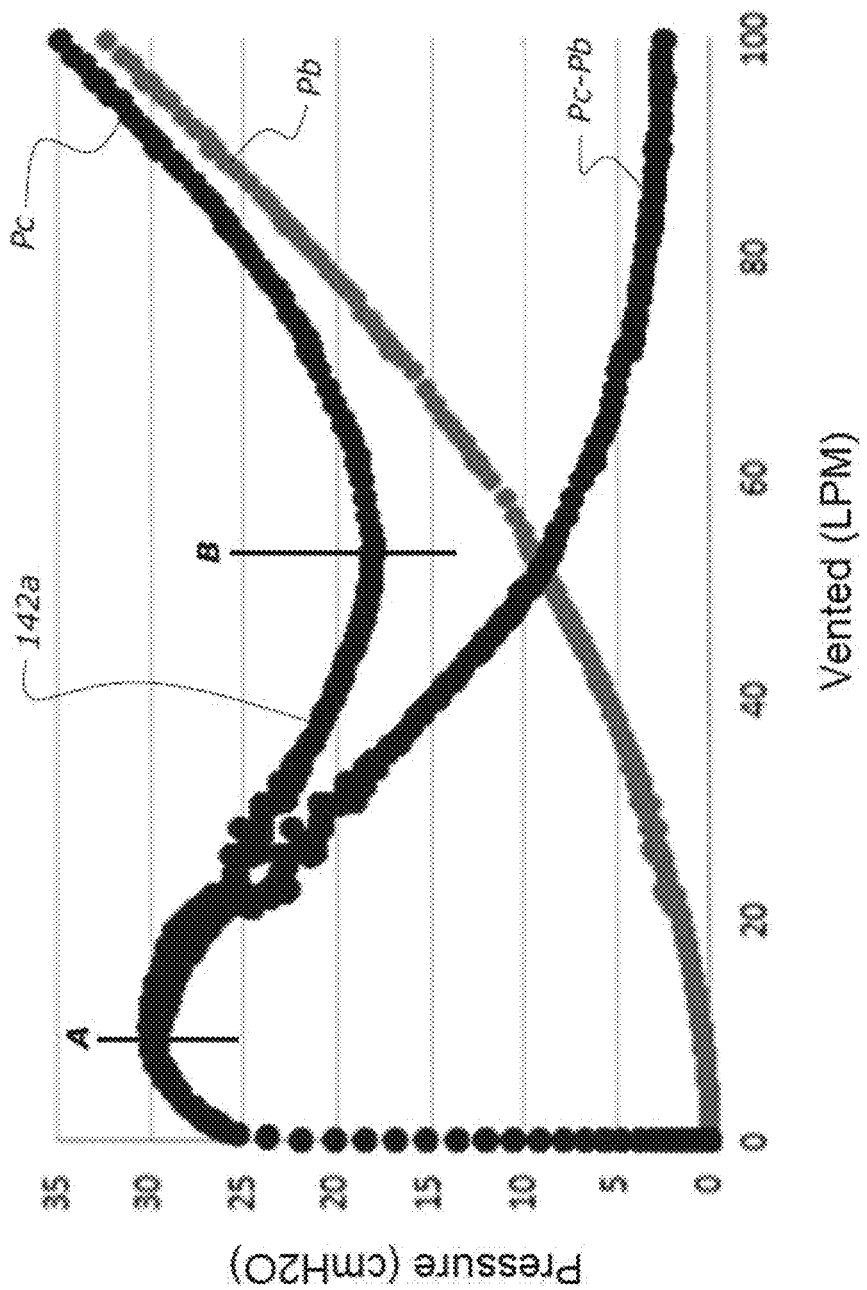
FIG. 34A shows a chart of the inlet pressure and outlet chamber pressure of a PRV vs venting flowrate through a PRV tuned to be used as a flow compensating PRV.

Various embodiments of FCPRV's comprising a sensing mechanism to adjust the relief pressure of the valve dependent on flow rate have been described. However, a PRV without a flow sensing mechanism, for example embodiments described above with reference to FIGS. 2A to 12E, may be configured to operate as a flow compensating pressure relief valve for a fixed input flow. With reference to the chart of FIG. 34A, a PRV may be tuned to have a 'knee', as described earlier with reference to FIGS. 3 to 8. From the knee in the Pc curve, the Pc pressure reduces for increases venting flow rate, for example between points A and B in FIG. 34A. As the flow rate to the patient is equal to the flow rate to the PRV minus the venting flow rate, the negative gradient of the venting flow rate curve between points A and B corresponds to a positive gradient for flow to the patient in the same pressure band (which in the example is approximately 18cmH$_2$O to about 30cmH$_2$O).

Figure 34B:
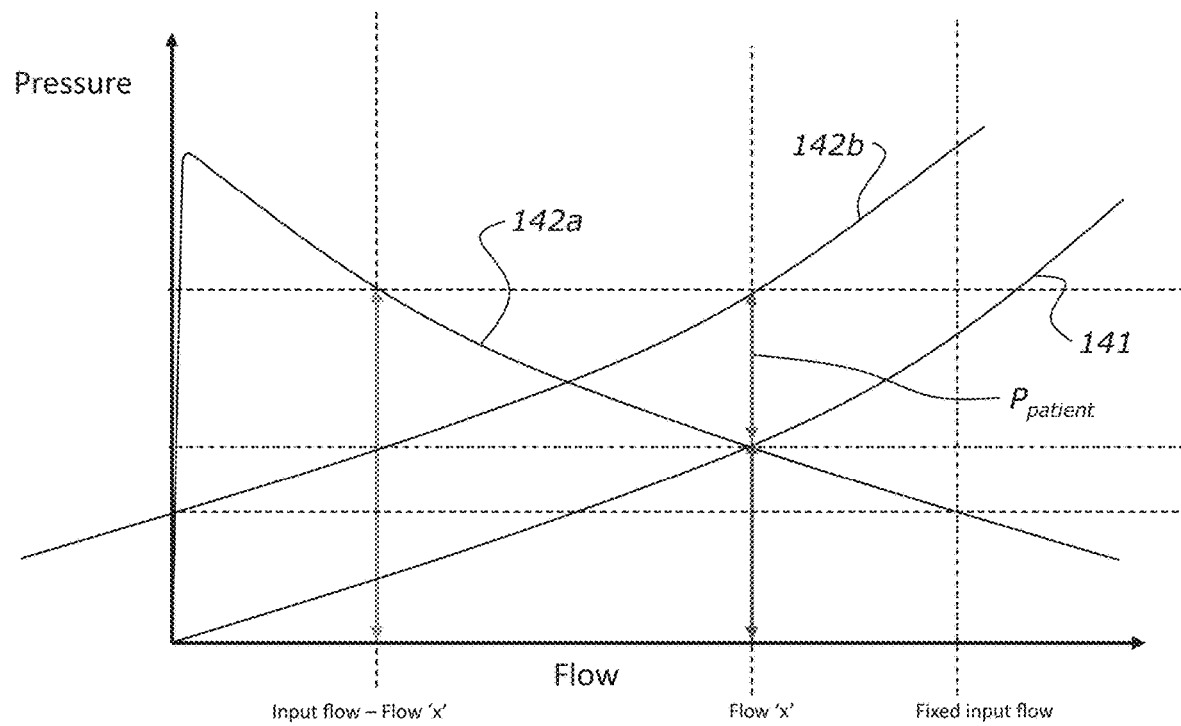
FIG. 34B presents shows system pressure (drop) vs flow rate curve and a relief pressure vs flow rate curve for a PRV tuned to be used as a FCPRV. The horizontal axis is flow delivered to a patient downstream of the PRV inlet.

FIG. 34B illustrates a relief pressure flow curve 142b for flow to the patient, which is the flow rate to the PRV minus the venting flow curve 142a for the PRV. Thus, as the system pressure Pc at the valve increases for flow to the patient, the relief pressure 142b also increases. The PRV is tuned so that the valve is continually venting in the operating range for the valve, thus the system pressure Pc at the PRV is equal to the venting pressure 142b at the PRV. The pressure to the patient for any flow rate to the patient is equal to the venting pressure Pc (curve 142b) minus the system pressure drop from the PRV to the patient at that flow rate (curve 141), i.e. the offset between curve 142b and curve 141. For a known system resistance to flow 141 and a fixed input flow, it is possible to design a required valve response to achieve a driving pressure 142a required to vent excess flow to achieve a safe patient pressure. The venting pressure 142b for a given flow rate x to the patient is equal to the system resistance to flow 141 at that flow rate plus the safe patient pressure Ppatient. The patient pressure for a given flow rate to the patient can be determined as the venting pressure 142a for a venting flow rate (the flow rate equal to the input flow rate minus the patient flow rate) minus the system resistance to flow at the patient flow rate.

Figure 35A:
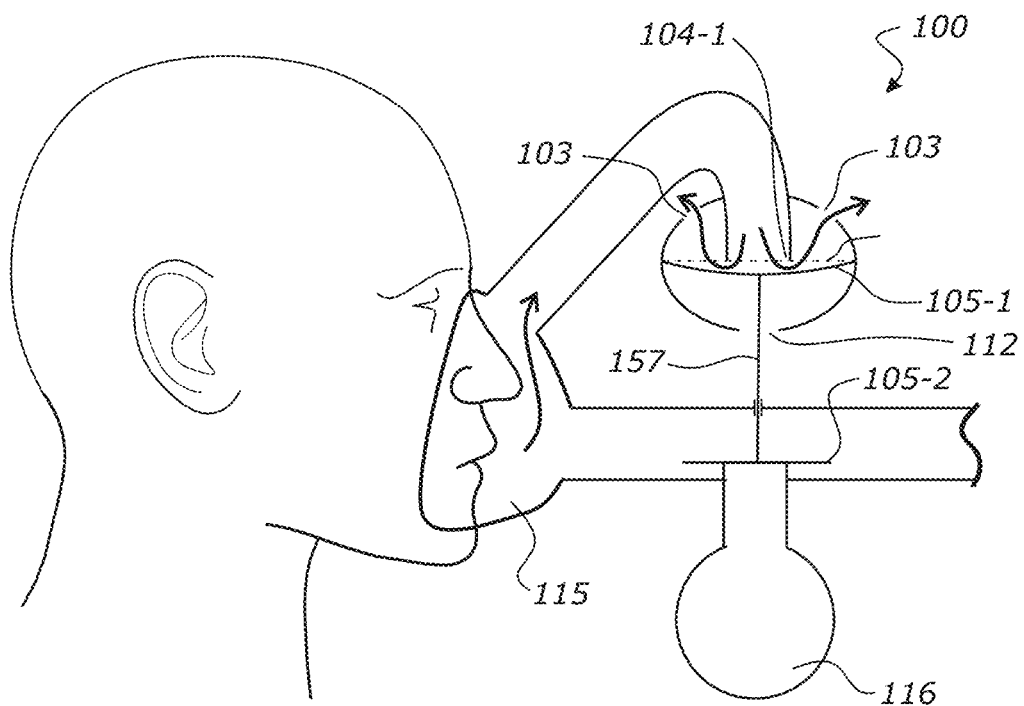
FIGS. 35A and 35B are schematic representations of a pressure relief valve arranged to vent expired respiratory gases and to control the opening and closing of a nebulizer port providing medication into a flow of gases to a patient.
Figure 35B:
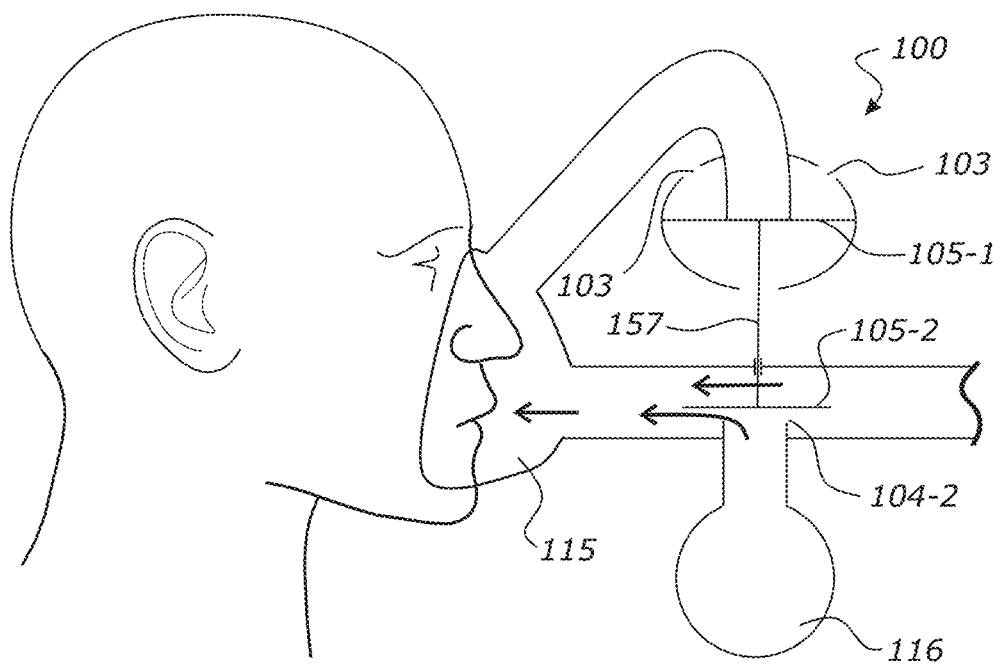

Various embodiments for a PRV 100 have been described above for venting pressure from a flow of gases being provided to a user via a patient interface. A further use and arrangement for a PRV according to embodiments described herein is illustrated in FIGS. 35A and 35B. As illustrated, the valve member 105-1 of the PRV 100 is coupled via a mechanical link 157 to a second valve member 105-2. The second valve member 105-2 is arranged to seal a port of a nebulizer 116 located within a respiratory flow of gases to the patient. As illustrated in FIG. 35A, when the patient breaths out, expired gases flow from the patient interface 115 through the PRV 100 to vent from the vent outlets 103 of the PRV 100. When venting expired gases through the PRV 100, the valve member lifts off the valve seat 104 and the displacement of the valve member 105-1 holds the second valve member 105-2 against a valve seat 104-2 of the nebuliser 116. Thus as the patient exhales, medicament provided by the nebuliser 116 is sealed from being released into the flow of gases to the patient. As shown in FIG. 35B, when the patient inhales, the PRV is in the closed or non-venting configuration with the valve member 105-1 against the valve seat 104-1. The displacement of the valve member 105-1 against the valve seat 104-1 lifts the second valve member 105-2 off the nebuliser valve seat 104-2 so that medicament is released from the nebuliser 116 into the flow of gases being provided to the patient via the patient interface 115. The above arrangement therefore prevents venting medication to atmosphere and therefore prevents medication being wasted.

In some embodiments the PRV (e.g. PRV 100) or FCPRV (e.g. FCPRV 800) comprises a vent indicator to indicate when flow if venting from the PRV or FCPRV via the outlet chamber 102 and outlet vents 103. A number of vent indicator embodiments are described below with reference to FIGS. 36 to 40.

Figure 36:
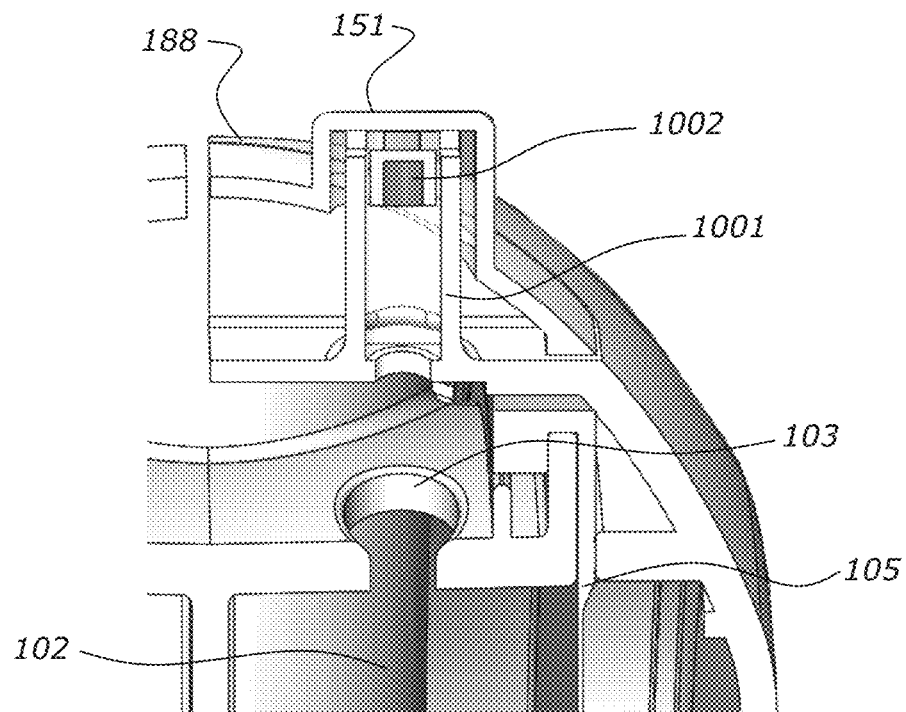
FIGS. 36 to 40 illustrate venting flow indicators that may be implemented in one or more of the PRV or FCPRV embodiments described.

In some embodiments, as illustrated in FIG. 36, the FCPRV compromises a guide or sight tube 1001 and a shuttle 1002 that moves along the tube 1001 in response to a flow of gases exiting the outlet chamber 102. The tube 1001 may be aligned with outlet vent aperture 103. When the shuttle moves with flow through the vent aperture 103 the shuttle becomes visible from an outside of the housing 180, e.g. via a clear portion of the housing and/or sight tube.

Figure 37:
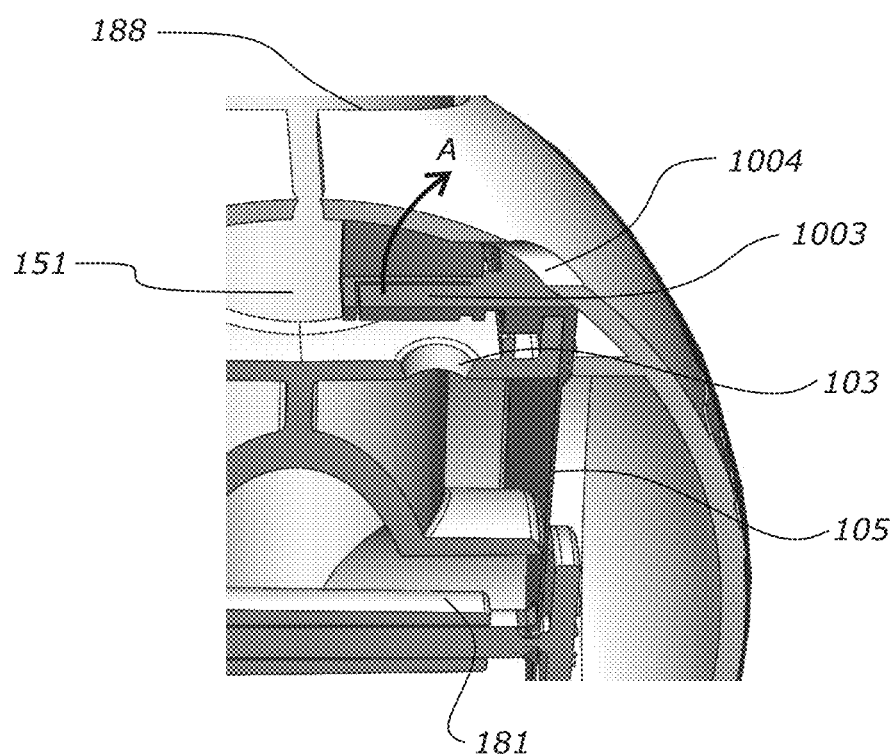

In some embodiments, as illustrated in FIG. 37, the FCPRV compromise a flap 1003 that moves about a hinge axis in response to a flow of gases exiting the outlet chamber 102, e.g. in the direction indicated by arrow A. The flap 1003 is located adjacent to or in proximity to the outlet vent 103. The housing may have a sight aperture 1004 so that when the flap bends in response to flow from the vent 103 the flap covers the sight aperture to be visible from the outside of the housing. Through the aperture 1004 the flap shows as a coloured 'dot' when in the bending or venting configuration.

Figure 38:
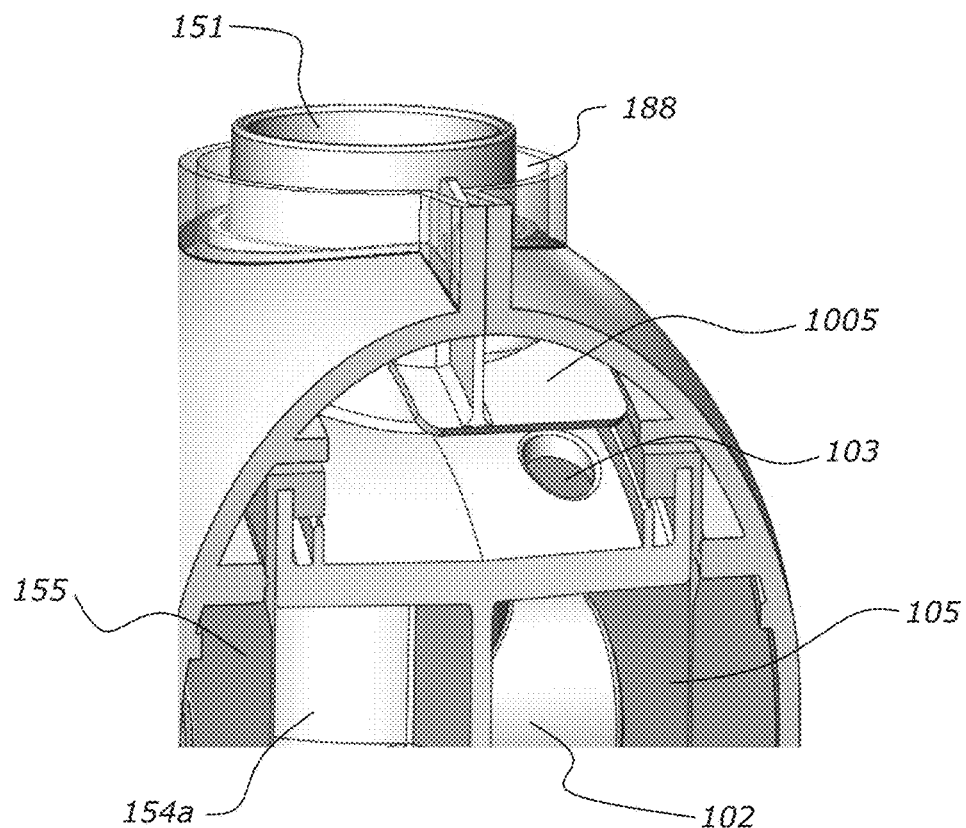
Figure 39:
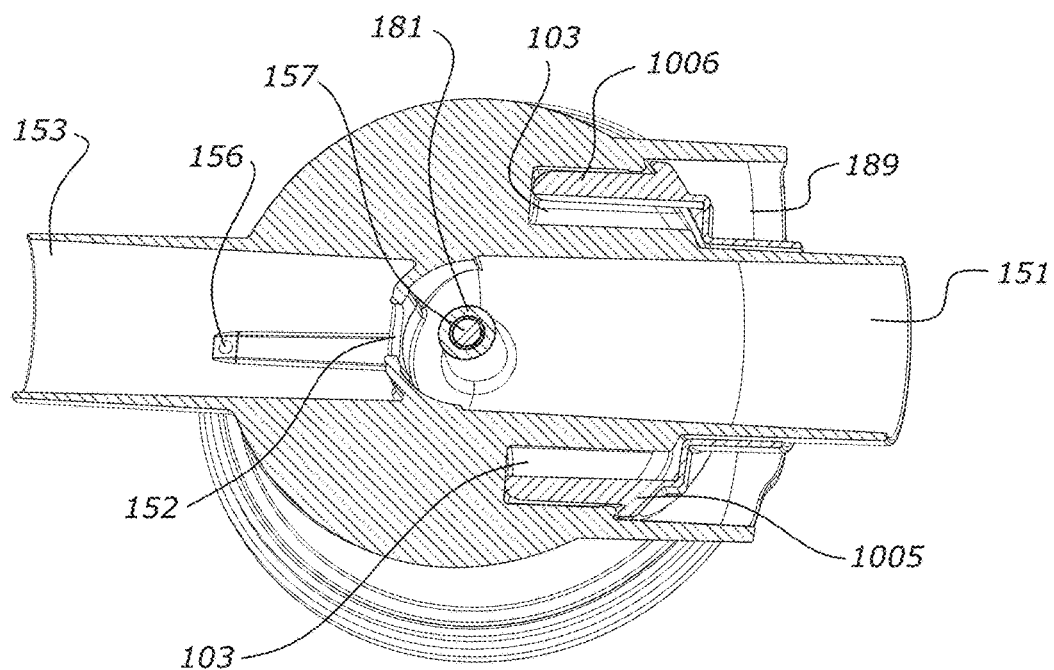

In some embodiments, as illustrated in FIG. 38, the FCPRV comprises a plunger or shuttle received in a guide to move in response to a flow of gases exiting the outlet chamber 102. The shuttle 1005 may comprise an annular portion or cuff received in the housing outlet 188, e.g. coaxially received in the housing outlet 188. The annular housing outlet 188 may guide the shuttle. In a venting configuration the shuttle moves to be visible from an outside of the housing, e.g. may extend external from the housing, or may become visible through a clear portion of the housing. For example the housing outlet 188 may be clear. A remainder of the housing may be opaque. FIG. 39 illustrates a similar embodiment comprising a shuttle 1005 that moves in response to gases exiting the outlet chamber, In the embodiment of FIG. 39, the shuttle comprises a member receive in the outlet chamber vent outlet 103, for example there are two elongate members 1006, each elongate member received in a respective vent outlet 103.

Figure 40:
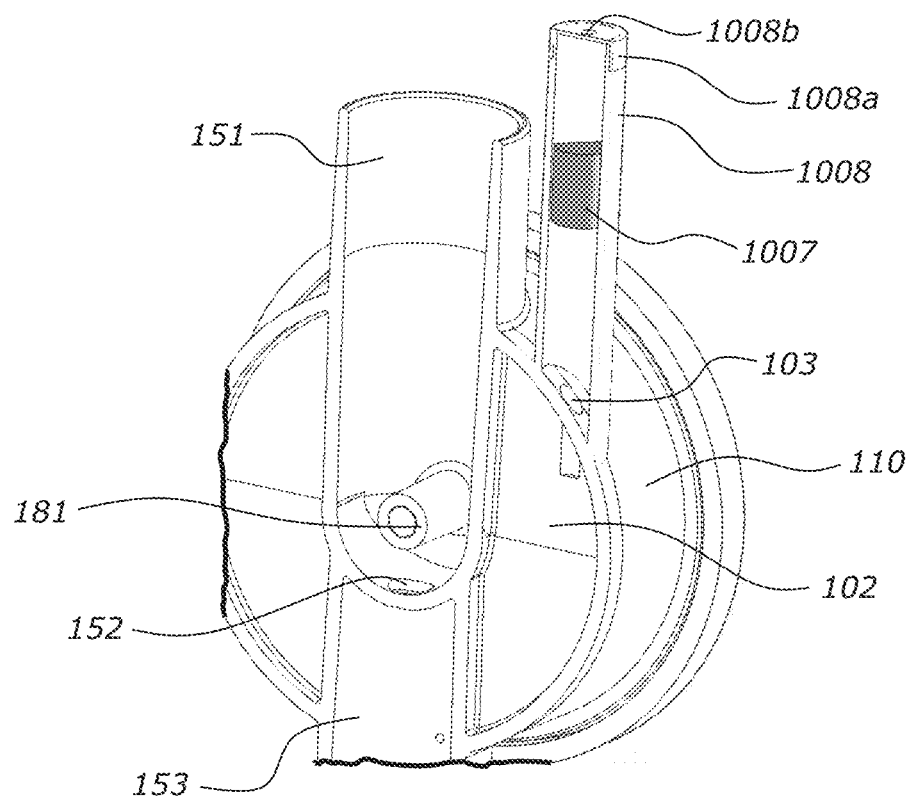

In some embodiments, as illustrated in FIG. 40, the FCPRV comprises a plunger or shuttle 1007 received in a guide, e.g. guide tube 1008, to move in response to a pressure in the outlet chamber. The pressure in the outlet chamber 102 is proportional to the flow of gases venting from the outlet chamber and is thus an indication of the rate of gases venting from the FCPRV. When the shuttle moves along the guide it becomes visible from an outside of the housing 180, e.g. via a clear portion of the housing and/or sight tube/guide 1008. As shown in FIG. 40, the guide tube may be marked with a scale relating the position of the shuttle along the guide tube to a flow rate. An annular space may be formed between an outer surface of the shuttle and an inner surface of the guide 1008. Venting gases may enter the sight tube 1008 through the outlet vent 103 and travel along the guide and around the shuttle 1007 and exit the guide via an outlet end of the tube. A cap 1008a may be fitted to the outlet end of the tube, the cap comprising a hole or aperture 1008b. The hole may be smaller than the cross section of the guide 1008, and may be sized to calibrate the shuttle to indicate the flow rate of the venting gases.

In the venting indicator arrangements described may provide a binary indication of a venting flow from the PRV/FCPRV, e.g. indicating venting or no venting (above a threshold). Such an arrangement may be described as a 'pop-up' indicator, comprising a member that 'pops up' to be visible from outside of the housing when flow is venting from the valve. Alternatively in some embodiments a venting indicator may provide a proportional indication of venting, indicative of the rate of flow of gases venting from the outlet chamber. For example the housing or shuttle guide 1001, 1008 or portion of a housing 180 may comprises a marking or indicia indicating an amount of travel of the shuttle that is indicative of the venting flow rate.

Figure 41A:
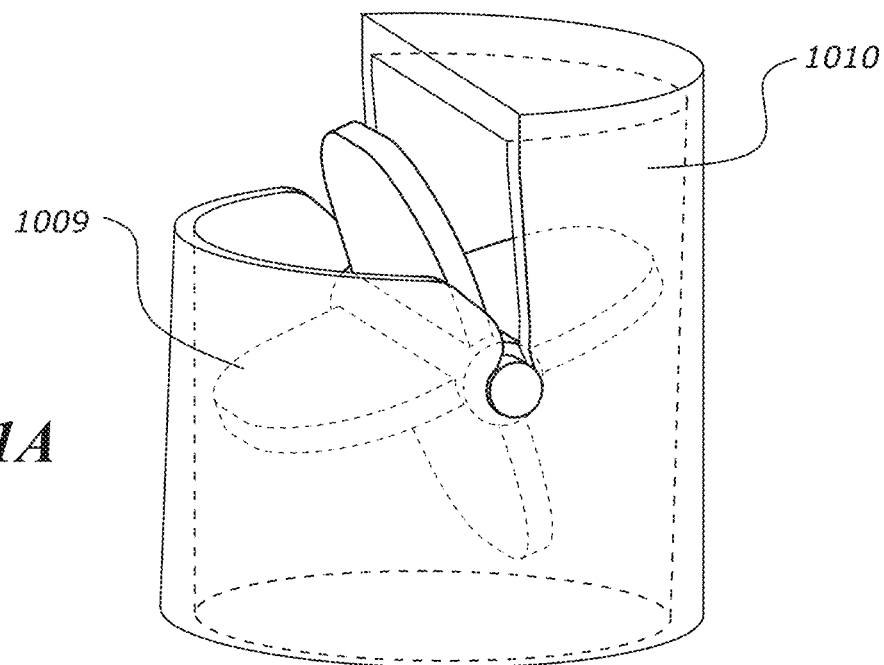
FIG. 41A illustrates an impeller flow indicator and FIG. 41B illustrates a FCPRV comprising an impeller in an outlet to indicate flow from the outlet of the FCPRV.
Figure 41B:
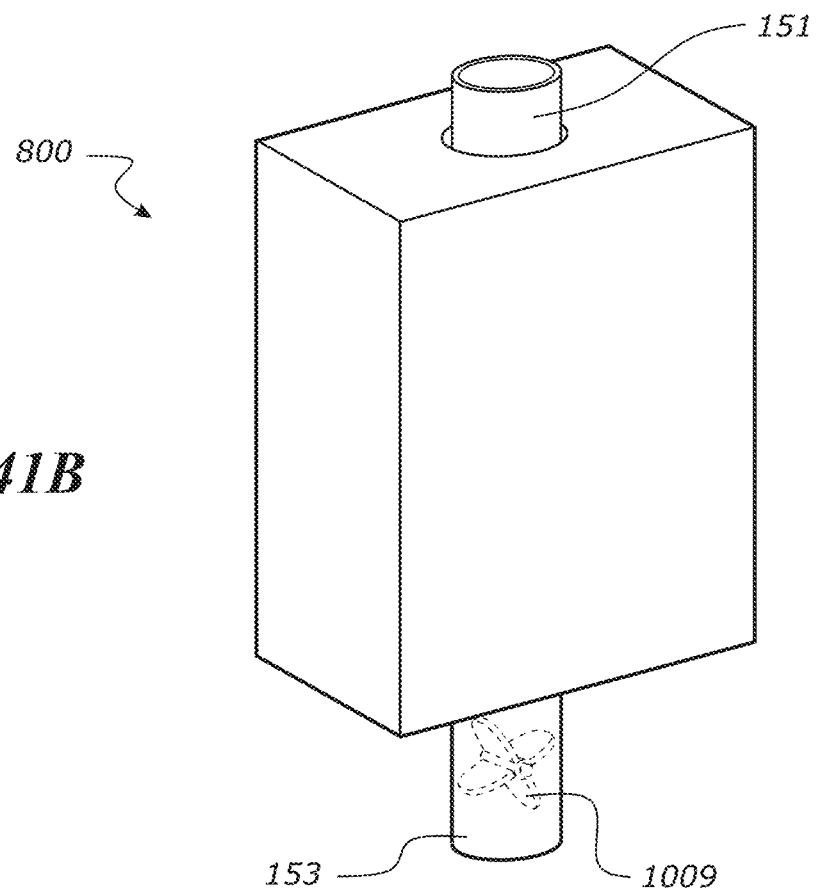

In some embodiments a PRV or a FCPRV may comprise an indicator to indicate a flow of gases being provided from an outlet of the PRV/FCPRV to a patient or user. For example, with reference to FIGS. 41A and 41B, in some embodiments a flow indicator comprises an impeller 1009 to be located in an outlet 153 of the FCPRV. As a flow of gases passes along the outlet 153 the flow causes the impeller to spin to indicate the flow. The impeller may be visible from an end of the outlet 153 or the outlet 153 may be transparent so that the impeller is visible through a wall of the outlet. The impeller 1009 may be rotationally mounted in an impeller housing 1010, and the impeller housing 1010 may be received in the outlet 153.

Figure 42A:
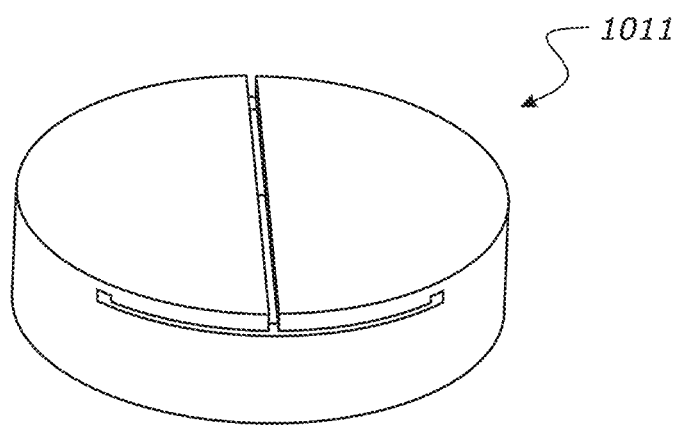
FIG. 42A illustrates a flap flow indicator.
Figure 42B:
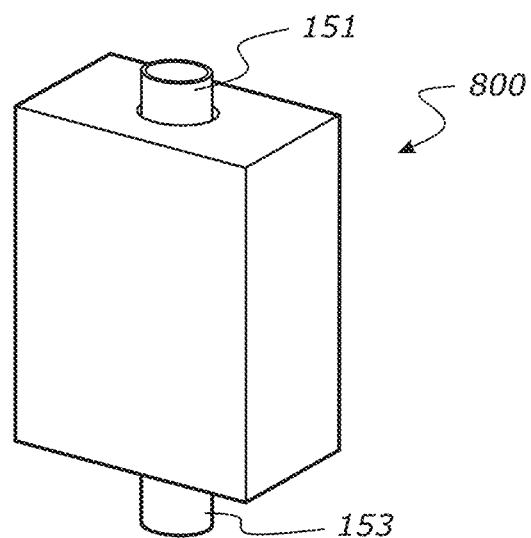
FIG. 42B shows a FCPRV comprising a flap flow indicator not visible in a no-flow condition.
Figure 42C:
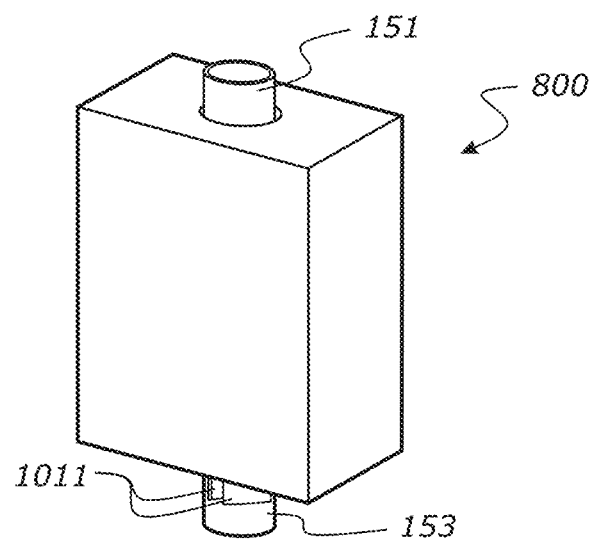
FIG. 42C illustrates the FCPRV of FIG. 42B with a flow of gases from an outlet of the FCPRV indicated by the flap moved to a flow condition.

With reference to FIGS. 42A to 42C, in some embodiments, a flow indicator may comprise a flap 1011 to be located in the outlet 153 of the PRV. The flap is movable between a closed position at least partially occluding the outlet, and an open position. Flow causes the flap to move to the open position to provide an indication of flow through the outlet to the patient. The flap may be visible from an end of the outlet 153 or the outlet 153 may be transparent so that the flap is visible through a wall of the outlet.

Figure 43:
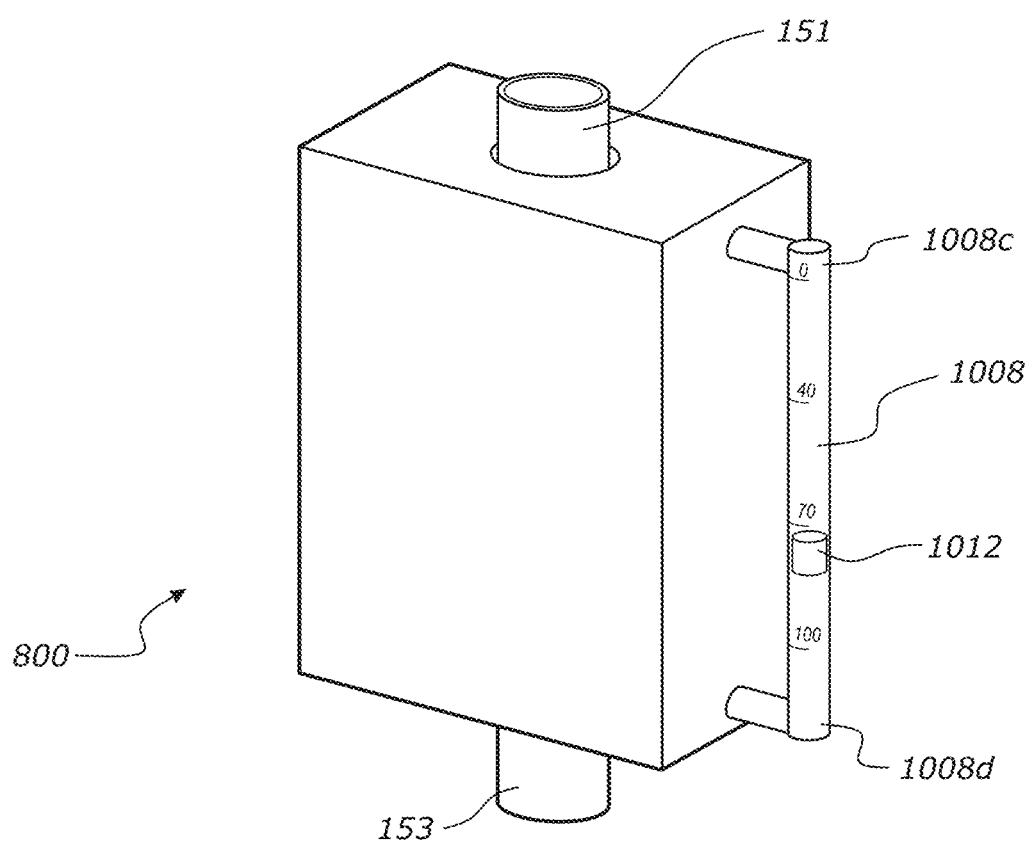
FIG. 43 illustrates a FCPRV comprising a flow indicator comprising a guide tube and shuttle or plunger.

As shown in FIG. 43, in some embodiments, a flow indicator may comprise a plunger or shuttle 1012 received in a guide tube 1008. An inlet end 1008c of the guide tube may be in fluid communication with the inlet 151 of the FCPRV and an outlet end 1008d may be in fluid communication with the outlet 153 of the FCPRV, such that the guide tube senses a pressure differential across the flow restriction 152 (e.g. as shown in FIG. 27A) between the inlet 151 and the outlet 153 of the FCPRV. The shuttle 1012 is adapted to move within the guide tube in response to the pressure differential across the flow restriction 152 to provide an indication of the flow through the FCPRV to the patient. As shown in FIG. 43, the guide tube may be marked with a scale relating the position of the shuttle along the guide tube to a flow rate. A spring (not shown in FIG. 43) may bias the shuttle or plunger against movement in response to increasing flow rate. In other words, a spring may bias the plunger or shuttle towards a zero flow indication. As the flow increases, the flow moves the shuttle or plunger against the bias of the spring to indicate a flow rate through the FCPRV.

In some embodiments, a PRV as described above with reference to FIGS. 2A to 12E may include a damper. In some embodiments, a FCPRV described above with reference to FIGS. 14A to 26B may include a damper. In some embodiments, a damping member (damper) may be disposed or located in contact with the sensing member 155, 255, 280 and/or the valve member 105, 205. In some embodiments a damper is positioned in contact with the valve member 105, 205. The damper may be attached to the valve member 105, 205. The damper may be positioned in the displacement chamber 107, 207, or if in contact with the sensing member, in the second chamber 154b, 254b. The damper may comprise a damping material such as foam or cotton pads, a sponge or tissue. In some embodiments, the damper is preferably formed from a soft, spongy material. In some embodiments, the damper comprises a porous material with a plurality of pores. In some embodiments the damper acts as a muffler configured to damp or muffle noise of the various moving valve components. In some embodiments the damper also increases the stability of the valve over a wider operating flow range. In some embodiments the damper damps mechanical oscillations of the moving parts of the PRV or FCPRV which in turn may reduce noise and/or increase the stability of the valve over a wider operating flow range.

In some embodiments the pressure relieve valve of the flow compensated pressure relief valve may be without an outlet chamber.

In some embodiment a PRV or FCPRV described herein may be provided as a disposable or consumable item, to be discarded after a short-time use, such that no cleaning of the PRV or FCPRV is required. Where a conduit is provided with the PRV or FCPRV, the conduit may also be disposable together with the PRV or FCPRV. Alternatively, a PRV or FCPRV described herein may be provided as a reusable device. Such an item would preferably be cleanable, for example sterilisable via autoclave. The device may be capable of being disassembled for cleaning, and reassembled post cleaning, for example by a medical professional.

The foregoing description of the invention includes preferred forms thereof. Modifications may be made thereto without departing from the scope of the invention.

Where, in the foregoing description reference has been made to integers or components having known equivalents thereof, those integers are herein incorporated as if individually set forth.

The invention may also be said broadly to consist in the parts, elements and features referred to or indicated in the specification of the application, individually or collectively, in any or all combinations of two or more of said parts, elements or features.

The invention claimed is:

1. A flow compensated pressure regulating or pressure relief device for a system providing a flow of gases, the device comprising:
   a main inlet to receive a flow of gases from a gases source and a main outlet to provide at least a portion of the flow of gases received by the main inlet to flow from the device,
   a pressure relief valve adapted to vent at least a portion of the flow of gases received by the inlet when a pressure of the flow of gases increases above a pressure threshold, wherein the pressure relief valve comprises:
   a valve inlet in fluid communication with the main inlet,
   a vent outlet,
   a valve seat between the valve inlet and the vent outlet, and
   a valve member configured to seal against the valve seat and to displace from the valve seat by an inlet pressure at the valve inlet increasing above the pressure threshold to vent at least a portion of the flow of gases from the valve inlet to the vent outlet, and
   a sensing mechanism to dynamically adjust the pressure threshold based on a flow rate of the flow of gases from the main outlet to a patient, wherein the sensing mechanism comprises:

a sensing member to sense a differential pressure indicative of the flow rate of the flow of gases from the main outlet to the patient, and a mechanical link acting between the sensing member and the valve member to transfer a force applied by the sensing member to the valve member to adjust a biasing of the valve member against the valve seat in response to the flow rate of the flow of gases through the main outlet.

2. A device as claimed in claim 1, wherein the sensing mechanism comprises a flow restriction or constriction to generate the differential pressure sensed by the sensing member to displace the sensing member in response to the flow rate of the gases through the main outlet.

3. A device as claimed in claim 1, wherein the sensing mechanism comprises:

a flow constriction or restriction downstream of the valve inlet, a sensing chamber, and the sensing member located in the sensing chamber dividing the sensing chamber into a first chamber and a second chamber, the first chamber in fluid communication with the flow of gases upstream of the flow constriction or restriction, and the second chamber in fluid communication with the flow of gases at the flow constriction or downstream of the flow restriction, a resulting differential pressure caused by the flow of gases through the flow constriction or restriction and the main outlet sensed by the sensing member.

4. A device as claimed in claim 3, wherein the sensing member is a piston, and the sensing chamber is a cylinder in which the piston moves, and the piston pneumatically seals the first chamber from the second chamber.

5. A device as claimed in claim 3, wherein the mechanical link is a rod or shaft and the device comprises a link guide supporting the mechanical link between the valve member and the sensing member, and wherein the main inlet is in fluid communication with the sensing chamber via an annular space between the link and the link guide.

6. A device as claimed in claim 3, further comprising a housing to enclose the pressure relief valve and the sensing mechanism.

7. A device as claimed in claim 6, comprising a body, the body comprising the main inlet and the main outlet, and at least an outlet chamber of the device and the first chamber of the sensing chamber, and the housing substantially encloses the body.

8. A device as claimed in claim 7, wherein the housing provides a space or cavity around the body, and wherein a displacement chamber of the device and/or the outlet chamber is in fluid communication with the cavity or space.

9. A device as claimed in claim 8, wherein the housing comprises a housing outlet from the housing space.

10. A device as claimed in claim 8, wherein the housing comprises a housing vent outlet in communication with a vent outlet from the outlet chamber, and where the housing vent outlet is coaxial with the main inlet or the main outlet.

11. A device as claimed in claim 8, wherein the housing comprises an aperture in fluid communication with the displacement chamber, and the aperture is coaxial with the main inlet or the main outlet.

12. A device as claimed in claim 7, wherein the valve member is a plunger or diaphragm.

13. A device as claimed in claim 1, wherein the mechanical link is coupled to the valve member and the sensing member to bias the valve member against the valve seat in response to the flow rate of the flow gases through the main outlet; or wherein the mechanical link is uncoupled from the valve member or the sensing member or the valve member and the sensing member, and with no flow of gases through the main outlet the valve member is biased against the valve seat and with the mechanical link bearing against the valve member and the sensing member, and as the flow of gases through the main outlet increases, the differential pressure across the sensing member increases to reduce a force applied by the mechanical link to the valve member to reduce a bias of the valve member against the valve seat until the mechanical link loses contact with the valve member or the sensing member or both when the flow rate of the flow of gases through the main outlet increases above a threshold.

14. A device as claimed in claim 1, wherein the mechanical link is uncoupled from the valve member or the sensing member or the valve member and the sensing member, and with no flow of gases through the main outlet the valve member is biased against the valve seat and with the mechanical link bearing against the valve member and the sensing member, and as the flow of gases through the main outlet increases, the differential pressure across the sensing member increases to reduce a force applied by the mechanical link to the valve member to reduce a bias of the valve member against the valve seat until the mechanical link loses contact with the valve member or the sensing member or both when the flow rate of the flow of gases through the main outlet increases above a threshold.

15. A device as claimed in claim 1, wherein the pressure relief valve comprises:

an outlet chamber comprising the vent outlet, the valve member adapted to displace from the valve seat by the inlet pressure at the valve inlet increasing above the pressure threshold to vent at least a portion of the flow of gases received by the main inlet from the valve inlet to the vent outlet via the outlet chamber, the flow of gases through the vent outlet causing an outlet pressure in the outlet chamber to act on the valve member together with the inlet pressure to displace the valve member from the valve seat.

16. A device as claimed in 1, wherein the valve member comprises a membrane and/or the sensing member comprises a membrane.

17. A device as claimed in claim 16, wherein the valve member and/or the sensing member comprises a frame supporting the membrane in a tensioned state.

18. A device as claimed in claim 1, wherein the mechanical link comprises a flange at one end to support the valve member against the valve seat.

19. A device as claimed in claim 1, wherein the device is configured to limit an amount of travel or deformation of the sensing member to set an upper pressure limit for the pressure threshold that is independent of flow rate.

20. A device as claimed in claim 19, wherein the device comprises a mechanical limit to limit the amount of travel or deformation of the sensing member.

21. A respiratory gases system comprising a flow compensated pressure regulating or pressure relief device as claimed in claim 1, wherein the system is a high flow respiratory gases system comprising a flow source and an unsealed patient interface.

22. A flow compensated pressure regulating or pressure relief device for a system providing a flow of gases, the device comprising:
- a main inlet configured to receive a flow of gases from a gases source and a main outlet configured to provide at least a portion of the flow of gases received by the main inlet to flow from the device,
- a pressure relief valve adapted to vent at least a portion of the flow of gases received by the inlet when a pressure of the flow of gases increases above a pressure threshold, wherein the pressure relief valve comprises:
  - a valve inlet in fluid communication with the main inlet,
  - a vent outlet,
  - a valve seat between the valve inlet and the vent outlet, and
  - a valve member configured to seal against the valve seat and to displace from the valve seat by an inlet pressure at the valve inlet increasing above the pressure threshold to vent at least a portion of the flow of gases from the valve inlet to the vent outlet, and
- a sensing mechanism configured to dynamically adjust the pressure threshold based on a flow rate of the flow of gases at the main outlet, wherein the sensing mechanism comprises:
  - a sensing member to sense a differential pressure indicative of the flow rate of the flow of gases at the main outlet, and
  - a mechanical link acting between the sensing member and the valve member to transfer a force applied by the sensing member to the valve member to adjust a biasing of the valve member against the valve seat in response to the flow rate of the flow of gases at the main outlet.

23. A device as claimed in claim 22, wherein the sensing mechanism comprises a flow restriction or constriction to generate the differential pressure sensed by the sensing member to displace the sensing member in response to the flow rate of the gases at the main outlet.

24. A device as claimed in claim 22, wherein the sensing mechanism comprises:
- a flow constriction or restriction downstream of the valve inlet,
- a sensing chamber, and the sensing member located in the sensing chamber dividing the sensing chamber into a first chamber and a second chamber, the first chamber in fluid communication with the flow of gases upstream of the flow constriction or restriction, and the second chamber in fluid communication with the flow of gases at the flow constriction or downstream of the flow restriction, a resulting differential pressure caused by the flow of gases through the flow constriction or restriction and the main outlet sensed by the sensing member.

25. A device as claimed in claim 24, wherein the sensing member is a piston, and the sensing chamber is a cylinder in which the piston moves, and the piston pneumatically seals the first chamber from the second chamber.

26. A device as claimed in claim 24, wherein the mechanical link is a rod or shaft and the device comprises a link guide supporting the mechanical link between the valve member and the sensing member, and wherein the main inlet is in fluid communication with the sensing chamber via an annular space between the link and the link guide.

27. A device as claimed in claim 24, further comprising a housing to enclose the pressure relief valve and the sensing mechanism.

28. A device as claimed in claim 27, comprising a body, the body comprising the main inlet and the main outlet, and at least an outlet chamber of the device and the first chamber of the sensing chamber, and the housing substantially encloses the body.

29. A device as claimed in claim 28, wherein the housing provides a space or cavity around the body, and wherein a displacement chamber of the device and/or the outlet chamber is in fluid communication with the cavity or space.

30. A device as claimed in claim 29, wherein the housing comprises a housing outlet from the housing space.

31. A device as claimed in claim 29, wherein the housing comprises a housing vent outlet in communication with a vent outlet from the outlet chamber, and where the housing vent outlet is coaxial with the main inlet or the main outlet.

32. A device as claimed in claim 29, wherein the housing comprises an aperture in fluid communication with the displacement chamber, and the aperture is coaxial with the main inlet or the main outlet.

33. A device as claimed in claim 28, wherein the valve member is a plunger or diaphragm.

34. A device as claimed in claim 22,
- wherein the mechanical link is coupled to the valve member and the sensing member to bias the valve member against the valve seat in response to the flow rate of the flow gases at the main outlet; or
- wherein the mechanical link is uncoupled from the valve member or the sensing member or the valve member and the sensing member, and
- with no flow of gases through the main outlet the valve member is biased against the valve seat and with the mechanical link bearing against the valve member and the sensing member, and
- as the flow of gases through the main outlet increases, the differential pressure across the sensing member increases to reduce a force applied by the mechanical link to the valve member to reduce a bias of the valve member against the valve seat until the mechanical link loses contact with the valve member or the sensing member or both when the flow rate of the flow of gases at the main outlet increases above a threshold.

35. A device as claimed in claim 22, wherein the mechanical link is uncoupled from the valve member or the sensing member or the valve member and the sensing member, and
- with no flow of gases through the main outlet the valve member is biased against the valve seat and with the mechanical link bearing against the valve member and the sensing member, and
- as the flow of gases through the main outlet increases, the differential pressure across the sensing member increases to reduce a force applied by the mechanical link to the valve member to reduce a bias of the valve member against the valve seat until the mechanical link loses contact with the valve member or the sensing member or both when the flow rate of the flow of gases at the main outlet increases above a threshold.

36. A device as claimed in claim 22, wherein the pressure relief valve comprises:
- an outlet chamber comprising the vent outlet,
- the valve member adapted to displace from the valve seat by the inlet pressure at the valve inlet increasing above the pressure threshold to vent at least a portion of the flow of gases received by the main inlet from the valve inlet to the vent outlet via the outlet chamber, the flow of gases through the vent outlet causing an outlet pressure in the outlet chamber to act on the valve member together with the inlet pressure to displace the valve member from the valve seat.

37. A device as claimed in 22, wherein the valve member comprises a membrane and/or the sensing member comprises a membrane.

38. A device as claimed in claim 37, wherein the valve member and/or the sensing member comprises a frame supporting the membrane in a tensioned state.

39. A device as claimed in claim 22, wherein the mechanical link comprises a flange at one end to support the valve member against the valve seat.

40. A device as claimed in claim 22, wherein the device is configured to limit an amount of travel or deformation of the sensing member to set an upper pressure limit for the pressure threshold that is independent of flow rate.

41. A device as claimed in claim 40, wherein the device comprises a mechanical limit to limit the amount of travel or deformation of the sensing member.

42. A respiratory gases system comprising a flow compensated pressure regulating or pressure relief device as claimed in claim 22, wherein the system is a high flow respiratory gases system comprising a flow source and an unsealed patient interface.

43. A flow compensated pressure regulating or pressure relief device for a system providing a flow of gases, the device comprising:
    a main inlet configured to receive a flow of gases from a gases source and a main outlet configured to provide at least a portion of the flow of gases received by the main inlet to flow from the device,
    a pressure relief valve adapted to vent at least a portion of the flow of gases received by the inlet when a pressure of the flow of gases increases above a pressure threshold, wherein the pressure relief valve comprises:
        a valve inlet in fluid communication with the main inlet,
        a vent outlet,
        a valve seat between the valve inlet and the vent outlet, and
        a valve member configured to seal against the valve seat and to displace from the valve inlet by an inlet pressure at the valve inlet increasing above the pressure threshold to vent at least a portion of the flow of gases from the valve inlet to the vent outlet, and
    a sensing mechanism configured to dynamically adjust the pressure threshold based on a flow rate of the flow of gases downstream of the main inlet, wherein the sensing mechanism comprises:
        a sensing member to sense a differential pressure indicative of the flow rate of the flow of gases downstream of the main inlet, and
        a mechanical link acting between the sensing member and the valve member to transfer a force applied by the sensing member to the valve member to adjust a biasing of the valve member against the valve seat in response to the flow rate of the flow of gases downstream of the main inlet.

44. A device as claimed in claim 43, wherein the sensing mechanism comprises a flow restriction or constriction to generate the differential pressure sensed by the sensing member to displace the sensing member in response to the flow rate of the gases downstream of the main inlet.

45. A device as claimed in claim 43, wherein the sensing mechanism comprises:
    a flow constriction or restriction downstream of the valve inlet,
    a sensing chamber, and the sensing member located in the sensing chamber dividing the sensing chamber into a first chamber and a second chamber, the first chamber in fluid communication with the flow of gases upstream of the flow constriction or restriction, and the second chamber in fluid communication with the flow of gases at the flow constriction or downstream of the flow restriction, a resulting differential pressure caused by the flow of gases through the flow constriction or restriction and the main outlet sensed by the sensing member.

46. A device as claimed in claim 45, wherein the sensing member is a piston, and the sensing chamber is a cylinder in which the piston moves, and the piston pneumatically seals the first chamber from the second chamber.

47. A device as claimed in claim 45, wherein the mechanical link is a rod or shaft and the device comprises a link guide supporting the mechanical link between the valve member and the sensing member, and wherein the main inlet is in fluid communication with the sensing chamber via an annular space between the link and the link guide.

48. A device as claimed in claim 45, further comprising a housing to enclose the pressure relief valve and the sensing mechanism.

49. A device as claimed in claim 48, comprising a body, the body comprising the main inlet and the main outlet, and at least an outlet chamber of the device and the first chamber of the sensing chamber, and the housing substantially encloses the body.

50. A device as claimed in claim 49, wherein the housing provides a space or cavity around the body, and wherein a displacement chamber of the device and/or the outlet chamber is in fluid communication with the cavity or space.

51. A device as claimed in claim 50, wherein the housing comprises a housing outlet from the housing space.

52. A device as claimed in claim 50, wherein the housing comprises a housing vent outlet in communication with a vent outlet from the outlet chamber, and where the housing vent outlet is coaxial with the main inlet or the main outlet.

53. A device as claimed in claim 50, wherein the housing comprises an aperture in fluid communication with the displacement chamber, and the aperture is coaxial with the main inlet or the main outlet.

54. A device as claimed in claim 49, wherein the valve member is a plunger or diaphragm.

55. A device as claimed in claim 43,
    wherein the mechanical link is coupled to the valve member and the sensing member to bias the valve member against the valve seat in response to the flow rate of the flow gases downstream of the main inlet; or
    wherein the mechanical link is uncoupled from the valve member or the sensing member or the valve member and the sensing member, and
    with no flow of gases through the main outlet the valve member is biased against the valve seat and with the mechanical link bearing against the valve member and the sensing member, and
    as the flow of gases through the main outlet increases, the differential pressure across the sensing member increases to reduce a force applied by the mechanical link to the valve member to reduce a bias of the valve member against the valve seat until the mechanical link loses contact with the valve member or the sensing member or both when the flow rate of the flow of gases downstream of the main inlet increases above a threshold.

56. A device as claimed in claim 43, wherein the mechanical link is uncoupled from the valve member or the sensing member or the valve member and the sensing member, and with no flow of gases through the main outlet the valve member is biased against the valve seat and with the mechanical link bearing against the valve member and the sensing member, and as the flow of gases through the main outlet increases, the differential pressure across the sensing member increases to reduce a force applied by the mechanical link to the valve member to reduce a bias of the valve member against the valve seat until the mechanical link loses contact with the valve member or the sensing member or both when the flow rate of the flow of gases downstream of the main inlet increases above a threshold.

57. A device as claimed in claim 43, wherein the pressure relief valve comprises:

an outlet chamber comprising the vent outlet, the valve member adapted to displace from the valve seat by the inlet pressure at the valve inlet increasing above the pressure threshold to vent at least a portion of the flow of gases received by the main inlet from the valve inlet to the vent outlet via the outlet chamber, the flow of gases through the vent outlet causing an outlet pressure in the outlet chamber to act on the valve member together with the inlet pressure to displace the valve member from the valve seat.

58. A device as claimed in 43, wherein the valve member comprises a membrane and/or the sensing member comprises a membrane.

59. device as claimed in claim 58, wherein the valve member and/or the sensing member comprises a frame supporting the membrane in a tensioned state.

60. A device as claimed in claim 45, wherein the mechanical link comprises a flange at one end to support the valve member against the valve seat.

61. A device as claimed in claim 45, wherein the device is configured to limit an amount of travel or deformation of the sensing member to set an upper pressure limit for the pressure threshold that is independent of flow rate.

62. A device as claimed in claim 61, wherein the device comprises a mechanical limit to limit the amount of travel or deformation of the sensing member.

63. A respiratory gases system comprising a flow compensated pressure regulating or pressure relief device as claimed in claim 43, wherein the system is a high flow respiratory gases system comprising a flow source and an unsealed patient interface.

\* \* \* \* \*

UNITED STATES PATENT AND TRADEMARK OFFICE
CERTIFICATE OF CORRECTION

| | | |
|---|---|---|
| PATENT NO. | : 11,235,123 B2 | Page 1 of 1 |
| APPLICATION NO. | : 16/325853 | |
| DATED | : February 1, 2022 | |
| INVENTOR(S) | : Barnes et al. | |

It is certified that error appears in the above-identified patent and that said Letters Patent is hereby corrected as shown below:

In the Claims

In Column 66, Claim 16, Line 47, after "in" insert --claim--.

In Column 69, Claim 37, Line 5, after "in" insert --claim--.

In Column 72, Claim 58, Line 5, after "in" insert --claim--.

In Column 72, Claim 59, Line 8, before "device" insert --A--.

In Column 72, Claim 60, Line 11 (approx.), delete "45," and insert --43,--.

In Column 72, Claim 61, Line 14 (approx.), delete "45," and insert --43,--.

Signed and Sealed this
Third Day of May, 2022

Katherine Kelly Vidal
*Director of the United States Patent and Trademark Office*